United States Patent
Soergel et al.

(10) Patent No.: US 10,385,012 B2
(45) Date of Patent: Aug. 20, 2019

(54) THIOAMIDES AND AMIDES FOR CONTROLLING ANIMAL PESTS

(71) Applicant: BASF SE, Ludwigshafen (DE)

(72) Inventors: Sebastian Soergel, Ludwigshafen (DE); Pascal Bindschaedler, Roemerberg (DE); Matthias Pohlman, Freinsheim (DE); Ralph Paulini, Cary, NC (US)

(73) Assignee: BASF SE, Ludwigshafen (DE)

( * ) Notice: Subject to any disclaimer, the term of this patent is extended or adjusted under 35 U.S.C. 154(b) by 35 days.

(21) Appl. No.: 15/105,062

(22) PCT Filed: Dec. 15, 2014

(86) PCT No.: PCT/EP2014/077737
§ 371 (c)(1),
(2) Date: Jun. 16, 2016

(87) PCT Pub. No.: WO2015/091343
PCT Pub. Date: Jun. 25, 2015

(65) Prior Publication Data
US 2016/0318854 A1 Nov. 3, 2016

Related U.S. Application Data

(60) Provisional application No. 61/918,690, filed on Dec. 20, 2013.

(51) Int. Cl.
| | |
|---|---|
| C07C 255/61 | (2006.01) |
| C07C 327/44 | (2006.01) |
| C07D 213/57 | (2006.01) |
| A01N 41/12 | (2006.01) |
| A01N 37/34 | (2006.01) |
| A01N 43/40 | (2006.01) |
| A01N 43/54 | (2006.01) |
| A01N 43/58 | (2006.01) |
| A01N 43/60 | (2006.01) |
| A01N 53/00 | (2006.01) |
| C07C 255/57 | (2006.01) |

(52) U.S. Cl.
CPC ............ *C07C 255/61* (2013.01); *A01N 37/34* (2013.01); *A01N 41/12* (2013.01); *A01N 43/40* (2013.01); *A01N 43/54* (2013.01); *A01N 43/58* (2013.01); *A01N 43/60* (2013.01); *A01N 53/00* (2013.01); *C07C 255/57* (2013.01); *C07C 327/44* (2013.01); *C07D 213/57* (2013.01)

(58) Field of Classification Search
None
See application file for complete search history.

(56) References Cited

U.S. PATENT DOCUMENTS

| | | | |
|---|---|---|---|
| 2002/0169203 A1* | 11/2002 | Jensen | C07C 69/65 514/450 |
| 2004/0138065 A1 | 7/2004 | Otaka et al. | |
| 2005/0176784 A1 | 8/2005 | Otaka et al. | |

FOREIGN PATENT DOCUMENTS

| | | |
|---|---|---|
| EP | 0445698 | 9/1991 |
| EP | 1555259 | 7/2005 |
| JP | 05059003 | 3/1993 |
| WO | WO 2000037422 | 6/2000 |

OTHER PUBLICATIONS

Patani, G. et al. "Bioisosterism: A Rational approach in drug design" Chem. Rev. 1996, 96, 3147-3176.*
U.S. Environmental Protection Agency (Insect Repellents: Uses and Effectiveness; updated Apr. 2013, no pagination.*
Pest Control Methods (Pest control methods: Natural vs. Chemical; © 2012), no pagination.*
Technicide "pest control" cached May 4, 2013. no pagination http://technicide.com/Pest-Control.*
International Search Report, issued in PCT/EP2014/077737, dated Feb. 18, 2015.
International Preliminary Report on Patentability, issued in PCT/EP2014/077737, dated Dec. 11, 2015.
Database Caplus [online] Chemical Abstracts Service, Columbus, Ohio, He et al., Copper-Catalyzed Enantioselective Intramolecular Aryl C—N Coupling: Synthesis of Enantioenriched 2-Oxo-1,2,3,4-tetrahydroquinoline-3-carboxamides via an Asymmetric Desymmetrization Strategy. XP002735071, Search Report.
He et al., "Copper-Catalyzed Enantioselective Intramolecular Aryl C—N Coupling: Synthesis of Enantioenriched 2-Oxo-1,2,3,4-tetrahydroquinoline-3-carboxamides via an Asymmetric Desymmetrization Strategy," Organic Letters, vol. 17, No. 2, (2015), pp. 374-377, Search Report.
Database Caplus [online] Chemical Abstracts Service, Columbus, Ohio, Okujima et al., "Preparation of Cyanophenylthioacetamides as Antihypertensives." XP002735072, Search Report.
Shimo et al., "Solvent-Catalyzed Alkylations of Active Methylene Groups in Liquid Ammonia," Journal of Organic Chemistry, vol. 26, (1961), pp. 4868-4871.

* cited by examiner

*Primary Examiner* — Mina Haghighatian
*Assistant Examiner* — Erin E Hirt
(74) *Attorney, Agent, or Firm* — Brinks Gilson & Lione

(57) ABSTRACT

The invention relates to the use of a compound of formula (I)

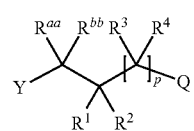

or a salt thereof for combating animal pests, where the symbols and indices are defined in the specification.

30 Claims, No Drawings

THIOAMIDES AND AMIDES FOR CONTROLLING ANIMAL PESTS

This application is a National Stage application of International Application No. PCT/EP2014/077737, filed Dec. 15, 2014, which claims the benefit of U.S. Provisional Application No. 61/918,690, filed Dec. 20, 2013.

The invention relates to aryl alkyl thioamides and amides, a method for their preparation and their use for combating animal pests, an agricultural composition or seeds comprising said malononitriles, a method for combating animal pests, a method for protecting crops from attack or infestation by animal pests, a method for protecting seeds from soil insects and the seedlings' roots and shoots from soil and foliar insects.

Animal pests destroy growing and harvested crops and attack wooden dwelling and commercial structures, causing large economic loss to the food supply and to property. While a large number of pesticidal agents are known, due to the ability of target pests to develop resistance to said agents, there is an ongoing need for new agents for combating animal pests. In particular, animal pests such as insects and acaridae are difficult to be effectively controlled. However, it is a continuing objective to provide further pesticidal compounds which, at least in some aspects, offer advantages over the known compounds.

Pesticidal compounds having a dicyanoalkane moiety have been disclosed in a number of patent applications, e.g. JP 2002 284608, WO 02/089579, WO 02/090320, WO 02/090321, WO 04/006677, WO 04/020399, JP 2004 99593, JP 2004 99597, WO 05/068432, WO 05/064823, EP 1555259, WO 05/063694, WO 2007/071609, and WO 2007/147888.

It has now been found that particular aryl alkyl thioamides and amides bearing an additional carbocyclic or 6-membered aromatic heterocyclic ring on the aforementioned alkyl group are particularly useful for controlling pests, in particular invertebrate pests.

Accordingly, in one aspect of the invention there is provided the use of a compound of formula (I)

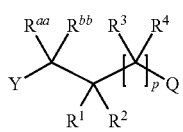

(I)

or a salt thereof for combating animal pests, wherein

Y is phenyl unsubstituted or substituted with 1, 2, 3, 4 or 5 substituents $R^5$; or naphthyl unsubstituted or substituted with 1, 2, 3, 4, 5, 6 or 7 substituents $R^5$;

Q is phenyl unsubstituted or substituted with 1, 2, 3, 4 or 5 substituents $R^6$; $C_3$-$C_8$ cycloalkyl unsubstituted or substituted with one or more substituents $R^6$; $C_3$-$C_8$ cycloalkenyl unsubstituted or substituted with one or more substituents $R^6$; or a 6-membered aromatic heterocyclic ring containing 1, 2, 3 or 4 nitrogen atoms in the ring, wherein the aforementioned ring is unsubstituted or substituted with 1, 2, 3 or 4 substituents $R^6$;

$R^1$ is hydrogen, halogen, cyano, hydroxy, $C_1$-$C_6$-alkyl, $C_2$-$C_6$-alkenyl, $C_2$-$C_6$-alkynyl, $C_3$-$C_8$-cycloalkyl, $C_3$-$C_8$-cycloalkenyl, $C_1$-$C_6$-alkoxy, $C_2$-$C_6$-alkenyloxy, $C_1$-$C_6$-alkylthio, ($C_1$-$C_6$-alkoxy)carbonyl, wherein the carbon atoms of the aforementioned aliphatic or cycloaliphatic radicals are unsubstituted or substituted with 1, 2 or 3 substituents $R^7$;

$R^2$ is hydrogen or halogen;
or
$R^1$ and $R^2$ form together with the carbon atom to which they are attached a methylene group or a cyclopropyl group;

$R^3$ is hydrogen, halogen, cyano, hydroxy, $C_1$-$C_6$-alkyl, $C_2$-$C_6$-alkenyl, $C_2$-$C_6$-alkynyl, $C_3$-$C_8$-cycloalkyl, $C_3$-$C_8$-cycloalkenyl, $C_1$-$C_6$-alkoxy, $C_2$-$C_6$-alkenyloxy, $C_1$-$C_6$-alkylthio, ($C_1$-$C_6$-alkoxy)carbonyl, wherein the carbon atoms of the aforementioned aliphatic or cycloaliphatic radicals are unsubstituted or substituted with 1, 2 or 3 substituents $R^7$;

$R^4$ is hydrogen or halogen;
or
$R^3$ and $R^4$ form together with the carbon atom to which they are attached a methylene group or a cyclopropyl group;

each $R^5$, $R^6$ is independently halogen, cyano, azido, nitro, —SCN, $SF_5$, $C_1$-$C_6$ alkyl, $C_2$-$C_6$ alkenyl, $C_2$-$C_6$ alkynyl, wherein the carbon atoms of the aforementioned aliphatic radicals are unsubstituted or substituted with one or more $R^a$;

$C_3$-$C_8$ cycloalkyl or $C_3$-$C_8$ cycloalkenyl, wherein the carbon atoms of the aforementioned cycloaliphatic radicals are unsubstituted or substituted with one or more $R^b$;

phenyl unsubstituted or substituted with up to 5 $R^c$;
a 3-, 4-, 5-, 6- or 7-membered saturated, partially unsaturated or aromatic heterocyclic ring containing 1, 2 or 3 heteroatoms or heteroatom groups selected from N, O, S, NO, SO, $SO_2$, wherein the aforementioned ring is unsubstituted or substituted with up to 5 $R^d$;

$Si(R^e)_3$, $OR^f$, $SR^f$, $OS(O)_xR^h$, $S(O)_xR^h$, $N(R^i)_2$, $N(R^i)C(=O)R^m$, $OC(=O)R^m$, $C(=O)R^m$, $C(=O)OR^f$, $C(=NR^i)R^m$, $C(=S)R^m$;
or
two $R^5$ on two adjacent carbon atoms present on one phenyl ring are together a bridge selected from $CH_2CH_2CH_2CH_2$, N=CH—CH=CH, CH=N—CH=CH, N=CH—N=CH, N=CH—CH=N, $OCH_2CH_2CH_2$, OCH=$CHCH_2$, $CH_2OCH_2CH_2$, $OCH_2CH_2O$, $OCH_2OCH_2$, $CH_2CH_2CH_2$, CH=$CHCH_2$, $CH_2CH_2O$, CH=CHO, $CH_2OCH_2$, $CH_2C(=O)O$, C(=O)$OCH_2$, $O(CH_2)O$, $SCH_2CH_2CH_2$, SCH=$CHCH_2$, $CH_2SCH_2CH_2$, $SCH_2CH_2S$, $SCH_2SCH_2$, $CH_2CH_2S$, CH=CHS, $CH_2SCH_2$, $CH_2C(=S)S$, C(=S)$SCH_2$, $S(CH_2)S$, $CH_2CH_2NR^K$, $CH_2CH=N$, CH=CH—$NR^K$, OCH=N, SCH=N and form together with the carbon atoms the two $R^5$ are bonded to a 5- or 6-membered partially unsaturated or aromatic carbocyclic or heterocyclic ring, wherein the ring is unsubstituted or substituted with 1 or 2 substituents selected from =O, OH, $CH_3$, $OCH_3$, halogen, halomethyl and halomethoxy;

each $R^7$ is independently halogen, cyano, hydroxy, $C_1$-$C_6$-alkyl, $C_2$-$C_6$-alkenyl, $C_2$-$C_6$-alkynyl, $C_3$-$C_8$-cycloalkyl, $C_3$-$C_8$-cycloalkenyl, $C_1$-$C_6$-alkoxy, $C_2$-$C_6$-alkenyloxy, $C_1$-$C_6$-alkylthio, ($C_1$-$C_6$-alkoxy)carbonyl, $OSi(R^e)_3$, wherein the carbon atoms of the aforementioned aliphatic or cycloaliphatic radicals are unsubstituted, partially or fully halogenated and/or oxygenated;

$R^{aa}$ is —C(=S)N($R^{cc}$)$_2$, —C(=$NR^{dd}$)$SR^{ee}$, or —C(=O)N($R^{ff}$)$_2$;

$R^{bb}$ is —C(=S)N($R^{cc}$)$_2$, —C(=$NR^{dd}$)$SR^{ee}$, —C(=O)N($R^{ff}$)$_2$, or CN;

each $R^{cc}$ is independently hydrogen, cyano, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_6$-cycloalkyl, $C_3$-$C_6$-halocycloalkyl, $C_1$-$C_6$-alkoxy-$C_1$-$C_6$-alkyl, $C_1$-$C_6$-haloalkoxy-$C_1$-$C_6$-alkyl, $C_1$-$C_6$-alkylthio-$C_1$-$C_6$-alkyl, $C_1$-$C_6$-haloalkylthio-$C_1$-$C_6$-alkyl;

each $R^{dd}$ is independently hydrogen, cyano, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_6$-cycloalkyl, $C_3$-$C_6$-halocycloalkyl, $C_1$-$C_6$-alkoxy-$C_1$-$C_6$-alkyl, $C_1$-$C_6$-haloalkoxy-$C_1$-$C_6$-alkyl, $C_1$-$C_6$-alkylthio-$C_1$-$C_6$-alkyl, $C_1$-$C_6$-haloalkylthio-$C_1$-$C_6$-alkyl;

each $R^{ee}$ is independently cyano, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_6$-cycloalkyl, $C_3$-$C_6$-halocycloalkyl, $C_1$-$C_6$-alkoxy-$C_1$-$C_6$-alkyl, $C_1$-$C_6$-haloalkoxy-$C_1$-$C_6$-alkyl, $C_1$-$C_6$-alkylthio-$C_1$-$C_6$-alkyl, $C_1$-$C_6$-haloalkylthio-$C_1$-$C_6$-alkyl;

each $R^{ff}$ is independently hydrogen, cyano, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_6$-cycloalkyl, $C_3$-$C_6$-halocycloalkyl, $C_1$-$C_6$-alkoxy-$C_1$-$C_6$-alkyl, $C_1$-$C_6$-haloalkoxy-$C_1$-$C_6$-alkyl, $C_1$-$C_6$-alkylthio-$C_1$-$C_6$-alkyl, $C_1$-$C_6$-haloalkylthio-$C_1$-$C_6$-alkyl;

each $R^a$ is independently halogen, cyano, azido, nitro, —SCN, $SF_5$, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$ haloalkynyl, $C_1$-$C_6$-alkyl-$C_3$-$C_8$-cycloalkyl, $Si(R^e)_3$, $OR^A$, $SR^A$, $OSO_2R^B$, $S(O)_xR^B$, —$S(O)_xN(R^D)_2$, $N(R^D)_2$, $C(=O)N(R^D)_2$, $C(=S)N(R^D)_2$, $C(=O)OR^A$, phenyl unsubstituted or substituted with up to 5 $R^E$;

a 3-, 4-, 5-, 6- or 7-membered saturated, partially unsaturated or aromatic heterocyclic ring containing 1, 2 or 3 heteroatoms or heteroatom groups selected from N, O, S, NO, SO, $SO_2$, wherein the aforementioned ring is unsubstituted or substituted with up to 5 $R^E$, or two $R^a$ present on one carbon atom are together =O, =$C(R^F)_2$, =$NR^D$, =$NOR^A$, =$NNR^D$, or two $R^a$ form a 3-, 4-, 5-, 6-, 7- or 8-membered saturated or partially unsaturated carbocyclic or heterocyclic ring together with the carbon atoms the two $R^a$ are bonded to;

each $R^b$ is independently halogen, cyano, azido, nitro, —SCN, $SF_5$, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$ haloalkynyl, $C_1$-$C_6$-alkyl-$C_3$-$C_8$-cycloalkyl, $Si(R^G)_3$, $OR^H$, $SR^H$, $OSO_2R^J$, $S(O)_xR^J$, —$S(O)_xN(R^K)_2$, $N(R^K)_2$, $C(=O)N(R^K)_2$, $C(=S)N(R^K)_2$, $C(=O)OR^H$, or two $R^b$ present on one carbon atom are together =O, =$C(R^L)_2$, =$NR^K$, =$NOR^H$, =$NNR^K$, or two $R^b$ form a 3-, 4-, 5-, 6-, 7- or 8-membered saturated or partially unsaturated carbocyclic or heterocyclic ring together with the carbon atoms the two $R^b$ are bonded to;

each $R^c$ is independently halogen, cyano, azido, nitro, —SCN, $SF_5$, $C_1$-$C_6$-alkyl, $C_2$-$C_6$-alkenyl, $C_2$-$C_6$-alkynyl, $C_3$-$C_8$-cycloalkyl, wherein the carbon atoms of the aforementioned aliphatic or cycloaliphatic radicals are unsubstituted or substituted with one or more $R^M$;

$Si(R^G)_3$, $OR^H$, $SR^H$, $OS(O)_xR^J$, $S(O)_xR^J$, —$S(O)_xN(R^K)_2$, $N(R^K)_2$, $C(=O)R^N$, $C(=O)OR^H$, $C(=NR^K)R^N$, $C(=O)N(R^K)_2$, $C(=S)N(R^K)_2$;

each $R^d$ is independently halogen, cyano, azido, nitro, —SCN, $SF_5$, $C_1$-$C_6$-alkyl, $C_2$-$C_6$-alkenyl, $C_2$-$C_6$-alkynyl, $C_3$-$C_8$-cycloalkyl, wherein the carbon atoms of the aforementioned aliphatic or cycloaliphatic radicals are unsubstituted or substituted with one or more $R^M$;

$Si(R^G)_3$, $OR^H$, $SR^H$, $OS(O)_xR^J$, $S(O)_xR^J$, —$S(O)_xN(R^K)_2$, $N(R^K)_2$, $C(=O)R^N$, $C(=O)OR^H$, $C(=NR^K)R^N$, $C(=O)N(R^K)_2$, $C(=S)N(R^K)_2$, or two $R^d$ present on one atom of a saturated or partially unsaturated heterocyclic ring are together =O, =$C(R^L)_2$; =$NR^K$, =$NOR^H$ or =$NNR^K$;

each $R^e$ is independently halogen, $C_1$-$C_6$ alkyl, $C_1$-$C_6$ haloalkyl, $C_1$-$C_6$ alkoxyalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_8$ cycloalkyl, $C_3$-$C_8$ halocycloalkyl, $C_1$-$C_6$ haloalkoxyalkyl, phenyl, a 3-, 4-, 5-, 6- or 7-membered saturated, partially unsaturated or aromatic heterocyclic ring containing 1, 2 or 3 heteroatoms or heteroatom groups selected from N, O, S, NO, SO, $SO_2$;

each $R^f$ is independently hydrogen, cyano, $C_1$-$C_6$-alkyl, $C_1$-$C_6$-alkylsulfinyl, $C_1$-$C_6$-alkylsulfonyl, $C_3$-$C_8$-cycloalkyl, $C_2$-$C_6$-alkenyl, $C_2$-$C_6$-alkynyl, wherein the carbon atoms of the aforementioned aliphatic or cycloaliphatic radicals are unsubstituted or substituted with one or more $R^M$;

$Si(R^e)_3$, $S(O)_xR^B$, —$S(O)_xN(R^D)_2$, $N(R^D)_2$, —N=$C(R^F)_2$, $C(=O)R^Q$, $C(=O)N(R^D)_2$, $C(=S)N(R^D)_2$, $C(=O)OR^A$, phenyl, a 3-, 4-, 5-, 6- or 7-membered saturated, partially unsaturated or aromatic heterocyclic ring containing 1, 2 or 3 heteroatoms or heteroatom groups selected from N, O, S, NO, SO, $SO_2$;

each $R^h$ is independently hydrogen, cyano, $C_1$-$C_6$-alkyl, $C_1$-$C_6$-alkoxy, $C_1$-$C_6$-alkylthio, $C_3$-$C_8$-cycloalkyl, $C_2$-$C_6$-alkenyl, $C_2$-$C_6$-alkynyl, wherein the carbon atoms of the aforementioned aliphatic or cycloaliphatic radicals are unsubstituted or substituted with one or more $R^M$;

$N(R^D)_2$, —N=$C(R^F)_2$, $C(=O)R^Q$, $C(=O)N(R^D)_2$, $C(=S)N(R^D)_2$, $C(=O)OR^A$, phenyl, a 3-, 4-, 5-, 6- or 7-membered saturated, partially unsaturated or aromatic heterocyclic ring containing 1, 2 or 3 heteroatoms or heteroatom groups selected from N, O, S, NO, SO, $SO_2$;

each $R^i$ is independently hydrogen, $C_1$-$C_6$-alkyl, $C_1$-$C_6$-alkoxy, $C_1$-$C_6$-alkylthio, $C_3$-$C_8$-cycloalkyl, $C_2$-$C_6$-alkenyl, $C_2$-$C_6$-alkynyl, wherein the carbon atoms of the aforementioned aliphatic or cycloaliphatic radicals are unsubstituted or substituted with one or more $R^M$;

$S(O)_xR^B$, —$S(O)_xN(R^D)_2$, $C(=O)R^S$, $C(=O)OR^A$, $C(=O)N(R^D)_2$, $C(=S)R^s$, $C(=S)SR^A$, $C(=S)N(R^D)_2$, $C(=NR^D)R^S$, phenyl unsubstituted or substituted with up to 5 $R^E$;

a 3-, 4-, 5-, 6- or 7-membered saturated, partially unsaturated or aromatic heterocyclic ring containing 1, 2 or 3 heteroatoms or heteroatom groups selected from N, O, S, NO, SO, $SO_2$, wherein the aforementioned ring is unsubstituted or substituted with up to 5 $R^E$, or two $R^i$ on one nitrogen atom are together a $C_2$-$C_7$ alkylene chain and form together with the nitrogen atom they are bonded to a 3-, 4-, 5-, 6-, 7- or 8-membered saturated, partially unsaturated or aromatic ring, wherein the alkylene chain may contain 1 or 2 heteroatoms or heteroatom groups selected from N, O, S, NO, SO, $SO_2$, and wherein the alkylene chain is unsubstituted or substituted with halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_2$-$C_6$-alkenyl, $C_2$-$C_6$-haloalkenyl, $C_2$-$C_6$-alkynyl, $C_2$-$C_6$-haloalkynyl;

each $R^m$ is independently hydrogen, —SCN, $SF_5$, $C_1$-$C_6$-alkyl, $C_1$-$C_6$-alkoxy, $C_1$-$C_6$-alkylthio, $C_3$-$C_8$-cycloalkyl, $C_2$-$C_6$-alkenyl, $C_2$-$C_6$-alkynyl, wherein the carbon atoms of the aforementioned aliphatic or cycloaliphatic radicals are unsubstituted or substituted with one or more $R^M$;

$Si(R^e)_3$, $OR^A$, $SR^A$, $OSO_2R^B$, $N(R^D)_2$, $C(=O)N(R^D)_2$, $C(=S)N(R^D)_2$, $C(=O)OR^A$, phenyl unsubstituted or substituted with up to 5 $R^E$;

a 3-, 4-, 5-, 6- or 7-membered saturated, partially unsaturated or aromatic heterocyclic ring containing 1, 2 or 3 heteroatoms or heteroatom groups selected from N, O, S, NO, SO, $SO_2$, wherein the aforementioned ring is unsubstituted or substituted with up to 5 $R^E$;

each $R^A$ is independently hydrogen, cyano, $C_1$-$C_6$-alkylsulfinyl, $C_1$-$C_6$-alkylsulfonyl, trimethylsilyl, triethylsilyl, tert-butyldimethylsilyl, $C_1$-$C_6$-alkyl, $C_2$-$C_6$-alkenyl, $C_2$-$C_6$-alkynyl, $C_3$-$C_8$-cycloalkyl, wherein the four last mentioned radicals are unsubstituted, partially or fully halogenated and/or oxygenated and/or carry 1 or 2 radicals selected from $C_1$-$C_4$ alkoxy;

phenyl, benzyl, pyridyl, phenoxy, wherein the four last mentioned radicals are unsubstituted, partially or fully halogenated and/or carry 1, 2 or 3 substituents selected from $C_1$-$C_6$-alkyl, $C_1$-$C_6$-haloalkyl, $C_1$-$C_6$-alkoxy, $C_1$-$C_6$ haloalkoxy and ($C_1$-$C_6$-alkoxy)carbonyl;

each $R^B$ is independently hydrogen, cyano, $C_1$-$C_6$-alkoxy, $C_1$-$C_6$-haloalkoxy, $C_1$-$C_6$-alkylthio, $C_1$-$C_6$-haloalkylthio, trimethylsilyl, triethylsilyl, tert-butyldimethylsilyl, $C_1$-$C_6$-alkyl, $C_2$-$C_6$-alkenyl, $C_2$-$C_6$-alkynyl, $C_3$-$C_8$-cycloalkyl, wherein the four last mentioned radicals are unsubstituted, partially or fully halogenated and/or oxygenated and/or carry 1 or 2 radicals selected from $C_1$-$C_4$ alkoxy;

phenyl, benzyl, pyridyl, phenoxy, wherein the four last mentioned radicals are unsubstituted, partially or fully halogenated and/or carry 1, 2 or 3 substituents selected from $C_1$-$C_6$-alkyl, $C_1$-$C_6$-haloalkyl, $C_1$-$C_6$-alkoxy, $C_1$-$C_6$ haloalkoxy and ($C_1$-$C_6$-alkoxy)carbonyl;

each $R^D$ is independently hydrogen, cyano, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, trimethylsilyl, triethylsilyl, tert-butyldimethylsilyl, $C_1$-$C_6$-alkyl, $C_2$-$C_6$-alkenyl, $C_2$-$C_6$-alkynyl, $C_3$-$C_8$-cycloalkyl, wherein the four last mentioned radicals are unsubstituted, partially or fully halogenated and/or oxygenated and/or carry 1 or 2 radicals selected from $C_1$-$C_4$-alkoxy;

phenyl, benzyl, pyridyl, phenoxy, wherein the four last mentioned radicals are unsubstituted, partially or fully halogenated and/or carry 1, 2 or 3 substituents selected from $C_1$-$C_6$-alkyl, $C_1$-$C_6$-haloalkyl, $C_1$-$C_6$-alkoxy, $C_1$-$C_6$ haloalkoxy and ($C_1$-$C_6$-alkoxy)carbonyl, or two $R^D$ on one nitrogen atom are together a $C_2$-$C_6$ alkylene chain and form together with the nitrogen atom they are bonded to a 3-, 4-, 5-, 6-, or 7-membered saturated, partially unsaturated or aromatic ring, wherein the alkylene chain may contain 1 or 2 heteroatoms or heteroatom groups selected from N, O, S, NO, SO, $SO_2$, and wherein the alkylene chain is unsubstituted or substituted with halogen, $C_1$-$C_4$-haloalkyl, $C_1$-$C_4$-alkoxy or $C_1$-$C_4$-haloalkoxy;

each $R^E$ is independently cyano, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, trimethylsilyl, triethylsilyl, tert-butyldimethylsilyl, $C_1$-$C_6$-alkyl, $C_2$-$C_6$-alkenyl, $C_2$-$C_6$-alkynyl, wherein the four last mentioned radicals are unsubstituted, partially or fully halogenated and/or oxygenated and/or carry 1 or 2 radicals selected from $C_1$-$C_4$-alkoxy, or two $R^E$ present on one atom of a saturated or partially unsaturated heterocyclic ring are together $=O$, $=N(C_1$-$C_6$-alkyl), $=NO(C_1$-$C_6$-alkyl), $=CH(C_1$-$C_4$-alkyl) or $=C(C_1$-$C_4$-alkyl)$C_1$-$C_4$-alkyl;

each $R^F$ is independently $C_1$-$C_4$ alkyl, $C_1$-$C_6$ cycloalkyl, $C_1$-$C_4$ alkoxyalkyl, phenyl or benzyl;

each $R^G$ is independently halogen, $C_1$-$C_6$ alkyl, $C_1$-$C_6$ haloalkyl, $C_1$-$C_6$ alkoxyalkyl, $C_2$-$C_6$ alkenyl, $C_2$-$C_6$ haloalkenyl, $C_2$-$C_6$ alkynyl, $C_2$-$C_6$ haloalkynyl, $C_1$-$C_6$ haloalkoxyalkyl;

each $R^H$ is independently hydrogen, cyano, $C_1$-$C_6$-alkylsulfinyl, $C_1$-$C_6$-alkylsulfonyl, trimethylsilyl, triethylsilyl, tert-butyldimethylsilyl, $C_1$-$C_6$-alkyl, $C_2$-$C_6$-alkenyl, $C_2$-$C_6$-alkynyl, wherein the three last mentioned radicals are unsubstituted, partially or fully halogenated and/or oxygenated and/or carry 1 or 2 radicals selected from $C_1$-$C_4$ alkoxy;

each $R^J$ is independently hydrogen, cyano, $C_1$-$C_6$-alkoxy, $C_1$-$C_6$-haloalkoxy, $C_1$-$C_6$-alkylthio, $C_1$-$C_6$-haloalkylthio, trimethylsilyl, triethylsilyl, tert-butyldimethylsilyl, $C_1$-$C_6$-alkyl, $C_2$-$C_6$-alkenyl, $C_2$-$C_6$-alkynyl, wherein the three last mentioned radicals are unsubstituted, partially or fully halogenated and/or oxygenated and/or carry 1 or 2 radicals selected from $C_1$-$C_4$ alkoxy;

each $R^K$ is independently hydrogen, cyano, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, trimethylsilyl, triethylsilyl, tert-butyldimethylsilyl, $C_1$-$C_6$-alkyl, $C_2$-$C_6$-alkenyl, $C_2$-$C_6$-alkynyl, wherein the three last mentioned radicals are unsubstituted, partially or fully halogenated and/or oxygenated and/or carry 1 or 2 radicals selected from $C_1$-$C_4$-alkoxy;

each $R^L$ is independently $C_1$-$C_4$ alkyl or $C_1$-$C_4$ alkoxyalkyl;

each $R^M$ is independently halogen, cyano, azido, nitro, OH, SH, —SCN, $SF_5$, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, trimethylsilyl, triethylsilyl, tert-butyldimethylsilyl, $C_1$-$C_6$-alkyl, $C_2$-$C_6$-alkenyl, $C_2$-$C_6$-alkynyl, $C_3$-$C_8$-cycloalkyl, $C_1$-$C_6$-alkyl-$C_3$-$C_8$-cycloalkyl, wherein the five last mentioned radicals are unsubstituted, partially or fully halogenated and/or oxygenated and/or carry 1 or 2 radicals selected from $C_1$-$C_4$ alkoxy, or two $R^M$ present on one carbon atom are together $=O$, $=CH(C_1$-$C_4$-alkyl), $=C(C_1$-$C_4$-alkyl)$C_1$-$C_4$-alkyl, $=N(C_1$-$C_6$-alkyl) or $=NO(C_1$-$C_6$-alkyl);

each $R^N$ is independently hydrogen, OH, SH, —SCN, $SF_5$, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, trimethylsilyl, triethylsilyl, tert-butyldimethylsilyl, $C_1$-$C_6$-alkyl, $C_2$-$C_6$-alkenyl, $C_2$-$C_6$-alkynyl, wherein the three last mentioned radicals are unsubstituted, partially or fully halogenated and/or oxygenated and/or carry 1 or 2 radicals selected from $C_1$-$C_4$ alkoxy;

each $R^Q$ is independently hydrogen, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, trimethylsilyl, triethylsilyl, tert-butyldimethylsilyl, $C_1$-$C_6$-alkyl, $C_2$-$C_6$-alkenyl, $C_2$-$C_6$-alkynyl, $C_3$-$C_8$-cycloalkyl, wherein the four last mentioned radicals are unsubstituted, partially or fully halogenated and/or oxygenated and/or carry 1 or 2 radicals selected from $C_1$-$C_4$ alkoxy;

phenyl, benzyl, pyridyl, phenoxy, wherein the four last mentioned radicals are unsubstituted, partially or fully halogenated and/or carry 1, 2 or 3 substituents selected from $C_1$-$C_6$-alkyl, $C_1$-$C_6$-haloalkyl, $C_1$-$C_6$-alkoxy, $C_1$-$C_6$ haloalkoxy and ($C_1$-$C_6$-alkoxy)carbonyl;

each $R^S$ is independently hydrogen, OH, SH, —SCN, $SF_5$, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, trimethylsilyl, triethylsilyl, tert-butyldimethylsilyl, $C_1$-$C_6$-alkyl, $C_2$-$C_6$-alkenyl, $C_2$-$C_6$-alkynyl, $C_3$-$C_8$-cycloalkyl, wherein the four last mentioned radicals are unsubstituted, partially or fully halogenated and/or oxygenated and/or carry 1 or 2 radicals selected from $C_1$-$C_4$ alkoxy;

phenyl, benzyl, pyridyl, phenoxy, wherein the four last mentioned radicals are unsubstituted, partially or fully halogenated and/or carry 1, 2 or 3 substituents selected from $C_1$-$C_6$-alkyl, $C_1$-$C_6$-haloalkyl, $C_1$-$C_6$-alkoxy, $C_1$-$C_6$ haloalkoxy, ($C_1$-$C_6$-alkoxy)carbonyl, ($C_1$-$C_6$-alkyl)amino and di-($C_1$-$C_6$-alkyl)amino;

p is 0 or 1;

x is 1 or 2.

Compounds of this type are disclosed in e.g. EP 0445698; JP 05059003; and K. Shimo, S.

Wakamatsu, T. Inoue, Journal of Organic Chemistry 1961, 26, 4868-4871.

In a further aspect of the invention there is provided an agricultural and/or veterinary composition comprising at least one compound of formula (I) according to the invention or a salt thereof. In a preferred embodiment said composition further comprises at least one inert liquid and/or at least one solid carrier.

In yet a further aspect of the invention there is provided a method for combating animal pests, which comprises contacting the animal pests, their habit, breeding ground, food supply, plant, seed, soil, area, material or environment in which the animal pests are growing or may grow, or the materials, plants, seeds, soils, surfaces or spaces to be protected from animal attack or infestation with a pesticidally effective amount of at least one compound of formula (I) according to the invention or a salt thereof.

In a further aspect of the invention there is provided a method for protecting crops from attack or infestation by animal pests, which comprises contacting the crop with a pesticidally effective amount of at least one compound of formula (I) according to the invention or a salt thereof.

In yet a further aspect of the invention there is provided a method for protecting seeds from soil insects and the seedlings' roots and shoots from soil and foliar insects, which comprises contacting the seeds before sowing and/or after pregermination with at least one compound of formula (I) according to the invention or a salt thereof.

In a further aspect of the invention there are provided seeds comprising at least one compound of formula (I) according to the invention or a salt thereof.

In yet a further aspect of the invention there is provided the use of a compound of formula (I) according to the invention or a salt thereof for combating parasites in and on animals.

In a further aspect of the invention there is provided a method for treating or protecting animals against infestation or infection by parasites, which comprises orally, topically or parenterally administering or applying to the animals a parasiticidally effective amount of at least one compound of formula (I) according to the invention or a salt thereof.

In yet a further aspect of the invention there is provided a method for the preparation of a composition for treating or protecting animals against infestation or infection by parasites, which comprises mixing a parasiticidally effective amount of at least one compound of formula (I) according to the invention or a salt thereof and at least one solid carrier.

In a further aspect of the invention there is provided the use of a compound of formula (I) according to the invention or a salt thereof for the preparation of a medicament for treating or protecting animals against infestation or infection by parasites.

In yet a further aspect of the invention there is provided a compound of formula (I) according to the invention or a salt thereof, with the proviso that $R^{cc}$ is H when $R^{bb}$ is CN, and with the proviso that the following compound is excluded:

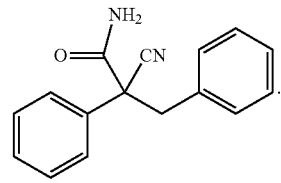 [SMILES: N#CC(Cc1ccccc1)(C(N)=O)c1ccccc1]

In a further aspect of the invention there is provided a compound of formula (I) according to the invention or a salt thereof as a medicament.

The present invention also relates to plant propagation materials, in particular seeds, comprising at least one compound of formula I or a salt thereof.

The present invention relates to every possible stereoisomer of the compounds of formula I, i.e. to single enantiomers or diastereomers, as well as to mixtures thereof.

The compounds of the present invention may be amorphous or may exist in one or more different crystalline states (polymorphs) or modifications which may have different macroscopic properties such as stability or show different biological properties such as activities. The present invention includes both amorphous and crystalline compounds of formula I, mixtures of different crystalline states or modifications of the respective compound I, as well as amorphous or crystalline salts thereof.

Salts of the compounds of formula I are preferably agriculturally and/or veterinarily acceptable salts. They can be formed in a customary manner, e.g. by reacting the compound with an acid of the anion in question if the compound of formula I has a basic functionality or by reacting an acidic compound of formula I with a suitable base.

Suitable agriculturally or veterinarilly useful salts are especially the salts of those cations or the acid addition salts of those acids whose cations and anions, respectively, do not have any adverse effect on the action of the compounds according to the present invention. Suitable cations are in particular ions of the alkali metals, preferably lithium, sodium and potassium, of the alkaline earth metals, preferably calcium, magnesium and barium, and of the transition metals, preferably manganese, copper, zinc and iron, and also ammonium ($NH_4^+$) and substituted ammonium in which one to four of the hydrogen atoms are replaced by $C_1$-$C_4$-alkyl, $C_1$-$C_4$-hydroxyalkyl, $C_1$-$C_4$-alkoxy, $C_1$-$C_4$-alkoxy-$C_1$-$C_4$-alkyl, hydroxy-$C_1$-$C_4$-alkoxy-$C_1$-$C_4$-alkyl, phenyl or benzyl. Examples of substituted ammonium ions comprise methylammonium, isopropylammonium, dimethylammonium, diisopropylammonium, trimethylammonium, tetramethylammonium, tetraethylammonium, tetrabutylammonium, 2-hydroxyethylammonium, 2-(2-hydroxyethoxy) ethylammonium, bis(2-hydroxyethyl)ammonium, benzyltrimethylammonium and benzyltriethylammonium, furthermore phosphonium ions, sulfonium ions, preferably tri($C_1$-$C_4$-alkyl)sulfonium, and sulfoxonium ions, preferably tri($C_1$-$C_4$-alkyl)sulfoxonium.

Anions of useful acid addition salts are primarily chloride, bromide, fluoride, hydrogen sulfate, sulfate, dihydrogen phosphate, hydrogen phosphate, phosphate, nitrate, hydrogen carbonate, carbonate, hexafluorosilicate, hexafluorophosphate, benzoate, and the anions of $C_1$-$C_4$-alkanoic acids, preferably formate, acetate, propionate and butyrate. They can be formed by reacting the compounds of formula I with an acid of the corresponding anion, preferably of hydrochloric acid, hydrobromic acid, sulfuric acid, phosphoric acid or nitric acid.

The organic moieties mentioned in the above definitions of the variables are—like the term halogen—collective terms for individual listings of the individual group members. The prefix $C_n$-$C_m$ indicates in each case the possible number of carbon atoms in the group.

The term "halogen" as used herein refers to fluoro, chloro, bromo and iodo.

The term "partially or fully halogenated" as used herein means that 1 or more, e.g. 1, 2, 3, 4 or 5 or all of the hydrogen atoms of a given radical have been replaced by a halogen atom, in particular by fluorine or chlorine.

The term "$C_n$-$C_m$-alkyl" as used herein (and also in $C_n$-$C_m$-alkylamino, di-$C_n$-$C_m$-alkylamino, $C_n$-$C_m$-alkylaminocarbonyl, di-($C_n$-$C_m$-alkylamino)carbonyl, $C_n$-$C_m$-alkylthio, $C_n$-$C_m$-alkylsulfinyl and $C_n$-$C_m$-alkylsulfonyl) refers to a branched or unbranched saturated hydrocarbon group having n to m, e.g. 1 to 10 carbon atoms, preferably 1 to 6 carbon atoms, for example methyl, ethyl, propyl, 1-methylethyl, butyl, 1-methylpropyl, 2-methylpropyl, 1,1-dimethylethyl, pentyl, 1-methyl-butyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, heptyl, octyl, 2-ethylhexyl, nonyl and decyl and their isomers. $C_1$-$C_4$-alkyl means for example methyl, ethyl, propyl, 1-methylethyl, butyl, 1-methylpropyl, 2-methylpropyl or 1,1-dimethylethyl.

The term "$C_n$-$C_m$-haloalkyl" as used herein (and also in $C_n$-$C_m$-haloalkylsulfinyl and $C_n$-$C_m$-haloalkylsulfonyl) refers to a straight-chain or branched alkyl group having n to m carbon atoms, e.g. 1 to 10, in particular 1 to 6 carbon atoms (as mentioned above), where some or all of the hydrogen atoms in these groups may be replaced by halogen atoms as mentioned above, for example $C_1$-$C_4$-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl and the like. The term $C_1$-$C_{10}$-haloalkyl in particular comprises $C_1$-$C_2$-fluoroalkyl, which is synonym with methyl or ethyl, wherein 1, 2, 3, 4 or 5 hydrogen atoms are substituted by fluorine atoms, such as fluoromethyl, difluoromethyl, trifluoromethyl, 1-fluoroethyl, 2-fluoroethyl, 2,2-difluoroethyl, 2,2,2-trifluoroethyl and pentafluoromethyl.

Similarly, the terms "$C_n$-$C_m$-alkoxy" and "$C_n$-$C_m$-alkylthio" (or the term "$C_n$-$C_m$-alkylsulfenyl", respectively) refer to straight-chain or branched alkyl groups having n to m carbon atoms, e.g. 1 to 10, in particular 1 to 6 or 1 to 4 carbon atoms (as mentioned above) bonded through oxygen or sulfur linkages, respectively, at any bond in the alkyl group. Examples include $C_1$-$C_4$-alkoxy such as methoxy, ethoxy, propoxy, isopropoxy, butoxy, sec-butoxy, isobutoxy and tert-butoxy, further $C_1$-$C_4$-alkylthio such as methylthio, ethylthio, propylthio, isopropylthio, and n-butylthio.

Accordingly, the terms "$C_n$-$C_m$-haloalkoxy" and "$C_n$-$C_m$-haloalkylthio" (or the term "$C_n$-$C_m$-haloalkylsulfenyl", respectively) refer to straight-chain or branched alkyl groups having n to m carbon atoms, e.g. 1 to 10, in particular 1 to 6 or 1 to 4 carbon atoms (as mentioned above) bonded through oxygen or sulfur linkages, respectively, at any bond in the alkyl group, where some or all of the hydrogen atoms in these groups may be replaced by halogen atoms as mentioned above, for example $C_1$-$C_2$-haloalkoxy, such as chloromethoxy, bromomethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-chloroethoxy, 1-bromoethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy and pentafluoroethoxy, further $C_1$-$C_2$-haloalkylthio, such as chloromethylthio, bromomethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-chloroethylthio, 1-bromoethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio and pentafluoroethylthio and the like. Similarly the terms "$C_1$-$C_2$-fluoroalkoxy" and "$C_1$-$C_2$-fluoroalkylthio" refer to $C_1$-$C_2$-fluoroalkyl which is bound to the remainder of the molecule via an oxygen atom or a sulfur atom, respectively.

The term "$C_2$-$C_m$-alkenyl" as used herein refers to a branched or unbranched unsaturated hydrocarbon group having 2 to m, e.g. 2 to 10 or 2 to 6 carbon atoms and a double bond in any position, such as ethenyl, 1-propenyl, 2-propenyl, 1-methyl-ethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl.

The term "$C_2$-$C_m$-alkynyl" as used herein refers to a branched or unbranched unsaturated hydrocarbon group having 2 to m, e.g. 2 to 10 or 2 to 6 carbon atoms and containing at least one triple bond, such as ethynyl, propynyl, 1-butynyl, 2-butynyl and the like.

The term "$C_1$-$C_4$-alkoxy-$C_1$-$C_4$-alkyl" as used herein refers to alkyl having 1 to 4 carbon atoms, e.g. like specific examples mentioned above, wherein one hydrogen atom of the alkyl radical is replaced by an $C_1$-$C_4$-alkoxy group.

The term "$C_3$-$C_m$-cycloalkyl" as used herein refers to a monocyclic 3- to m-membered saturated cycloaliphatic radicals, e.g. cyclopropyl, cyclobutyl, cyclopentyl, cyclohexyl, cycloheptyl, cyclooctyl and cyclodecyl.

The term "aryl" as used herein refers to an aromatic hydrocarbon radical such as naphthyl or in particular phenyl.

The term "naphthyl" as used herein refers to 1-naphthyl and 2-naphthyl. Preferably, naphthyl is 2-naphthyl.

The term "3- to 6-membered carbocyclic ring" as used herein refers to cyclopropane, cyclobutane, cyclopentane and cyclohexane rings.

The term "3-, 4-, 5-, 6- or 7-membered saturated, partially unsaturated or aromatic heterocyclic ring containing 1, 2 or 3 heteroatoms or heteroatom groups selected from N, O, S, NO, SO, $SO_2$" as used herein refers to monocyclic radicals, the monocyclic radicals being saturated, partially unsaturated or aromatic. The heterocyclic radical may be attached to the remainder of the molecule via a carbon ring member or via a nitrogen ring member.

Examples of 3-, 4-, 5-, 6- or 7-membered saturated heterocyclyl include: oxiranyl, aziridinyl, azetidinyl, 2 tetrahydrofuranyl, 3-tetrahydrofuranyl, 2 tetrahydrothienyl, 3 tetrahydrothienyl, 2-pyrrolidinyl, 3-pyrrolidinyl, 3 pyrazolidinyl, 4 pyrazolidinyl, 5-pyrazolidinyl, 2 imidazolidinyl, 4 imidazolidinyl, 2-oxazolidinyl, 4-oxazolidinyl, 5 oxazolidinyl, 3-isoxazolidinyl, 4 isoxazolidinyl, 5 isoxazolidinyl, 2 thiazolidinyl, 4-thiazolidinyl, 5-thiazolidinyl, 3 isothiazolidinyl, 4-isothiazolidinyl, 5 isothiazolidinyl, 1,2,4-oxadiazolidin-3-yl, 1,2,4 oxadiazolidin 5 yl, 1,2,4-thiadiazolidin-3-yl, 1,2,4 thiadiazolidin-5-yl, 1,2,4 triazolidin-3-yl, 1,3,4-oxadiazolidin-2-yl, 1,3,4 thiadiazolidin-2-yl, 1,3,4 triazolidin-2-yl, 2-tetrahydropyranyl, 4 tetrahydropyranyl, 1,3-dioxan-5-yl, 1,4-dioxan-2-yl, 2-piperidinyl, 3-piperidinyl, 4-piperidinyl, 3-hexahydropyridazinyl, 4 hexahydropyridazinyl, 2-hexahydropyrimidinyl, 4-hexahydropyrimidinyl, 5 hexahydropyrimidinyl, 2-piperazinyl, 1,3,5-hexahydrotriazin-2-yl and 1,2,4 hexahydrotriazin-3-yl, 2-morpholinyl, 3-morpholinyl, 2-thiomorpholinyl, 3-thiomorpholinyl, 1-oxothiomorpholin-2-yl, 1-oxothiomorpholin-3-yl, 1,1-dioxothiomorpholin-2-yl, 1,1-dioxothiomorpholin-3-yl, hexahydroazepin-1-, -2-, -3- or -4-yl, hexahydrooxepinyl, hexahydro-1,3-diazepinyl, hexahydro-1,4-diazepinyl, hexahydro-1,3-oxazepinyl, hexahydro-1,4-oxazepinyl, hexahydro-1,3-dioxepinyl, hexahydro-1,4-dioxepinyl and the like.

Examples of 3-, 4-, 5-, 6- or 7-membered partially unsaturated heterocyclyl include: 2,3-dihydrofur-2-yl, 2,3-dihydrofur-3-yl, 2,4-dihydrofur-2-yl, 2,4-dihydrofur-3-yl, 2,3-dihydrothien-2-yl, 2,3 dihydrothien-3-yl, 2,4 dihydrothien-2-yl, 2,4-dihydrothien-3-yl, 2-pyrrolin-2-yl, 2-pyrrolin-3-yl, 3 pyrrolin-2-yl, 3-pyrrolin-3-yl, 2-isoxazolin-3-yl, 3-isoxazolin-3-yl, 4 isoxazolin 3 yl, 2-isoxazolin-4-yl, 3-isoxazolin-4-yl, 4-isoxazolin-4-yl, 2 isoxazolin-5-yl, 3-isoxazolin-5-yl, 4-isoxazolin-5-yl, 2-isothiazolin-3-yl, 3 isothiazolin-3-yl, 4-isothiazolin-3-yl, 2-isothiazolin-4-yl, 3-isothiazolin-4-yl, 4 isothiazolin-4-yl, 2-isothiazolin-5-yl, 3-isothiazolin-5-yl, 4-isothiazolin-5-yl, 2,3 dihydropyrazol-1-yl, 2,3-dihydropyrazol-2-yl, 2,3-dihydropyrazol-3-yl, 2,3 dihydropyrazol-4-yl, 2,3-dihydropyrazol-5-yl, 3,4-dihydropyrazol-1-yl, 3,4 dihydropyrazol-3-yl, 3,4-dihydropyrazol-4-yl, 3,4-dihydropyrazol-5-yl, 4,5 dihydropyrazol-1-yl, 4,5-dihydropyrazol-3-yl, 4,5-dihydropyrazol-4-yl, 4,5 dihydropyrazol-5-yl, 2,3-dihydrooxazol-2-yl, 2,3-dihydrooxazol-3-yl, 2,3 dihydrooxazol-4-yl, 2,3-dihydrooxazol-5-yl, 3,4-dihydrooxazol-2-yl, 3,4 dihydrooxazol-3-yl, 3,4-dihydrooxazol-4-yl, 3,4-dihydrooxazol-5-yl, 3,4 dihydrooxazol-2-yl, 3,4-dihydrooxazol-3-yl, 3,4-dihydrooxazol-4-yl, 2-, 3-, 4-, 5- or 6-di- or tetrahydropyridinyl, 3-di- or tetrahydropyridazinyl, 4 di- or tetrahydropyridazinyl, 2-di- or tetrahydropyrimidinyl, 4-di- or tetrahydropyrimidinyl, 5 di- or tetrahydropyrimidinyl, di- or tetrahydropyrazinyl, 1,3,5-di- or tetrahydrotriazin-2-yl, 1,2,4-di- or tetrahydrotriazin-3-yl, 2,3,4,5-tetrahydro[1H]azepin-1-, -2-, -3-, -4-, -5-, -6- or -7-yl, 3,4,5,6-tetrahydro[2H]azepin-2-, -3-, -4-, -5-, -6- or -7-yl, 2,3,4,7 tetrahydro[1H]azepin-1-, -2-, -3-, -4-, -5-, -6- or -7-yl, 2,3,6,7 tetrahydro[1H]azepin-1-, -2-, -3-, -4-, -5-, -6- or -7-yl, tetrahydrooxepinyl, such as 2,3,4,5-tetrahydro[1H]oxepin-2-, -3-, -4-, -5-, -6- or -7-yl, 2,3,4,7 tetrahydro[1H]oxepin-2-, -3-, -4-, -5-, -6- or -7-yl, 2,3,6,7 tetrahydro[1H]oxepin-2-, -3-, -4-, -5-, -6- or -7-yl, tetrahydro-1,3-diazepinyl, tetrahydro-1,4-diazepinyl, tetrahydro-1,3-oxazepinyl, tetrahydro-1,4-oxazepinyl, tetrahydro-1,3-dioxepinyl and tetrahydro-1,4-dioxepinyl.

3-, 4-, 5-, 6- or 7-membered aromatic heterocyclyl is 5- or 6-membered aromatic heterocyclyl (hetaryl). Examples are: 2-furyl, 3-furyl, 2-thienyl, 3-thienyl, 2-pyrrolyl, 3-pyrrolyl, 3-pyrazolyl, 4-pyrazolyl, 5-pyrazolyl, 2-oxazolyl, 4-oxazolyl, 5-oxazolyl, 2-thiazolyl, 4 thiazolyl, 5-thiazolyl, 2-imidazolyl, 4-imidazolyl, 1,3,4-triazol-2-yl, 2-pyridinyl, 3-pyridinyl, 4-pyridinyl, 3-pyridazinyl, 4-pyridazinyl, 2-pyrimidinyl, 4-pyrimidinyl, 5-pyrimidinyl and 2-pyrazinyl.

The term "$C_2$-$C_7$-alkylene" as used herein refers to a divalent branched or preferably unbranched saturated aliphatic chain having 2 to 7 carbon atoms, for example $CH_2CH_2$, —$CH(CH_3)$—, $CH_2CH_2CH_2$, $CH(CH_3)CH_2$, $CH_2CH(CH_3)$, $CH_2CH_2CH_2CH_2$, $CH_2CH_2CH_2CH_2CH_2$, $CH_2CH_2CH_2CH_2CH_2CH_2$ and $CH_2CH_2CH_2CH_2CH_2CH_2CH_2$.

The term "tri-($C_1$-$C_4$)silyl-$C_2$-$C_4$-alkynyl" as used herein refers to $C_2$-$C_4$-alkynyl substituted with tri-($C_1$-$C_4$)silyl. The term "(trimethylsilyl)ethynyl" as used herein refers to ethynyl substituted with trimethylsilyl.

The term "$C_1$-$C_6$-alkyl-$C_3$-$C_8$-cycloalkyl" as used herein refers to $C_3$-$C_8$-cycloalkyl substituted with $C_1$-$C_6$-alkyl. The term "$C_1$-$C_4$-alkyl-$C_3$-$C_6$-cycloalkyl" as used herein refers to $C_3$-$C_6$-cycloalkyl substituted with $C_1$-$C_4$-alkyl.

Preferably, the term "phenyl unsubstituted or substituted with 1, 2, 3, 4 or 5 substituents $R^5/R^6$" means "phenyl unsubstituted or substituted with up to 3 or in the case of halogen up to the maximum possible number of substituents $R^5/R^6$", and also preferably "phenyl unsubstituted or substituted with 1, 2, 3 or 4 substituents $R^5/R^6$", more preferably "phenyl unsubstituted or substituted with 1, 2 or 3 substituents $R^5/R^6$", even more preferably "phenyl unsubstituted or substituted with 1 or 2 substituents $R^5/R^6$", and particularly preferably "phenyl unsubstituted or substituted with 1 substituent $R^5/R^6$".

Preferably, the term "naphthyl unsubstituted or substituted with 1, 2, 3, 4, 5, 6 or 7 substituents $R^5$" means "naphthyl unsubstituted or substituted with up to 3 or in the case of halogen up to the maximum possible number of substituents $R^5$", more preferably "naphthyl unsubstituted or substituted with up to 3 substituents $R^5$", even more preferably "naphthyl unsubstituted or substituted with up to 2 substituents $R^5$", and particularly preferably "naphthyl unsubstituted or substituted with up to 1 substituent $R^5$".

Preferably, the term "unsubstituted or substituted with up to 5 $R^c/R^d/R^E$, e.g. in connection with phenyl or a heterocyclic ring, means "unsubstituted or substituted with up to 3 or in the case of halogen up to the maximum possible number of $R^c/R^d/R^E$", more preferably "unsubstituted or substituted with up to 2 or in the case of halogen up to the maximum possible number of $R^c/R^d/R^E$", also more preferably "unsubstituted or substituted with up to 3 $R^c/R^d/R^E$", and even more preferably "unsubstituted or substituted with up to 2 $R^c/R^d/R^E$".

Preferably, the term "unsubstituted or substituted with one or more", e.g. in connection with substituents $R^6$, $R^a$, $R^b$ or $R^M$, means "unsubstituted or substituted with up to 5 or in the case of halogen up to the maximum possible number of", more preferably "unsubstituted or substituted with up to 3 or in the case of halogen up to the maximum possible number of", even more preferably "unsubstituted or substituted with up to 2 or in the case of halogen up to the maximum possible number of", also more preferably "unsubstituted or substituted with up to 5", also even more preferably "unsubstituted or substituted with up to 3", and particularly preferably "unsubstituted or substituted with up to 2".

The preferred, more preferred, even more preferred and particularly preferred substituents and embodiments described herein are to be understood as preferred either independently of each other or in every possible combination with each other.

These preferences and embodiments apply to the compounds of the invention, to the use of the compounds of the invention as well as to methods using the compounds of the invention.

Preferred are compounds of formula (I) wherein Y is phenyl unsubstituted or substituted with 1, 2, 3, 4 or 5 substituents $R^5$; or naphthyl unsubstituted or substituted with 1 or 2 substituents $R^5$.

Preferred are compounds of formula (I) wherein Q is phenyl unsubstituted or substituted with 1, 2, 3 or 4 substituents $R^6$; cyclohexyl unsubstituted or substituted with 1 or 2 substituents $R^6$; cyclopentyl unsubstituted or substituted with 1 or 2 substituents $R^6$; or a 6-membered aromatic heterocyclic ring containing 1, 2 or 3 nitrogen atoms in the ring, wherein the aforementioned ring is unsubstituted or substituted with 1, 2, 3 or 4 substituents $R^6$.

Also preferred are compounds of formula (I) wherein Q is phenyl unsubstituted or substituted with 1, 2, 3 or 4 substituents $R^6$; cyclohexyl unsubstituted or substituted with 1 or 2 substituents $R^6$; or cyclopentyl unsubstituted or substituted with 1 or 2 substituents $R^6$.

Also preferred are compounds of formula (I) wherein Q is a 6-membered aromatic heterocyclic ring containing 1, 2 or 3 nitrogen atoms in the ring, wherein the aforementioned ring is unsubstituted or substituted with 1, 2, 3 or 4 substituents $R^6$.

Preferred are compounds of formula (I) wherein $R^1$ is H, halogen, cyano, $C_1$-$C_6$-alkyl, $C_2$-$C_6$-alkenyl, $C_2$-$C_6$-alkynyl, $C_3$-$C_6$-cycloalkyl or ($C_1$-$C_6$-alkoxy)carbonyl, wherein the five radicals last mentioned are unsubstituted or substituted with 1, 2 or 3 substituents selected from halogen, cyano, hydroxy, $OSi(C_1$-$C_6$-alkyl$)_3$, $C_1$-$C_6$-alkyl, $C_2$-$C_6$-alkenyl, $C_2$-$C_6$-alkynyl, $C_3$-$C_6$-cycloalkyl, $C_1$-$C_6$-alkoxy and ($C_1$-$C_6$-alkoxy)carbonyl, wherein the six radicals last mentioned are unsubstituted or partially or fully halogenated, and in particular the ones wherein $R^1$ is H, Me, Et, iPr, cPr, $CH_2CN$, $CF_3$, $CHF_2$, $CH_2F$, $CH_2CH_2F$, $CH_2CHF_2$, $CH_2CF_3$, CN, halogen, $CH_2OH$, $CH_2OMe$, $CH_2OEt$, $CO_2Me$, $CO_2Et$, $CH_2CO_2Me$, $CH_2CO_2Et$, $CH_2OSi(Me)_3$ or $CH_2OSi(Et)_3$.

Preferred are compounds of formula (I) wherein $R^2$ is H or halogen.

Also preferred are compounds of formula (I) wherein $R^1$ and $R^2$ form together with the carbon atom to which they are attached a methylene group.

Preferred are compounds of formula (I) wherein $R^3$ is H, halogen, cyano, $C_1$-$C_6$-alkyl, $C_2$-$C_6$-alkenyl, $C_2$-$C_6$-alkynyl, $C_3$-$C_6$-cycloalkyl or ($C_1$-$C_6$-alkoxy)carbonyl, wherein the five radicals last mentioned are unsubstituted or substituted with 1, 2 or 3 substituents selected from halogen, cyano, hydroxy, $OSi(C_1$-$C_6$-alkyl$)_3$, $C_1$-$C_6$-alkyl, $C_2$-$C_6$-alkenyl, $C_2$-$C_6$-alkynyl, $C_3$-$C_6$-cycloalkyl, $C_1$-$C_6$-alkoxy and ($C_1$-$C_6$-alkoxy)carbonyl, wherein the six radicals last mentioned are unsubstituted or partially or fully halogenated, and in particular the ones wherein $R^3$ is H, Me, Et, iPr, cPr, $CH_2CN$, $CF_3$, $CHF_2$, $CH_2F$, $CH_2CH_2F$, $CH_2CHF_2$, $CH_2CF_3$, CN, halogen, $CH_2OH$, $CH_2OMe$, $CH_2OEt$, $CO_2Me$, $CO_2Et$, $CH_2CO_2Me$, $CH_2CO_2Et$, $CH_2OSi(Me)_3$ or $CH_2OSi(Et)_3$.

Preferred are compounds of formula (I) wherein $R^4$ is H or halogen.

Also preferred are compounds of formula (I) wherein $R^3$ and $R^4$ form together with the carbon atom to which they are attached a methylene group.

Preferred are compounds of formula (I) wherein $R^5$ is halogen, cyano, $SF_5$, tri-($C_1$-$C_4$)silyl-$C_2$-$C_4$-alkynyl, ($C_1$-$C_6$-alkyl)aminocarbonyl, di-($C_1$-$C_6$-alkyl)aminocarbonyl, $C_1$-$C_6$-alkyl, $C_2$-$C_6$-alkenyl, $C_2$-$C_6$-alkynyl, $C_3$-$C_6$-cycloalkyl, phenyl, $C_1$-$C_6$-alkoxy, $C_1$-$C_6$-alkylthio, $C_1$-$C_6$-alkylsulfinyl, $C_1$-$C_6$-alkylsulfonyl, ($C_1$-$C_6$-alkoxy)carbonyl, ($C_1$-$C_6$-alkyl)amino, di-($C_1$-$C_6$-alkyl)amino, ($C_1$-$C_6$-alkyl)carbonyl or ($C_1$-$C_6$-alkyl)carbonyloxy, wherein the 14 radicals last mentioned are unsubstituted or substituted with one or more substituents selected from halogen, cyano, $C_1$-$C_4$-alkyl-$C_3$-$C_6$-cycloalkyl, $C_1$-$C_6$-alkyl, $C_2$-$C_6$-alkenyl, $C_2$-$C_6$-alkynyl, $C_3$-$C_6$-cycloalkyl and $C_1$-$C_6$-alkoxy, wherein the five radicals last mentioned are unsubstituted or partially or fully halogenated;

or two $R^5$ on two adjacent carbon atoms present on one phenyl ring are together a bridge selected from N=CH—CH=CH, N=CH—CH=N, $OCH_2CH_2O$, $O(CH_2)O$ and form together with the carbon atoms the two $R^5$ are bonded to a 5- or 6-membered partially unsaturated or aromatic heterocyclic ring, wherein the ring is unsubstituted.

Also preferred are compounds of formula (I) wherein $R^5$ is halogen, cyano, $SF_5$, tri-($C_1$-$C_4$)silyl-$C_2$-$C_4$-alkynyl, ($C_1$-$C_6$-alkyl)aminocarbonyl, di-($C_1$-$C_6$-alkyl)aminocarbonyl, $C_1$-$C_6$-alkyl, $C_2$-$C_6$-alkenyl, $C_2$-$C_6$-alkynyl, $C_3$-$C_6$-cycloalkyl, phenyl, $C_1$-$C_6$-alkoxy, $C_1$-$C_6$-alkylthio, $C_1$-$C_6$-alkylsulfinyl, $C_1$-$C_6$-alkylsulfonyl, ($C_1$-$C_6$-alkoxy)carbonyl, ($C_1$-$C_6$-alkyl)amino, di-($C_1$-$C_6$-alkyl)amino, ($C_1$-$C_6$-alkyl)carbonyl or ($C_1$-$C_6$-alkyl)carbonyloxy, wherein the 14 radicals last mentioned are unsubstituted or substituted with one or more (particularly up to 3 or in the case of halogen up to the maximum possible number) substituents selected from halogen, cyano, $C_1$-$C_4$-alkyl-$C_3$-$C_6$-cycloalkyl, $C_1$-$C_6$-alkyl, $C_2$-$C_6$-alkenyl, $C_2$-$C_6$-alkynyl, $C_3$-$C_6$-cycloalkyl and $C_1$-$C_6$-alkoxy, wherein the five radicals last mentioned are unsubstituted or partially or fully halogenated, and in particular the ones wherein $R^5$ is halogen (particularly F, Cl, Br), Me, Et, iPr, cPr, OMe, OEt, OiPr, ethynyl, (trimethylsilyl)ethynyl, vinyl, Ph, CN, $CF_3$, $OCF_3$, $SF_5$, $CHF_2$, $OCHF_2$, SMe, S(O)Me, S(O)$_2$Me, SCF$_3$, S(O)CF$_3$, S(O)$_2$CF$_3$, SCHF$_2$, S(O)CHF$_2$, S(O)$_2$CHF$_2$, CO$_2$Me, CO$_2$Et, C(O)Me, OAc, C(O)NHMe, C(O)NMe$_2$, CH$_2$OMe or CH$_2$OEt.

Also preferred are compounds of formula (I) wherein R$^5$ is halogen, Me, Et, iPr, cPr, OMe, OEt, OiPr, ethynyl, (trimethylsilyl)ethynyl, vinyl, Ph, CN, CF$_3$, OCF$_3$, SF$_5$, CHF$_2$, OCHF$_2$, SMe, S(O)Me, S(O)$_2$Me, SCF$_3$, S(O)CF$_3$, S(O)$_2$CF$_3$, SCHF$_2$, S(O)CHF$_2$, S(O)$_2$CHF$_2$, CO$_2$Me, CO$_2$Et, C(O)Me, OAc, C(O)NHMe, C(O)NMe$_2$, CH$_2$OMe or CH$_2$OEt;

or two R$^5$ on two adjacent carbon atoms present on one phenyl ring are together a bridge selected from N=CH—CH=CH, N=CH—CH=N, OCH$_2$CH$_2$O, O(CH$_2$)O and form together with the carbon atoms the two R$^5$ are bonded to a 5- or 6-membered partially unsaturated or aromatic heterocyclic ring, wherein the ring is unsubstituted.

Preferred are compounds of formula (I) wherein R$^6$ is halogen, nitro, cyano, SF$_5$, tri-(C$_1$-C$_4$)silyl-C$_2$-C$_4$-alkynyl, 2,2,2-trifluoro-1-hydroxy-1-(trifluoromethyl)ethyl, (C$_1$-C$_6$-alkyl)aminocarbonyl, di-(C$_1$-C$_6$-alkyl)aminocarbonyl, dimethylcarbamoylsulfanyl, morpholine-4-carbonyl, acetamido, pyridyl, pyrrolyl, pyrazolyl, imidazolyl, triazolyl, C$_1$-C$_6$-alkyl, C$_2$-C$_6$-alkenyl, C$_2$-C$_6$-alkynyl, C$_3$-C$_6$-cycloalkyl, phenyl, C$_1$-C$_6$-alkoxy, C$_3$-C$_6$-cycloalkoxy, phenoxy, C$_1$-C$_6$-alkylthio, C$_1$-C$_6$-alkylsulfinyl, C$_1$-C$_6$-alkylsulfonyl, (C$_1$-C$_6$-alkoxy)carbonyl, (C$_1$-C$_6$-alkyl)amino, di-(C$_1$-C$_6$-alkyl)amino, (C$_1$-C$_6$-alkyl)carbonyl or (C$_1$-C$_6$-alkyl)carbonyloxy, wherein the 16 radicals last mentioned are unsubstituted or substituted with one or more substituents selected from halogen, cyano, C$_1$-C$_4$-alkyl-C$_3$-C$_6$-cycloalkyl, C$_1$-C$_6$-alkyl, C$_2$-C$_6$-alkenyl, C$_2$-C$_6$-alkynyl, C$_3$-C$_6$-cycloalkyl and C$_1$-C$_6$-alkoxy, wherein the five radicals last mentioned are unsubstituted or partially or fully halogenated.

Also preferred are compounds of formula (I) wherein R$^6$ is halogen, cyano, SF$_5$, tri-(C$_1$-C$_4$)silyl-C$_2$-C$_4$-alkynyl, (C$_1$-C$_6$-alkyl)aminocarbonyl, di-(C$_1$-C$_6$-alkyl)aminocarbonyl, C$_1$-C$_6$-alkyl, C$_2$-C$_6$-alkenyl, C$_2$-C$_6$-alkynyl, C$_3$-C$_6$-cycloalkyl, phenyl, C$_1$-C$_6$-alkoxy, C$_1$-C$_6$-alkylthio, C$_1$-C$_6$-alkylsulfinyl, C$_1$-C$_6$-alkylsulfonyl, (C$_1$-C$_6$-alkoxy)carbonyl, (C$_1$-C$_6$-alkyl)amino, di-(C$_1$-C$_6$-alkyl)amino, (C$_1$-C$_6$-alkyl)carbonyl or (C$_1$-C$_6$-alkyl)carbonyloxy, wherein the 14 radicals last mentioned are unsubstituted or substituted with one or more (particularly up to 3 or in the case of halogen up to the maximum possible number) substituents selected from halogen, cyano, C$_1$-C$_4$-alkyl-C$_3$-C$_6$-cycloalkyl, C$_1$-C$_6$-alkyl, C$_2$-C$_6$-alkenyl, C$_2$-C$_6$-alkynyl, C$_3$-C$_6$-cycloalkyl and C$_1$-C$_6$-alkoxy, wherein the five radicals last mentioned are unsubstituted or partially or fully halogenated, and in particular the ones wherein R$^6$ is halogen (particularly F, Cl, Br), Me, Et, iPr, cPr, OMe, OEt, OiPr, ethynyl, (trimethylsilyl)ethynyl, vinyl, Ph, CN, CF$_3$, OCF$_3$, SF$_5$, CHF$_2$, OCHF$_2$, SMe, S(O)Me, S(O)$_2$Me, SCF$_3$, S(O)CF$_3$, S(O)$_2$CF$_3$, SCHF$_2$, S(O)CHF$_2$, S(O)$_2$CHF$_2$, CO$_2$Me, CO$_2$Et, C(O)Me, OAc, C(O)NHMe, C(O)NMe$_2$, CH$_2$OMe or CH$_2$OEt.

Also preferred are compounds of formula (I) wherein R$^6$ is halogen, Me, Et, iPr, cPr, tBu, OMe, OEt, OnPr, OiPr, OtBu, OPh, ethynyl, (trimethylsilyl)ethynyl, vinyl, Ph, NO$_2$, CN, CF$_3$, OCF$_3$, SF$_5$, CHF$_2$, OCHF$_2$, SMe, S(O)Me, S(O)$_2$Me, SCF$_3$, S(O)CF$_3$, S(O)$_2$CF$_3$, SCHF$_2$, S(O)CHF$_2$, S(O)$_2$CHF$_2$, CO$_2$Me, CO$_2$Et, CO$_2$iPr, C(O)Me, OAc, C(O)NHMe, C(O)NMe$_2$, CH$_2$OMe, CH$_2$OEt, fluoromethyl, 2,2,2-trifluoroethyl, 1,2,2,2-tetrafluoro-1-(trifluoromethyl)ethyl, 2,2,2-trifluoro-1-hydroxy-1-(trifluoromethyl)ethyl, dimethoxymethyl, chloro(difluoro)methoxy, 2,2,2-trifluoroethoxy, 2,2-difluorocyclopropoxy, tert-butylsulfanyl, dimethylcarbamoylsulfanyl, morpholine-4-carbonyl, acetamido, 2-pyridyl, 3-pyridyl, 4-pyridyl, pyrrol-1-yl, pyrazol-1-yl, imidazol-1-yl or 1,2,4-triazol-1-yl.

More preferred are compounds of formula (I) wherein R$^{aa}$ is —C(=S)N(R$^{cc}$)$_2$ or —C(=O)N(R$^{ff}$)$_2$.

More preferred are compounds of formula (I) wherein R$^{bb}$ is CN.

More preferred are compounds of formula (I) wherein each R$^{cc}$ is independently hydrogen, C$_1$-C$_4$-alkyl, C$_2$-C$_4$-alkenyl, C$_2$-C$_4$-alkynyl, C$_3$-C$_6$-cycloalkyl, C$_1$-C$_4$-alkoxy-C$_1$-C$_2$-alkyl.

More preferred are compounds of formula (I) wherein each R$^{ff}$ is independently hydrogen, C$_1$-C$_4$-alkyl, C$_2$-C$_4$-alkenyl, C$_2$-C$_4$-alkynyl, C$_3$-C$_6$-cycloalkyl, C$_1$-C$_4$-alkoxy-C$_1$-C$_2$-alkyl.

Also more preferred are compounds of formula (I) wherein R$^{aa}$ is —C(=S)N(R$^{cc}$)$_2$ or —C(=O)N(R$^{ff}$)$_2$; each R$^{cc}$ is independently hydrogen, C$_1$-C$_4$-alkyl, C$_2$-C$_4$-alkenyl, C$_2$-C$_4$-alkynyl, C$_3$-C$_6$-cycloalkyl, C$_1$-C$_4$-alkoxy-C$_1$-C$_2$-alkyl; and each R$^{ff}$ is independently hydrogen, C$_1$-C$_4$-alkyl, C$_2$-C$_4$-alkenyl, C$_2$-C$_4$-alkynyl, C$_3$-C$_6$-cycloalkyl, C$_1$-C$_4$-alkoxy-C$_1$-C$_2$-alkyl.

Preferred are compounds of formula (I) wherein p is 0 or 1, and in particular the ones wherein p is 0.

More preferred are compounds of formula (I) wherein Y is phenyl unsubstituted or substituted with 1, 2, 3, 4 or 5 substituents R$^5$; or naphthyl unsubstituted or substituted with 1 substituent R$^5$.

More preferred are compounds of formula (I) wherein Q is phenyl unsubstituted or substituted with 1, 2 or 3 substituents R$^6$; cyclohexyl unsubstituted or substituted with 1 substituent R$^6$; or a 6-membered aromatic heterocyclic ring containing 1, 2 or 3 nitrogen atoms in the ring, wherein the aforementioned ring is unsubstituted or substituted with 1, 2 or 3 substituents R$^6$.

Also more preferred are compounds of formula (I) wherein Q is phenyl unsubstituted or substituted with 1, 2 or 3 substituents R$^6$; or cyclohexyl unsubstituted or substituted with 1 substituent R$^6$.

Also more preferred are compounds of formula (I) wherein Q is a 6-membered aromatic heterocyclic ring containing 1, 2 or 3 nitrogen atoms in the ring, wherein the aforementioned ring is unsubstituted or substituted with 1, 2 or 3 substituents R$^6$.

More preferred are compounds of formula (I) wherein R$^1$ is H, Me, Et, CN, CH$_2$CN, CH$_2$CF$_3$, halogen, CH$_2$OH, CH$_2$OMe, CH$_2$OEt, CH$_2$CO$_2$Me, CH$_2$CO$_2$Et, CH$_2$OSi(Me)$_3$ or CH$_2$OSi(Et)$_3$.

More preferred are compounds of formula (I) wherein R$^2$ is H or halogen.

More preferred are compounds of formula (I) wherein R$^3$ is H, Me, Et, CN, CH$_2$CN, CH$_2$CF$_3$, halogen, CH$_2$OH, CH$_2$OMe, CH$_2$OEt, CH$_2$CO$_2$Me, CH$_2$CO$_2$Et, CH$_2$OSi(Me)$_3$ or CH$_2$OSi(Et)$_3$.

More preferred are compounds of formula (I) wherein R$^4$ is H or halogen.

More preferred are compounds of formula (I) wherein R$^5$ is halogen, cyano, tri-(C$_1$-C$_4$)silyl-C$_2$-C$_4$-alkynyl, C$_1$-C$_6$-alkyl, C$_2$-C$_6$-alkenyl, C$_2$-C$_6$-alkynyl, C$_3$-C$_6$-cycloalkyl, phenyl, C$_1$-C$_6$-alkoxy, C$_1$-C$_6$-alkylthio or (C$_1$-C$_6$-alkoxy)carbonyl, wherein the eight radicals last mentioned are unsubstituted or partially or fully halogenated;

or two R$^5$ on two adjacent carbon atoms present on one phenyl ring are together a bridge selected from N=CH—

CH=CH, N=CH—CH=N, OCH$_2$CH$_2$O, O(CH$_2$)O and form together with the carbon atoms the two R$^5$ are bonded to a 5- or 6-membered partially unsaturated or aromatic heterocyclic ring, wherein the ring is unsubstituted.

Also more preferred are compounds of formula (I) wherein R$^5$ is halogen, cyano, tri-(C$_1$-C$_4$)silyl-C$_2$-C$_4$-alkynyl, C$_1$-C$_6$-alkyl, C$_2$-C$_6$-alkenyl, C$_2$-C$_6$-alkynyl, C$_3$-C$_6$-cycloalkyl, phenyl, C$_1$-C$_6$-alkoxy, C$_1$-C$_6$-alkylthio or (C$_1$-C$_6$-alkoxy)carbonyl, wherein the eight radicals last mentioned are unsubstituted or partially or fully halogenated, and in particular the ones wherein R$^5$ is halogen (particularly Cl, F, Br), Me, OMe, CN, CF$_3$, OCF$_3$ or ethynyl.

More preferred are compounds of formula (I) wherein R$^6$ is halogen, nitro, cyano, tri-(C$_1$-C$_4$)silyl-C$_2$-C$_4$-alkynyl, 2,2,2-trifluoro-1-hydroxy-1-(trifluoromethyl)ethyl, dimethoxymethyl, dimethylcarbamoylsulfanyl, morpholine-4-carbonyl, acetamido, pyridyl, pyrrolyl, pyrazolyl, imidazolyl, triazolyl, C$_1$-C$_6$-alkyl, C$_2$-C$_6$-alkenyl, C$_2$-C$_6$-alkynyl, C$_3$-C$_6$-cycloalkyl, phenyl, C$_1$-C$_6$-alkoxy, C$_3$-C$_6$-cycloalkoxy, phenoxy, C$_1$-C$_6$-alkylthio, C$_1$-C$_6$-alkylsulfonyl or (C$_1$-C$_6$-alkoxy)carbonyl, wherein the eleven radicals last mentioned are unsubstituted or partially or fully halogenated.

Also more preferred are compounds of formula (I) wherein R$^6$ is halogen, cyano, tri-(C$_1$-C$_4$)silyl-C$_2$-C$_4$-alkynyl, C$_1$-C$_6$-alkyl, C$_2$-C$_6$-alkenyl, C$_2$-C$_6$-alkynyl, C$_3$-C$_6$-cycloalkyl, phenyl, C$_1$-C$_6$-alkoxy, C$_1$-C$_6$-alkylthio or (C$_1$-C$_6$-alkoxy)carbonyl, wherein the eight radicals last mentioned are unsubstituted or partially or fully halogenated, and in particular the ones wherein R$^6$ is halogen (particularly Cl, F, Br), Me, OMe, CN, CF$_3$, OCF$_3$ or ethynyl.

More preferred are compounds of formula (I) wherein R$^{aa}$ is —C(=S)N(R$^{cc}$)$_2$.

More preferred are compounds of formula (I) wherein R$^{bb}$ is CN.

More preferred are compounds of formula (I) wherein each R$^{cc}$ is independently H, Me, Et, propargyl, allyl, CH$_2$OMe, CH$_2$OEt.

Also more preferred are compounds of formula (I) wherein R$^{aa}$ is —C(=S)N(R$^{cc}$)$_2$; and R$^{cc}$ is independently H, Me, Et, propargyl, allyl, CH$_2$OMe, CH$_2$OEt.

More preferred are compounds of formula (I) wherein p is 0 or 1, and in particular the ones wherein p is 0.

Even more preferred are compounds of formula (I) wherein Y is phenyl unsubstituted or substituted with 1, 2 or 3 substituents R$^5$.

Even more preferred are compounds of formula (I) wherein Q is phenyl unsubstituted or substituted with 1 or 2 substituents R$^6$; pyridyl, pyrimidinyl, pyrazinyl or pyridazinyl, wherein the four rings last mentioned are unsubstituted or substituted with 1 or 2 substituents R$^6$.

Also even more preferred are compounds of formula (I) wherein Q is phenyl unsubstituted or substituted with 1 or 2 substituents R$^6$, and in particular the ones wherein Q is phenyl unsubstituted or substituted with 1 substituent R$^6$.

Also even more preferred are compounds of formula (I) wherein Q is pyridyl, pyrimidinyl, pyrazinyl or pyridazinyl, wherein the aforementioned rings are unsubstituted or substituted with 1 or 2 substituents R$^6$, and in particular the ones wherein Q is pyridyl, pyrimidinyl, pyrazinyl or pyridazinyl, wherein the aforementioned rings are unsubstituted or substituted with 1 substituent R$^6$.

Even more preferred are compounds of formula (I) wherein R$^1$ is H, F, Me, Et, CN, CH$_2$CN or CH$_2$OMe, and in particular the ones wherein R$^1$ is H.

Even more preferred are compounds of formula (I) wherein R$^2$ is H.

Even more preferred are compounds of formula (I) wherein R$^5$ is F, Cl, Br or CF$_3$.

Even more preferred are compounds of formula (I) wherein R$^6$ is F, ethynyl or CF$_3$.

Even more preferred are compounds of formula (I) wherein R$^{aa}$ is —C(=S)NH$_2$.

Even more preferred are compounds of formula (I) wherein R$^{bb}$ is ON.

Even more preferred are compounds of formula (I) wherein p is 0.

Also preferred are compounds of formula (I) wherein all symbols and indices have the preferred meanings.

Also more preferred are compounds of formula (I) wherein all symbols and indices have the more preferred meanings.

Also even more preferred are compounds of formula (I) wherein all symbols and indices have the even more preferred meanings.

Preferred are compounds of formula (I) wherein

Y is phenyl unsubstituted or substituted with 1, 2, 3, 4 or 5 substituents R$^5$; or naphthyl unsubstituted or substituted with 1 or 2 substituents R$^5$;

Q is phenyl unsubstituted or substituted with 1, 2, 3 or 4 substituents R$^6$; cyclohexyl unsubstituted or substituted with 1 or 2 substituents R$^6$; cyclopentyl unsubstituted or substituted with 1 or 2 substituents R$^6$; or a 6-membered aromatic heterocyclic ring containing 1, 2 or 3 nitrogen atoms in the ring, wherein the aforementioned ring is unsubstituted or substituted with 1, 2, 3 or 4 substituents R$^6$;

R$^1$ is H, halogen, cyano, C$_1$-C$_6$-alkyl, C$_2$-C$_6$-alkenyl, C$_2$-C$_6$-alkynyl, C$_3$-C$_6$-cycloalkyl or (C$_1$-C$_6$-alkoxy)carbonyl, wherein the five radicals last mentioned are unsubstituted or substituted with 1, 2 or 3 substituents selected from halogen, cyano, hydroxy, OSi(C$_1$-C$_6$-alkyl)$_3$, C$_1$-C$_6$-alkyl, C$_2$-C$_6$-alkenyl, C$_2$-C$_6$-alkynyl, C$_3$-C$_6$-cycloalkyl, C$_1$-C$_6$-alkoxy and (C$_1$-C$_6$-alkoxy)carbonyl, wherein the six radicals last mentioned are unsubstituted or partially or fully halogenated;

R$^2$ is H or halogen;

or

R$^1$ and R$^2$ form together with the carbon atom to which they are attached a methylene group;

R$^3$ is H, halogen, cyano, C$_1$-C$_6$-alkyl, C$_2$-C$_6$-alkenyl, C$_2$-C$_6$-alkynyl, C$_3$-C$_6$-cycloalkyl or (C$_1$-C$_6$-alkoxy)carbonyl, wherein the five radicals last mentioned are unsubstituted or substituted with 1, 2 or 3 substituents selected from halogen, cyano, hydroxy, OSi(C$_1$-C$_6$-alkyl)$_3$, C$_1$-C$_6$-alkyl, C$_2$-C$_6$-alkenyl, C$_2$-C$_6$-alkynyl, C$_3$-C$_6$-cycloalkyl, C$_1$-C$_6$-alkoxy and (C$_1$-C$_6$-alkoxy)carbonyl, wherein the six radicals last mentioned are unsubstituted or partially or fully halogenated;

R$^4$ is H or halogen;

or

R$^3$ and R$^4$ form together with the carbon atom to which they are attached a methylene group;

R$^5$ is halogen, cyano, SF$_5$, tri-(C$_1$-C$_4$)silyl-C$_2$-C$_4$-alkynyl, (C$_1$-C$_6$-alkyl)aminocarbonyl, di-(C$_1$-C$_6$-alkyl)aminocarbonyl, C$_1$-C$_6$-alkyl, C$_2$-C$_6$-alkenyl, C$_2$-C$_6$-alkynyl, C$_3$-C$_6$-cycloalkyl, phenyl, C$_1$-C$_6$-alkoxy, C$_1$-C$_6$-alkylthio, C$_1$-C$_6$-alkylsulfinyl, C$_1$-C$_6$-alkylsulfonyl, (C$_1$-C$_6$-alkoxy)carbonyl, (C$_1$-C$_6$-alkyl)amino, di-(C$_1$-C$_6$-alkyl)amino, (C$_1$-C$_6$-alkyl)carbonyl or (C$_1$-C$_6$-alkyl)carbonyloxy, wherein the 14 radicals last mentioned are unsubstituted or substituted with one or more substituents selected from halogen, cyano, $C_1$-$C_4$-alkyl-$C_3$-$C_6$-cycloalkyl, $C_1$-$C_6$-alkyl, $C_2$-$C_6$-alkenyl, $C_2$-$C_6$-alkynyl, $C_3$-$C_6$-cycloalkyl and $C_1$-$C_6$-alkoxy, wherein the five radicals last mentioned are unsubstituted or partially or fully halogenated;

or two $R^5$ on two adjacent carbon atoms present on one phenyl ring are together a bridge selected from N=CH—CH=CH, N=CH—CH=N, OCH$_2$CH$_2$O, O(CH$_2$)O and form together with the carbon atoms the two $R^5$ are bonded to a 5- or 6-membered partially unsaturated or aromatic heterocyclic ring, wherein the ring is unsubstituted;

$R^6$ is halogen, nitro, cyano, SF$_5$, tri-($C_1$-$C_4$)silyl-$C_2$-$C_4$-alkynyl, 2,2,2-trifluoro-1-hydroxy-1-(trifluoromethyl)ethyl, ($C_1$-$C_6$-alkyl)aminocarbonyl, di-($C_1$-$C_6$-alkyl)aminocarbonyl, dimethylcarbamoylsulfanyl, morpholine-4-carbonyl, acetamido, pyridyl, pyrrolyl, pyrazolyl, imidazolyl, triazolyl, $C_1$-$C_6$-alkyl, $C_2$-$C_6$-alkenyl, $C_2$-$C_6$-alkynyl, $C_3$-$C_6$-cycloalkyl, phenyl, $C_1$-$C_6$-alkoxy, $C_3$-$C_6$-cycloalkoxy, phenoxy, $C_1$-$C_6$-alkylthio, $C_1$-$C_6$-alkylsulfinyl, $C_1$-$C_6$-alkylsulfonyl, ($C_1$-$C_6$-alkoxy)carbonyl, ($C_1$-$C_6$-alkyl)amino, di-($C_1$-$C_6$-alkyl)amino, ($C_1$-$C_6$-alkyl)carbonyl or ($C_1$-$C_6$-alkyl)carbonyloxy, wherein the 16 radicals last mentioned are unsubstituted or substituted with one or more substituents selected from halogen, cyano, $C_1$-$C_4$-alkyl-$C_3$-$C_6$-cycloalkyl, $C_1$-$C_6$-alkyl, $C_2$-$C_6$-alkenyl, $C_2$-$C_6$-alkynyl, $C_3$-$C_6$-cycloalkyl and $C_1$-$C_6$-alkoxy, wherein the five radicals last mentioned are unsubstituted or partially or fully halogenated;

$R^{aa}$ is —C(=S)N($R^{cc}$)$_2$ or —C(=O)N($R^{ff}$)$_2$;
$R^{bb}$ is CN;
each $R^{cc}$ is independently hydrogen, $C_1$-$C_4$-alkyl, $C_2$-$C_4$-alkenyl, $C_2$-$C_4$-alkynyl, $C_3$-$C_6$-cycloalkyl, $C_1$-$C_4$-alkoxy-$C_1$-$C_2$-alkyl;
each $R^{ff}$ is independently hydrogen, $C_1$-$C_4$-alkyl, $C_2$-$C_4$-alkenyl, $C_2$-$C_4$-alkynyl, $C_3$-$C_6$-cycloalkyl, $C_1$-$C_4$-alkoxy-$C_1$-$C_2$-alkyl;
p is 0 or 1.

More preferred are compounds of formula (I) wherein

Y is phenyl unsubstituted or substituted with 1, 2, 3, 4 or 5 substituents $R^5$; or naphthyl unsubstituted or substituted with 1 substituent $R^5$;

Q is phenyl unsubstituted or substituted with 1, 2 or 3 substituents $R^6$; cyclohexyl unsubstituted or substituted with 1 substituent $R^6$; or a 6-membered aromatic heterocyclic ring containing 1, 2 or 3 nitrogen atoms in the ring, wherein the aforementioned ring is unsubstituted or substituted with 1, 2 or 3 substituents $R^6$;

$R^1$ is H, Me, Et, CN, CH$_2$CN, CH$_2$CF$_3$, halogen, CH$_2$OH, CH$_2$OMe, CH$_2$OEt, CH$_2$CO$_2$Me, CH$_2$CO$_2$Et, CH$_2$OSi(Me)$_3$ or CH$_2$OSi(Et)$_3$;
$R^2$ is H or halogen;
$R^3$ is H, Me, Et, CN, CH$_2$CN, CH$_2$CF$_3$, halogen, CH$_2$OH, CH$_2$OMe, CH$_2$OEt, CH$_2$CO$_2$Me, CH$_2$CO$_2$Et, CH$_2$OSi(Me)$_3$ or CH$_2$OSi(Et)$_3$;
$R^4$ is H or halogen;
$R^5$ is halogen, cyano, tri-($C_1$-$C_4$)silyl-$C_2$-$C_4$-alkynyl, $C_1$-$C_6$-alkyl, $C_2$-$C_6$-alkenyl, $C_2$-$C_6$-alkynyl, $C_3$-$C_6$-cycloalkyl, phenyl, $C_1$-$C_6$-alkoxy, $C_1$-$C_6$-alkylthio or ($C_1$-$C_6$-alkoxy)carbonyl, wherein the eight radicals last mentioned are unsubstituted or partially or fully halogenated;

or two $R^5$ on two adjacent carbon atoms present on one phenyl ring are together a bridge selected from N=CH—CH=CH, N=CH—CH=N, OCH$_2$CH$_2$O, O(CH$_2$)O and form together with the carbon atoms the two $R^5$ are bonded to a 5- or 6-membered partially unsaturated or aromatic heterocyclic ring, wherein the ring is unsubstituted;

$R^6$ is halogen, nitro, cyano, tri-($C_1$-$C_4$)silyl-$C_2$-$C_4$-alkynyl, 2,2,2-trifluoro-1-hydroxy-1-(trifluoromethyl)ethyl, dimethoxymethyl, dimethylcarbamoylsulfanyl, morpholine-4-carbonyl, acetamido, pyridyl, pyrrolyl, pyrazolyl, imidazolyl, triazolyl, $C_1$-$C_6$-alkyl, $C_2$-$C_6$-alkenyl, $C_2$-$C_6$-alkynyl, $C_3$-$C_6$-cycloalkyl, phenyl, $C_1$-$C_6$-alkoxy, $C_3$-$C_6$-cycloalkoxy, phenoxy, $C_1$-$C_6$-alkylthio, $C_1$-$C_6$-alkylsulfonyl or ($C_1$-$C_6$-alkoxy)carbonyl, wherein the eleven radicals last mentioned are unsubstituted or partially or fully halogenated;

$R^{aa}$ is —C(=S)N($R^{cc}$)$_2$;
$R^{bb}$ is CN;
each $R^{cc}$ is independently H, Me, Et, propargyl, allyl, CH$_2$OMe, CH$_2$OEt;
p is 0 or 1.

Even more preferred are compounds of formula (I) wherein

Y is phenyl unsubstituted or substituted with 1, 2 or 3 substituents $R^5$;

Q is phenyl unsubstituted or substituted with 1 or 2 substituents $R^6$; pyridyl, pyrimidinyl, pyrazinyl or pyridazinyl, wherein the four rings last mentioned are unsubstituted or substituted with 1 or 2 substituents $R^6$;

$R^1$ is H, F, Me, Et, CN, CH$_2$CN or CH$_2$OMe;
$R^2$ is H;
$R^5$ is F, Cl, Br or CF$_3$;
$R^6$ is F, ethynyl or CF$_3$;
$R^{aa}$ is —C(=S)NH$_2$;
$R^{bb}$ is CN;
p is 0.

Particularly preferred are compounds of formula (I) wherein Y is 4-fluorophenyl, 3-fluorophenyl, 2-fluorophenyl, 4-chlorophenyl, 3-cyanophenyl, 4-bromophenyl, 3-methylphenyl, 3-methoxyphenyl, 4-trifluoromethylphenyl, 3,5-difluorophenyl or 3,4,5-trifluorophenyl.

Also particularly preferred are compounds of formula (I) wherein Y is 4-fluorophenyl, 3-fluorophenyl, 4-bromophenyl, 4-trifluoromethylphenyl, 3,5-difluorophenyl or 3,4,5-trifluorophenyl.

Also particularly preferred are compounds of formula (I) wherein Y is 3,4,5-trifluorophenyl.

Particularly preferred are compounds of formula (I) wherein Q is 4-fluorophenyl, 4-ethynylphenyl or 4-trifluoromethylphenyl.

Also particularly preferred are compounds of formula (I) wherein Q is 2-pyridyl, 3-pyridyl or 5-pyrimidinyl, wherein the aforementioned rings are unsubstituted or substituted with one or more $R^6$, particularly 2-pyridyl, 3-pyridyl or 5-pyrimidinyl, wherein the aforementioned rings are unsubstituted or substituted with 1 or 2 $R^6$ (particularly F, ethynyl, Br, CF$_3$).

Particular preference is given to compounds of formula (I) wherein $R^1$, $R^2$, $R^3$ and $R^4$ are H.

Very particular preference is given to compounds of formula (I) wherein $R^1$ and $R^2$ are H; and p is 0.

In a preferred embodiment Q is phenyl unsubstituted or substituted with one or more $R^6$; pyridyl or pyrimidinyl, wherein the two rings last mentioned are unsubstituted or substituted with one or more $R^6$.

In another preferred embodiment Q is phenyl unsubstituted or substituted with one or more $R^6$.

In another preferred embodiment Q is pyridyl or pyrimidinyl, wherein the aforementioned rings are unsubstituted or substituted with one or more $R^6$, particularly pyridyl or pyrimidinyl, wherein the aforementioned rings are unsubstituted or substituted with 1 or 2 $R^6$.

In another embodiment Q is cyclohexyl unsubstituted or substituted with 1 or 2 $R^6$.

In one embodiment $R^{cc}$ is H when $R^{bb}$ is CN.

In a further embodiment $R^{cc}$ is H. In a further embodiment $R^{ff}$ is H.

In a further embodiment $R^{cc}$ is H; and $R^{ff}$ is H.

In a preferred embodiment $R^{aa}$ is —C(=S)NH$_2$ or —C(=O)NH$_2$.

In a more preferred embodiment $R^{aa}$ is —C(=S)NH$_2$.

In another preferred embodiment $R^{aa}$ is —C(=O)NH$_2$.

In a preferred embodiment $R^{bb}$ is —C(=S)NH$_2$, —C(=O)NH$_2$, or CN.

In a further preferred embodiment $R^{bb}$ is —C(=S)NH$_2$ or CN.

In another preferred embodiment $R^{bb}$ is —C(=O)NH$_2$ or CN.

In a more preferred embodiment $R^{bb}$ is CN.

In a preferred embodiment $R^{aa}$ is —C(=S)NH$_2$ or —C(=O)NH$_2$; and $R^{bb}$ is CN.

In a more preferred embodiment $R^{aa}$ is —C(=S)NH$_2$; and $R^{bb}$ is CN.

In another preferred embodiment $R^{aa}$ is —C(=O)NH$_2$; and $R^{bb}$ is CN.

In another preferred embodiment $R^{cc}$ is H or Me. In another preferred embodiment $R^{ff}$ is H or Me. In another preferred embodiment $R^{cc}$ is H or Me; and $R^{ff}$ is H or Me.

In another embodiment $R^{cc}$ is Me. In another embodiment $R^{ff}$ is Me.

In another embodiment $R^{cc}$ is Me; and $R^{ff}$ is Me.

In another preferred embodiment $R^{aa}$ is —C(=S)NH$_2$, —C(=S)NHMe, —C(=O)NH$_2$ or —C(=O)NHMe.

In another preferred embodiment $R^{aa}$ is —C(=S)NH$_2$ or —C(=S)NHMe.

In another preferred embodiment $R^{aa}$ is —C(=O)NH$_2$ or —C(=O)NHMe.

In another embodiment $R^{aa}$ is —C(=S)NHMe or —C(=O)NHMe.

In another embodiment $R^{aa}$ is —C(=S)NHMe.

In another embodiment $R^{aa}$ is —C(=O)NHMe.

In another preferred embodiment $R^{aa}$ is —C(=S)NH$_2$, —C(=S)NHMe, —C(=O)NH$_2$ or —C(=O)NHMe; and $R^{bb}$ is CN.

In another preferred embodiment $R^{aa}$ is —C(=S)NH$_2$ or —C(=S)NHMe; and $R^{bb}$ is CN.

In another preferred embodiment $R^{aa}$ is —C(=O)NH$_2$ or —C(=O)NHMe; and $R^{bb}$ is CN.

In another embodiment $R^{aa}$ is —C(=S)NHMe or —C(=O)NHMe; and $R^{bb}$ is CN.

In another embodiment $R^{aa}$ is —C(=S)NHMe; and $R^{bb}$ is CN.

In another embodiment $R^{aa}$ is —C(=O)NHMe; and $R^{bb}$ is CN.

In one embodiment $R^1$ and $R^2$ do not form together with the carbon atom to which they are attached a methylene group. In a further embodiment $R^3$ and $R^4$ do not form together with the carbon atom to which they are attached a methylene group. In yet a further embodiment neither $R^1$ and $R^2$ nor $R^3$ and $R^4$ form together with the carbon atom to which they are attached a methylene group.

Further preferred compounds of formula (I) are compounds of formulae (Ia-1), (Ia-2) or (Ia-3),

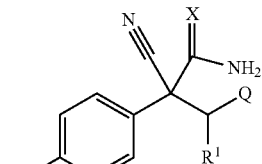
(Ia-1)

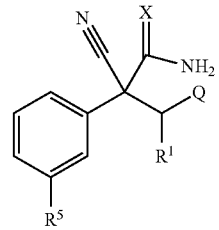
(Ia-2)

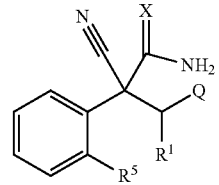
(Ia-3)

wherein Y is phenyl substituted with 1 substituent $R^5$; $R^2$ is H; $R^{aa}$ is —C(=X)NH$_2$; $R^{bb}$ is CN; p is 0; Q is as defined in formula (I); and $R^1$, $R^5$ and X are as defined in Table A.

The compounds of formulae (Ia-1), (Ia-2) or (Ia-3) include the respective compounds wherein Y=unsubstituted phenyl. In line with this, the symbol "–" in column "$R^5$" in table A means that the corresponding compounds do not carry a substituent $R^5$, i.e. Y=unsubstituted phenyl.

TABLE A

| No.   | $R^1$ | $R^5$   | X |
|-------|-------|---------|---|
| A-001 | H     | —       | S |
| A-002 | H     | F       | S |
| A-003 | H     | Cl      | S |
| A-004 | H     | Br      | S |
| A-005 | H     | Me      | S |
| A-006 | H     | OMe     | S |
| A-007 | H     | vinyl   | S |
| A-008 | H     | ethynyl | S |
| A-009 | H     | CN      | S |
| A-010 | H     | $CF_3$  | S |
| A-011 | H     | $OCF_3$ | S |
| A-012 | H     | $CHF_2$ | S |
| A-013 | H     | $OCHF_2$| S |
| A-014 | H     | $SCF_3$ | S |
| A-015 | Me    | —       | S |
| A-016 | Me    | F       | S |
| A-017 | Me    | Cl      | S |
| A-018 | Me    | Br      | S |
| A-019 | Me    | Me      | S |
| A-020 | Me    | OMe     | S |
| A-021 | Me    | vinyl   | S |
| A-022 | Me    | ethynyl | S |
| A-023 | Me    | CN      | S |
| A-024 | Me    | $CF_3$  | S |
| A-025 | Me    | $OCF_3$ | S |
| A-026 | Me    | $CHF_2$ | S |
| A-027 | Me    | $OCHF_2$| S |
| A-028 | Me    | $SCF_3$ | S |
| A-029 | Et    | —       | S |
| A-030 | Et    | F       | S |
| A-031 | Et    | Cl      | S |
| A-032 | Et    | Br      | S |
| A-033 | Et    | Me      | S |

TABLE A-continued

| No. | R¹ | R⁵ | X |
|---|---|---|---|
| A-034 | Et | OMe | S |
| A-035 | Et | vinyl | S |
| A-036 | Et | ethynyl | S |
| A-037 | Et | CN | S |
| A-038 | Et | $CF_3$ | S |
| A-039 | Et | $OCF_3$ | S |
| A-040 | Et | $CHF_2$ | S |
| A-041 | Et | $OCHF_2$ | S |
| A-042 | Et | $SCF_3$ | S |
| A-043 | CN | — | S |
| A-044 | CN | F | S |
| A-045 | CN | Cl | S |
| A-046 | CN | Br | S |
| A-047 | CN | Me | S |
| A-048 | CN | OMe | S |
| A-049 | CN | vinyl | S |
| A-050 | CN | ethynyl | S |
| A-051 | CN | CN | S |
| A-052 | CN | $CF_3$ | S |
| A-053 | CN | $OCF_3$ | S |
| A-054 | CN | $CHF_2$ | S |
| A-055 | CN | $OCHF_2$ | S |
| A-056 | CN | $SCF_3$ | S |
| A-057 | $CF_3$ | — | S |
| A-058 | $CF_3$ | F | S |
| A-059 | $CF_3$ | Cl | S |
| A-060 | $CF_3$ | Br | S |
| A-061 | $CF_3$ | Me | S |
| A-062 | $CF_3$ | OMe | S |
| A-063 | $CF_3$ | vinyl | S |
| A-064 | $CF_3$ | ethynyl | S |
| A-065 | $CF_3$ | CN | S |
| A-066 | $CF_3$ | $CF_3$ | S |
| A-067 | $CF_3$ | $OCF_3$ | S |
| A-068 | $CF_3$ | $CHF_2$ | S |
| A-069 | $CF_3$ | $OCHF_2$ | S |
| A-070 | $CF_3$ | $SCF_3$ | S |
| A-071 | $CH_2CN$ | — | S |
| A-072 | $CH_2CN$ | F | S |
| A-073 | $CH_2CN$ | Cl | S |
| A-074 | $CH_2CN$ | Br | S |
| A-075 | $CH_2CN$ | Me | S |
| A-076 | $CH_2CN$ | OMe | S |
| A-077 | $CH_2CN$ | vinyl | S |
| A-078 | $CH_2CN$ | ethynyl | S |
| A-079 | $CH_2CN$ | CN | S |
| A-080 | $CH_2CN$ | $CF_3$ | S |
| A-081 | $CH_2CN$ | $OCF_3$ | S |
| A-082 | $CH_2CN$ | $CHF_2$ | S |
| A-083 | $CH_2CN$ | $OCHF_2$ | S |
| A-084 | $CH_2CN$ | $SCF_3$ | S |
| A-085 | $CH_2OMe$ | — | S |
| A-086 | $CH_2OMe$ | F | S |
| A-087 | $CH_2OMe$ | Cl | S |
| A-088 | $CH_2OMe$ | Br | S |
| A-089 | $CH_2OMe$ | Me | S |
| A-090 | $CH_2OMe$ | OMe | S |
| A-091 | $CH_2OMe$ | vinyl | S |
| A-092 | $CH_2OMe$ | ethynyl | S |
| A-093 | $CH_2OMe$ | CN | S |
| A-094 | $CH_2OMe$ | $CF_3$ | S |
| A-095 | $CH_2OMe$ | $OCF_3$ | S |
| A-096 | $CH_2OMe$ | $CHF_2$ | S |
| A-097 | $CH_2OMe$ | $OCHF_2$ | S |
| A-098 | $CH_2OMe$ | $SCF_3$ | S |
| A-099 | H | — | O |
| A-100 | H | F | O |
| A-101 | H | Cl | O |
| A-102 | H | Br | O |
| A-103 | H | Me | O |
| A-104 | H | OMe | O |
| A-105 | H | vinyl | O |
| A-106 | H | ethynyl | O |
| A-107 | H | CN | O |
| A-108 | H | $CF_3$ | O |
| A-109 | H | $OCF_3$ | O |
| A-110 | H | $CHF_2$ | O |
| A-111 | H | $OCHF_2$ | O |
| A-112 | H | $SCF_3$ | O |
| A-113 | Me | — | O |
| A-114 | Me | F | O |
| A-115 | Me | Cl | O |
| A-116 | Me | Br | O |
| A-117 | Me | Me | O |
| A-118 | Me | OMe | O |
| A-119 | Me | vinyl | O |
| A-120 | Me | ethynyl | O |
| A-121 | Me | CN | O |
| A-122 | Me | $CF_3$ | O |
| A-123 | Me | $OCF_3$ | O |
| A-124 | Me | $CHF_2$ | O |
| A-125 | Me | $OCHF_2$ | O |
| A-126 | Me | $SCF_3$ | O |
| A-127 | Et | — | O |
| A-128 | Et | F | O |
| A-129 | Et | Cl | O |
| A-130 | Et | Br | O |
| A-131 | Et | Me | O |
| A-132 | Et | OMe | O |
| A-133 | Et | vinyl | O |
| A-134 | Et | ethynyl | O |
| A-135 | Et | CN | O |
| A-136 | Et | $CF_3$ | O |
| A-137 | Et | $OCF_3$ | O |
| A-138 | Et | $CHF_2$ | O |
| A-139 | Et | $OCHF_2$ | O |
| A-140 | Et | $SCF_3$ | O |
| A-141 | CN | — | O |
| A-142 | CN | F | O |
| A-143 | CN | Cl | O |
| A-144 | CN | Br | O |
| A-145 | CN | Me | O |
| A-146 | CN | OMe | O |
| A-147 | CN | vinyl | O |
| A-148 | CN | ethynyl | O |
| A-149 | CN | CN | O |
| A-150 | CN | $CF_3$ | O |
| A-151 | CN | $OCF_3$ | O |
| A-152 | CN | $CHF_2$ | O |
| A-153 | CN | $OCHF_2$ | O |
| A-154 | CN | $SCF_3$ | O |
| A-155 | $CF_3$ | — | O |
| A-156 | $CF_3$ | F | O |
| A-157 | $CF_3$ | Cl | O |
| A-158 | $CF_3$ | Br | O |
| A-159 | $CF_3$ | Me | O |
| A-160 | $CF_3$ | OMe | O |
| A-161 | $CF_3$ | vinyl | O |
| A-162 | $CF_3$ | ethynyl | O |
| A-163 | $CF_3$ | CN | O |
| A-164 | $CF_3$ | $CF_3$ | O |
| A-165 | $CF_3$ | $OCF_3$ | O |
| A-166 | $CF_3$ | $CHF_2$ | O |
| A-167 | $CF_3$ | $OCHF_2$ | O |
| A-168 | $CF_3$ | $SCF_3$ | O |
| A-169 | $CH_2CN$ | — | O |
| A-170 | $CH_2CN$ | F | O |
| A-171 | $CH_2CN$ | Cl | O |
| A-172 | $CH_2CN$ | Br | O |
| A-173 | $CH_2CN$ | Me | O |
| A-174 | $CH_2CN$ | OMe | O |
| A-175 | $CH_2CN$ | vinyl | O |
| A-176 | $CH_2CN$ | ethynyl | O |
| A-177 | $CH_2CN$ | CN | O |
| A-178 | $CH_2CN$ | $CF_3$ | O |
| A-179 | $CH_2CN$ | $OCF_3$ | O |
| A-180 | $CH_2CN$ | $CHF_2$ | O |
| A-181 | $CH_2CN$ | $OCHF_2$ | O |
| A-182 | $CH_2CN$ | $SCF_3$ | O |
| A-183 | $CH_2OMe$ | — | O |
| A-184 | $CH_2OMe$ | F | O |
| A-185 | $CH_2OMe$ | Cl | O |
| A-186 | $CH_2OMe$ | Br | O |
| A-187 | $CH_2OMe$ | Me | O |
| A-188 | $CH_2OMe$ | OMe | O |
| A-189 | $CH_2OMe$ | vinyl | O |

TABLE A-continued

| No. | R¹ | R⁵ | X |
|---|---|---|---|
| A-190 | CH₂OMe | ethynyl | O |
| A-191 | CH₂OMe | CN | O |
| A-192 | CH₂OMe | CF₃ | O |
| A-193 | CH₂OMe | OCF₃ | O |
| A-194 | CH₂OMe | CHF₂ | O |
| A-195 | CH₂OMe | OCHF₂ | O |
| A-196 | CH₂OMe | SCF₃ | O |

Further preferred compounds of formula (I) are compounds of formulae (Ib-1), (Ib-2), (Ib-3), (Ib-4), (Ib-5) or (Ib-6),

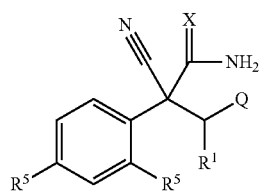
(Ib-1)

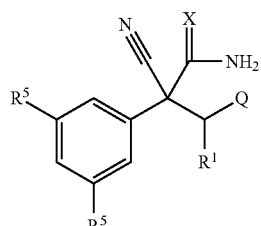
(Ib-2)

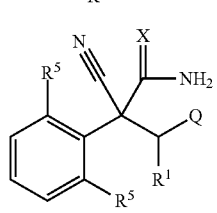
(Ib-3)

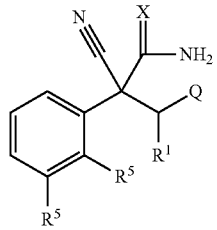
(Ib-4)

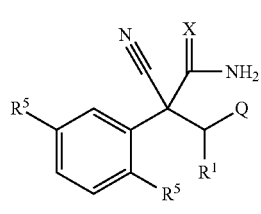
(Ib-5)

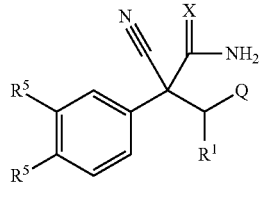
(Ib-6)

wherein Y is phenyl substituted with 2 substituents R⁵; R² is H; $R^{aa}$ is —C(=X)NH₂; $R^{bb}$ is CN; p is 0; Q is as defined in formula (I); and R¹, R⁵ and X are as defined in Table B.

Further preferred compounds of formula (I) are compounds of formulae (Ib-7), (Ib-8), (Ib-9), (Ib-10), (Ib-11) or (Ib-12),

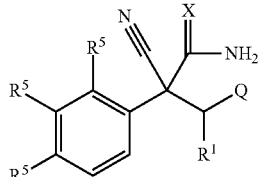
(Ib-7)

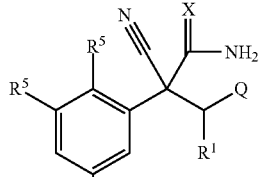
(Ib-8)

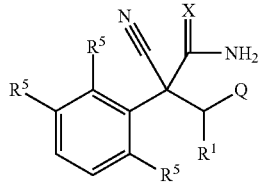
(Ib-9)

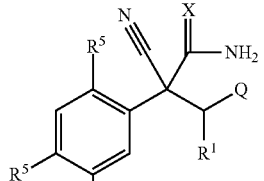
(Ib-10)

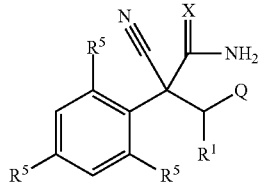
(Ib-11)

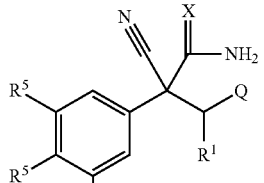
(Ib-12)

wherein Y is phenyl substituted with 3 substituents R⁵; R² is H; $R^{aa}$ is —C(=X)NH₂; $R^{bb}$ is CN; p is 0; Q is as defined in formula (I); and R¹, R⁵ and X are as defined in Table B.

TABLE B

| No. | R¹ | R⁵ | X |
|---|---|---|---|
| B-001 | H | F | S |
| B-002 | H | Cl | S |
| B-003 | H | Br | S |
| B-004 | H | Me | S |
| B-005 | H | OMe | S |
| B-006 | H | SCF₃ | S |
| B-007 | H | CF₃ | S |
| B-008 | H | OCF₃ | S |
| B-009 | Me | F | S |
| B-010 | Me | Cl | S |
| B-011 | Me | Br | S |
| B-012 | Me | Me | S |
| B-013 | Me | OMe | S |
| B-014 | Me | SCF₃ | S |
| B-015 | Me | CF₃ | S |
| B-016 | Me | OCF₃ | S |
| B-017 | Et | F | S |
| B-018 | Et | Cl | S |
| B-019 | Et | Br | S |
| B-020 | Et | Me | S |
| B-021 | Et | OMe | S |
| B-022 | Et | SCF₃ | S |
| B-023 | Et | CF₃ | S |
| B-024 | Et | OCF₃ | S |
| B-025 | CN | F | S |
| B-026 | CN | Cl | S |
| B-027 | CN | Br | S |
| B-028 | CN | Me | S |
| B-029 | CN | OMe | S |
| B-030 | CN | SCF₃ | S |
| B-031 | CN | CF₃ | S |
| B-032 | CN | OCF₃ | S |
| B-033 | CF₃ | F | S |
| B-034 | CF₃ | Cl | S |
| B-035 | CF₃ | Br | S |
| B-036 | CF₃ | Me | S |
| B-037 | CF₃ | OMe | S |
| B-038 | CF₃ | SCF₃ | S |
| B-039 | CF₃ | CF₃ | S |
| B-040 | CF₃ | OCF₃ | S |
| B-041 | CH₂CN | F | S |
| B-042 | CH₂CN | Cl | S |
| B-043 | CH₂CN | Br | S |
| B-044 | CH₂CN | Me | S |
| B-045 | CH₂CN | OMe | S |
| B-046 | CH₂CN | SCF₃ | S |
| B-047 | CH₂CN | CF₃ | S |
| B-048 | CH₂CN | OCF₃ | S |
| B-049 | CH₂OMe | F | S |
| B-050 | CH₂OMe | Cl | S |
| B-051 | CH₂OMe | Br | S |
| B-052 | CH₂OMe | Me | S |
| B-053 | CH₂OMe | OMe | S |
| B-054 | CH₂OMe | SCF₃ | S |
| B-055 | CH₂OMe | CF₃ | S |
| B-056 | CH₂OMe | OCF₃ | S |
| B-057 | H | F | O |
| B-058 | H | Cl | O |
| B-059 | H | Br | O |
| B-060 | H | Me | O |
| B-061 | H | OMe | O |
| B-062 | H | SCF₃ | O |
| B-063 | H | CF₃ | O |
| B-064 | H | OCF₃ | O |
| B-065 | Me | F | O |
| B-066 | Me | Cl | O |
| B-067 | Me | Br | O |
| B-068 | Me | Me | O |
| B-069 | Me | OMe | O |
| B-070 | Me | SCF₃ | O |
| B-071 | Me | CF₃ | O |
| B-072 | Me | OCF₃ | O |
| B-073 | Et | F | O |
| B-074 | Et | Cl | O |
| B-075 | Et | Br | O |
| B-076 | Et | Me | O |
| B-077 | Et | OMe | O |
| B-078 | Et | SCF₃ | O |
| B-079 | Et | CF₃ | O |
| B-080 | Et | OCF₃ | O |
| B-081 | CN | F | O |
| B-082 | CN | Cl | O |
| B-083 | CN | Br | O |
| B-084 | CN | Me | O |
| B-085 | CN | OMe | O |
| B-086 | CN | SCF₃ | O |
| B-087 | CN | CF₃ | O |
| B-088 | CN | OCF₃ | O |
| B-089 | CF₃ | F | O |
| B-090 | CF₃ | Cl | O |
| B-091 | CF₃ | Br | O |
| B-092 | CF₃ | Me | O |
| B-093 | CF₃ | OMe | O |
| B-094 | CF₃ | SCF₃ | O |
| B-095 | CF₃ | CF₃ | O |
| B-096 | CF₃ | OCF₃ | O |
| B-097 | CH₂CN | F | O |
| B-098 | CH₂CN | Cl | O |
| B-099 | CH₂CN | Br | O |
| B-100 | CH₂CN | Me | O |
| B-101 | CH₂CN | OMe | O |
| B-102 | CH₂CN | SCF₃ | O |
| B-103 | CH₂CN | CF₃ | O |
| B-104 | CH₂CN | OCF₃ | O |
| B-105 | CH₂OMe | F | O |
| B-106 | CH₂OMe | Cl | O |
| B-107 | CH₂OMe | Br | O |
| B-108 | CH₂OMe | Me | O |
| B-109 | CH₂OMe | OMe | O |
| B-110 | CH₂OMe | SCF₃ | O |
| B-111 | CH₂OMe | CF₃ | O |
| B-112 | CH₂OMe | OCF₃ | O |

Further preferred compounds of formula (I) are compounds of formulae (Ic-1), (Ic-2), (Ic-3), (Ic-4), (Ic-5) (Ic-6), (Ic-7), (Ic-8) or (Ic-9),

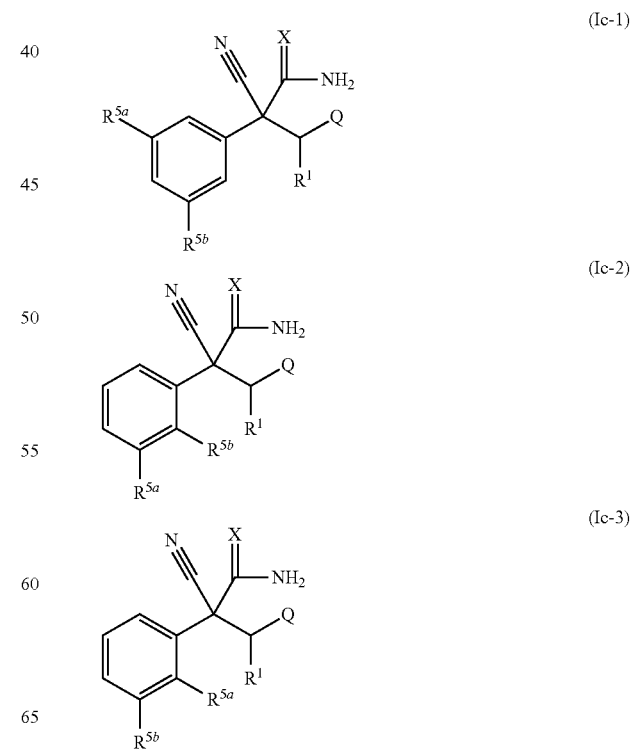

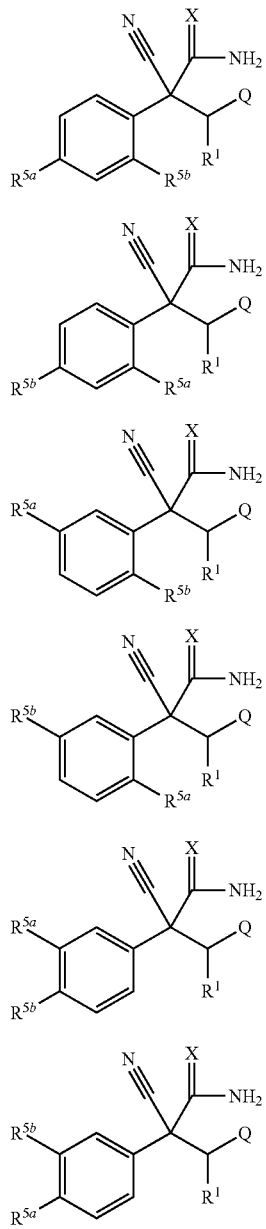

wherein Y is phenyl substituted with 2 substituents R⁵; one R⁵ is $R^{5a}$ and the other R⁵ is $R^{5b}$; $R^2$ is H; $R^{aa}$ is —C(=X)NH₂; $R^{bb}$ is CN; p is 0; Q is as defined in formula (I); and $R^1$, $R^{5a}$, $R^{5b}$ and X are as defined in Table C.

TABLE C

| No. | $R^1$ | $R^{5a}$ | $R^{5b}$ | X |
|---|---|---|---|---|
| C-001 | H | F | Cl | S |
| C-002 | H | F | Me | S |
| C-003 | H | Cl | Me | S |
| C-004 | H | CF₃ | F | S |
| C-005 | H | CF₃ | Cl | S |
| C-006 | H | CF₃ | Me | S |
| C-007 | H | CN | F | S |
| C-008 | H | CN | Cl | S |
| C-009 | H | Br | F | S |
| C-010 | H | Br | Cl | S |

TABLE C-continued

| No. | $R^1$ | $R^{5a}$ | $R^{5b}$ | X |
|---|---|---|---|---|
| C-011 | H | Br | Me | S |
| C-012 | H | Br | CF₃ | S |
| C-013 | H | OCF₃ | F | S |
| C-014 | H | OCF₃ | Cl | S |
| C-015 | H | OCF₃ | Me | S |
| C-016 | H | OCF₃ | Br | S |
| C-017 | H | SCF₃ | F | S |
| C-018 | H | SCF₃ | Cl | S |
| C-019 | H | SCF₃ | Me | S |
| C-020 | H | SCF₃ | Br | S |
| C-021 | Me | F | Cl | S |
| C-022 | Me | F | Me | S |
| C-023 | Me | Cl | Me | S |
| C-024 | Me | CF₃ | F | S |
| C-025 | Me | CF₃ | Cl | S |
| C-026 | Me | CF₃ | Me | S |
| C-027 | Me | CN | F | S |
| C-028 | Me | CN | Cl | S |
| C-029 | Me | Br | F | S |
| C-030 | Me | Br | Cl | S |
| C-031 | Me | Br | Me | S |
| C-032 | Me | Br | CF₃ | S |
| C-033 | Me | OCF₃ | F | S |
| C-034 | Me | OCF₃ | Cl | S |
| C-035 | Me | OCF₃ | Me | S |
| C-036 | Me | OCF₃ | Br | S |
| C-037 | Me | SCF₃ | F | S |
| C-038 | Me | SCF₃ | Cl | S |
| C-039 | Me | SCF₃ | Me | S |
| C-040 | Me | SCF₃ | Br | S |
| C-041 | Et | F | Cl | S |
| C-042 | Et | F | Me | S |
| C-043 | Et | Cl | Me | S |
| C-044 | Et | CF₃ | F | S |
| C-045 | Et | CF₃ | Cl | S |
| C-046 | Et | CF₃ | Me | S |
| C-047 | Et | CN | F | S |
| C-048 | Et | CN | Cl | S |
| C-049 | Et | CN | Me | S |
| C-050 | Et | Br | F | S |
| C-051 | Et | Br | Cl | S |
| C-052 | Et | Br | Me | S |
| C-053 | Et | Br | CF₃ | S |
| C-054 | Et | OCF₃ | F | S |
| C-055 | Et | OCF₃ | Cl | S |
| C-056 | Et | OCF₃ | Me | S |
| C-057 | Et | OCF₃ | Br | S |
| C-058 | Et | SCF₃ | F | S |
| C-059 | Et | SCF₃ | Cl | S |
| C-060 | Et | SCF₃ | Me | S |
| C-061 | Et | SCF₃ | Br | S |
| C-062 | CN | F | Cl | S |
| C-063 | CN | F | Me | S |
| C-064 | CN | Cl | Me | S |
| C-065 | CN | CF₃ | F | S |
| C-066 | CN | CF₃ | Cl | S |
| C-067 | CN | CF₃ | Me | S |
| C-068 | CN | CN | F | S |
| C-069 | CN | CN | Cl | S |
| C-070 | CN | Br | F | S |
| C-071 | CN | Br | Cl | S |
| C-072 | CN | Br | Me | S |
| C-073 | CN | Br | CF₃ | S |
| C-074 | CN | OCF₃ | F | S |
| C-075 | CN | OCF₃ | Cl | S |
| C-076 | CN | OCF₃ | Me | S |
| C-077 | CN | OCF₃ | Br | S |
| C-078 | CN | SCF₃ | F | S |
| C-079 | CN | SCF₃ | Cl | S |
| C-080 | CN | SCF₃ | Me | S |
| C-081 | CN | SCF₃ | Br | S |
| C-082 | CF₃ | F | Cl | S |
| C-083 | CF₃ | F | Me | S |
| C-084 | CF₃ | Cl | Me | S |
| C-085 | CF₃ | CF₃ | F | S |
| C-086 | CF₃ | CF₃ | Cl | S |
| C-087 | CF₃ | CF₃ | Me | S |
| C-088 | CF₃ | CN | F | S |

TABLE C-continued

| No. | R¹ | R⁵ᵃ | R⁵ᵇ | X |
|---|---|---|---|---|
| C-089 | CF₃ | CN | Cl | S |
| C-090 | CF₃ | Br | F | S |
| C-091 | CF₃ | Br | Cl | S |
| C-092 | CF₃ | Br | Me | S |
| C-093 | CF₃ | Br | CF₃ | S |
| C-094 | CF₃ | OCF₃ | F | S |
| C-095 | CF₃ | OCF₃ | Cl | S |
| C-096 | CF₃ | OCF₃ | Me | S |
| C-097 | CF₃ | OCF₃ | Br | S |
| C-098 | CF₃ | SCF₃ | F | S |
| C-099 | CF₃ | SCF₃ | Cl | S |
| C-100 | CF₃ | SCF₃ | Me | S |
| C-101 | CF₃ | SCF₃ | Br | S |
| C-102 | CH₂CN | F | Cl | S |
| C-103 | CH₂CN | F | Me | S |
| C-104 | CH₂CN | Cl | Me | S |
| C-105 | CH₂CN | CF₃ | F | S |
| C-106 | CH₂CN | CF₃ | Cl | S |
| C-107 | CH₂CN | CF₃ | Me | S |
| C-108 | CH₂CN | CN | F | S |
| C-109 | CH₂CN | CN | Cl | S |
| C-110 | CH₂CN | Br | F | S |
| C-111 | CH₂CN | Br | Cl | S |
| C-112 | CH₂CN | Br | Me | S |
| C-113 | CH₂CN | Br | CF₃ | S |
| C-114 | CH₂CN | OCF₃ | F | S |
| C-115 | CH₂CN | OCF₃ | Cl | S |
| C-116 | CH₂CN | OCF₃ | Me | S |
| C-117 | CH₂CN | OCF₃ | Br | S |
| C-118 | CH₂CN | SCF₃ | F | S |
| C-119 | CH₂CN | SCF₃ | Cl | S |
| C-120 | CH₂CN | SCF₃ | Me | S |
| C-121 | CH₂CN | SCF₃ | Br | S |
| C-122 | CH₂OMe | F | Cl | S |
| C-123 | CH₂OMe | F | Me | S |
| C-124 | CH₂OMe | Cl | Me | S |
| C-125 | CH₂OMe | CF₃ | F | S |
| C-126 | CH₂OMe | CF₃ | Cl | S |
| C-127 | CH₂OMe | CF₃ | Me | S |
| C-128 | CH₂OMe | CN | F | S |
| C-129 | CH₂OMe | CN | Cl | S |
| C-130 | CH₂OMe | Br | F | S |
| C-131 | CH₂OMe | Br | Cl | S |
| C-132 | CH₂OMe | Br | Me | S |
| C-133 | CH₂OMe | Br | CF₃ | S |
| C-134 | CH₂OMe | OCF₃ | F | S |
| C-135 | CH₂OMe | OCF₃ | Cl | S |
| C-136 | CH₂OMe | OCF₃ | Me | S |
| C-137 | CH₂OMe | OCF₃ | Br | S |
| C-138 | CH₂OMe | SCF₃ | F | S |
| C-139 | CH₂OMe | SCF₃ | Cl | S |
| C-140 | CH₂OMe | SCF₃ | Me | S |
| C-141 | CH₂OMe | SCF₃ | Br | S |
| C-142 | H | F | Cl | O |
| C-143 | H | F | Me | O |
| C-144 | H | Cl | Me | O |
| C-145 | H | CF₃ | F | O |
| C-146 | H | CF₃ | Cl | O |
| C-147 | H | CF₃ | Me | O |
| C-148 | H | CN | F | O |
| C-149 | H | CN | Cl | O |
| C-150 | H | Br | F | O |
| C-151 | H | Br | Cl | O |
| C-152 | H | Br | Me | O |
| C-153 | H | Br | CF₃ | O |
| C-154 | H | OCF₃ | F | O |
| C-155 | H | OCF₃ | Cl | O |
| C-156 | H | OCF₃ | Me | O |
| C-157 | H | OCF₃ | Br | O |
| C-158 | H | SCF₃ | F | O |
| C-159 | H | SCF₃ | Cl | O |
| C-160 | H | SCF₃ | Me | O |
| C-161 | H | SCF₃ | Br | O |
| C-162 | Me | F | Cl | O |
| C-163 | Me | F | Me | O |
| C-164 | Me | Cl | Me | O |
| C-165 | Me | CF₃ | F | O |
| C-166 | Me | CF₃ | Cl | O |
| C-167 | Me | CF₃ | Me | O |
| C-168 | Me | CN | F | O |
| C-169 | Me | CN | Cl | O |
| C-170 | Me | Br | F | O |
| C-171 | Me | Br | Cl | O |
| C-172 | Me | Br | Me | O |
| C-173 | Me | Br | CF₃ | O |
| C-174 | Me | OCF₃ | F | O |
| C-175 | Me | OCF₃ | Cl | O |
| C-176 | Me | OCF₃ | Me | O |
| C-177 | Me | OCF₃ | Br | O |
| C-178 | Me | SCF₃ | F | O |
| C-179 | Me | SCF₃ | Cl | O |
| C-180 | Me | SCF₃ | Me | O |
| C-181 | Me | SCF₃ | Br | O |
| C-182 | Et | F | Cl | O |
| C-183 | Et | F | Me | O |
| C-184 | Et | Cl | Me | O |
| C-185 | Et | CF₃ | F | O |
| C-186 | Et | CF₃ | Cl | O |
| C-187 | Et | CF₃ | Me | O |
| C-188 | Et | CN | F | O |
| C-189 | Et | CN | Cl | O |
| C-190 | Et | CN | Me | O |
| C-191 | Et | Br | F | O |
| C-192 | Et | Br | Cl | O |
| C-193 | Et | Br | Me | O |
| C-194 | Et | Br | CF₃ | O |
| C-195 | Et | OCF₃ | F | O |
| C-196 | Et | OCF₃ | Cl | O |
| C-197 | Et | OCF₃ | Me | O |
| C-198 | Et | OCF₃ | Br | O |
| C-199 | Et | SCF₃ | F | O |
| C-200 | Et | SCF₃ | Cl | O |
| C-201 | Et | SCF₃ | Me | O |
| C-202 | Et | SCF₃ | Br | O |
| C-203 | CN | F | Cl | O |
| C-204 | CN | F | Me | O |
| C-205 | CN | Cl | Me | O |
| C-206 | CN | CF₃ | F | O |
| C-207 | CN | CF₃ | Cl | O |
| C-208 | CN | CF₃ | Me | O |
| C-209 | CN | CN | F | O |
| C-210 | CN | CN | Cl | O |
| C-211 | CN | Br | F | O |
| C-212 | CN | Br | Cl | O |
| C-213 | CN | Br | Me | O |
| C-214 | CN | Br | CF₃ | O |
| C-215 | CN | OCF₃ | F | O |
| C-216 | CN | OCF₃ | Cl | O |
| C-217 | CN | OCF₃ | Me | O |
| C-218 | CN | OCF₃ | Br | O |
| C-219 | CN | SCF₃ | F | O |
| C-220 | CN | SCF₃ | Cl | O |
| C-221 | CN | SCF₃ | Me | O |
| C-222 | CN | SCF₃ | Br | O |
| C-223 | CF₃ | F | Cl | O |
| C-224 | CF₃ | F | Me | O |
| C-225 | CF₃ | Cl | Me | O |
| C-226 | CF₃ | CF₃ | F | O |
| C-227 | CF₃ | CF₃ | Cl | O |
| C-228 | CF₃ | CF₃ | Me | O |
| C-229 | CF₃ | CN | F | O |
| C-230 | CF₃ | CN | Cl | O |
| C-231 | CF₃ | Br | F | O |
| C-232 | CF₃ | Br | Cl | O |
| C-233 | CF₃ | Br | Me | O |
| C-234 | CF₃ | Br | CF₃ | O |
| C-235 | CF₃ | OCF₃ | F | O |
| C-236 | CF₃ | OCF₃ | Cl | O |
| C-237 | CF₃ | OCF₃ | Me | O |
| C-238 | CF₃ | OCF₃ | Br | O |
| C-239 | CF₃ | SCF₃ | F | O |
| C-240 | CF₃ | SCF₃ | Cl | O |
| C-241 | CF₃ | SCF₃ | Me | O |
| C-242 | CF₃ | SCF₃ | Br | O |
| C-243 | CH₂CN | F | Cl | O |
| C-244 | CH₂CN | F | Me | O |

TABLE C-continued

| No. | R¹ | R⁵ᵃ | R⁵ᵇ | X |
|---|---|---|---|---|
| C-245 | CH₂CN | Cl | Me | O |
| C-246 | CH₂CN | CF₃ | F | O |
| C-247 | CH₂CN | CF₃ | Cl | O |
| C-248 | CH₂CN | CF₃ | Me | O |
| C-249 | CH₂CN | CN | F | O |
| C-250 | CH₂CN | CN | Cl | O |
| C-251 | CH₂CN | Br | F | O |
| C-252 | CH₂CN | Br | Cl | O |
| C-253 | CH₂CN | Br | Me | O |
| C-254 | CH₂CN | Br | CF₃ | O |
| C-255 | CH₂CN | OCF₃ | F | O |
| C-256 | CH₂CN | OCF₃ | Cl | O |
| C-257 | CH₂CN | OCF₃ | Me | O |
| C-258 | CH₂CN | OCF₃ | Br | O |
| C-259 | CH₂CN | SCF₃ | F | O |
| C-260 | CH₂CN | SCF₃ | Cl | O |
| C-261 | CH₂CN | SCF₃ | Me | O |
| C-262 | CH₂CN | SCF₃ | Br | O |
| C-263 | CH₂OMe | F | Cl | O |
| C-264 | CH₂OMe | F | Me | O |
| C-265 | CH₂OMe | Cl | Me | O |
| C-266 | CH₂OMe | CF₃ | F | O |
| C-267 | CH₂OMe | CF₃ | Cl | O |
| C-268 | CH₂OMe | CF₃ | Me | O |
| C-269 | CH₂OMe | CN | F | O |
| C-270 | CH₂OMe | CN | Cl | O |
| C-271 | CH₂OMe | Br | F | O |
| C-272 | CH₂OMe | Br | Cl | O |
| C-273 | CH₂OMe | Br | Me | O |
| C-274 | CH₂OMe | Br | CF₃ | O |
| C-275 | CH₂OMe | OCF₃ | F | O |
| C-276 | CH₂OMe | OCF₃ | Cl | O |
| C-277 | CH₂OMe | OCF₃ | Me | O |
| C-278 | CH₂OMe | OCF₃ | Br | O |
| C-279 | CH₂OMe | SCF₃ | F | O |
| C-280 | CH₂OMe | SCF₃ | Cl | O |
| C-281 | CH₂OMe | SCF₃ | Me | O |
| C-282 | CH₂OMe | SCF₃ | Br | O |

Further preferred compounds of formula (I) are compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) or (Id-30),

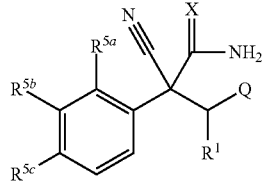

(Id-1)

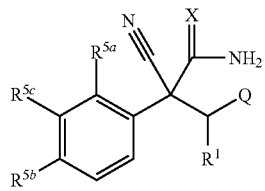

(Id-2)

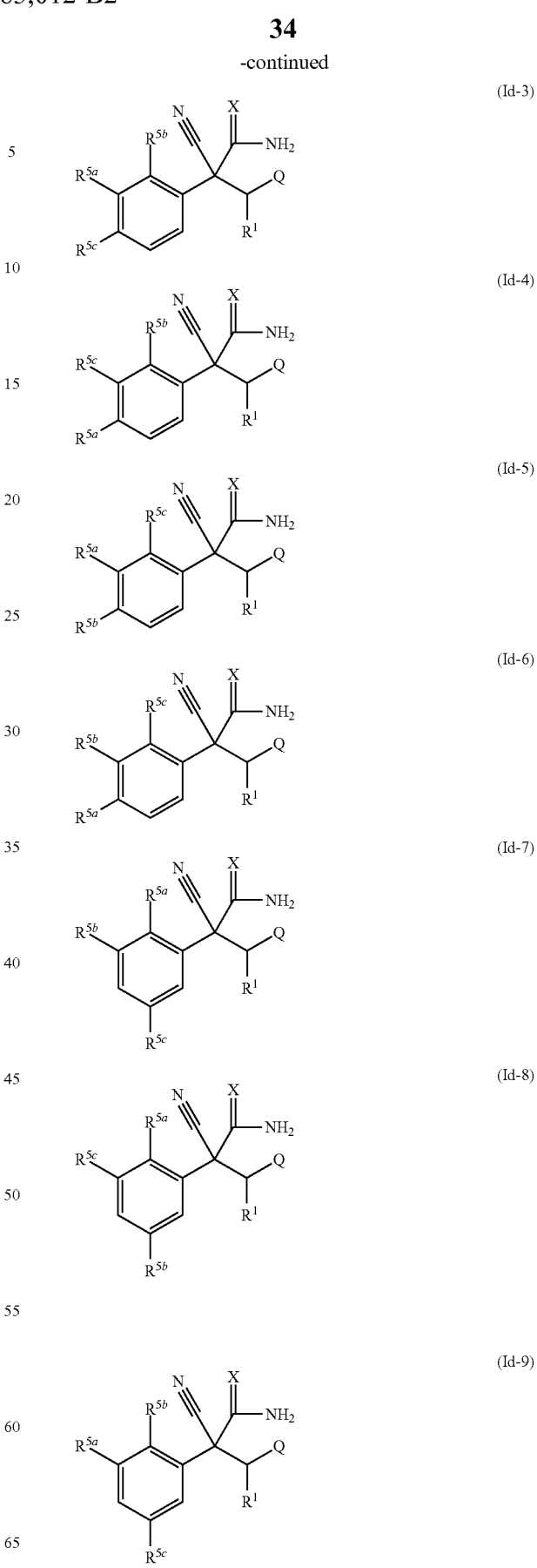

(Id-3)

(Id-4)

(Id-5)

(Id-6)

(Id-7)

(Id-8)

(Id-9)

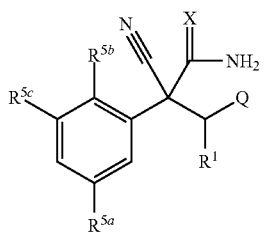
(Id-10)
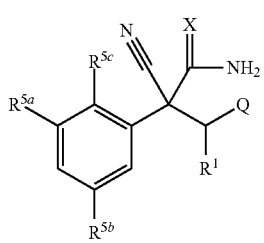
(Id-11)
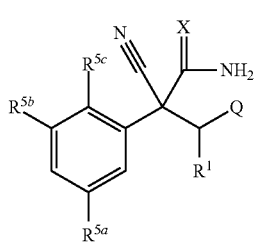
(Id-12)
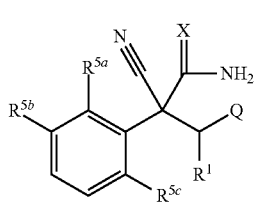
(Id-13)
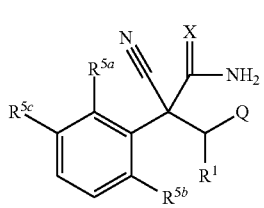
(Id-14)
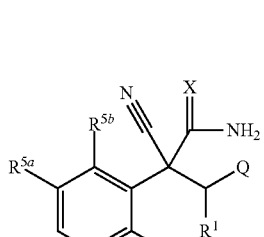
(Id-15)
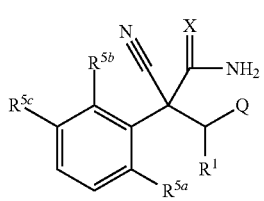
(Id-16)
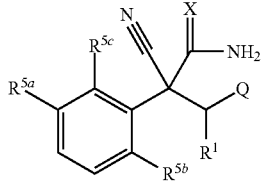
(Id-17)
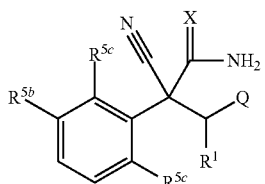
(Id-18)
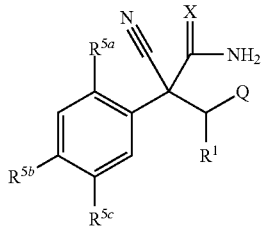
(Id-19)
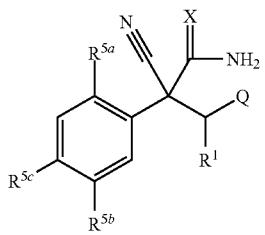
(Id-20)
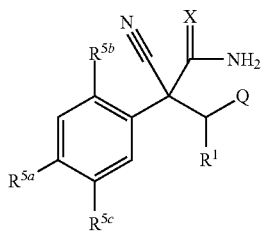
(Id-21)
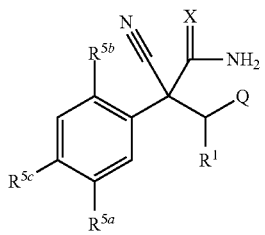
(Id-22)
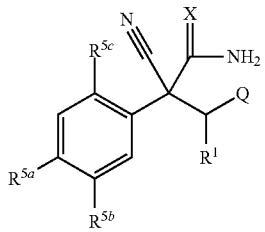
(Id-23)

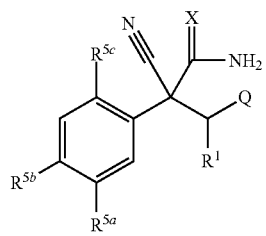 (Id-24)

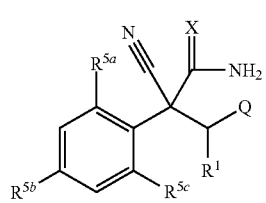 (Id-25)

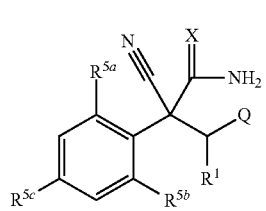 (Id-26)

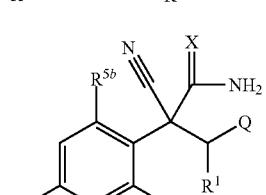 (Id-27)

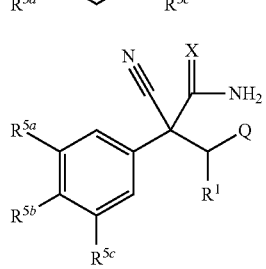 (Id-28)

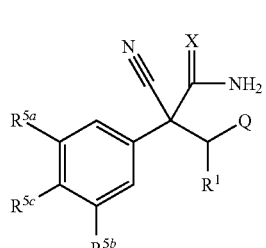 (Id-29)

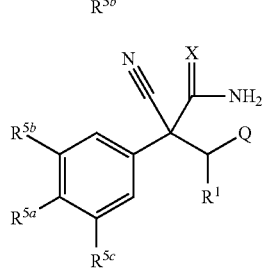 (Id-30)

wherein Y is phenyl substituted with 3 substituents $R^5$; one $R^5$ is $R^{5a}$, one $R^5$ is $R^{5b}$, and the other $R^5$ is $R^{5c}$; $R^2$ is H; $R^{aa}$ is —C(=X)NH$_2$; $R^{bb}$ is CN; p is 0; Q is as defined in formula (I); and $R^1$, $R^{5a}$, $R^{5b}$, $R^{5c}$ and X are as defined in Table D.

TABLE D

| No. | $R^1$ | $R^{5a}$ | $R^{5b}$ | $R^{5c}$ | X |
|---|---|---|---|---|---|
| D-001 | H | F | Cl | F | S |
| D-002 | H | F | Me | F | S |
| D-003 | H | Cl | Me | F | S |
| D-004 | H | CF$_3$ | F | F | S |
| D-005 | H | CF$_3$ | Cl | F | S |
| D-006 | H | CF$_3$ | Me | F | S |
| D-007 | H | CN | F | F | S |
| D-008 | H | CN | Cl | F | S |
| D-009 | H | Br | F | F | S |
| D-010 | H | Br | Cl | F | S |
| D-011 | H | Br | Me | F | S |
| D-012 | H | Br | CF$_3$ | F | S |
| D-013 | H | OCF$_3$ | F | F | S |
| D-014 | H | OCF$_3$ | Cl | F | S |
| D-015 | H | OCF$_3$ | Me | F | S |
| D-016 | H | OCF$_3$ | Br | F | S |
| D-017 | H | SCF$_3$ | F | F | S |
| D-018 | H | SCF$_3$ | Cl | F | S |
| D-019 | H | SCF$_3$ | Me | F | S |
| D-020 | H | SCF$_3$ | Br | F | S |
| D-021 | H | F | Cl | Cl | S |
| D-022 | H | F | Me | Cl | S |
| D-023 | H | Cl | Me | Cl | S |
| D-024 | H | CF$_3$ | F | Cl | S |
| D-025 | H | CF$_3$ | Cl | Cl | S |
| D-026 | H | CF$_3$ | Me | Cl | S |
| D-027 | H | CN | F | Cl | S |
| D-028 | H | CN | Cl | Cl | S |
| D-029 | H | Br | F | Cl | S |
| D-030 | H | Br | Cl | Cl | S |
| D-031 | H | Br | Me | Cl | S |
| D-032 | H | Br | CF$_3$ | Cl | S |
| D-033 | H | OCF$_3$ | F | Cl | S |
| D-034 | H | OCF$_3$ | Cl | Cl | S |
| D-035 | H | OCF$_3$ | Me | Cl | S |
| D-036 | H | OCF$_3$ | Br | Cl | S |
| D-037 | H | SCF$_3$ | F | Cl | S |
| D-038 | H | SCF$_3$ | Cl | Cl | S |
| D-039 | H | SCF$_3$ | Me | Cl | S |
| D-040 | H | SCF$_3$ | Br | Cl | S |
| D-041 | H | F | Cl | Br | S |
| D-042 | H | F | Me | Br | S |
| D-043 | H | Cl | Me | Br | S |
| D-044 | H | CF$_3$ | F | Br | S |
| D-045 | H | CF$_3$ | Cl | Br | S |
| D-046 | H | CF$_3$ | Me | Br | S |
| D-047 | H | CN | F | Br | S |
| D-048 | H | CN | Cl | Br | S |
| D-049 | H | Br | F | Br | S |
| D-050 | H | Br | Cl | Br | S |
| D-051 | H | Br | Me | Br | S |
| D-052 | H | Br | CF$_3$ | Br | S |
| D-053 | H | OCF$_3$ | F | Br | S |
| D-054 | H | OCF$_3$ | Cl | Br | S |
| D-055 | H | OCF$_3$ | Me | Br | S |
| D-056 | H | OCF$_3$ | Br | Br | S |
| D-057 | H | SCF$_3$ | F | Br | S |
| D-058 | H | SCF$_3$ | Cl | Br | S |
| D-059 | H | SCF$_3$ | Me | Br | S |
| D-060 | H | SCF$_3$ | Br | Br | S |
| D-061 | H | F | Cl | CF$_3$ | S |
| D-062 | H | F | Me | CF$_3$ | S |
| D-063 | H | Cl | Me | CF$_3$ | S |
| D-064 | H | CF$_3$ | F | CF$_3$ | S |
| D-065 | H | CF$_3$ | Cl | CF$_3$ | S |
| D-066 | H | CF$_3$ | Me | CF$_3$ | S |
| D-067 | H | CN | F | CF$_3$ | S |
| D-068 | H | CN | Cl | CF$_3$ | S |
| D-069 | H | Br | F | CF$_3$ | S |
| D-070 | H | Br | Cl | CF$_3$ | S |
| D-071 | H | Br | Me | CF$_3$ | S |
| D-072 | H | Br | CF$_3$ | CF$_3$ | S |
| D-073 | H | OCF$_3$ | F | CF$_3$ | S |

TABLE D-continued

| No. | R¹ | R⁵ᵃ | R⁵ᵇ | R⁵ᶜ | X |
|---|---|---|---|---|---|
| D-074 | H | OCF₃ | Cl | CF₃ | S |
| D-075 | H | OCF₃ | Me | CF₃ | S |
| D-076 | H | OCF₃ | Br | CF₃ | S |
| D-077 | H | SCF₃ | F | CF₃ | S |
| D-078 | H | SCF₃ | Cl | CF₃ | S |
| D-079 | H | SCF₃ | Me | CF₃ | S |
| D-080 | H | SCF₃ | Br | CF₃ | S |
| D-081 | Me | F | Cl | F | S |
| D-082 | Me | F | Me | F | S |
| D-083 | Me | Cl | Me | F | S |
| D-084 | Me | CF₃ | F | F | S |
| D-085 | Me | CF₃ | Cl | F | S |
| D-086 | Me | CF₃ | Me | F | S |
| D-087 | Me | CN | F | F | S |
| D-088 | Me | CN | Cl | F | S |
| D-089 | Me | Br | F | F | S |
| D-090 | Me | Br | Cl | F | S |
| D-091 | Me | Br | Me | F | S |
| D-092 | Me | Br | CF₃ | F | S |
| D-093 | Me | OCF₃ | F | F | S |
| D-094 | Me | OCF₃ | Cl | F | S |
| D-095 | Me | OCF₃ | Me | F | S |
| D-096 | Me | OCF₃ | Br | F | S |
| D-097 | Me | SCF₃ | F | F | S |
| D-098 | Me | SCF₃ | Cl | F | S |
| D-099 | Me | SCF₃ | Me | F | S |
| D-100 | Me | SCF₃ | Br | F | S |
| D-101 | Me | F | Cl | Cl | S |
| D-102 | Me | F | Me | Cl | S |
| D-103 | Me | Cl | Me | Cl | S |
| D-104 | Me | CF₃ | F | Cl | S |
| D-105 | Me | CF₃ | Cl | Cl | S |
| D-106 | Me | CF₃ | Me | Cl | S |
| D-107 | Me | CN | F | Cl | S |
| D-108 | Me | CN | Cl | Cl | S |
| D-109 | Me | Br | F | Cl | S |
| D-110 | Me | Br | Cl | Cl | S |
| D-111 | Me | Br | Me | Cl | S |
| D-112 | Me | Br | CF₃ | Cl | S |
| D-113 | Me | OCF₃ | F | Cl | S |
| D-114 | Me | OCF₃ | Cl | Cl | S |
| D-115 | Me | OCF₃ | Me | Cl | S |
| D-116 | Me | OC₃ | Br | Cl | S |
| D-117 | Me | SCF₃ | F | Cl | S |
| D-118 | Me | SCF₃ | Cl | Cl | S |
| D-119 | Me | SCF₃ | Me | Cl | S |
| D-120 | Me | SCF₃ | Br | Cl | S |
| D-121 | Me | F | Cl | Br | S |
| D-122 | Me | F | Me | Br | S |
| D-123 | Me | Cl | Me | Br | S |
| D-124 | Me | CF₃ | F | Br | S |
| D-125 | Me | CF₃ | Cl | Br | S |
| D-126 | Me | CF₃ | Me | Br | S |
| D-127 | Me | CN | F | Br | S |
| D-128 | Me | CN | Cl | Br | S |
| D-129 | Me | Br | F | Br | S |
| D-130 | Me | Br | Cl | Br | S |
| D-131 | Me | Br | Me | Br | S |
| D-132 | Me | Br | CF₃ | Br | S |
| D-133 | Me | OCF₃ | F | Br | S |
| D-134 | Me | OCF₃ | Cl | Br | S |
| D-135 | Me | OCF₃ | Me | Br | S |
| D-136 | Me | OCF₃ | Br | Br | S |
| D-137 | Me | SCF₃ | F | Br | S |
| D-138 | Me | SCF₃ | Cl | Br | S |
| D-139 | Me | SCF₃ | Me | Br | S |
| D-140 | Me | SCF₃ | Br | Br | S |
| D-141 | Me | F | Cl | CF₃ | S |
| D-142 | Me | F | Me | CF₃ | S |
| D-143 | Me | Cl | Me | CF₃ | S |
| D-144 | Me | CF₃ | F | CF₃ | S |
| D-145 | Me | CF₃ | Cl | CF₃ | S |
| D-146 | Me | CF₃ | Me | CF₃ | S |
| D-147 | Me | CN | F | CF₃ | S |
| D-148 | Me | CN | Cl | CF₃ | S |
| D-149 | Me | Br | F | CF₃ | S |
| D-150 | Me | Br | Cl | CF₃ | S |
| D-151 | Me | Br | Me | CF₃ | S |
| D-152 | Me | Br | CF₃ | CF₃ | S |
| D-153 | Me | OCF₃ | F | CF₃ | S |
| D-154 | Me | OCF₃ | Cl | CF₃ | S |
| D-155 | Me | OCF₃ | Me | CF₃ | S |
| D-156 | Me | OCF₃ | Br | CF₃ | S |
| D-157 | Me | SCF₃ | F | CF₃ | S |
| D-158 | Me | SCF₃ | Cl | CF₃ | S |
| D-159 | Me | SCF₃ | Me | CF₃ | S |
| D-160 | Me | SCF₃ | Br | CF₃ | S |
| D-161 | Et | F | Cl | F | S |
| D-162 | Et | F | Me | F | S |
| D-163 | Et | Cl | Me | F | S |
| D-164 | Et | CF₃ | F | F | S |
| D-165 | Et | CF₃ | Cl | F | S |
| D-166 | Et | CF₃ | Me | F | S |
| D-167 | Et | CN | F | F | S |
| D-168 | Et | CN | Cl | F | S |
| D-169 | Et | Br | F | F | S |
| D-170 | Et | Br | Cl | F | S |
| D-171 | Et | Br | Me | F | S |
| D-172 | Et | Br | CF₃ | F | S |
| D-173 | Et | OCF₃ | F | F | S |
| D-174 | Et | OCF₃ | Cl | F | S |
| D-175 | Et | OCF₃ | Me | F | S |
| D-176 | Et | OCF₃ | Br | F | S |
| D-177 | Et | SCF₃ | F | F | S |
| D-178 | Et | SCF₃ | Cl | F | S |
| D-179 | Et | SCF₃ | Me | F | S |
| D-180 | Et | SCF₃ | Br | F | S |
| D-181 | Et | F | Cl | Cl | S |
| D-182 | Et | F | Me | Cl | S |
| D-183 | Et | Cl | Me | Cl | S |
| D-184 | Et | CF₃ | F | Cl | S |
| D-185 | Et | CF₃ | Cl | Cl | S |
| D-186 | Et | CF₃ | Me | Cl | S |
| D-187 | Et | CN | F | Cl | S |
| D-188 | Et | CN | Cl | Cl | S |
| D-189 | Et | Br | F | Cl | S |
| D-190 | Et | Br | Cl | Cl | S |
| D-191 | Et | Br | Me | Cl | S |
| D-192 | Et | Br | CF₃ | Cl | S |
| D-193 | Et | OCF₃ | F | Cl | S |
| D-194 | Et | OCF₃ | Cl | Cl | S |
| D-195 | Et | OCF₃ | Me | Cl | S |
| D-196 | Et | OCF₃ | Br | Cl | S |
| D-197 | Et | SCF₃ | F | Cl | S |
| D-198 | Et | SCF₃ | Cl | Cl | S |
| D-199 | Et | SCF₃ | Me | Cl | S |
| D-200 | Et | SCF₃ | Br | Cl | S |
| D-201 | Et | F | Cl | Br | S |
| D-202 | Et | F | Me | Br | S |
| D-203 | Et | Cl | Me | Br | S |
| D-204 | Et | CF₃ | F | Br | S |
| D-205 | Et | CF₃ | Cl | Br | S |
| D-206 | Et | CF₃ | Me | Br | S |
| D-207 | Et | CN | F | Br | S |
| D-208 | Et | CN | Cl | Br | S |
| D-209 | Et | Br | F | Br | S |
| D-210 | Et | Br | Cl | Br | S |
| D-211 | Et | Br | Me | Br | S |
| D-212 | Et | Br | CF₃ | Br | S |
| D-213 | Et | OCF₃ | F | Br | S |
| D-214 | Et | OCF₃ | Cl | Br | S |
| D-215 | Et | OCF₃ | Me | Br | S |
| D-216 | Et | OCF₃ | Br | Br | S |
| D-217 | Et | SCF₃ | F | Br | S |
| D-218 | Et | SCF₃ | Cl | Br | S |
| D-219 | Et | SCF₃ | Me | Br | S |
| D-220 | Et | SCF₃ | Br | Br | S |
| D-221 | Et | F | Cl | CF₃ | S |
| D-222 | Et | F | Me | CF₃ | S |
| D-223 | Et | Cl | Me | CF₃ | S |
| D-224 | Et | CF₃ | F | CF₃ | S |
| D-225 | Et | CF₃ | Cl | CF₃ | S |
| D-226 | Et | CF₃ | Me | CF₃ | S |
| D-227 | Et | CN | F | CF₃ | S |
| D-228 | Et | CN | Cl | CF₃ | S |
| D-229 | Et | Br | F | CF₃ | S |

TABLE D-continued

| No. | R¹ | R⁵ᵃ | R⁵ᵇ | R⁵ᶜ | X |
|---|---|---|---|---|---|
| D-230 | Et | Br | Cl | CF₃ | S |
| D-231 | Et | Br | Me | CF₃ | S |
| D-232 | Et | Br | CF₃ | CF₃ | S |
| D-233 | Et | OCF₃ | F | CF₃ | S |
| D-234 | Et | OCF₃ | Cl | CF₃ | S |
| D-235 | Et | OCF₃ | Me | CF₃ | S |
| D-236 | Et | OCF₃ | Br | CF₃ | S |
| D-237 | Et | SCF₃ | F | CF₃ | S |
| D-238 | Et | SCF₃ | Cl | CF₃ | S |
| D-239 | Et | SCF₃ | Me | CF₃ | S |
| D-240 | Et | SCF₃ | Br | CF₃ | S |
| D-241 | H | F | Cl | F | O |
| D-242 | H | F | Me | F | O |
| D-243 | H | Cl | Me | F | O |
| D-244 | H | CF₃ | F | F | O |
| D-245 | H | CF₃ | Cl | F | O |
| D-246 | H | CF₃ | Me | F | O |
| D-247 | H | CN | F | F | O |
| D-248 | H | CN | Cl | F | O |
| D-249 | H | Br | F | F | O |
| D-250 | H | Br | Cl | F | O |
| D-251 | H | Br | Me | F | O |
| D-252 | H | Br | CF₃ | F | O |
| D-253 | H | OCF₃ | F | F | O |
| D-254 | H | OCF₃ | Cl | F | O |
| D-255 | H | OCF₃ | Me | F | O |
| D-256 | H | OCF₃ | Br | F | O |
| D-257 | H | SCF₃ | F | F | O |
| D-258 | H | SCF₃ | Cl | F | O |
| D-259 | H | SCF₃ | Me | F | O |
| D-260 | H | SCF₃ | Br | F | O |
| D-261 | H | F | Cl | Cl | O |
| D-262 | H | F | Me | Cl | O |
| D-263 | H | Cl | Me | Cl | O |
| D-264 | H | CF₃ | F | Cl | O |
| D-265 | H | CF₃ | Cl | Cl | O |
| D-266 | H | CF₃ | Me | Cl | O |
| D-267 | H | CN | F | Cl | O |
| D-268 | H | CN | Cl | Cl | O |
| D-269 | H | Br | F | Cl | O |
| D-270 | H | Br | Cl | Cl | O |
| D-271 | H | Br | Me | Cl | O |
| D-272 | H | Br | CF₃ | Cl | O |
| D-273 | H | OCF₃ | F | Cl | O |
| D-274 | H | OCF₃ | Cl | Cl | O |
| D-275 | H | OCF₃ | Me | Cl | O |
| D-276 | H | OCF₃ | Br | Cl | O |
| D-277 | H | SCF₃ | F | Cl | O |
| D-278 | H | SCF₃ | Cl | Cl | O |
| D-279 | H | SCF₃ | Me | Cl | O |
| D-280 | H | SCF₃ | Br | Cl | O |
| D-281 | H | F | Cl | Br | O |
| D-282 | H | F | Me | Br | O |
| D-283 | H | Cl | Me | Br | O |
| D-284 | H | CF₃ | F | Br | O |
| D-285 | H | CF₃ | Cl | Br | O |
| D-286 | H | CF₃ | Me | Br | O |
| D-287 | H | CN | F | Br | O |
| D-288 | H | CN | Cl | Br | O |
| D-289 | H | Br | F | Br | O |
| D-290 | H | Br | Cl | Br | O |
| D-291 | H | Br | Me | Br | O |
| D-292 | H | Br | CF₃ | Br | O |
| D-293 | H | OCF₃ | F | Br | O |
| D-294 | H | OCF₃ | Cl | Br | O |
| D-295 | H | OCF₃ | Me | Br | O |
| D-296 | H | OCF₃ | Br | Br | O |
| D-297 | H | SCF₃ | F | Br | O |
| D-298 | H | SCF₃ | Cl | Br | O |
| D-299 | H | SCF₃ | Me | Br | O |
| D-300 | H | SCF₃ | Br | Br | O |
| D-301 | H | F | Cl | CF₃ | O |
| D-302 | H | F | Me | CF₃ | O |
| D-303 | H | Cl | Me | CF₃ | O |
| D-304 | H | CF₃ | F | CF₃ | O |
| D-305 | H | CF₃ | Cl | CF₃ | O |
| D-306 | H | CF₃ | Me | CF₃ | O |
| D-307 | H | CN | F | CF₃ | O |
| D-308 | H | CN | Cl | CF₃ | O |
| D-309 | H | Br | F | CF₃ | O |
| D-310 | H | Br | Cl | CF₃ | O |
| D-311 | H | Br | Me | CF₃ | O |
| D-312 | H | Br | CF₃ | CF₃ | O |
| D-313 | H | OCF₃ | F | CF₃ | O |
| D-314 | H | OCF₃ | Cl | CF₃ | O |
| D-315 | H | OCF₃ | Me | CF₃ | O |
| D-316 | H | OCF₃ | Br | CF₃ | O |
| D-317 | H | SCF₃ | F | CF₃ | O |
| D-318 | H | SCF₃ | Cl | CF₃ | O |
| D-319 | H | SCF₃ | Me | CF₃ | O |
| D-320 | H | SCF₃ | Br | CF₃ | O |
| D-321 | Me | F | Cl | F | O |
| D-322 | Me | F | Me | F | O |
| D-323 | Me | Cl | Me | F | O |
| D-324 | Me | CF₃ | F | F | O |
| D-325 | Me | CF₃ | Cl | F | O |
| D-326 | Me | CF₃ | Me | F | O |
| D-327 | Me | CN | F | F | O |
| D-328 | Me | CN | Cl | F | O |
| D-329 | Me | Br | F | F | O |
| D-330 | Me | Br | Cl | F | O |
| D-331 | Me | Br | Me | F | O |
| D-332 | Me | Br | CF₃ | F | O |
| D-333 | Me | OCF₃ | F | F | O |
| D-334 | Me | OCF₃ | Cl | F | O |
| D-335 | Me | OCF₃ | Me | F | O |
| D-336 | Me | OCF₃ | Br | F | O |
| D-337 | Me | SCF₃ | F | F | O |
| D-338 | Me | SCF₃ | Cl | F | O |
| D-339 | Me | SCF₃ | Me | F | O |
| D-340 | Me | SCF₃ | Br | F | O |
| D-341 | Me | F | Cl | Cl | O |
| D-342 | Me | F | Me | Cl | O |
| D-343 | Me | Cl | Me | Cl | O |
| D-344 | Me | CF₃ | F | Cl | O |
| D-345 | Me | CF₃ | Cl | Cl | O |
| D-346 | Me | CF₃ | Me | Cl | O |
| D-347 | Me | CN | F | Cl | O |
| D-348 | Me | CN | Cl | Cl | O |
| D-349 | Me | Br | F | Cl | O |
| D-350 | Me | Br | Cl | Cl | O |
| D-351 | Me | Br | Me | Cl | O |
| D-352 | Me | Br | CF₃ | Cl | O |
| D-353 | Me | OCF₃ | F | Cl | O |
| D-354 | Me | OCF₃ | Cl | Cl | O |
| D-355 | Me | OCF₃ | Me | Cl | O |
| D-356 | Me | OCF₃ | Br | Cl | O |
| D-357 | Me | SCF₃ | F | Cl | O |
| D-358 | Me | SCF₃ | Cl | Cl | O |
| D-359 | Me | SCF₃ | Me | Cl | O |
| D-360 | Me | SCF₃ | Br | Cl | O |
| D-361 | Me | F | Cl | Br | O |
| D-362 | Me | F | Me | Br | O |
| D-363 | Me | Cl | Me | Br | O |
| D-364 | Me | CF₃ | F | Br | O |
| D-365 | Me | CF₃ | Cl | Br | O |
| D-366 | Me | CF₃ | Me | Br | O |
| D-367 | Me | CN | F | Br | O |
| D-368 | Me | CN | Cl | Br | O |
| D-369 | Me | Br | F | Br | O |
| D-370 | Me | Br | Cl | Br | O |
| D-371 | Me | Br | Me | Br | O |
| D-372 | Me | Br | CF₃ | Br | O |
| D-373 | Me | OCF₃ | F | Br | O |
| D-374 | Me | OCF₃ | Cl | Br | O |
| D-375 | Me | OCF₃ | Me | Br | O |
| D-376 | Me | OCF₃ | Br | Br | O |
| D-377 | Me | SCF₃ | F | Br | O |
| D-378 | Me | SCF₃ | Cl | Br | O |
| D-379 | Me | SCF₃ | Me | Br | O |
| D-380 | Me | SCF₃ | Br | Br | O |
| D-381 | Me | F | Cl | CF₃ | O |
| D-382 | Me | F | Me | CF₃ | O |
| D-383 | Me | Cl | Me | CF₃ | O |
| D-384 | Me | CF₃ | F | CF₃ | O |
| D-385 | Me | CF₃ | Cl | CF₃ | O |

TABLE D-continued

| No. | R$^1$ | R$^{5a}$ | R$^{5b}$ | R$^{5c}$ | X |
|---|---|---|---|---|---|
| D-386 | Me | CF$_3$ | Me | CF$_3$ | O |
| D-387 | Me | CN | F | CF$_3$ | O |
| D-388 | Me | CN | Cl | CF$_3$ | O |
| D-389 | Me | Br | F | CF$_3$ | O |
| D-390 | Me | Br | Cl | CF$_3$ | O |
| D-391 | Me | Br | Me | CF$_3$ | O |
| D-392 | Me | Br | CF$_3$ | CF$_3$ | O |
| D-393 | Me | OCF$_3$ | F | CF$_3$ | O |
| D-394 | Me | OCF$_3$ | Cl | CF$_3$ | O |
| D-395 | Me | OCF$_3$ | Me | CF$_3$ | O |
| D-396 | Me | OCF$_3$ | Br | CF$_3$ | O |
| D-397 | Me | SCF$_3$ | F | CF$_3$ | O |
| D-398 | Me | SCF$_3$ | Cl | CF$_3$ | O |
| D-399 | Me | SCF$_3$ | Me | CF$_3$ | O |
| D-400 | Me | SCF$_3$ | Br | CF$_3$ | O |
| D-401 | Et | F | Cl | F | O |
| D-402 | Et | F | Me | F | O |
| D-403 | Et | Cl | Me | F | O |
| D-404 | Et | CF$_3$ | F | F | O |
| D-405 | Et | CF$_3$ | Cl | F | O |
| D-406 | Et | CF$_3$ | Me | F | O |
| D-407 | Et | CN | F | F | O |
| D-408 | Et | CN | Cl | F | O |
| D-409 | Et | Br | F | F | O |
| D-410 | Et | Br | Cl | F | O |
| D-411 | Et | Br | Me | F | O |
| D-412 | Et | Br | CF$_3$ | F | O |
| D-413 | Et | OCF$_3$ | F | F | O |
| D-414 | Et | OCF$_3$ | Cl | F | O |
| D-415 | Et | OCF$_3$ | Me | F | O |
| D-416 | Et | OCF$_3$ | Br | F | O |
| D-417 | Et | SCF$_3$ | F | F | O |
| D-418 | Et | SCF$_3$ | Cl | F | O |
| D-419 | Et | SCF$_3$ | Me | F | O |
| D-420 | Et | SCF$_3$ | Br | F | O |
| D-421 | Et | F | Cl | Cl | O |
| D-422 | Et | F | Me | Cl | O |
| D-423 | Et | Cl | Me | Cl | O |
| D-424 | Et | CF$_3$ | F | Cl | O |
| D-425 | Et | CF$_3$ | Cl | Cl | O |
| D-426 | Et | CF$_3$ | Me | Cl | O |
| D-427 | Et | CN | F | Cl | O |
| D-428 | Et | CN | Cl | Cl | O |
| D-429 | Et | Br | F | Cl | O |
| D-430 | Et | Br | Cl | Cl | O |
| D-431 | Et | Br | Me | Cl | O |
| D-432 | Et | Br | CF$_3$ | Cl | O |
| D-433 | Et | OCF$_3$ | F | Cl | O |
| D-434 | Et | OCF$_3$ | Cl | Cl | O |
| D-435 | Et | OCF$_3$ | Me | Cl | O |
| D-436 | Et | OCF$_3$ | Br | Cl | O |
| D-437 | Et | SCF$_3$ | F | Cl | O |
| D-438 | Et | SCF$_3$ | Cl | Cl | O |
| D-439 | Et | SCF$_3$ | Me | Cl | O |
| D-440 | Et | SCF$_3$ | Br | Cl | O |
| D-441 | Et | F | Cl | Br | O |
| D-442 | Et | F | Me | Br | O |
| D-443 | Et | Cl | Me | Br | O |
| D-444 | Et | CF$_3$ | F | Br | O |
| D-445 | Et | CF$_3$ | Cl | Br | O |
| D-446 | Et | CF$_3$ | Me | Br | O |
| D-447 | Et | CN | F | Br | O |
| D-448 | Et | CN | Cl | Br | O |
| D-449 | Et | Br | F | Br | O |
| D-450 | Et | Br | Cl | Br | O |
| D-451 | Et | Br | Me | Br | O |
| D-452 | Et | Br | CF$_3$ | Br | O |
| D-453 | Et | OCF$_3$ | F | Br | O |
| D-454 | Et | OCF$_3$ | Cl | Br | O |
| D-455 | Et | OCF$_3$ | Me | Br | O |
| D-456 | Et | OCF$_3$ | Br | Br | O |
| D-457 | Et | SCF$_3$ | F | Br | O |
| D-458 | Et | SCF$_3$ | Cl | Br | O |
| D-459 | Et | SCF$_3$ | Me | Br | O |
| D-460 | Et | SCF$_3$ | Br | Br | O |
| D-461 | Et | F | Cl | CF$_3$ | O |
| D-462 | Et | F | Me | CF$_3$ | O |
| D-463 | Et | Cl | Me | CF$_3$ | O |
| D-464 | Et | CF$_3$ | F | CF$_3$ | O |
| D-465 | Et | CF$_3$ | Cl | CF$_3$ | O |
| D-466 | Et | CF$_3$ | Me | CF$_3$ | O |
| D-467 | Et | CN | F | CF$_3$ | O |
| D-468 | Et | CN | Cl | CF$_3$ | O |
| D-469 | Et | Br | F | CF$_3$ | O |
| D-470 | Et | Br | Cl | CF$_3$ | O |
| D-471 | Et | Br | Me | CF$_3$ | O |
| D-472 | Et | Br | CF$_3$ | CF$_3$ | O |
| D-473 | Et | OCF$_3$ | F | CF$_3$ | O |
| D-474 | Et | OCF$_3$ | Cl | CF$_3$ | O |
| D-475 | Et | OCF$_3$ | Me | CF$_3$ | O |
| D-476 | Et | OCF$_3$ | Br | CF$_3$ | O |
| D-477 | Et | SCF$_3$ | F | CF$_3$ | O |
| D-478 | Et | SCF$_3$ | Cl | CF$_3$ | O |
| D-479 | Et | SCF$_3$ | Me | CF$_3$ | O |
| D-480 | Et | SCF$_3$ | Br | CF$_3$ | O |

Further preferred meanings of Q are given in Table E.

TABLE E

| No. | ring | substituents |
|---|---|---|
| E-001 | 4-substituted cyclohexyl | H |
| E-002 | 4-substituted cyclohexyl | F |
| E-003 | 4-substituted cyclohexyl | Cl |
| E-004 | 4-substituted cyclohexyl | Br |
| E-005 | 4-substituted cyclohexyl | Me |
| E-006 | 4-substituted cyclohexyl | OMe |
| E-007 | 4-substituted cyclohexyl | vinyl |
| E-008 | 4-substituted cyclohexyl | ethynyl |
| E-009 | 4-substituted cyclohexyl | CN |
| E-010 | 4-substituted cyclohexyl | CF$_3$ |
| E-011 | 4-substituted cyclohexyl | OCF$_3$ |
| E-012 | 4-substituted cyclohexyl | CHF$_2$ |
| E-013 | 4-substituted cyclohexyl | OCHF$_2$ |
| E-014 | 4-substituted cyclohexyl | SCF$_3$ |
| E-015 | 4-substituted phenyl | H |
| E-016 | 4-substituted phenyl | F |
| E-017 | 4-substituted phenyl | Cl |
| E-018 | 4-substituted phenyl | Br |
| E-019 | 4-substituted phenyl | Me |
| E-020 | 4-substituted phenyl | OMe |
| E-021 | 4-substituted phenyl | vinyl |
| E-022 | 4-substituted phenyl | ethynyl |
| E-023 | 4-substituted phenyl | CN |
| E-024 | 4-substituted phenyl | CF$_3$ |
| E-025 | 4-substituted phenyl | OCF$_3$ |
| E-026 | 4-substituted phenyl | CHF$_2$ |
| E-027 | 4-substituted phenyl | OCHF$_2$ |
| E-028 | 4-substituted phenyl | SCF$_3$ |
| E-029 | 3-substituted phenyl | H |
| E-030 | 3-substituted phenyl | F |
| E-031 | 3-substituted phenyl | Cl |
| E-032 | 3-substituted phenyl | Br |
| E-033 | 3-substituted phenyl | Me |
| E-034 | 3-substituted phenyl | OMe |
| E-035 | 3-substituted phenyl | vinyl |
| E-036 | 3-substituted phenyl | ethynyl |
| E-037 | 3-substituted phenyl | CN |
| E-038 | 3-substituted phenyl | CF$_3$ |
| E-039 | 3-substituted phenyl | OCF$_3$ |
| E-040 | 3-substituted phenyl | CHF$_2$ |
| E-041 | 3-substituted phenyl | OCHF$_2$ |
| E-042 | 3-substituted phenyl | SCF$_3$ |
| E-043 | 2-substituted phenyl | H |
| E-044 | 2-substituted phenyl | F |
| E-045 | 2-substituted phenyl | Cl |
| E-046 | 2-substituted phenyl | Br |
| E-047 | 2-substituted phenyl | Me |
| E-048 | 2-substituted phenyl | OMe |
| E-049 | 2-substituted phenyl | vinyl |
| E-050 | 2-substituted phenyl | ethynyl |
| E-051 | 2-substituted phenyl | CN |
| E-052 | 2-substituted phenyl | CF$_3$ |

TABLE E-continued

| No. | ring | substituents |
|---|---|---|
| E-053 | 2-substituted phenyl | OCF$_3$ |
| E-054 | 2-substituted phenyl | CHF$_2$ |
| E-055 | 2-substituted phenyl | OCHF$_2$ |
| E-056 | 2-substituted phenyl | SCF$_3$ |
| E-057 | 2,4-disubstituted phenyl | F, F |
| E-058 | 2,4-disubstituted phenyl | Cl, Cl |
| E-059 | 2,4-disubstituted phenyl | Br, Br |
| E-060 | 2,4-disubstituted phenyl | Me, Me |
| E-061 | 2,4-disubstituted phenyl | OMe, OMe |
| E-062 | 2,4-disubstituted phenyl | SCF$_3$, SCF$_3$ |
| E-063 | 2,4-disubstituted phenyl | CF$_3$, CF$_3$ |
| E-064 | 2,4-disubstituted phenyl | OCF$_3$, OCF$_3$ |
| E-065 | 3,5-disubstituted phenyl | F, F |
| E-066 | 3,5-disubstituted phenyl | Cl, Cl |
| E-067 | 3,5-disubstituted phenyl | Br, Br |
| E-068 | 3,5-disubstituted phenyl | Me, Me |
| E-069 | 3,5-disubstituted phenyl | OMe, OMe |
| E-070 | 3,5-disubstituted phenyl | SCF$_3$, SCF$_3$ |
| E-071 | 3,5-disubstituted phenyl | CF$_3$, CF$_3$ |
| E-072 | 3,5-disubstituted phenyl | OCF$_3$, OCF$_3$ |
| E-073 | 2,6-disubstituted phenyl | F, F |
| E-074 | 2,6-disubstituted phenyl | Cl, Cl |
| E-075 | 2,6-disubstituted phenyl | Br, Br |
| E-076 | 2,6-disubstituted phenyl | Me, Me |
| E-077 | 2,6-disubstituted phenyl | OMe, OMe |
| E-078 | 2,6-disubstituted phenyl | SCF$_3$, SCF$_3$ |
| E-079 | 2,6-disubstituted phenyl | CF$_3$, CF$_3$ |
| E-080 | 2,6-disubstituted phenyl | OCF$_3$, OCF$_3$ |
| E-081 | 2,3-disubstituted phenyl | F, F |
| E-082 | 2,3-disubstituted phenyl | Cl, Cl |
| E-083 | 2,3-disubstituted phenyl | Br, Br |
| E-084 | 2,3-disubstituted phenyl | Me, Me |
| E-085 | 2,3-disubstituted phenyl | OMe, OMe |
| E-086 | 2,3-disubstituted phenyl | SCF$_3$, SCF$_3$ |
| E-087 | 2,3-disubstituted phenyl | CF$_3$, CF$_3$ |
| E-088 | 2,3-disubstituted phenyl | OCF$_3$, OCF$_3$ |
| E-089 | 2,5-disubstituted phenyl | F, F |
| E-090 | 2,5-disubstituted phenyl | Cl, Cl |
| E-091 | 2,5-disubstituted phenyl | Br, Br |
| E-092 | 2,5-disubstituted phenyl | Me, Me |
| E-093 | 2,5-disubstituted phenyl | OMe, OMe |
| E-094 | 2,5-disubstituted phenyl | SCF$_3$, SCF$_3$ |
| E-095 | 2,5-disubstituted phenyl | CF$_3$, CF$_3$ |
| E-096 | 2,5-disubstituted phenyl | OCF$_3$, OCF$_3$ |
| E-097 | 3,4-disubstituted phenyl | F, F |
| E-098 | 3,4-disubstituted phenyl | Cl, Cl |
| E-099 | 3,4-disubstituted phenyl | Br, Br |
| E-100 | 3,4-disubstituted phenyl | Me, Me |
| E-101 | 3,4-disubstituted phenyl | OMe, OMe |
| E-102 | 3,4-disubstituted phenyl | SCF$_3$, SCF$_3$ |
| E-103 | 3,4-disubstituted phenyl | CF$_3$, CF$_3$ |
| E-104 | 3,4-disubstituted phenyl | OCF$_3$, OCF$_3$ |
| E-105 | 3,5-disubstituted phenyl | F, Cl |
| E-106 | 3,5-disubstituted phenyl | F, Me |
| E-107 | 3,5-disubstituted phenyl | Cl, Me |
| E-108 | 3,5-disubstituted phenyl | CF$_3$, Cl |
| E-109 | 3,5-disubstituted phenyl | CF$_3$, Me |
| E-110 | 3,5-disubstituted phenyl | CF$_3$, CN |
| E-111 | 3,5-disubstituted phenyl | CN, F |
| E-112 | 3,5-disubstituted phenyl | CN, Cl |
| E-113 | 3,5-disubstituted phenyl | CN, Me |
| E-114 | 3,5-disubstituted phenyl | ethynyl, F |
| E-115 | 3,5-disubstituted phenyl | ethynyl, Cl |
| E-116 | 3,5-disubstituted phenyl | ethynyl, Me |
| E-117 | 3,5-disubstituted phenyl | ethynyl, CF$_3$ |
| E-118 | 3,5-disubstituted phenyl | OCF$_3$, F |
| E-119 | 3,5-disubstituted phenyl | OCF$_3$, Cl |
| E-120 | 3,5-disubstituted phenyl | OCF$_3$, Me |
| E-121 | 3,5-disubstituted phenyl | OCF$_3$, ethynyl |
| E-122 | 3,5-disubstituted phenyl | SCF$_3$, F |
| E-123 | 3,5-disubstituted phenyl | SCF$_3$, Cl |
| E-124 | 3,5-disubstituted phenyl | SCF$_3$, Me |
| E-125 | 3,5-disubstituted phenyl | SCF$_3$, ethynyl |
| E-126 | 2,3-disubstituted phenyl | 2-F, 3-Cl |
| E-127 | 2,3-disubstituted phenyl | 2-F, 3-Me |
| E-128 | 2,3-disubstituted phenyl | 2-Cl, 3-Me |
| E-129 | 2,3-disubstituted phenyl | 2-CF$_3$, 3-F |
| E-130 | 2,3-disubstituted phenyl | 2-CF$_3$, 3-Cl |
| E-131 | 2,3-disubstituted phenyl | 2-CF$_3$, 3-Me |
| E-132 | 2,3-disubstituted phenyl | 2-CN, 3-F |
| E-133 | 2,3-disubstituted phenyl | 2-CN, 3-Cl |
| E-134 | 2,3-disubstituted phenyl | 2-ethynyl, 3-F |
| E-135 | 2,3-disubstituted phenyl | 2-ethynyl, 3-Cl |
| E-136 | 2,3-disubstituted phenyl | 2-ethynyl, 3-Me |
| E-137 | 2,3-disubstituted phenyl | 2-ethynyl, 3-CF$_3$ |
| E-138 | 2,3-disubstituted phenyl | 2-OCF$_3$, 3-F |
| E-139 | 2,3-disubstituted phenyl | 2-OCF$_3$, 3-Cl |
| E-140 | 2,3-disubstituted phenyl | 2-OCF$_3$, 3-Me |
| E-141 | 2,3-disubstituted phenyl | 2-OCF$_3$, 3-ethynyl |
| E-142 | 2,3-disubstituted phenyl | 2-SCF$_3$, 3-F |
| E-143 | 2,3-disubstituted phenyl | 2-SCF$_3$, 3-Cl |
| E-144 | 2,3-disubstituted phenyl | 2-SCF$_3$, 3-Me |
| E-145 | 2,3-disubstituted phenyl | 2-SCF$_3$, 3-ethynyl |
| E-146 | 3,2-disubstituted phenyl | 3-F, 2-Cl |
| E-147 | 3,2-disubstituted phenyl | 3-F, 2-Me |
| E-148 | 3,2-disubstituted phenyl | 3-Cl, 2-Me |
| E-149 | 3,2-disubstituted phenyl | 3-CF$_3$, 2-F |
| E-150 | 3,2-disubstituted phenyl | 3-CF$_3$, 2-Cl |
| E-151 | 3,2-disubstituted phenyl | 3-CF$_3$, 2-Me |
| E-152 | 3,2-disubstituted phenyl | 3-CN, 2-F |
| E-153 | 3,2-disubstituted phenyl | 3-CN, 2-Cl |
| E-154 | 3,2-disubstituted phenyl | 3-ethynyl, 2-F |
| E-155 | 3,2-disubstituted phenyl | 3-ethynyl, 2-Cl |
| E-156 | 3,2-disubstituted phenyl | 3-ethynyl, 2-Me |
| E-157 | 3,2-disubstituted phenyl | 3-ethynyl, 2-CF$_3$ |
| E-158 | 3,2-disubstituted phenyl | 3-OCF$_3$, 2-F |
| E-159 | 3,2-disubstituted phenyl | 3-OCF$_3$, 2-Cl |
| E-160 | 3,2-disubstituted phenyl | 3-OCF$_3$, 2-Me |
| E-161 | 3,2-disubstituted phenyl | 3-OCF$_3$, 2-ethynyl |
| E-162 | 3,2-disubstituted phenyl | 3-SCF$_3$, 2-F |
| E-163 | 3,2-disubstituted phenyl | 3-SCF$_3$, 2-Cl |
| E-164 | 3,2-disubstituted phenyl | 3-SCF$_3$, 2-Me |
| E-165 | 3,2-disubstituted phenyl | 3-SCF$_3$, 2-ethynyl |
| E-166 | 2,4-disubstituted phenyl | 2-F, 4-Cl |
| E-167 | 2,4-disubstituted phenyl | 2-F, 4-Me |
| E-168 | 2,4-disubstituted phenyl | 2-Cl, 4-Me |
| E-169 | 2,4-disubstituted phenyl | 2-CF$_3$, 4-F |
| E-170 | 2,4-disubstituted phenyl | 2-CF$_3$, 4-Cl |
| E-171 | 2,4-disubstituted phenyl | 2-CF$_3$, 4-Me |
| E-172 | 2,4-disubstituted phenyl | 2-CN, 4-F |
| E-173 | 2,4-disubstituted phenyl | 2-CN, 4-Cl |
| E-174 | 2,4-disubstituted phenyl | 2-ethynyl, 4-F |
| E-175 | 2,4-disubstituted phenyl | 2-ethynyl, 4-Cl |
| E-176 | 2,4-disubstituted phenyl | 2-ethynyl, 4-Me |
| E-177 | 2,4-disubstituted phenyl | 2-ethynyl, 4-CF$_3$ |
| E-178 | 2,4-disubstituted phenyl | 2-OCF$_3$, 4-F |
| E-179 | 2,4-disubstituted phenyl | 2-OCF$_3$, 4-Cl |
| E-180 | 2,4-disubstituted phenyl | 2-OCF$_3$, 4-Me |
| E-181 | 2,4-disubstituted phenyl | 2-OCF$_3$, 4-ethynyl |
| E-182 | 2,4-disubstituted phenyl | 2-SCF$_3$, 4-F |
| E-183 | 2,4-disubstituted phenyl | 2-SCF$_3$, 4-Cl |
| E-184 | 2,4-disubstituted phenyl | 2-SCF$_3$, 4-Me |
| E-185 | 2,4-disubstituted phenyl | 2-SCF$_3$, 4-ethynyl |
| E-186 | 4,2-disubstituted phenyl | 4-F, 2-Cl |
| E-187 | 4,2-disubstituted phenyl | 4-F, 2-Me |
| E-188 | 4,2-disubstituted phenyl | 4-Cl, 2-Me |
| E-189 | 4,2-disubstituted phenyl | 4-CF$_3$, 2-F |
| E-190 | 4,2-disubstituted phenyl | 4-CF$_3$, 2-Cl |
| E-191 | 4,2-disubstituted phenyl | 4-CF$_3$, 2-Me |
| E-192 | 4,2-disubstituted phenyl | 4-CN, 2-F |
| E-193 | 4,2-disubstituted phenyl | 4-CN, 2-Cl |
| E-194 | 4,2-disubstituted phenyl | 4-ethynyl, 2-F |
| E-195 | 4,2-disubstituted phenyl | 4-ethynyl, 2-Cl |
| E-196 | 4,2-disubstituted phenyl | 4-ethynyl, 2-Me |
| E-197 | 4,2-disubstituted phenyl | 4-ethynyl, 2-CF$_3$ |
| E-198 | 4,2-disubstituted phenyl | 4-OCF$_3$, 2-F |
| E-199 | 4,2-disubstituted phenyl | 4-OCF$_3$, 2-Cl |
| E-200 | 4,2-disubstituted phenyl | 4-OCF$_3$, 2-Me |
| E-201 | 4,2-disubstituted phenyl | 4-OCF$_3$, 2-ethynyl |
| E-202 | 4,2-disubstituted phenyl | 4-SCF$_3$, 2-F |
| E-203 | 4,2-disubstituted phenyl | 4-SCF$_3$, 2-Cl |
| E-204 | 4,2-disubstituted phenyl | 4-SCF$_3$, 2-Me |
| E-205 | 4,2-disubstituted phenyl | 4-SCF$_3$, 2-ethynyl |
| E-206 | 2,5-disubstituted phenyl | 2-F, 5-Cl |
| E-207 | 2,5-disubstituted phenyl | 2-F, 5-Me |
| E-208 | 2,5-disubstituted phenyl | 2-Cl, 5-Me |

TABLE E-continued

| No. | ring | substituents |
|---|---|---|
| E-209 | 2,5-disubstituted phenyl | 2-CF$_3$, 5-F |
| E-210 | 2,5-disubstituted phenyl | 2-CF$_3$, 5-Cl |
| E-211 | 2,5-disubstituted phenyl | 2-CF$_3$, 5-Me |
| E-212 | 2,5-disubstituted phenyl | 2-CN, 5-F |
| E-213 | 2,5-disubstituted phenyl | 2-CN, 5-Cl |
| E-214 | 2,5-disubstituted phenyl | 2-ethynyl, 5-F |
| E-215 | 2,5-disubstituted phenyl | 2-ethynyl, 5-Cl |
| E-216 | 2,5-disubstituted phenyl | 2-ethynyl, 5-Me |
| E-217 | 2,5-disubstituted phenyl | 2-ethynyl, 5-CF$_3$ |
| E-218 | 2,5-disubstituted phenyl | 2-OCF$_3$, 5-F |
| E-219 | 2,5-disubstituted phenyl | 2-OCF$_3$, 5-Cl |
| E-220 | 2,5-disubstituted phenyl | 2-OCF$_3$, 5-Me |
| E-221 | 2,5-disubstituted phenyl | 2-OCF$_3$, 5-ethynyl |
| E-222 | 2,5-disubstituted phenyl | 2-SCF$_3$, 5-F |
| E-223 | 2,5-disubstituted phenyl | 2-SCF$_3$, 5-Cl |
| E-224 | 2,5-disubstituted phenyl | 2-SCF$_3$, 5-Me |
| E-225 | 2,5-disubstituted phenyl | 2-SCF$_3$, 5-ethynyl |
| E-226 | 5,2-disubstituted phenyl | 5-F, 2-Cl |
| E-227 | 5,2-disubstituted phenyl | 5-F, 2-Me |
| E-228 | 5,2-disubstituted phenyl | 5-Cl, 2-Me |
| E-229 | 5,2-disubstituted phenyl | 5-CF$_3$, 2-F |
| E-230 | 5,2-disubstituted phenyl | 5-CF$_3$, 2-Cl |
| E-231 | 5,2-disubstituted phenyl | 5-CF$_3$, 2-Me |
| E-232 | 5,2-disubstituted phenyl | 5-CN, 2-F |
| E-233 | 5,2-disubstituted phenyl | 5-CN, 2-Cl |
| E-234 | 5,2-disubstituted phenyl | 5-ethynyl, 2-F |
| E-235 | 5,2-disubstituted phenyl | 5-ethynyl, 2-Cl |
| E-236 | 5,2-disubstituted phenyl | 5-ethynyl, 2-Me |
| E-237 | 5,2-disubstituted phenyl | 5-ethynyl, 2-CF$_3$ |
| E-238 | 5,2-disubstituted phenyl | 5-OCF$_3$, 2-F |
| E-239 | 5,2-disubstituted phenyl | 5-OCF$_3$, 2-Cl |
| E-240 | 5,2-disubstituted phenyl | 5-OCF$_3$, 2-Me |
| E-241 | 5,2-disubstituted phenyl | 5-OCF$_3$, 2-ethynyl |
| E-242 | 5,2-disubstituted phenyl | 5-SCF$_3$, 2-F |
| E-243 | 5,2-disubstituted phenyl | 5-SCF$_3$, 2-Cl |
| E-244 | 5,2-disubstituted phenyl | 5-SCF$_3$, 2-Me |
| E-245 | 5,2-disubstituted phenyl | 5-SCF$_3$, 2-ethynyl |
| E-246 | 3,4-disubstituted phenyl | 3-F, 4-Cl |
| E-247 | 3,4-disubstituted phenyl | 3-F, 4-Me |
| E-248 | 3,4-disubstituted phenyl | 3-Cl, 4-Me |
| E-249 | 3,4-disubstituted phenyl | 3-CF$_3$, 4-F |
| E-250 | 3,4-disubstituted phenyl | 3-CF$_3$, 4-Cl |
| E-251 | 3,4-disubstituted phenyl | 3-CF$_3$, 4-Me |
| E-252 | 3,4-disubstituted phenyl | 3-CN, 4-F |
| E-253 | 3,4-disubstituted phenyl | 3-CN, 4-Cl |
| E-254 | 3,4-disubstituted phenyl | 3-ethynyl, 4-F |
| E-255 | 3,4-disubstituted phenyl | 3-ethynyl, 4-Cl |
| E-256 | 3,4-disubstituted phenyl | 3-ethynyl, 4-Me |
| E-257 | 3,4-disubstituted phenyl | 3-ethynyl, 4-CF$_3$ |
| E-258 | 3,4-disubstituted phenyl | 3-OCF$_3$, 4-F |
| E-259 | 3,4-disubstituted phenyl | 3-OCF$_3$, 4-Cl |
| E-260 | 3,4-disubstituted phenyl | 3-OCF$_3$, 4-Me |
| E-261 | 3,4-disubstituted phenyl | 3-OCF$_3$, 4-ethynyl |
| E-262 | 3,4-disubstituted phenyl | 3-SCF$_3$, 4-F |
| E-263 | 3,4-disubstituted phenyl | 3-SCF$_3$, 4-Cl |
| E-264 | 3,4-disubstituted phenyl | 3-SCF$_3$, 4-Me |
| E-265 | 3,4-disubstituted phenyl | 3-SCF$_3$, 4-ethynyl |
| E-266 | 4,3-disubstituted phenyl | 4-F, 3-Cl |
| E-267 | 4,3-disubstituted phenyl | 4-F, 3-Me |
| E-268 | 4,3-disubstituted phenyl | 4-Cl, 3-Me |
| E-269 | 4,3-disubstituted phenyl | 4-CF$_3$, 3-F |
| E-270 | 4,3-disubstituted phenyl | 4-CF$_3$, 3-Cl |
| E-271 | 4,3-disubstituted phenyl | 4-CF$_3$, 3-Me |
| E-272 | 4,3-disubstituted phenyl | 4-CN, 3-F |
| E-273 | 4,3-disubstituted phenyl | 4-CN, 3-Cl |
| E-274 | 4,3-disubstituted phenyl | 4-ethynyl, 3-F |
| E-275 | 4,3-disubstituted phenyl | 4-ethynyl, 3-Cl |
| E-276 | 4,3-disubstituted phenyl | 4-ethynyl, 3-Me |
| E-277 | 4,3-disubstituted phenyl | 4-ethynyl, 3-CF$_3$ |
| E-278 | 4,3-disubstituted phenyl | 4-OCF$_3$, 3-F |
| E-279 | 4,3-disubstituted phenyl | 4-OCF$_3$, 3-Cl |
| E-280 | 4,3-disubstituted phenyl | 4-OCF$_3$, 3-Me |
| E-281 | 4,3-disubstituted phenyl | 4-OCF$_3$, 3-ethynyl |
| E-282 | 4,3-disubstituted phenyl | 4-SCF$_3$, 3-F |
| E-283 | 4,3-disubstituted phenyl | 4-SCF$_3$, 3-Cl |
| E-284 | 4,3-disubstituted phenyl | 4-SCF$_3$, 3-Me |
| E-285 | 4,3-disubstituted phenyl | 4-SCF$_3$, 3-ethynyl |

Further preferred meanings of Q are given in Table F.

TABLE F

| No. | Q |
|---|---|
| F-001 | pyridin-2-yl |
| F-002 | 5-fluoropyridin-2-yl |
| F-003 | 5-chloropyridin-2-yl |
| F-004 | 5-bromopyridin-2-yl |
| F-005 | 5-methylpyridin-2-yl |
| F-006 | 5-methoxypyridin-2-yl |
| F-007 | 5-vinylpyridin-2-yl |
| F-008 | 5-ethynylpyridin-2-yl |
| F-009 | 5-cyanopyridin-2-yl |
| F-010 | 5-(trifluoromethyl)pyridin-2-yl |
| F-011 | 5-(trifluoromethoxy)pyridin-2-yl |
| F-012 | 5-(difluoromethyl)pyridin-2-yl |

TABLE F-continued

| No. | Q |
|---|---|
| F-013 | 5-OCHF₂-pyridin-2-yl (#) |
| F-014 | 5-SCF₃-pyridin-2-yl (#) |
| F-015 | pyridin-3-yl (#) |
| F-016 | 6-F-pyridin-3-yl (#) |
| F-017 | 6-Cl-pyridin-3-yl (#) |
| F-018 | 6-Br-pyridin-3-yl (#) |
| F-019 | 6-Me-pyridin-3-yl (#) |
| F-020 | 6-OMe-pyridin-3-yl (#) |
| F-021 | 6-vinyl-pyridin-3-yl (#) |
| F-022 | 6-ethynyl-pyridin-3-yl (#) |
| F-023 | 6-CN-pyridin-3-yl (#) |
| F-024 | 6-CF₃-pyridin-3-yl (#) |
| F-025 | 6-OCF₃-pyridin-3-yl (#) |

TABLE F-continued

| No. | Q |
|---|---|
| F-026 | 6-CHF₂-pyridin-3-yl (#) |
| F-027 | 6-OCHF₂-pyridin-3-yl (#) |
| F-028 | 6-SCF₃-pyridin-3-yl (#) |
| F-029 | pyrazin-2-yl (#) |
| F-030 | 5-F-pyrazin-2-yl (#) |
| F-031 | 5-Cl-pyrazin-2-yl (#) |
| F-032 | 5-Br-pyrazin-2-yl (#) |
| F-033 | 5-Me-pyrazin-2-yl (#) |
| F-034 | 5-OMe-pyrazin-2-yl (#) |
| F-035 | 5-vinyl-pyrazin-2-yl (#) |
| F-036 | 5-ethynyl-pyrazin-2-yl (#) |
| F-037 | 5-CN-pyrazin-2-yl (#) |

TABLE F-continued

| No. | Q |
|---|---|
| F-038 | 5-(trifluoromethyl)pyrazin-2-yl |
| F-039 | 5-(trifluoromethoxy)pyrazin-2-yl |
| F-040 | 5-(difluoromethyl)pyrazin-2-yl |
| F-041 | 5-(difluoromethoxy)pyrazin-2-yl |
| F-042 | 5-((trifluoromethyl)thio)pyrazin-2-yl |
| F-043 | pyrimidin-5-yl |
| F-044 | 2-fluoropyrimidin-5-yl |
| F-045 | 2-chloropyrimidin-5-yl |
| F-046 | 2-bromopyrimidin-5-yl |
| F-047 | 2-methylpyrimidin-5-yl |
| F-048 | 2-methoxypyrimidin-5-yl |
| F-049 | 2-vinylpyrimidin-5-yl |
| F-050 | 2-ethynylpyrimidin-5-yl |

TABLE F-continued

| No. | Q |
|---|---|
| F-051 | 2-cyanopyrimidin-5-yl |
| F-052 | 2-(trifluoromethyl)pyrimidin-5-yl |
| F-053 | 2-(trifluoromethoxy)pyrimidin-5-yl |
| F-054 | 2-(difluoromethyl)pyrimidin-5-yl |
| F-055 | 2-(difluoromethoxy)pyrimidin-5-yl |
| F-056 | 2-((trifluoromethyl)thio)pyrimidin-5-yl |
| F-057 | pyrimidin-2-yl |
| F-058 | 5-fluoropyrimidin-2-yl |
| F-059 | 5-chloropyrimidin-2-yl |
| F-060 | 5-bromopyrimidin-2-yl |
| F-061 | 5-methylpyrimidin-2-yl |
| F-062 | 5-methoxypyrimidin-2-yl |
| F-063 | 5-vinylpyrimidin-2-yl |

TABLE F-continued

| No. | Q |
|---|---|
| F-064 | 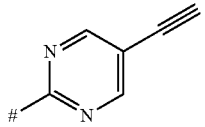 |
| F-065 | 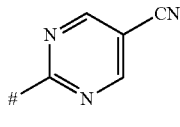 |
| F-066 | 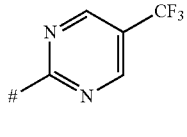 |
| F-067 | 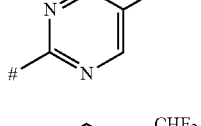 |
| F-068 | 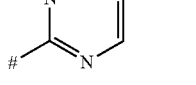 |
| F-069 | 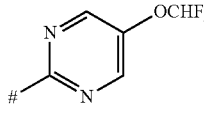 |
| F-070 | 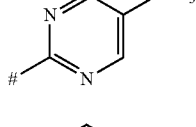 |
| F-071 | 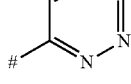 |
| F-072 | 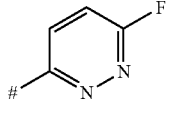 |
| F-073 | 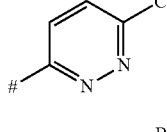 |
| F-074 | 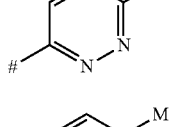 |
| F-075 | 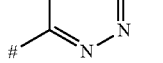 |

TABLE F-continued

| No. | Q |
|---|---|
| F-076 | 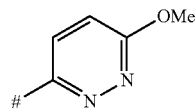 |
| F-077 | 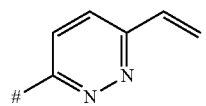 |
| F-078 | 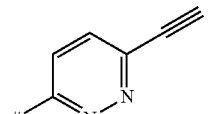 |
| F-079 | 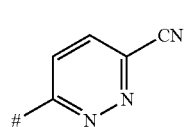 |
| F-080 | 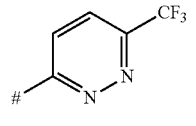 |
| F-081 | 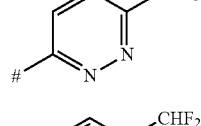 |
| F-082 | 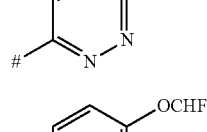 |
| F-083 | 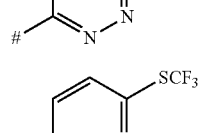 |
| F-084 | 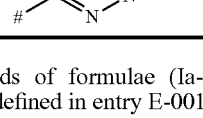 |

Table 1e: Compounds of formulae (Ia-1), (Ia-2) and (Ia-3), wherein Q is as defined in entry E-001 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-001 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-001 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-001 of table E and $R^1$, $R^{5a}$, $R^{5b}$, $R^{5c}$ and X correspond in each case to a row of table D.

Table 2e: Compounds of formulae (Ia-1), (Ia-2) and (Ia-3), wherein Q is as defined in entry E-002 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-002 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-002 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-002 of table E and $R^1$, $R^{5a}$, $R^{5b}$, $R^{5c}$ and X correspond in each case to a row of table D.

Table 3e: Compounds of formulae (Ia-1), (Ia-2) and (Ia-3), wherein Q is as defined in entry E-003 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-003 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-003 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-003 of table E and $R^1$, $R^{5a}$, $R^{5b}$, $R^{5c}$ and X correspond in each case to a row of table D.

Table 4e: Compounds of formulae (Ia-1), (Ia-2) and (Ia-3), wherein Q is as defined in entry E-004 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-004 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-004 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-004 of table E and $R^1$, $R^{5a}$, $R^{5b}$, $R^{5c}$ and X correspond in each case to a row of table D.

Table 5e: Compounds of formulae (Ia-1), (Ia-2) and (Ia-3), wherein Q is as defined in entry E-005 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-005 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-005 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-005 of table E and $R^1$, $R^{5a}$, $R^{5b}$, $R^{5c}$ and X correspond in each case to a row of table D.

Table 6e: Compounds of formulae (Ia-1), (Ia-2) and (Ia-3), wherein Q is as defined in entry E-006 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-006 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-006 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-006 of table E and $R^1$, $R^{5a}$, $R^{5b}$, $R^{5c}$ and X correspond in each case to a row of table D.

Table 7e: Compounds of formulae (Ia-1), (Ia-2) and (Ia-3), wherein Q is as defined in entry E-007 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-007 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-007 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-007 of table E and $R^1$, $R^{5a}$, $R^{5b}$, $R^{5c}$ and X correspond in each case to a row of table D.

Table 8e: Compounds of formulae (Ia-1), (Ia-2) and (Ia-3), wherein Q is as defined in entry E-008 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-008 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-008 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-008 of table E and $R^1$, $R^{5a}$, $R^{5b}$, $R^{5c}$ and X correspond in each case to a row of table D.

Table 9e: Compounds of formulae (Ia-1), (Ia-2) and (Ia-3), wherein Q is as defined in entry E-009 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-009 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-009 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-009 of table E and $R^1$, $R^{5a}$, $R^{5b}$, $R^{5c}$ and X correspond in each case to a row of table D.

Table 10e: Compounds of formulae (Ia-1), (Ia-2) and (Ia-3), wherein Q is as defined in entry E-010 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-010 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-010 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-010 of table E and $R^1$, $R^{5a}$, $R^{5b}$, $R^{5c}$ and X correspond in each case to a row of table D.

Table 11e: Compounds of formulae (Ia-1), (Ia-2) and (Ia-3), wherein Q is as defined in entry E-011 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-011 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-011 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-011 of table E and $R^1$, $R^{5a}$, $R^{5b}$, $R^{5c}$ and X correspond in each case to a row of table D.

Table 12e: Compounds of formulae (Ia-1), (Ia-2) and (Ia-3), wherein Q is as defined in entry E-012 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-012 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-012 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-012 of table E and $R^1$, $R^{5a}$, $R^{5b}$, $R^{5c}$ and X correspond in each case to a row of table D.

Table 13e: Compounds of formulae (Ia-1), (Ia-2) and (Ia-3), wherein Q is as defined in entry E-013 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-013 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-013 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-013 of table E and $R^1$, $R^{5a}$, $R^{5b}$, $R^{5c}$ and X correspond in each case to a row of table D.

Table 14e: Compounds of formulae (Ia-1), (Ia-2) and (Ia-3), wherein Q is as defined in entry E-014 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-014 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-014 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-014 of table E and $R^1$, $R^{5a}$, $R^{5b}$, $R^{5c}$ and X correspond in each case to a row of table D.

Table 15e: Compounds of formulae (Ia-1), (Ia-2) and (Ia-3), wherein Q is as defined in entry E-015 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-015 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-015 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-015 of table E and $R^1$, $R^{5a}$, $R^{5b}$, $R^{5c}$ and X correspond in each case to a row of table D.

Table 16e: Compounds of formulae (Ia-1), (Ia-2) and (Ia-3), wherein Q is as defined in entry E-016 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-016 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-016 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-016 of table E and $R^1$, $R^{5a}$, $R^{5b}$, $R^{5c}$ and X correspond in each case to a row of table D.

Table 17e: Compounds of formulae (Ia-1), (Ia-2) and (Ia-3), wherein Q is as defined in entry E-017 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-017 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-017 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-017 of table E and $R^1$, $R^{5a}$, $R^{5b}$, $R^{5c}$ and X correspond in each case to a row of table D.

Table 18e: Compounds of formulae (Ia-1), (Ia-2) and (Ia-3), wherein Q is as defined in entry E-018 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-018 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-018 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-018 of table E and $R^1$, $R^{5a}$, $R^{5b}$, $R^{5c}$ and X correspond in each case to a row of table D.

Table 19e: Compounds of formulae (Ia-1), (Ia-2) and (Ia-3), wherein Q is as defined in entry E-019 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-019 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-019 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-019 of table E and $R^1$, $R^{5a}$, $R^{5b}$, $R^{5c}$ and X correspond in each case to a row of table D.

Table 20e: Compounds of formulae (Ia-1), (Ia-2) and (Ia-3), wherein Q is as defined in entry E-020 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-020 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-020 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-020 of table E and $R^1$, $R^{5a}$, $R^{5b}$, $R^{5c}$ and X correspond in each case to a row of table D.

Table 21e: Compounds of formulae (Ia-1), (Ia-2) and (Ia-3), wherein Q is as defined in entry E-021 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-021 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-021 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-021 of table E and $R^1$, $R^{5a}$, $R^{5b}$, $R^{5c}$ and X correspond in each case to a row of table D.

Table 22e: Compounds of formulae (Ia-1), (Ia-2) and (Ia-3), wherein Q is as defined in entry E-022 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-022 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-022 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-022 of table E and $R^1$, $R^{5a}$, $R^{5b}$, $R^{5c}$ and X correspond in each case to a row of table D.

Table 23e: Compounds of formulae (Ia-1), (Ia-2) and (Ia-3), wherein Q is as defined in entry E-023 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-023 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-023 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-023 of table E and $R^1$, $R^{5a}$, $R^{5b}$, $R^{5c}$ and X correspond in each case to a row of table D.

Table 24e: Compounds of formulae (Ia-1), (Ia-2) and (Ia-3), wherein Q is as defined in entry E-024 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-024 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-024 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-024 of table E and $R^1$, $R^{5a}$, $R^{5b}$, $R^{5c}$ and X correspond in each case to a row of table D.

Table 25e: Compounds of formulae (Ia-1), (Ia-2) and (Ia-3), wherein Q is as defined in entry E-025 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-025 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-025 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-025 of table E and $R^1$, $R^{5a}$, $R^{5b}$, $R^{5c}$ and X correspond in each case to a row of table D.

Table 26e: Compounds of formulae (Ia-1), (Ia-2) and (Ia-3), wherein Q is as defined in entry E-026 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-026 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-026 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-026 of table E and $R^1$, $R^{5a}$, $R^{5b}$, $R^{5c}$ and X correspond in each case to a row of table D.

Table 27e: Compounds of formulae (Ia-1), (Ia-2) and (Ia-3), wherein Q is as defined in entry E-027 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-027 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-027 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-027 of table E and $R^1$, $R^{5a}$, $R^{5b}$, $R^{5c}$ and X correspond in each case to a row of table D.

Table 28e: Compounds of formulae (Ia-1), (Ia-2) and (Ia-3), wherein Q is as defined in entry E-028 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-028 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-028 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-028 of table E and $R^1$, $R^{5a}$, $R^{5b}$, $R^{5c}$ and X correspond in each case to a row of table D.

Table 29e: Compounds of formulae (Ia-1), (Ia-2) and (Ia-3), wherein Q is as defined in entry E-029 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-029 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-029 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-029 of table E and $R^1$, $R^{5a}$, $R^{5b}$, $R^{5c}$ and X correspond in each case to a row of table D.

Table 30e: Compounds of formulae (Ia-1), (Ia-2) and (Ia-3), wherein Q is as defined in entry E-030 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-030 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-030 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-030 of table E and $R^1$, $R^{5a}$, $R^{5b}$, $R^{5c}$ and X correspond in each case to a row of table D.

Table 31e: Compounds of formulae (Ia-1), (Ia-2) and (Ia-3), wherein Q is as defined in entry E-031 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-031 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-031 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29)

and (Id-30), wherein Q is as defined in entry E-031 of table E and $R^1$, $R^{5a}$, $R^{5b}$, $R^{5c}$ and X correspond in each case to a row of table D.

Table 32e: Compounds of formulae (Ia-1), (Ia-2) and (Ia-3), wherein Q is as defined in entry E-032 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-032 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-032 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-032 of table E and $R^1$, $R^{5a}$, $R^{5b}$, $R^{5c}$ and X correspond in each case to a row of table D.

Table 33e: Compounds of formulae (Ia-1), (Ia-2) and (Ia-3), wherein Q is as defined in entry E-033 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-033 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-033 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-033 of table E and $R^1$, $R^{5a}$, $R^{5b}$, $R^{5c}$ and X correspond in each case to a row of table D.

Table 34e: Compounds of formulae (Ia-1), (Ia-2) and (Ia-3), wherein Q is as defined in entry E-034 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-034 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-034 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-034 of table E and $R^1$, $R^{5a}$, $R^{5b}$, $R^{5c}$ and X correspond in each case to a row of table D.

Table 35e: Compounds of formulae (Ia-1), (Ia-2) and (Ia-3), wherein Q is as defined in entry E-035 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-035 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-035 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-035 of table E and $R^1$, $R^{5a}$, $R^{5b}$, $R^{5c}$ and X correspond in each case to a row of table D.

Table 36e: Compounds of formulae (Ia-1), (Ia-2) and (Ia-3), wherein Q is as defined in entry E-036 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-036 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-036 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-036 of table E and $R^1$, $R^{5a}$, $R^{5b}$, $R^{5c}$ and X correspond in each case to a row of table D.

Table 37e: Compounds of formulae (Ia-1), (Ia-2) and (Ia-3), wherein Q is as defined in entry E-037 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-037 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-037 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-037 of table E and $R^1$, $R^{5a}$, $R^{5b}$, $R^{5c}$ and X correspond in each case to a row of table D.

Table 38e: Compounds of formulae (Ia-1), (Ia-2) and (Ia-3), wherein Q is as defined in entry E-038 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-038 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-038 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-038 of table E and $R^1$, $R^{5a}$, $R^{5b}$, $R^{5c}$ and X correspond in each case to a row of table D.

Table 39e: Compounds of formulae (Ia-1), (Ia-2) and (Ia-3), wherein Q is as defined in entry E-039 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-039 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-039 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-039 of table E and $R^1$, $R^{5a}$, $R^{5b}$, $R^{5c}$ and X correspond in each case to a row of table D.

Table 40e: Compounds of formulae (Ia-1), (Ia-2) and (Ia-3), wherein Q is as defined in entry E-040 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-040 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-040 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-040 of table E and $R^1$, $R^{5a}$, $R^{5b}$, $R^{5c}$ and X correspond in each case to a row of table D.

Table 41e: Compounds of formulae (Ia-1), (Ia-2) and (Ia-3), wherein Q is as defined in entry E-041 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-041 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-041 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-041 of table E and $R^1$, $R^{5a}$, $R^{5b}$, $R^{5c}$ and X correspond in each case to a row of table D.

Table 42e: Compounds of formulae (Ia-1), (Ia-2) and (Ia-3), wherein Q is as defined in entry E-042 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-042 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-042 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-042 of table E and $R^1$, $R^{5a}$, $R^{5b}$, $R^{5c}$ and X correspond in each case to a row of table D.

Table 43e: Compounds of formulae (Ia-1), (Ia-2) and (Ia-3), wherein Q is as defined in entry E-043 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-043 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-043 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-043 of table E and $R^1$, $R^{5a}$, $R^{5b}$, $R^{5c}$ and X correspond in each case to a row of table D.

Table 44e: Compounds of formulae (Ia-1), (Ia-2) and (Ia-3), wherein Q is as defined in entry E-044 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-044 of table E and $R^1$, $R^5$ and X correspond in each case to a row of table B; compounds of formulae (Id-1), (Ic-2), (Ic-3), (Ic-4), (Ic-5), (Ic-6), (Ic-7), (Ic-8), and (Ic-9), wherein Q is as defined in entry E-044 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-044 of table E and $R^1$, $R^{5a}$, $R^{5b}$, $R^{5c}$ and X correspond in each case to a row of table D.

Table 45e: Compounds of formulae (Ia-1), (Ia-2) and (Ia-3), wherein Q is as defined in entry E-045 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-045 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-045 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-045 of table E and $R^1$, $R^{5a}$, $R^{5b}$, $R^{5c}$ and X correspond in each case to a row of table D.

Table 46e: Compounds of formulae (Ia-1), (Ia-2) and (Ia-3), wherein Q is as defined in entry E-046 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-046 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-046 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-046 of table E and $R^1$, $R^{5a}$, $R^{5b}$, $R^{5c}$ and X correspond in each case to a row of table D.

Table 47e: Compounds of formulae (Ia-1), (Ia-2) and (Ia-3), wherein Q is as defined in entry E-047 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-047 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-047 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-047 of table E and $R^1$, $R^{5a}$, $R^{5b}$, $R^{5c}$ and X correspond in each case to a row of table D.

Table 48e: Compounds of formulae (Ia-1), (Ia-2) and (Ia-3), wherein Q is as defined in entry E-048 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-048 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-048 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-048 of table E and $R^1$, $R^{5a}$, $R^{5b}$, $R^{5c}$ and X correspond in each case to a row of table D.

Table 49e: Compounds of formulae (Ia-1), (Ia-2) and (Ia-3), wherein Q is as defined in entry E-049 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-049 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-049 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-049 of table E and $R^1$, $R^{5a}$, $R^{5b}$, $R^{5c}$ and X correspond in each case to a row of table D.

Table 50e: Compounds of formulae (Ia-1), (Ia-2) and (Ia-3), wherein Q is as defined in entry E-050 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-050 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-050 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-050 of table E and $R^1$, $R^{5a}$, $R^{5b}$, $R^{5c}$ and X correspond in each case to a row of table D.

Table 51e: Compounds of formulae (Ia-1), (Ia-2) and (Ia-3), wherein Q is as defined in entry E-051 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-051 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-051 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-051 of table E and $R^1$, $R^{5a}$, $R^{5b}$, $R^{5c}$ and X correspond in each case to a row of table D.

Table 52e: Compounds of formulae (Ia-1), (Ia-2) and (Ia-3), wherein Q is as defined in entry E-052 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-052 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-052 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-052 of table E and $R^1$, $R^{5a}$, $R^{5b}$, $R^{5c}$ and X correspond in each case to a row of table D.

Table 53e: Compounds of formulae (Ia-1), (Ia-2) and (Ia-3), wherein Q is as defined in entry E-053 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-053 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-053 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-053 of table E and $R^1$, $R^{5a}$, $R^{5b}$, $R^{5c}$ and X correspond in each case to a row of table D.

Table 54e: Compounds of formulae (Ia-1), (Ia-2) and (Ia-3), wherein Q is as defined in entry E-054 of table E and $R^1$, $R^5$ and X correspond in each case to a row of table A;

compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-054 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-054 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-054 of table E and $R^1$, $R^{5a}$, $R^{5b}$, $R^{5c}$ and X correspond in each case to a row of table D.

Table 55e: Compounds of formulae (Ia-1), (Ia-2) and (Ia-3), wherein Q is as defined in entry E-055 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-055 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-055 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-055 of table E and $R^1$, $R^{5a}$, $R^{5b}$, $R^{5c}$ and X correspond in each case to a row of table D.

Table 56e: Compounds of formulae (Ia-1), (Ia-2) and (Ia-3), wherein Q is as defined in entry E-056 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-056 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-056 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-056 of table E and $R^1$, $R^{5a}$, $R^{5b}$, $R^{5c}$ and X correspond in each case to a row of table D.

Table 57e: Compounds of formulae (Ia-1), (Ia-2) and (Ia-3), wherein Q is as defined in entry E-057 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-057 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-057 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-057 of table E and $R^1$, $R^{5a}$, $R^{5b}$, $R^{5c}$ and X correspond in each case to a row of table D.

Table 58e: Compounds of formulae (Ia-1), (Ia-2) and (Ia-3), wherein Q is as defined in entry E-058 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-058 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-058 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-058 of table E and $R^1$, $R^{5a}$, $R^{5b}$, $R^{5c}$ and X correspond in each case to a row of table D.

Table 59e: Compounds of formulae (Ia-1), (Ia-2) and (Ia-3), wherein Q is as defined in entry E-059 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-059 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-059 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-059 of table E and $R^1$, $R^{5a}$, $R^{5b}$, $R^{5c}$ and X correspond in each case to a row of table D.

Table 60e: Compounds of formulae (Ia-1), (Ia-2) and (Ia-3), wherein Q is as defined in entry E-060 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-060 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-060 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-060 of table E and $R^1$, $R^{5a}$, $R^{5b}$, $R^{5c}$ and X correspond in each case to a row of table D.

Table 61e: Compounds of formulae (Ia-1), (Ia-2) and (Ia-3), wherein Q is as defined in entry E-061 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-061 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-061 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-061 of table E and $R^1$, $R^{5a}$, $R^{5b}$, $R^{5c}$ and X correspond in each case to a row of table D.

Table 62e: Compounds of formulae (Ia-1), (Ia-2) and (Ia-3), wherein Q is as defined in entry E-062 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-062 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-062 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-062 of table E and $R^1$, $R^{5a}$, $R^{5b}$, $R^{5c}$ and X correspond in each case to a row of table D.

Table 63e: Compounds of formulae (Ia-1), (Ia-2) and (Ia-3), wherein Q is as defined in entry E-063 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-063 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-063 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-063 of table E and $R^1$, $R^{5a}$, $R^{5b}$, $R^{5c}$ and X correspond in each case to a row of table D.

Table 64e: Compounds of formulae (Ia-1), (Ia-2) and (Ia-3), wherein Q is as defined in entry E-064 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-064 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-064 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-064 of table E and $R^1$, $R^{5a}$, $R^{5b}$, $R^{5c}$ and X correspond in each case to a row of table D.

Table 65e: Compounds of formulae (Ia-1), (Ia-2) and (Ia-3), wherein Q is as defined in entry E-065 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-065 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-066 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-066 of table E and $R^1$, $R^{5a}$, $R^{5b}$, $R^{5c}$ and X correspond in each case to a row of table D.

Table 66e: Compounds of formulae (Ia-1), (Ia-2) and (Ia-3), wherein Q is as defined in entry E-066 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-066 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-066 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-066 of table E and $R^1$, $R^{5a}$, $R^{5b}$, $R^{5c}$ and X correspond in each case to a row of table D.

Table 67e: Compounds of formulae (Ia-1), (Ia-2) and (Ia-3), wherein Q is as defined in entry E-067 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-067 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-067 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-067 of table E and $R^1$, $R^{5a}$, $R^{5b}$, $R^{5c}$ and X correspond in each case to a row of table D.

Table 68e: Compounds of formulae (Ia-1), (Ia-2) and (Ia-3), wherein Q is as defined in entry E-068 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-068 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-068 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-068 of table E and $R^1$, $R^{5a}$, $R^{5b}$, $R^{5c}$ and X correspond in each case to a row of table D.

Table 69e: Compounds of formulae (Ia-1), (Ia-2) and (Ia-3), wherein Q is as defined in entry E-069 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-069 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-069 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-069 of table E and $R^1$, $R^{5a}$, $R^{5b}$, $R^{5c}$ and X correspond in each case to a row of table D.

Table 70e: Compounds of formulae (Ia-1), (Ia-2) and (Ia-3), wherein Q is as defined in entry E-070 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-070 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-070 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-070 of table E and $R^1$, $R^{5a}$, $R^{5b}$, $R^{5c}$ and X correspond in each case to a row of table D.

Table 71e: Compounds of formulae (Ia-1), (Ia-2) and (Ia-3), wherein Q is as defined in entry E-071 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-071 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-071 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-071 of table E and $R^1$, $R^{5a}$, $R^{5b}$, $R^{5c}$ and X correspond in each case to a row of table D.

Table 72e: Compounds of formulae (Ia-1), (Ia-2) and (Ia-3), wherein Q is as defined in entry E-072 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-072 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-072 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-072 of table E and $R^1$, $R^{5a}$, $R^{5b}$, $R^{5c}$ and X correspond in each case to a row of table D.

Table 73e: Compounds of formulae (Ia-1), (Ia-2) and (Ia-3), wherein Q is as defined in entry E-073 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-073 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-073 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-073 of table E and $R^1$, $R^{5a}$, $R^{5b}$, $R^{5c}$ and X correspond in each case to a row of table D.

Table 74e: Compounds of formulae (Ia-1), (Ia-2) and (Ia-3), wherein Q is as defined in entry E-074 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-074 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-074 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-074 of table E and $R^1$, $R^{5a}$, $R^{5b}$, $R^{5c}$ and X correspond in each case to a row of table D.

Table 75e: Compounds of formulae (Ia-1), (Ia-2) and (Ia-3), wherein Q is as defined in entry E-075 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-075 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-075 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-075 of table E and $R^1$, $R^{5a}$, $R^{5b}$, $R^{5c}$ and X correspond in each case to a row of table D.

Table 76e: Compounds of formulae (Ia-1), (Ia-2) and (Ia-3), wherein Q is as defined in entry E-076 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-076 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-076 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-076 of table E and $R^1$, $R^{5a}$, $R^{5b}$, $R^{5c}$ and X correspond in each case to a row of table D.

Table 77e: Compounds of formulae (Ia-1), (Ia-2) and (Ia-3), wherein Q is as defined in entry E-077 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-077 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-077 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-077 of table E and $R^1$, $R^{5a}$, $R^{5b}$, $R^{5c}$ and X correspond in each case to a row of table D.

Table 78e: Compounds of formulae (Ia-1), (Ia-2) and (Ia-3), wherein Q is as defined in entry E-078 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-078 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-078 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-078 of table E and $R^1$, $R^{5a}$, $R^{5b}$, $R^{5c}$ and X correspond in each case to a row of table D.

Table 79e: Compounds of formulae (Ia-1), (Ia-2) and (Ia-3), wherein Q is as defined in entry E-079 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-079 of table E and $R^1$, $R^5$ and X correspond in each case in each case to a row of table B; compounds of formulae (Ic-1), (Ic-2), (Ic-3), (Ic-4), (Ic-5), (Ic-6), (Ic-7), (Ic-8), and (Ic-9), wherein Q is as defined in entry E-079 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-079 of table E and $R^1$, $R^{5a}$, $R^{5b}$, $R^{5c}$ and X correspond in each case to a row of table D.

Table 80e: Compounds of formulae (Ia-1), (Ia-2) and (Ia-3), wherein Q is as defined in entry E-080 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-080 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-080 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-080 of table E and $R^1$, $R^{5a}$, $R^{5b}$, $R^{5c}$ and X correspond in each case to a row of table D.

Table 81e: Compounds of formulae (Ia-1), (Ia-2) and (Ia-3), wherein Q is as defined in entry E-081 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-081 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-081 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-081 of table E and $R^1$, $R^{5a}$, $R^{5b}$, $R^{5c}$ and X correspond in each case to a row of table D.

Table 82e: Compounds of formulae (Ia-1), (Ia-2) and (Ia-3), wherein Q is as defined in entry E-082 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-082 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-082 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-082 of table E and $R^1$, $R^{5a}$, $R^{5b}$, $R^{5c}$ and X correspond in each case to a row of table D.

Table 83e: Compounds of formulae (Ia-1), (Ia-2) and (Ia-3), wherein Q is as defined in entry E-083 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-083 of table E and $R^1$, $R^5$ and X correspond in each case in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-083 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-083 of table E and $R^1$, $R^{5a}$, $R^{5b}$, $R^{5c}$ and X correspond in each case to a row of table D.

Table 84e: Compounds of formulae (Ia-1), (Ia-2) and (Ia-3), wherein Q is as defined in entry E-084 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-084 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-084 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-084 of table E and $R^1$, $R^{5a}$, $R^{5b}$, $R^{5c}$ and X correspond in each case to a row of table D.

Table 85e: Compounds of formulae (Ia-1), (Ia-2) and (Ia-3), wherein Q is as defined in entry E-085 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-085 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-085 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-085 of table E and $R^1$, $R^{5a}$, $R^{5b}$, $R^{5c}$ and X correspond in each case to a row of table D.

Table 86e: Compounds of formulae (Ia-1), (Ia-2) and (Ia-3), wherein Q is as defined in entry E-086 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-086 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-086 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-086 of table E and $R^1$, $R^{5a}$, $R^{5b}$, $R^{5c}$ and X correspond in each case to a row of table D.

Table 87e: Compounds of formulae (Ia-1), (Ia-2) and (Ia-3), wherein Q is as defined in entry E-087 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-087 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-087 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-087 of table E and $R^1$, $R^{5a}$, $R^{5b}$, $R^{5c}$ and X correspond in each case to a row of table D.

Table 88e: Compounds of formulae (Ia-1), (Ia-2) and (Ia-3), wherein Q is as defined in entry E-088 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-088 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-088 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-088 of table E and $R^1$, $R^{5a}$, $R^{5b}$, $R^{5c}$ and X correspond in each case to a row of table D.

Table 89e: Compounds of formulae (Ia-1), (Ia-2) and (Ia-3), wherein Q is as defined in entry E-089 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-089 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-089 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-089 of table E and $R^1$, $R^{5a}$, $R^{5b}$, $R^{5c}$ and X correspond in each case to a row of table D.

Table 90e: Compounds of formulae (Ia-1), (Ia-2) and (Ia-3), wherein Q is as defined in entry E-090 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-090 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-090 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-090 of table E and $R^1$, $R^{5a}$, $R^{5b}$, $R^{5c}$ and X correspond in each case to a row of table D.

Table 91e: Compounds of formulae (Ia-1), (Ia-2) and (Ia-3), wherein Q is as defined in entry E-091 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-091 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-091 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-091 of table E and $R^1$, $R^{5a}$, $R^{5b}$, $R^{5c}$ and X correspond in each case to a row of table D.

Table 92e: Compounds of formulae (Ia-1), (Ia-2) and (Ia-3), wherein Q is as defined in entry E-092 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-092 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-092 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-092 of table E and $R^1$, $R^{5a}$, $R^{5b}$, $R^{5c}$ and X correspond in each case to a row of table D.

Table 93e: Compounds of formulae (Ia-1), (Ia-2) and (Ia-3), wherein Q is as defined in entry E-093 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-093 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-093 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-093 of table E and $R^1$, $R^{5a}$, $R^{5b}$, $R^{5c}$ and X correspond in each case to a row of table D.

Table 94e: Compounds of formulae (Ia-1), (Ia-2) and (Ia-3), wherein Q is as defined in entry E-094 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-094 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-094 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-094 of table E and $R^1$, $R^{5a}$, $R^{5b}$, $R^{5c}$ and X correspond Table 95e: Compounds of formulae (Ia-1), (Ia-2) and (Ia-3), wherein Q is as defined in entry E-095 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-095 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-095 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-095 of table E and $R^1$, $R^{5a}$, $R^{5b}$, $R^{5c}$ and X correspond in each case to a row of table D.

Table 96e: Compounds of formulae (Ia-1), (Ia-2) and (Ia-3), wherein Q is as defined in entry E-096 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-096 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-096 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-096 of table E and $R^1$, $R^{5a}$, $R^{5b}$, $R^{5c}$ and X correspond in each case to a row of table D.

Table 97e: Compounds of formulae (Ia-1), (Ia-2) and (Ia-3), wherein Q is as defined in entry E-097 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-097 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-098 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-097 of table E and $R^1$, $R^{5a}$, $R^{5b}$, $R^{5c}$ and X correspond in each case to a row of table D.

Table 98e: Compounds of formulae (Ia-1), (Ia-2) and (Ia-3), wherein Q is as defined in entry E-098 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-098 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-098 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29)

and (Id-30), wherein Q is as defined in entry E-098 of table E and $R^1$, $R^{5a}$, $R^{5b}$, $R^{5c}$ and X correspond in each case to a row of table D.

Table 99e: Compounds of formulae (Ia-1), (Ia-2) and (Ia-3), wherein Q is as defined in entry E-099 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-099 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-099 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-099 of table E and $R^1$, $R^{5a}$, $R^{5b}$, $R^{5c}$ and X correspond in each case to a row of table D.

Table 100e: Compounds of formulae (Ia-1), (Ia-2) and (Ia-3), wherein Q is as defined in entry E-100 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-100 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-100 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-100 of table E and $R^1$, $R^{5a}$, $R^{5b}$, $R^{5c}$ and X correspond in each case to a row of table D.

Table 101e: Compounds of formulae (Ia-1), (Ia-2) and (Ia-3), wherein Q is as defined in entry E-101 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-101 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-101 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-101 of table E and $R^1$, $R^{5a}$, $R^{5b}$, $R^{5c}$ and X correspond in each case to a row of table D.

Table 102e: Compounds of formulae (Ia-1), (Ia-2) and (Ia-3), wherein Q is as defined in entry E-102 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-102 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-102 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-102 of table E and $R^1$, $R^{5a}$, $R^{5b}$, $R^{5c}$ and X correspond in each case to a row of table D.

Table 103e: Compounds of formulae (Ia-1), (Ia-2) and (Ia-3), wherein Q is as defined in entry E-103 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-103 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-103 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-103 of table E and $R^1$, $R^{5a}$, $R^{5b}$, $R^{5c}$ and X correspond in each case to a row of table D.

Table 104e: Compounds of formulae (Ia-1), (Ia-2) and (Ia-3), wherein Q is as defined in entry E-104 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-104 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-104 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-104 of table E and $R^1$, $R^{5a}$, $R^{5b}$, $R^{5c}$ and X correspond in each case to a row of table D.

Table 105e: Compounds of formulae (Ia-1), (Ia-2) and (Ia-3), wherein Q is as defined in entry E-105 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-105 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-105 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-105 of table E and $R^1$, $R^{5a}$, $R^{5b}$, $R^{5c}$ and X correspond in each case to a row of table D.

Table 106e: Compounds of formulae (Ia-1), (Ia-2) and (Ia-3), wherein Q is as defined in entry E-106 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-106 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-106 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-106 of table E and $R^1$, $R^{5a}$, $R^{5b}$, $R^{5c}$ and X correspond in each case to a row of table D.

Table 107e: Compounds of formulae (Ia-1), (Ia-2) and (Ia-3), wherein Q is as defined in entry E-107 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-107 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-107 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-107 of table E and $R^1$, $R^{5a}$, $R^{5b}$, $R^{5c}$ and X correspond in each case to a row of table D.

Table 108e: Compounds of formulae (Ia-1), (Ia-2) and (Ia-3), wherein Q is as defined in entry E-108 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-108 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-108 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-108 of table E and $R^1$, $R^{5a}$, $R^{5b}$, $R^{5c}$ and X correspond in each case to a row of table D.

Table 109e: Compounds of formulae (Ia-1), (Ia-2) and (Ia-3), wherein Q is as defined in entry E-109 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-109 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-109 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-109 of table E and $R^1$, $R^{5a}$, $R^{5b}$, $R^{5c}$ and X correspond in each case to a row of table D.

Table 110e: Compounds of formulae (Ia-1), (Ia-2) and (Ia-3), wherein Q is as defined in entry E-110 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-110 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-110 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-110 of table E and $R^1$, $R^{5a}$, $R^{5b}$, $R^{5c}$ and X correspond in each case to a row of table D.

Table 111e: Compounds of formulae (Ia-1), (Ia-2) and (Ia-3), wherein Q is as defined in entry E-111 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-111 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-111 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-111 of table E and $R^1$, $R^{5a}$, $R^{5b}$, $R^{5c}$ and X correspond in each case to a row of table D.

Table 112e: Compounds of formulae (Ia-1), (Ia-2) and (Ia-3), wherein Q is as defined in entry E-112 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-112 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-112 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-112 of table E and $R^1$, $R^{5a}$, $R^{5b}$, $R^{5c}$ and X correspond in each case to a row of table D.

Table 113e: Compounds of formulae (Ia-1), (Ia-2) and (Ia-3), wherein Q is as defined in entry E-113 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-113 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-113 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-113 of table E and $R^1$, $R^{5a}$, $R^{5b}$, $R^{5c}$ and X correspond in each case to a row of table D.

Table 114e: Compounds of formulae (Ia-1), (Ia-2) and (Ia-3), wherein Q is as defined in entry E-114 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-114 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-114 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-114 of table E and $R^1$, $R^{5a}$, $R^{5b}$, $R^{5c}$ and X correspond in each case to a row of table D.

Table 115e: Compounds of formulae (Ia-1), (Ia-2) and (Ia-3), wherein Q is as defined in entry E-115 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-115 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-115 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-115 of table E and $R^1$, $R^{5a}$, $R^{5b}$, $R^{5c}$ and X correspond in each case to a row of table D.

Table 116e: Compounds of formulae (Ia-1), (Ia-2) and (Ia-3), wherein Q is as defined in entry E-116 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-116 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-116 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-116 of table E and $R^1$, $R^{5a}$, $R^{5b}$, $R^{5c}$ and X correspond in each case to a row of table D.

Table 117e: Compounds of formulae (Ia-1), (Ia-2) and (Ia-3), wherein Q is as defined in entry E-117 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-117 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-117 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-117 of table E and $R^1$, $R^{5a}$, $R^{5b}$, $R^{5c}$ and X correspond in each case to a row of table D.

Table 118e: Compounds of formulae (Ia-1), (Ia-2) and (Ia-3), wherein Q is as defined in entry E-118 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-118 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-118 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-118 of table E and $R^1$, $R^{5a}$, $R^{5b}$, $R^{5c}$ and X correspond in each case to a row of table D.

Table 119e: Compounds of formulae (Ia-1), (Ia-2) and (Ia-3), wherein Q is as defined in entry E-119 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-119 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-119 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-119 of table E and $R^1$, $R^{5a}$, $R^{5b}$, $R^{5c}$ and X correspond in each case to a row of table D.

Table 120e: Compounds of formulae (Ia-1), (Ia-2) and (Ia-3), wherein Q is as defined in entry E-120 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-120 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-120 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-120 of table E and $R^1$, $R^{5a}$, $R^{5b}$, $R^{5c}$ and X correspond in each case to a row of table D.

Table 121e: Compounds of formulae (Ia-1), (Ia-2) and (Ia-3), wherein Q is as defined in entry E-121 of table E and $R^1$, $R^5$ and X correspond in each case to a row of table A;

compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-121 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-121 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-121 of table E and $R^1$, $R^{5a}$, $R^{5b}$, $R^{5c}$ and X correspond in each case to a row of table D.

Table 122e: Compounds of formulae (Ia-1), (Ia-2) and (Ia-3), wherein Q is as defined in entry E-122 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10),(Ib-11) and (Ib-12), wherein Q is as defined in entry E-122 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-122 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-122 of table E and $R^1$, $R^{5a}$, $R^{5b}$, $R^{5c}$ and X correspond in each case to a row of table D.

Table 123e: Compounds of formulae (Ia-1), (Ia-2) and (Ia-3), wherein Q is as defined in entry E-123 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-123 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-123 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-123 of table E and $R^1$, $R^{5a}$, $R^{5b}$, $R^{5c}$ and X correspond in each case to a row of table D.

Table 124e: Compounds of formulae (Ia-1), (Ia-2) and (Ia-3), wherein Q is as defined in entry E-124 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-124 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-124 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-124 of table E and $R^1$, $R^{5a}$, $R^{5b}$, $R^{5c}$ and X correspond in each case to a row of table D.

Table 125e: Compounds of formulae (Ia-1), (Ia-2) and (Ia-3), wherein Q is as defined in entry E-125 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-125 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-125 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-125 of table E and $R^1$, $R^{5a}$, $R^{5b}$, $R^{5c}$ and X correspond in each case to a row of table D.

Table 126e: Compounds of formulae (Ia-1), (Ia-2) and (Ia-3), wherein Q is as defined in entry E-126 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-126 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-126 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-126 of table E and $R^1$, $R^{5a}$, $R^{5b}$, $R^{5c}$ and X correspond in each case to a row of table D.

Table 127e: Compounds of formulae (Ia-1), (Ia-2) and (Ia-3), wherein Q is as defined in entry E-127 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-127 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-127 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-127 of table E and $R^1$, $R^{5a}$, $R^{5b}$, $R^{5c}$ and X correspond in each case to a row of table D.

Table 128e: Compounds of formulae (Ia-1), (Ia-2) and (Ia-3), wherein Q is as defined in entry E-128 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-128 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-128 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-128 of table E and $R^1$, $R^{5a}$, $R^{5b}$, $R^{5c}$ and X correspond in each case to a row of table D.

Table 129e: Compounds of formulae (Ia-1), (Ia-2) and (Ia-3), wherein Q is as defined in entry E-129 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-129 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-129 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-129 of table E and $R^1$, $R^{5a}$, $R^{5b}$, $R^{5c}$ and X correspond in each case to a row of table D.

Table 130e: Compounds of formulae (Ia-1), (Ia-2) and (Ia-3), wherein Q is as defined in entry E-130 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-130 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-130 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-130 of table E and $R^1$, $R^{5a}$, $R^{5b}$, $R^{5c}$ and X correspond in each case to a row of table D.

Table 131e: Compounds of formulae (Ia-1), (Ia-2) and (Ia-3), wherein Q is as defined in entry E-131 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-131 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-131 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-131 of table E and $R^1$, $R^{5a}$, $R^{5b}$, $R^{5c}$ and X correspond in each case to a row of table D.

Table 132e: Compounds of formulae (Ia-1), (Ia-2) and (Ia-3), wherein Q is as defined in entry E-132 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-132 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-132 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-132 of table E and $R^1$, $R^{5a}$, $R^{5b}$, $R^{5c}$ and X correspond in each case to a row of table D.

Table 133e: Compounds of formulae (Ia-1), (Ia-2) and (Ia-3), wherein Q is as defined in entry E-133 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-133 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-133 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-133 of table E and $R^1$, $R^{5a}$, $R^{5b}$, $R^{5c}$ and X correspond in each case to a row of table D.

Table 134e: Compounds of formulae (Ia-1), (Ia-2) and (Ia-3), wherein Q is as defined in entry E-134 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-134 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-134 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-134 of table E and $R^1$, $R^{5a}$, $R^{5b}$, $R^{5c}$ and X correspond in each case to a row of table D.

Table 135e: Compounds of formulae (Ia-1), (Ia-2) and (Ia-3), wherein Q is as defined in entry E-135 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-135 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-135 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-135 of table E and $R^1$, $R^{5a}$, $R^{5b}$, $R^{5c}$ and X correspond in each case to a row of table D.

Table 136e: Compounds of formulae (Ia-1), (Ia-2) and (Ia-3), wherein Q is as defined in entry E-136 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-136 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-136 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-136 of table E and $R^1$, $R^{5a}$, $R^{5b}$, $R^{5c}$ and X correspond in each case to a row of table D.

Table 137e: Compounds of formulae (Ia-1), (Ia-2) and (Ia-3), wherein Q is as defined in entry E-137 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-137 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-137 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-137 of table E and $R^1$, $R^{5a}$, $R^{5b}$, $R^{5c}$ and X correspond in each case to a row of table D.

Table 138e: Compounds of formulae (Ia-1), (Ia-2) and (Ia-3), wherein Q is as defined in entry E-138 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-138 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-138 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-138 of table E and $R^1$, $R^{5a}$, $R^{5b}$, $R^{5c}$ and X correspond in each case to a row of table D.

Table 139e: Compounds of formulae (Ia-1), (Ia-2) and (Ia-3), wherein Q is as defined in entry E-139 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-139 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-139 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-139 of table E and $R^1$, $R^{5a}$, $R^{5b}$, $R^{5c}$ and X correspond in each case to a row of table D.

Table 140e: Compounds of formulae (Ia-1), (Ia-2) and (Ia-3), wherein Q is as defined in entry E-140 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-140 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-140 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-140 of table E and $R^1$, $R^{5a}$, $R^{5b}$, $R^{5c}$ and X correspond in each case to a row of table D.

Table 141e: Compounds of formulae (Ia-1), (Ia-2) and (Ia-3), wherein Q is as defined in entry E-141 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-141 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-141 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-141 of table E and $R^1$, $R^{5a}$, $R^{5b}$, $R^{5c}$ and X correspond in each case to a row of table D.

Table 142e: Compounds of formulae (Ia-1), (Ia-2) and (Ia-3), wherein Q is as defined in entry E-142 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-142 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-142 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-142 of table E and $R^1$, $R^{5a}$, $R^{5b}$, $R^{5c}$ and X correspond in each case to a row of table D.

Table 143e: Compounds of formulae (Ia-1), (Ia-2) and (Ia-3), wherein Q is as defined in entry E-143 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-143 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-143 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-143 of table E and $R^1$, $R^{5a}$, $R^{5b}$, $R^{5c}$ and X correspond in each case to a row of table D.

Table 144e: Compounds of formulae (Ia-1), (Ia-2) and (Ia-3), wherein Q is as defined in entry E-144 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-144 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-144 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-144 of table E and $R^1$, $R^{5a}$, $R^{5b}$, $R^{5c}$ and X correspond in each case to a row of table D.

Table 145e: Compounds of formulae (Ia-1), (Ia-2) and (Ia-3), wherein Q is as defined in entry E-145 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-145 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-145 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-145 of table E and $R^1$, $R^{5a}$, $R^{5b}$, $R^{5c}$ and X correspond in each case to a row of table D.

Table 146e: Compounds of formulae (Ia-1), (Ia-2) and (Ia-3), wherein Q is as defined in entry E-146 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-146 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-146 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-146 of table E and $R^1$, $R^{5a}$, $R^{5b}$, $R^{5c}$ and X correspond in each case to a row of table D.

Table 147e: Compounds of formulae (Ia-1), (Ia-2) and (Ia-3), wherein Q is as defined in entry E-147 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-147 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-147 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-147 of table E and $R^1$, $R^{5a}$, $R^{5b}$, $R^{5c}$ and X correspond in each case to a row of table D.

Table 148e: Compounds of formulae (Ia-1), (Ia-2) and (Ia-3), wherein Q is as defined in entry E-148 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-148 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-148 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-148 of table E and $R^1$, $R^{5a}$, $R^{5b}$, $R^{5c}$ and X correspond in each case to a row of table D.

Table 149e: Compounds of formulae (Ia-1), (Ia-2) and (Ia-3), wherein Q is as defined in entry E-149 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-149 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-149 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-149 of table E and $R^1$, $R^{5a}$, $R^{5b}$, $R^{5c}$ and X correspond in each case to a row of table D.

Table 150e: Compounds of formulae (Ia-1), (Ia-2) and (Ia-3), wherein Q is as defined in entry E-150 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-150 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-150 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29)

and (Id-30), wherein Q is as defined in entry E-150 of table E and $R^1$, $R^{5a}$, $R^{5b}$, $R^{5c}$ and X correspond in each case to a row of table D.

Table 151e: Compounds of formulae (Ia-1), (Ia-2) and (Ia-3), wherein Q is as defined in entry E-151 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-151 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-151 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-151 of table E and $R^1$, $R^{5a}$, $R^{5b}$, $R^{5c}$ and X correspond in each case to a row of table D.

Table 152e: Compounds of formulae (Ia-1), (Ia-2) and (Ia-3), wherein Q is as defined in entry E-152 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-152 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-152 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-152 of table E and $R^1$, $R^{5a}$, $R^{5b}$, $R^{5c}$ and X correspond in each case to a row of table D.

Table 153e: Compounds of formulae (Ia-1), (Ia-2) and (Ia-3), wherein Q is as defined in entry E-153 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-153 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-153 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-153 of table E and $R^1$, $R^{5a}$, $R^{5b}$, $R^{5c}$ and X correspond in each case to a row of table D.

Table 154e: Compounds of formulae (Ia-1), (Ia-2) and (Ia-3), wherein Q is as defined in entry E-154 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-154 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-154 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-154 of table E and $R^1$, $R^{5a}$, $R^{5b}$, $R^{5c}$ and X correspond in each case to a row of table D.

Table 155e: Compounds of formulae (Ia-1), (Ia-2) and (Ia-3), wherein Q is as defined in entry E-155 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-155 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-155 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-155 of table E and $R^1$, $R^{5a}$, $R^{5b}$, $R^{5c}$ and X correspond in each case to a row of table D.

Table 156e: Compounds of formulae (Ia-1), (Ia-2) and (Ia-3), wherein Q is as defined in entry E-156 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-156 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-156 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-156 of table E and $R^1$, $R^{5a}$, $R^{5b}$, $R^{5c}$ and X correspond in each case to a row of table D.

Table 157e: Compounds of formulae (Ia-1), (Ia-2) and (Ia-3), wherein Q is as defined in entry E-157 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-157 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-157 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-157 of table E and $R^1$, $R^{5a}$, $R^{5b}$, $R^{5c}$ and X correspond in each case to a row of table D.

Table 158e: Compounds of formulae (Ia-1), (Ia-2) and (Ia-3), wherein Q is as defined in entry E-158 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-158 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-158 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-158 of table E and $R^1$, $R^{5a}$, $R^{5b}$, $R^{5c}$ and X correspond in each case to a row of table D.

Table 159e: Compounds of formulae (Ia-1), (Ia-2) and (Ia-3), wherein Q is as defined in entry E-159 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-159 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-159 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-159 of table E and $R^1$, $R^{5a}$, $R^{5b}$, $R^{5c}$ and X correspond in each case to a row of table D.

Table 160e: Compounds of formulae (Ia-1), (Ia-2) and (Ia-3), wherein Q is as defined in entry E-160 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-160 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E160 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-160 of table E and $R^1$, $R^{5a}$, $R^{5b}$, $R^{5c}$ and X correspond in each case to a row of table D.

Table 161e: Compounds of formulae (Ia-1), (Ia-2) and (Ia-3), wherein Q is as defined in entry E-161 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-161 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-161 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-161 of table E and $R^1$, $R^{5a}$, $R^{5b}$, $R^{5c}$ and X correspond in each case to a row of table D.

Table 162e: Compounds of formulae (Ia-1), (Ia-2) and (Ia-3), wherein Q is as defined in entry E-162 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-162 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-162 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-162 of table E and $R^1$, $R^{5a}$, $R^{5b}$, $R^{5c}$ and X correspond in each case to a row of table D.

Table 163e: Compounds of formulae (Ia-1), (Ia-2) and (Ia-3), wherein Q is as defined in entry E-163 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-163 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-163 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-163 of table E and $R^1$, $R^{5a}$, $R^{5b}$, $R^{5c}$ and X correspond in each case to a row of table D.

Table 164e: Compounds of formulae (Ia-1), (Ia-2) and (Ia-3), wherein Q is as defined in entry E-164 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-164 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-164 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-164 of table E and $R^1$, $R^{5a}$, $R^{5b}$, $R^{5c}$ and X correspond in each case to a row of table D.

Table 165e: Compounds of formulae (Ia-1), (Ia-2) and (Ia-3), wherein Q is as defined in entry E-165 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-165 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-165 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-165 of table E and $R^1$, $R^{5a}$, $R^{5b}$, $R^{5c}$ and X correspond in each case to a row of table D.

Table 166e: Compounds of formulae (Ia-1), (Ia-2) and (Ia-3), wherein Q is as defined in entry E-166 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-166 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-166 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-166 of table E and $R^1$, $R^{5a}$, $R^{5b}$, $R^{5c}$ and X correspond in each case to a row of table D.

Table 167e: Compounds of formulae (Ia-1), (Ia-2) and (Ia-3), wherein Q is as defined in entry E-167 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-167 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-167 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-167 of table E and $R^1$, $R^{5a}$, $R^{5b}$, $R^{5c}$ and X correspond in each case to a row of table D.

Table 168e: Compounds of formulae (Ia-1), (Ia-2) and (Ia-3), wherein Q is as defined in entry E-168 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-168 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-168 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-168 of table E and $R^1$, $R^{5a}$, $R^{5b}$, $R^{5c}$ and X correspond in each case to a row of table D.

Table 169e: Compounds of formulae (Ia-1), (Ia-2) and (Ia-3), wherein Q is as defined in entry E-169 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-169 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-169 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-169 of table E and $R^1$, $R^{5a}$, $R^{5b}$, $R^{5c}$ and X correspond in each case to a row of table D.

Table 170e: Compounds of formulae (Ia-1), (Ia-2) and (Ia-3), wherein Q is as defined in entry E-170 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-170 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-170 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-170 of table E and $R^1$, $R^{5a}$, $R^{5b}$, $R^{5c}$ and X correspond in each case to a row of table D.

Table 171e: Compounds of formulae (Ia-1), (Ia-2) and (Ia-3), wherein Q is as defined in entry E-171 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-171 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-171 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-171 of table E and $R^1$, $R^{5a}$, $R^{5b}$, $R^{5c}$ and X correspond in each case to a row of table D.

Table 172e: Compounds of formulae (Ia-1), (Ia-2) and (Ia-3), wherein Q is as defined in entry E-172 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E172 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-172 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-172 of table E and $R^1$, $R^{5a}$, $R^{5b}$, $R^{5c}$ and X correspond in each case to a row of table D.

Table 173e: Compounds of formulae (Ia-1), (Ia-2) and (Ia-3), wherein Q is as defined in entry E-173 of table E and $R^1$, $R^5$ and X correspond in each case to a row of table A;

compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-173 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-173 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-173 of table E and $R^1$, $R^{5a}$, $R^{5b}$, $R^{5c}$ and X correspond in each case to a row of table D.

Table 174e: Compounds of formulae (Ia-1), (Ia-2) and (Ia-3), wherein Q is as defined in entry E-174 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-174 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-174 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-174 of table E and $R^1$, $R^{5a}$, $R^{5b}$, $R^{5c}$ and X correspond in each case to a row of table D.

Table 175e: Compounds of formulae (Ia-1), (Ia-2) and (Ia-3), wherein Q is as defined in entry E-175 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-175 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-175 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-175 of table E and $R^1$, $R^{5a}$, $R^{5b}$, $R^{5c}$ and X correspond in each case to a row of table D.

Table 176e: Compounds of formulae (Ia-1), (Ia-2) and (Ia-3), wherein Q is as defined in entry E-176 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-176 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-176 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-176 of table E and $R^1$, $R^{5a}$, $R^{5b}$, $R^{5c}$ and X correspond in each case to a row of table D.

Table 177e: Compounds of formulae (Ia-1), (Ia-2) and (Ia-3), wherein Q is as defined in entry E-177 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-177 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-177 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-177 of table E and $R^1$, $R^{5a}$, $R^{5b}$, $R^{5c}$ and X correspond in each case to a row of table D.

Table 178e: Compounds of formulae (Ia-1), (Ia-2) and (Ia-3), wherein Q is as defined in entry E-178 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-178 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-178 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-178 of table E and $R^1$, $R^{5a}$, $R^{5b}$, $R^{5c}$ and X correspond in each case to a row of table D.

Table 179e: Compounds of formulae (Ia-1), (Ia-2) and (Ia-3), wherein Q is as defined in entry E-179 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-179 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-179 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-179 of table E and $R^1$, $R^{5a}$, $R^{5b}$, $R^{5c}$ and X correspond in each case to a row of table D.

Table 180e: Compounds of formulae (Ia-1), (Ia-2) and (Ia-3), wherein Q is as defined in entry E-180 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-180 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-180 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-180 of table E and $R^1$, $R^{5a}$, $R^{5b}$, $R^{5c}$ and X correspond in each case to a row of table D.

Table 181e: Compounds of formulae (Ia-1), (Ia-2) and (Ia-3), wherein Q is as defined in entry E-181 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-181 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-181 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-181 of table E and $R^1$, $R^{5a}$, $R^{5b}$, $R^{5c}$ and X correspond in each case to a row of table D.

Table 182e: Compounds of formulae (Ia-1), (Ia-2) and (Ia-3), wherein Q is as defined in entry E-182 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-182 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-182 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-182 of table E and $R^1$, $R^{5a}$, $R^{5b}$, $R^{5c}$ and X correspond in each case to a row of table D.

Table 183e: Compounds of formulae (Ia-1), (Ia-2) and (Ia-3), wherein Q is as defined in entry E-183 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-183 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-183 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-183 of table E and $R^1$, $R^{5a}$, $R^{5b}$, $R^{5c}$ and X correspond in each case to a row of table D.

Table 184e: Compounds of formulae (Ia-1), (Ia-2) and (Ia-3), wherein Q is as defined in entry E-184 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-184 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-184 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-184 of table E and $R^1$, $R^{5a}$, $R^{5b}$, $R^{5c}$ and X correspond in each case to a row of table D.

Table 185e: Compounds of formulae (Ia-1), (Ia-2) and (Ia-3), wherein Q is as defined in entry E-185 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-185 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-185 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-185 of table E and $R^1$, $R^{5a}$, $R^{5b}$, $R^{5c}$ and X correspond in each case to a row of table D.

Table 186e: Compounds of formulae (Ia-1), (Ia-2) and (Ia-3), wherein Q is as defined in entry E-186 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-186 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-186 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-186 of table E and $R^1$, $R^{5a}$, $R^{5b}$, $R^{5c}$ and X correspond in each case to a row of table D.

Table 187e: Compounds of formulae (Ia-1), (Ia-2) and (Ia-3), wherein Q is as defined in entry E-187 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-187 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-187 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-187 of table E and $R^1$, $R^{5a}$, $R^{5b}$, $R^{5c}$ and X correspond in each case to a row of table D.

Table 188e: Compounds of formulae (Ia-1), (Ia-2) and (Ia-3), wherein Q is as defined in entry E-188 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-188 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-188 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-188 of table E and $R^1$, $R^{5a}$, $R^{5b}$, $R^{5c}$ and X correspond in each case to a row of table D.

Table 189e: Compounds of formulae (Ia-1), (Ia-2) and (Ia-3), wherein Q is as defined in entry E-189 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-189 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-189 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-189 of table E and $R^1$, $R^{5a}$, $R^{5b}$, $R^{5c}$ and X correspond in each case to a row of table D.

Table 190e: Compounds of formulae (Ia-1), (Ia-2) and (Ia-3), wherein Q is as defined in entry E-190 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-190 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-190 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-190 of table E and $R^1$, $R^{5a}$, $R^{5b}$, $R^{5c}$ and X correspond in each case to a row of table D.

Table 191e: Compounds of formulae (Ia-1), (Ia-2) and (Ia-3), wherein Q is as defined in entry E-191 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-191 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-191 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-191 of table E and $R^1$, $R^{5a}$, $R^{5b}$, $R^{5c}$ and X correspond in each case to a row of table D.

Table 192e: Compounds of formulae (Ia-1), (Ia-2) and (Ia-3), wherein Q is as defined in entry E-192 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-192 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-192 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-192 of table E and $R^1$, $R^{5a}$, $R^{5b}$, $R^{5c}$ and X correspond in each case to a row of table D.

Table 193e: Compounds of formulae (Ia-1), (Ia-2) and (Ia-3), wherein Q is as defined in entry E-193 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-193 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-193 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-193 of table E and $R^1$, $R^{5a}$, $R^{5b}$, $R^{5c}$ and X correspond in each case to a row of table D.

Table 194e: Compounds of formulae (Ia-1), (Ia-2) and (Ia-3), wherein Q is as defined in entry E-194 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-194 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-194 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-194 of table E and $R^1$, $R^{5a}$, $R^{5b}$, $R^{5c}$ and X correspond in each case to a row of table D.

Table 195e: Compounds of formulae (Ia-1), (Ia-2) and (Ia-3), wherein Q is as defined in entry E-195 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-195 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-195 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-195 of table E and $R^1$, $R^{5a}$, $R^{5b}$, $R^{5c}$ and X correspond in each case to a row of table D.

Table 196e: Compounds of formulae (Ia-1), (Ia-2) and (Ia-3), wherein Q is as defined in entry E-196 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-196 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-196 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-196 of table E and $R^1$, $R^{5a}$, $R^{5b}$, $R^{5c}$ and X correspond in each case to a row of table D.

Table 197e: Compounds of formulae (Ia-1), (Ia-2) and (Ia-3), wherein Q is as defined in entry E-197 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-197 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-197 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-197 of table E and $R^1$, $R^{5a}$, $R^{5b}$, $R^{5c}$ and X correspond in each case to a row of table D.

Table 198e: Compounds of formulae (Ia-1), (Ia-2) and (Ia-3), wherein Q is as defined in entry E-198 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-198 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-198 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-198 of table E and $R^1$, $R^{5a}$, $R^{5b}$, $R^{5c}$ and X correspond in each case to a row of table D.

Table 199e: Compounds of formulae (Ia-1), (Ia-2) and (Ia-3), wherein Q is as defined in entry E-199 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-199 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-199 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-199 of table E and $R^1$, $R^{5a}$, $R^{5b}$, $R^{5c}$ and X correspond in each case to a row of table D.

Table 200e: Compounds of formulae (Ia-1), (Ia-2) and (Ia-3), wherein Q is as defined in entry E-200 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-200 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-200 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-200 of table E and $R^1$, $R^{5a}$, $R^{5b}$, $R^{5c}$ and X correspond in each case to a row of table D.

Table 201e: Compounds of formulae (Ia-1), (Ia-2) and (Ia-3), wherein Q is as defined in entry E-201 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-201 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-201 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-201 of table E and $R^1$, $R^{5a}$, $R^{5b}$, $R^{5c}$ and X correspond in each case to a row of table D.

Table 202e: Compounds of formulae (Ia-1), (Ia-2) and (Ia-3), wherein Q is as defined in entry E-202 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-202 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-202 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-202 of table E and $R^1$, $R^{5a}$, $R^{5b}$, $R^{5c}$ and X correspond in each case to a row of table D.

Table 203e: Compounds of formulae (Ia-1), (Ia-2) and (Ia-3), wherein Q is as defined in entry E-203 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-203 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-203 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-203 of table E and $R^1$, $R^{5a}$, $R^{5b}$, $R^{5c}$ and X correspond in each case to a row of table D.

Table 204e: Compounds of formulae (Ia-1), (Ia-2) and (Ia-3), wherein Q is as defined in entry E-204 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-204 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-204 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-204 of table E and $R^1$, $R^{5a}$, $R^{5b}$, $R^{5c}$ and X correspond in each case to a row of table D.

Table 205e: Compounds of formulae (Ia-1), (Ia-2) and (Ia-3), wherein Q is as defined in entry E-205 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-205 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-205 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-205 of table E and $R^1$, $R^{5a}$, $R^{5b}$, $R^{5c}$ and X correspond in each case to a row of table D.

Table 206e: Compounds of formulae (Ia-1), (Ia-2) and (Ia-3), wherein Q is as defined in entry E-206 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-206 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-206 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-206 of table E and $R^1$, $R^{5a}$, $R^{5b}$, $R^{5c}$ and X correspond in each case to a row of table D.

Table 207e: Compounds of formulae (Ia-1), (Ia-2) and (Ia-3), wherein Q is as defined in entry E-207 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-207 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-207 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-207 of table E and $R^1$, $R^{5a}$, $R^{5b}$, $R^{5c}$ and X correspond in each case to a row of table D.

Table 208e: Compounds of formulae (Ia-1), (Ia-2) and (Ia-3), wherein Q is as defined in entry E-208 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-208 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-208 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-208 of table E and $R^1$, $R^{5a}$, $R^{5b}$, $R^{5c}$ and X correspond in each case to a row of table D.

Table 209e: Compounds of formulae (Ia-1), (Ia-2) and (Ia-3), wherein Q is as defined in entry E-209 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-209 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-209 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-209 of table E and $R^1$, $R^{5a}$, $R^{5b}$, $R^{5c}$ and X correspond in each case to a row of table D.

Table 210e: Compounds of formulae (Ia-1), (Ia-2) and (Ia-3), wherein Q is as defined in entry E-210 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-210 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-210 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-210 of table E and $R^1$, $R^{5a}$, $R^{5b}$, $R^{5c}$ and X correspond in each case to a row of table D.

Table 211e: Compounds of formulae (Ia-1), (Ia-2) and (Ia-3), wherein Q is as defined in entry E-211 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-211 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-211 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-211 of table E and $R^1$, $R^{5a}$, $R^{5b}$, $R^{5c}$ and X correspond in each case to a row of table D.

Table 212e: Compounds of formulae (Ia-1), (Ia-2) and (Ia-3), wherein Q is as defined in entry E-212 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-212 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-212 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-212 of table E and $R^1$, $R^{5a}$, $R^{5b}$, $R^{5c}$ and X correspond in each case to a row of table D.

Table 213e: Compounds of formulae (Ia-1), (Ia-2) and (Ia-3), wherein Q is as defined in entry E-213 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-213 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-213 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-213 of table E and $R^1$, $R^{5a}$, $R^{5b}$, $R^{5c}$ and X correspond in each case to a row of table D.

Table 214e: Compounds of formulae (Ia-1), (Ia-2) and (Ia-3), wherein Q is as defined in entry E-214 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-214 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-214 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-214 of table E and $R^1$, $R^{5a}$, $R^{5b}$, $R^{5c}$ and X correspond in each case to a row of table D.

Table 215e: Compounds of formulae (Ia-1), (Ia-2) and (Ia-3), wherein Q is as defined in entry E-215 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-215 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-215 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-215 of table E and $R^1$, $R^{5a}$, $R^{5b}$, $R^{5c}$ and X correspond in each case to a row of table D.

Table 216e: Compounds of formulae (Ia-1), (Ia-2) and (Ia-3), wherein Q is as defined in entry E-216 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-216 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-216 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-216 of table E and $R^1$, $R^{5a}$, $R^{5b}$, $R^{5c}$ and X correspond in each case to a row of table D.

Table 217e: Compounds of formulae (Ia-1), (Ia-2) and (Ia-3), wherein Q is as defined in entry E-217 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-217 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-217 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-217 of table E and $R^1$, $R^{5a}$, $R^{5b}$, $R^{5c}$ and X correspond in each case to a row of table D.

Table 218e: Compounds of formulae (Ia-1), (Ia-2) and (Ia-3), wherein Q is as defined in entry E-218 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-218 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-218 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-218 of table E and $R^1$, $R^{5a}$, $R^{5b}$, $R^{5c}$ and X correspond in each case to a row of table D.

Table 219e: Compounds of formulae (Ia-1), (Ia-2) and (Ia-3), wherein Q is as defined in entry E-219 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-219 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-219 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-219 of table E and $R^1$, $R^{5a}$, $R^{5b}$, $R^{5c}$ and X correspond in each case to a row of table D.

Table 220e: Compounds of formulae (Ia-1), (Ia-2) and (Ia-3), wherein Q is as defined in entry E-220 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-220 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-220 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-220 of table E and $R^1$, $R^{5a}$, $R^{5b}$, $R^{5c}$ and X correspond in each case to a row of table D.

Table 221e: Compounds of formulae (Ia-1), (Ia-2) and (Ia-3), wherein Q is as defined in entry E-221 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-221 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-221 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-221 of table E and $R^1$, $R^{5a}$, $R^{5b}$, $R^{5c}$ and X correspond in each case to a row of table D.

Table 222e: Compounds of formulae (Ia-1), (Ia-2) and (Ia-3), wherein Q is as defined in entry E-222 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-222 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-222 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-222 of table E and $R^1$, $R^{5a}$, $R^{5b}$, $R^{5c}$ and X correspond in each case to a row of table D.

Table 223e: Compounds of formulae (Ia-1), (Ia-2) and (Ia-3), wherein Q is as defined in entry E-223 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-223 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-223 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-223 of table E and $R^1$, $R^{5a}$, $R^{5b}$, $R^{5c}$ and X correspond in each case to a row of table D.

Table 224e: Compounds of formulae (Ia-1), (Ia-2) and (Ia-3), wherein Q is as defined in entry E-224 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-224 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-224 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-224 of table E and $R^1$, $R^{5a}$, $R^{5b}$, $R^{5c}$ and X correspond in each case to a row of table D.

Table 225e: Compounds of formulae (Ia-1), (Ia-2) and (Ia-3), wherein Q is as defined in entry E-225 of table E and $R^1$, $R^5$ and X correspond in each case to a row of table A;

compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-225 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-225 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-225 of table E and $R^1$, $R^{5a}$, $R^{5b}$, $R^{5c}$ and X correspond in each case to a row of table D.

Table 226e: Compounds of formulae (Ia-1), (Ia-2) and (Ia-3), wherein Q is as defined in entry E-226 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-226 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-226 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-226 of table E and $R^1$, $R^{5a}$, $R^{5b}$, $R^{5c}$ and X correspond in each case to a row of table D.

Table 227e: Compounds of formulae (Ia-1), (Ia-2) and (Ia-3), wherein Q is as defined in entry E-227 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-227 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-227 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-227 of table E and $R^1$, $R^{5a}$, $R^{5b}$, $R^{5c}$ and X correspond in each case to a row of table D.

Table 228e: Compounds of formulae (Ia-1), (Ia-2) and (Ia-3), wherein Q is as defined in entry E-228 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-228 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-228 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-228 of table E and $R^1$, $R^{5a}$, $R^{5b}$, $R^{5c}$ and X correspond in each case to a row of table D.

Table 229e: Compounds of formulae (Ia-1), (Ia-2) and (Ia-3), wherein Q is as defined in entry E-229 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-229 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-229 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-229 of table E and $R^1$, $R^{5a}$, $R^{5b}$, $R^{5c}$ and X correspond in each case to a row of table D.

Table 230e: Compounds of formulae (Ia-1), (Ia-2) and (Ia-3), wherein Q is as defined in entry E-230 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-230 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-230 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-230 of table E and $R^1$, $R^{5a}$, $R^{5b}$, $R^{5c}$ and X correspond in each case to a row of table D.

Table 231e: Compounds of formulae (Ia-1), (Ia-2) and (Ia-3), wherein Q is as defined in entry E-231 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-231 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-231 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-231 of table E and $R^1$, $R^{5a}$, $R^{5b}$, $R^{5c}$ and X correspond in each case to a row of table D.

Table 232e: Compounds of formulae (Ia-1), (Ia-2) and (Ia-3), wherein Q is as defined in entry E-232 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-232 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-232 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-232 of table E and $R^1$, $R^{5a}$, $R^{5b}$, $R^{5c}$ and X correspond in each case to a row of table D.

Table 233e: Compounds of formulae (Ia-1), (Ia-2) and (Ia-3), wherein Q is as defined in entry E-233 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-233 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-233 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-233 of table E and $R^1$, $R^{5a}$, $R^{5b}$, $R^{5c}$ and X correspond in each case to a row of table D.

Table 234e: Compounds of formulae (Ia-1), (Ia-2) and (Ia-3), wherein Q is as defined in entry E-234 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-234 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-234 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-234 of table E and $R^1$, $R^{5a}$, $R^{5b}$, $R^{5c}$ and X correspond in each case to a row of table D.

Table 235e: Compounds of formulae (Ia-1), (Ia-2) and (Ia-3), wherein Q is as defined in entry E-235 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-235 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-235 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-235 of table E and $R^1$, $R^{5a}$, $R^{5b}$, $R^{5c}$ and X correspond in each case to a row of table D.

Table 236e: Compounds of formulae (Ia-1), (Ia-2) and (Ia-3), wherein Q is as defined in entry E-236 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-236 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-236 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-236 of table E and $R^1$, $R^{5a}$, $R^{5b}$, $R^{5c}$ and X correspond in each case to a row of table D.

Table 237e: Compounds of formulae (Ia-1), (Ia-2) and (Ia-3), wherein Q is as defined in entry E-237 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-237 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-237 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-237 of table E and $R^1$, $R^{5a}$, $R^{5b}$, $R^{5c}$ and X correspond in each case to a row of table D.

Table 238e: Compounds of formulae (Ia-1), (Ia-2) and (Ia-3), wherein Q is as defined in entry E-238 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-238 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-238 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-238 of table E and $R^1$, $R^{5a}$, $R^{5b}$, $R^{5c}$ and X correspond in each case to a row of table D.

Table 239e: Compounds of formulae (Ia-1), (Ia-2) and (Ia-3), wherein Q is as defined in entry E-239 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-239 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-239 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-239 of table E and $R^1$, $R^{5a}$, $R^{5b}$, $R^{5c}$ and X correspond in each case to a row of table D.

Table 240e: Compounds of formulae (Ia-1), (Ia-2) and (Ia-3), wherein Q is as defined in entry E-240 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-240 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-240 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-240 of table E and $R^1$, $R^{5a}$, $R^{5b}$, $R^{5c}$ and X correspond in each case to a row of table D.

Table 241e: Compounds of formulae (Ia-1), (Ia-2) and (Ia-3), wherein Q is as defined in entry E-241 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-241 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-241 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-241 of table E and $R^1$, $R^{5a}$, $R^{5b}$, $R^{5c}$ and X correspond in each case to a row of table D.

Table 242e: Compounds of formulae (Ia-1), (Ia-2) and (Ia-3), wherein Q is as defined in entry E-242 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-242 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-242 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-242 of table E and $R^1$, $R^{5a}$, $R^{5b}$, $R^{5c}$ and X correspond in each case to a row of table D.

Table 243e: Compounds of formulae (Ia-1), (Ia-2) and (Ia-3), wherein Q is as defined in entry E-243 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-243 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-243 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-243 of table E and $R^1$, $R^{5a}$, $R^{5b}$, $R^{5c}$ and X correspond in each case to a row of table D.

Table 244e: Compounds of formulae (Ia-1), (Ia-2) and (Ia-3), wherein Q is as defined in entry E-244 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-244 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-244 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-244 of table E and $R^1$, $R^{5a}$, $R^{5b}$, $R^{5c}$ and X correspond in each case to a row of table D.

Table 245e: Compounds of formulae (Ia-1), (Ia-2) and (Ia-3), wherein Q is as defined in entry E-245 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-245 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-245 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-245 of table E and $R^1$, $R^{5a}$, $R^{5b}$, $R^{5c}$ and X correspond in each case to a row of table D.

Table 246e: Compounds of formulae (Ia-1), (Ia-2) and (Ia-3), wherein Q is as defined in entry E-246 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-246 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-246 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-246 of table E and $R^1$, $R^{5a}$, $R^{5b}$, $R^{5c}$ and X correspond in each case to a row of table D.

Table 247e: Compounds of formulae (Ia-1), (Ia-2) and (Ia-3), wherein Q is as defined in entry E-247 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-247 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-247 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-247 of table E and $R^1$, $R^{5a}$, $R^{5b}$, $R^{5c}$ and X correspond in each case to a row of table D.

Table 248e: Compounds of formulae (Ia-1), (Ia-2) and (Ia-3), wherein Q is as defined in entry E-248 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-248 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-248 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-248 of table E and $R^1$, $R^{5a}$, $R^{5b}$, $R^{5c}$ and X correspond in each case to a row of table D.

Table 249e: Compounds of formulae (Ia-1), (Ia-2) and (Ia-3), wherein Q is as defined in entry E-249 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-249 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-249 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-249 of table E and $R^1$, $R^{5a}$, $R^{5b}$, $R^{5c}$ and X correspond in each case to a row of table D.

Table 250e: Compounds of formulae (Ia-1), (Ia-2) and (Ia-3), wherein Q is as defined in entry E-250 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-250 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-250 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-250 of table E and $R^1$, $R^{5a}$, $R^{5b}$, $R^{5c}$ and X correspond in each case to a row of table D.

Table 251e: Compounds of formulae (Ia-1), (Ia-2) and (Ia-3), wherein Q is as defined in entry E-251 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-251 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-251 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-251 of table E and $R^1$, $R^{5a}$, $R^{5b}$, $R^{5c}$ and X correspond in each case to a row of table D.

Table 252e: Compounds of formulae (Ia-1), (Ia-2) and (Ia-3), wherein Q is as defined in entry E-252 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-252 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-252 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-252 of table E and $R^1$, $R^{5a}$, $R^{5b}$, $R^{5c}$ and X correspond in each case to a row of table D.

Table 253e: Compounds of formulae (Ia-1), (Ia-2) and (Ia-3), wherein Q is as defined in entry E-253 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-253 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-253 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-253 of table E and $R^1$, $R^{5a}$, $R^{5b}$, $R^{5c}$ and X correspond in each case to a row of table D.

Table 254e: Compounds of formulae (Ia-1), (Ia-2) and (Ia-3), wherein Q is as defined in entry E-254 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-254 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-254 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29)

and (Id-30), wherein Q is as defined in entry E-254 of table E and $R^1$, $R^{5a}$, $R^{5b}$, $R^{5c}$ and X correspond in each case to a row of table D.

Table 255e: Compounds of formulae (Ia-1), (Ia-2) and (Ia-3), wherein Q is as defined in entry E-255 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-255 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-255 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-255 of table E and $R^1$, $R^{5a}$, $R^{5b}$, $R^{5c}$ and X correspond in each case to a row of table D.

Table 256e: Compounds of formulae (Ia-1), (Ia-2) and (Ia-3), wherein Q is as defined in entry E-256 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-256 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-256 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-256 of table E and $R^1$, $R^{5a}$, $R^{5b}$, $R^{5c}$ and X correspond in each case to a row of table D.

Table 257e: Compounds of formulae (Ia-1), (Ia-2) and (Ia-3), wherein Q is as defined in entry E-257 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-257 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-257 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-257 of table E and $R^1$, $R^{5a}$, $R^{5b}$, $R^{5c}$ and X correspond in each case to a row of table D.

Table 258e: Compounds of formulae (Ia-1), (Ia-2) and (Ia-3), wherein Q is as defined in entry E-258 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-258 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-258 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-258 of table E and $R^1$, $R^{5a}$, $R^{5b}$, $R^{5c}$ and X correspond in each case to a row of table D.

Table 259e: Compounds of formulae (Ia-1), (Ia-2) and (Ia-3), wherein Q is as defined in entry E-259 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-259 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-259 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-259 of table E and $R^1$, $R^{5a}$, $R^{5b}$, $R^{5c}$ and X correspond in each case to a row of table D.

Table 260e: Compounds of formulae (Ia-1), (Ia-2) and (Ia-3), wherein Q is as defined in entry E-260 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-260 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-260 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-260 of table E and $R^1$, $R^{5a}$, $R^{5b}$, $R^{5c}$ and X correspond in each case to a row of table D.

Table 261e: Compounds of formulae (Ia-1), (Ia-2) and (Ia-3), wherein Q is as defined in entry E-261 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-261 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-261 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-261 of table E and $R^1$, $R^{5a}$, $R^{5b}$, $R^{5c}$ and X correspond in each case to a row of table D.

Table 262e: Compounds of formulae (Ia-1), (Ia-2) and (Ia-3), wherein Q is as defined in entry E-262 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-262 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-262 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-262 of table E and $R^1$, $R^{5a}$, $R^{5b}$, $R^{5c}$ and X correspond in each case to a row of table D.

Table 263e: Compounds of formulae (Ia-1), (Ia-2) and (Ia-3), wherein Q is as defined in entry E-263 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-263 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-263 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-263 of table E and $R^1$, $R^{5a}$, $R^{5b}$, $R^{5c}$ and X correspond in each case to a row of table D.

Table 264e: Compounds of formulae (Ia-1), (Ia-2) and (Ia-3), wherein Q is as defined in entry E-264 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-264 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-264 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-264 of table E and $R^1$, $R^{5a}$, $R^{5b}$, $R^{5c}$ and X correspond in each case to a row of table D.

Table 265e: Compounds of formulae (Ia-1), (Ia-2) and (Ia-3), wherein Q is as defined in entry E-265 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-265 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-265 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-265 of table E and $R^1$, $R^{5a}$, $R^{5b}$, $R^{5c}$ and X correspond in each case to a row of table D.

Table 266e: Compounds of formulae (Ia-1), (Ia-2) and (Ia-3), wherein Q is as defined in entry E-266 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-266 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-266 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-266 of table E and $R^1$, $R^{5a}$, $R^{5b}$, $R^{5c}$ and X correspond in each case to a row of table D.

Table 267e: Compounds of formulae (Ia-1), (Ia-2) and (Ia-3), wherein Q is as defined in entry E-267 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-267 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-267 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-267 of table E and $R^1$, $R^{5a}$, $R^{5b}$, $R^{5c}$ and X correspond in each case to a row of table D.

Table 268e: Compounds of formulae (Ia-1), (Ia-2) and (Ia-3), wherein Q is as defined in entry E-268 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-268 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-268 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-268 of table E and $R^1$, $R^{5a}$, $R^{5b}$, $R^{5c}$ and X correspond in each case to a row of table D.

Table 269e: Compounds of formulae (Ia-1), (Ia-2) and (Ia-3), wherein Q is as defined in entry E-269 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-269 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-269 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-269 of table E and $R^1$, $R^{5a}$, $R^{5b}$, $R^{5c}$ and X correspond in each case to a row of table D.

Table 270e: Compounds of formulae (Ia-1), (Ia-2) and (Ia-3), wherein Q is as defined in entry E-270 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-270 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-270 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-270 of table E and $R^1$, $R^{5a}$, $R^{5b}$, $R^{5c}$ and X correspond in each case to a row of table D.

Table 271e: Compounds of formulae (Ia-1), (Ia-2) and (Ia-3), wherein Q is as defined in entry E-271 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-271 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-271 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-271 of table E and $R^1$, $R^{5a}$, $R^{5b}$, $R^{5c}$ and X correspond in each case to a row of table D.

Table 272e: Compounds of formulae (Ia-1), (Ia-2) and (Ia-3), wherein Q is as defined in entry E-272 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-272 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-272 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-272 of table E and $R^1$, $R^{5a}$, $R^{5b}$, $R^{5c}$ and X correspond in each case to a row of table D.

Table 273e: Compounds of formulae (Ia-1), (Ia-2) and (Ia-3), wherein Q is as defined in entry E-273 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-273 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-273 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-273 of table E and $R^1$, $R^{5a}$, $R^{5b}$, $R^{5c}$ and X correspond in each case to a row of table D.

Table 274e: Compounds of formulae (Ia-1), (Ia-2) and (Ia-3), wherein Q is as defined in entry E-274 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-274 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-274 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-274 of table E and $R^1$, $R^{5a}$, $R^{5b}$, $R^{5c}$ and X correspond in each case to a row of table D.

Table 275e: Compounds of formulae (Ia-1), (Ia-2) and (Ia-3), wherein Q is as defined in entry E-275 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-275 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-275 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-275 of table E and $R^1$, $R^{5a}$, $R^{5b}$, $R^{5c}$ and X correspond in each case to a row of table D.

Table 276e: Compounds of formulae (Ia-1), (Ia-2) and (Ia-3), wherein Q is as defined in entry E-276 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-276 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-276 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-276 of table E and $R^1$, $R^{5a}$, $R^{5b}$, $R^{5c}$ and X correspond in each case to a row of table D.

Table 277e: Compounds of formulae (Ia-1), (Ia-2) and (Ia-3), wherein Q is as defined in entry E-277 of table E and $R^1$, $R^5$ and X correspond in each case to a row of table A;

compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-277 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-277 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-277 of table E and $R^1$, $R^{5a}$, $R^{5b}$, $R^{5c}$ and X correspond in each case to a row of table D.

Table 278e: Compounds of formulae (Ia-1), (Ia-2) and (Ia-3), wherein Q is as defined in entry E-278 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-278 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-278 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-278 of table E and $R^1$, $R^{5a}$, $R^{5b}$, $R^{5c}$ and X correspond in each case to a row of table D.

Table 279e: Compounds of formulae (Ia-1), (Ia-2) and (Ia-3), wherein Q is as defined in entry E-279 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-279 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E279 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-279 of table E and $R^1$, $R^{5a}$, $R^{5b}$, $R^{5c}$ and X correspond in each case to a row of table D.

Table 280e: Compounds of formulae (Ia-1), (Ia-2) and (Ia-3), wherein Q is as defined in entry E-280 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-280 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-280 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-280 of table E and $R^1$, $R^{5a}$, $R^{5b}$, $R^{5c}$ and X correspond in each case to a row of table D.

Table 281e: Compounds of formulae (Ia-1), (Ia-2) and (Ia-3), wherein Q is as defined in entry E-281 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-281 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-281 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-281 of table E and $R^1$, $R^{5a}$, $R^{5b}$, $R^{5c}$ and X correspond in each case to a row of table D.

Table 282e: Compounds of formulae (Ia-1), (Ia-2) and (Ia-3), wherein Q is as defined in entry E-282 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-282 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-282 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-282 of table E and $R^1$, $R^{5a}$, $R^{5b}$, $R^{5c}$ and X correspond in each case to a row of table D.

Table 283e: Compounds of formulae (Ia-1), (Ia-2) and (Ia-3), wherein Q is as defined in entry E-283 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-283 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-283 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-283 of table E and $R^1$, $R^{5a}$, $R^{5b}$, $R^{5c}$ and X correspond in each case to a row of table D.

Table 284e: Compounds of formulae (Ia-1), (Ia-2) and (Ia-3), wherein Q is as defined in entry E-284 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-284 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-284 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-284 of table E and $R^1$, $R^{5a}$, $R^{5b}$, $R^{5c}$ and X correspond in each case to a row of table D.

Table 285e: Compounds of formulae (Ia-1), (Ia-2) and (Ia-3), wherein Q is as defined in entry E-285 of table E and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry E-285 of table E and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry E-285 of table E and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-285 of table E and $R^1$, $R^{5a}$, $R^{5b}$, $R^{5c}$ and X correspond in each case to a row of table D.

Table 1f: Compounds of formulae (Ia-1), (Ia-2) and (Ia-3), wherein Q is as defined in entry F-001 of table F and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry F-001 of table F and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry F-001 of table F and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry F-001 of table F and $R^1$, $R^{5a}$, $R^{5b}$, $R^{5c}$ and X correspond in each case to a row of table D.

Table 2f: Compounds of formulae (Ia-1), (Ia-2) and (Ia-3), wherein Q is as defined in entry F-002 of table F and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry F-002 of table F and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry F-002 of table F and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry F-002 of table F and $R^1$, $R^{5a}$, $R^{5b}$, $R^{5c}$ and X correspond in each case to a row of table D.

Table 3f: Compounds of formulae (Ia-1), (Ia-2) and (Ia-3), wherein Q is as defined in entry F-003 of table F and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry F-003 of table F and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry F-003 of table F and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry E-003 of table F and $R^1$, $R^{5a}$, $R^{5b}$, $R^{5c}$ and X correspond in each case to a row of table D.

Table 4f: Compounds of formulae (Ia-1), (Ia-2) and (Ia-3), wherein Q is as defined in entry F-004 of table F and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry F-004 of table F and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry F-004 of table F and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry F-004 of table F and $R^1$, $R^{5a}$, $R^{5b}$, $R^{5c}$ and X correspond in each case to a row of table D.

Table 5f: Compounds of formulae (Ia-1), (Ia-2) and (Ia-3), wherein Q is as defined in entry F-005 of table F and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry F-005 of table F and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry F-005 of table F and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry F-005 of table F and $R^1$, $R^{5a}$, $R^{5b}$, $R^{5c}$ and X correspond in each case to a row of table D.

Table 6f: Compounds of formulae (Ia-1), (Ia-2) and (Ia-3), wherein Q is as defined in entry F-006 of table F and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry F-006 of table F and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry F-006 of table F and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry F-006 of table F and $R^1$, $R^{5a}$, $R^{5b}$, $R^{5c}$ and X correspond in each case to a row of table D.

Table 7f: Compounds of formulae (Ia-1), (Ia-2) and (Ia-3), wherein Q is as defined in entry F-007 of table F and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry F-007 of table F and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry F-007 of table F and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry F-007 of table F and $R^1$, $R^{5a}$, $R^{5b}$, $R^{5c}$ and X correspond in each case to a row of table D.

Table 8f: Compounds of formulae (Ia-1), (Ia-2) and (Ia-3), wherein Q is as defined in entry F-008 of table F and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry F-008 of table F and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry F-008 of table F and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry F-008 of table F and $R^1$, $R^{5a}$, $R^{5b}$, $R^{5c}$ and X correspond in each case to a row of table D.

Table 9f: Compounds of formulae (Ia-1), (Ia-2) and (Ia-3), wherein Q is as defined in entry F-009 of table F and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry F-009 of table F and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry F-009 of table F and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry F-009 of table F and $R^1$, $R^{5a}$, $R^{5b}$, $R^{5c}$ and X correspond in each case to a row of table D.

Table 10f: Compounds of formulae (Ia-1), (Ia-2) and (Ia-3), wherein Q is as defined in entry F-010 of table F and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry F-010 of table F and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry F-010 of table F and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry F-010 of table F and $R^1$, $R^{5a}$, $R^{5b}$, $R^{5c}$ and X correspond in each case to a row of table D.

Table 11f: Compounds of formulae (Ia-1), (Ia-2) and (Ia-3), wherein Q is as defined in entry F-011 of table F and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry F-011 of table F and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry F-011 of table F and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry F-011 of table F and $R^1$, $R^{5a}$, $R^{5b}$, $R^{5c}$ and X correspond in each case to a row of table D.

Table 12f: Compounds of formulae (Ia-1), (Ia-2) and (Ia-3), wherein Q is as defined in entry F-012 of table F and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry F-012 of table F and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry F-012 of table F and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry F-012 of table F and $R^1$, $R^{5a}$, $R^{5b}$, $R^{5c}$ and X correspond in each case to a row of table D.

Table 13f: Compounds of formulae (Ia-1), (Ia-2) and (Ia-3), wherein Q is as defined in entry F-013 of table F and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry F-013 of table F and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry F-013 of table F and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry F-013 of table F and $R^1$, $R^{5a}$, $R^{5b}$, $R^{5c}$ and X correspond in each case to a row of table D.

Table 14f: Compounds of formulae (Ia-1), (Ia-2) and (Ia-3), wherein Q is as defined in entry F-014 of table F and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry F-014 of table F and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry F-014 of table F and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry F-014 of table F and $R^1$, $R^{5a}$, $R^{5b}$, $R^{5c}$ and X correspond in each case to a row of table D.

Table 15f: Compounds of formulae (Ia-1), (Ia-2) and (Ia-3), wherein Q is as defined in entry F-015 of table F and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry F-015 of table F and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry F-015 of table F and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry F-015 of table F and $R^1$, $R^{5a}$, $R^{5b}$, $R^{5c}$ and X correspond in each case to a row of table D.

Table 16f: Compounds of formulae (Ia-1), (Ia-2) and (Ia-3), wherein Q is as defined in entry F-016 of table F and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry F-016 of table F and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry F-016 of table F and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry F-016 of table F and $R^1$, $R^{5a}$, $R^{5b}$, $R^{5c}$ and X correspond in each case to a row of table D.

Table 17f: Compounds of formulae (Ia-1), (Ia-2) and (Ia-3), wherein Q is as defined in entry F-017 of table F and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry F-017 of table F and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry F-017 of table F and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry F-017 of table F and $R^1$, $R^{5a}$, $R^{5b}$, $R^{5c}$ and X correspond in each case to a row of table D.

Table 18f: Compounds of formulae (Ia-1), (Ia-2) and (Ia-3), wherein Q is as defined in entry F-018 of table F and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry F-018 of table F and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry F-018 of table F and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry F-018 of table F and $R^1$, $R^{5a}$, $R^{5b}$, $R^{5c}$ and X correspond in each case to a row of table D.

Table 19f: Compounds of formulae (Ia-1), (Ia-2) and (Ia-3), wherein Q is as defined in entry F-019 of table F and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry F-019 of table F and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry F-019 of table F and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry F-019 of table F and $R^1$, $R^{5a}$, $R^{5b}$, $R^{5c}$ and X correspond in each case to a row of table D.

Table 20f: Compounds of formulae (Ia-1), (Ia-2) and (Ia-3), wherein Q is as defined in entry F-020 of table F and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry F-020 of table F and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry F-020 of table F and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry F-020 of table F and $R^1$, $R^{5a}$, $R^{5b}$, $R^{5c}$ and X correspond in each case to a row of table D.

Table 21f: Compounds of formulae (Ia-1), (Ia-2) and (Ia-3), wherein Q is as defined in entry F-021 of table F and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry F-021 of table F and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry F-021 of table F and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29)

and (Id-30), wherein Q is as defined in entry F-021 of table F and $R^1$, $R^{5a}$, $R^{5b}$, $R^{5c}$ and X correspond in each case to a row of table D.

Table 22f: Compounds of formulae (Ia-1), (Ia-2) and (Ia-3), wherein Q is as defined in entry F-022 of table F and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry F-022 of table F and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry F-022 of table F and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry F-022 of table F and $R^1$, $R^{5a}$, $R^{5b}$, $R^{5c}$ and X correspond in each case to a row of table D.

Table 23f: Compounds of formulae (Ia-1), (Ia-2) and (Ia-3), wherein Q is as defined in entry F-023 of table F and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry F-023 of table F and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry F-023 of table F and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry F-023 of table F and $R^1$, $R^{5a}$, $R^{5b}$, $R^{5c}$ and X correspond in each case to a row of table D.

Table 24f: Compounds of formulae (Ia-1), (Ia-2) and (Ia-3), wherein Q is as defined in entry F-024 of table F and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry F-024 of table F and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry F-024 of table F and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry F-024 of table F and $R^1$, $R^{5a}$, $R^{5b}$, $R^{5c}$ and X correspond in each case to a row of table D.

Table 25f: Compounds of formulae (Ia-1), (Ia-2) and (Ia-3), wherein Q is as defined in entry F-025 of table F and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry F-025 of table F and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry F-025 of table F and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry F-025 of table F and $R^1$, $R^{5a}$, $R^{5b}$, $R^{5c}$ and X correspond in each case to a row of table D.

Table 26f: Compounds of formulae (Ia-1), (Ia-2) and (Ia-3), wherein Q is as defined in entry F-026 of table F and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry F-026 of table F and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry F-026 of table F and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry F-026 of table F and $R^1$, $R^{5a}$, $R^{5b}$, $R^{5c}$ and X correspond in each case to a row of table D.

Table 27f: Compounds of formulae (Ia-1), (Ia-2) and (Ia-3), wherein Q is as defined in entry F-027 of table F and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry F-027 of table F and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry F-027 of table F and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry F-027 of table F and $R^1$, $R^{5a}$, $R^{5b}$, $R^{5c}$ and X correspond in each case to a row of table D.

Table 28f: Compounds of formulae (Ia-1), (Ia-2) and (Ia-3), wherein Q is as defined in entry F-028 of table F and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry F-028 of table F and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry F-028 of table F and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry F-028 of table F and $R^1$, $R^{5a}$, $R^{5b}$, $R^{5c}$ and X correspond in each case to a row of table D.

Table 29f: Compounds of formulae (Ia-1), (Ia-2) and (Ia-3), wherein Q is as defined in entry F-029 of table F and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry F-029 of table F and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry F-029 of table F and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry F-029 of table F and $R^1$, $R^{5a}$, $R^{5b}$, $R^{5c}$ and X correspond in each case to a row of table D.

Table 30f: Compounds of formulae (Ia-1), (Ia-2) and (Ia-3), wherein Q is as defined in entry F-030 of table F and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry F-030 of table F and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry F-030 of table F and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry F-030 of table F and $R^1$, $R^{5a}$, $R^{5b}$, $R^{5c}$ and X correspond in each case to a row of table D.

Table 31f: Compounds of formulae (Ia-1), (Ia-2) and (Ia-3), wherein Q is as defined in entry F-031 of table F and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry F-031 of table F and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry F-031 of table F and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry F-031 of table F and $R^1$, $R^{5a}$, $R^{5b}$, $R^{5c}$ and X correspond in each case to a row of table D.

Table 32f: Compounds of formulae (Ia-1), (Ia-2) and (Ia-3), wherein Q is as defined in entry F-032 of table F and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry F-032 of table F and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry F-032 of table F and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry F-032 of table F and $R^1$, $R^{5a}$, $R^{5b}$, $R^{5c}$ and X correspond in each case to a row of table D.

Table 33f: Compounds of formulae (Ia-1), (Ia-2) and (Ia-3), wherein Q is as defined in entry F-033 of table F and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry F-033 of table F and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry F-033 of table F and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry F-033 of table F and $R^1$, $R^{5a}$, $R^{5b}$, $R^{5c}$ and X correspond in each case to a row of table D.

Table 34f: Compounds of formulae (Ia-1), (Ia-2) and (Ia-3), wherein Q is as defined in entry F-034 of table F and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry F-034 of table F and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry F-034 of table F and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry F-034 of table F and $R^1$, $R^{5a}$, $R^{5b}$, $R^{5c}$ and X correspond in each case to a row of table D.

Table 35f: Compounds of formulae (Ia-1), (Ia-2) and (Ia-3), wherein Q is as defined in entry F-035 of table F and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry F-035 of table F and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry F-035 of table F and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry F-035 of table F and $R^1$, $R^{5a}$, $R^{5b}$, $R^{5c}$ and X correspond in each case to a row of table D.

Table 36f: Compounds of formulae (Ia-1), (Ia-2) and (Ia-3), wherein Q is as defined in entry F-036 of table F and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry F-036 of table F and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry F-036 of table F and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry F-036 of table F and $R^1$, $R^{5a}$, $R^{5b}$, $R^{5c}$ and X correspond in each case to a row of table D.

Table 37f: Compounds of formulae (Ia-1), (Ia-2) and (Ia-3), wherein Q is as defined in entry F-037 of table F and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry F-037 of table F and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry F-037 of table F and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry F-037 of table F and $R^1$, $R^{5a}$, $R^{5b}$, $R^{5c}$ and X correspond in each case to a row of table D.

Table 38f: Compounds of formulae (Ia-1), (Ia-2) and (Ia-3), wherein Q is as defined in entry F-038 of table F and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry F-038 of table F and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry F-038 of table F and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry F-038 of table F and $R^1$, $R^{5a}$, $R^{5b}$, $R^{5c}$ and X correspond in each case to a row of table D.

Table 39f: Compounds of formulae (Ia-1), (Ia-2) and (Ia-3), wherein Q is as defined in entry F-039 of table F and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry F-039 of table F and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry F-039 of table F and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry F-039 of table F and $R^1$, $R^{5a}$, $R^{5b}$, $R^{5c}$ and X correspond in each case to a row of table D.

Table 40f: Compounds of formulae (Ia-1), (Ia-2) and (Ia-3), wherein Q is as defined in entry F-040 of table F and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry F-040 of table F and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry F-040 of table F and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry F-040 of table F and $R^1$, $R^{5a}$, $R^{5b}$, $R^{5c}$ and X correspond in each case to a row of table D.

Table 41f: Compounds of formulae (Ia-1), (Ia-2) and (Ia-3), wherein Q is as defined in entry F-041 of table F and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry F-041 of table F and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry F-041 of table F and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry F-041 of table F and $R^1$, $R^{5a}$, $R^{5b}$, $R^{5c}$ and X correspond in each case to a row of table D.

Table 42f: Compounds of formulae (Ia-1), (Ia-2) and (Ia-3), wherein Q is as defined in entry F-042 of table F and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry F-042 of table F and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry F-042 of table F and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry F-042 of table F and $R^1$, $R^{5a}$, $R^{5b}$, $R^{5c}$ and X correspond in each case to a row of table D.

Table 43f: Compounds of formulae (Ia-1), (Ia-2) and (Ia-3), wherein Q is as defined in entry F-043 of table F and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry F-043 of table F and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry F-043 of table F and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry F-043 of table F and $R^1$, $R^{5a}$, $R^{5b}$, $R^{5c}$ and X correspond in each case to a row of table D.

Table 44f: Compounds of formulae (Ia-1), (Ia-2) and (Ia-3), wherein Q is as defined in entry F-044 of table F and $R^1$, $R^5$ and X correspond in each case to a row of table A;

compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry F-044 of table F and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry F-044 of table F and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry F-044 of table F and $R^1$, $R^{5a}$, $R^{5b}$, $R^{5c}$ and X correspond in each case to a row of table D.

Table 45f: Compounds of formulae (Ia-1), (Ia-2) and (Ia-3), wherein Q is as defined in entry F-045 of table F and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry F-045 of table F and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry F-045 of table F and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry F-045 of table F and $R^1$, $R^{5a}$, $R^{5b}$, $R^{5c}$ and X correspond in each case to a row of table D.

Table 46f: Compounds of formulae (Ia-1), (Ia-2) and (Ia-3), wherein Q is as defined in entry F-046 of table F and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry F-046 of table F and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry F-046 of table F and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry F-046 of table F and $R^1$, $R^{5a}$, $R^{5b}$, $R^{5c}$ and X correspond in each case to a row of table D.

Table 47f: Compounds of formulae (Ia-1), (Ia-2) and (Ia-3), wherein Q is as defined in entry F-047 of table F and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry F-047 of table F and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry F-047 of table F and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry F-047 of table F and $R^1$, $R^{5a}$, $R^{5b}$, $R^{5c}$ and X correspond in each case to a row of table D.

Table 48f: Compounds of formulae (Ia-1), (Ia-2) and (Ia-3), wherein Q is as defined in entry F-048 of table F and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry F-048 of table F and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry F-048 of table F and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry F-048 of table F and $R^1$, $R^{5a}$, $R^{5b}$, $R^{5c}$ and X correspond in each case to a row of table D.

Table 49f: Compounds of formulae (Ia-1), (Ia-2) and (Ia-3), wherein Q is as defined in entry F-049 of table F and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry F-049 of table F and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry F-049 of table F and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry F-049 of table F and $R^1$, $R^{5a}$, $R^{5b}$, $R^{5c}$ and X correspond in each case to a row of table D.

Table 50f: Compounds of formulae (Ia-1), (Ia-2) and (Ia-3), wherein Q is as defined in entry F-050 of table F and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry F-050 of table F and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry F-050 of table F and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry F-050 of table F and $R^1$, $R^{5a}$, $R^{5b}$, $R^{5c}$ and X correspond in each case to a row of table D.

Table 51f: Compounds of formulae (Ia-1), (Ia-2) and (Ia-3), wherein Q is as defined in entry F-051 of table F and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry F-051 of table F and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry F-051 of table F and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry F-051 of table F and $R^1$, $R^{5a}$, $R^{5b}$, $R^{5c}$ and X correspond in each case to a row of table D.

Table 52f: Compounds of formulae (Ia-1), (Ia-2) and (Ia-3), wherein Q is as defined in entry F-052 of table F and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry F-052 of table F and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry F-052 of table F and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry F-052 of table F and $R^1$, $R^{5a}$, $R^{5b}$, $R^{5c}$ and X correspond in each case to a row of table D.

Table 53f: Compounds of formulae (Ia-1), (Ia-2) and (Ia-3), wherein Q is as defined in entry F-053 of table F and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry F-053 of table F and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry F-053 of table F and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry F-053 of table F and $R^1$, $R^{5a}$, $R^{5b}$, $R^{5c}$ and X correspond in each case to a row of table D.

Table 54f: Compounds of formulae (Ia-1), (Ia-2) and (Ia-3), wherein Q is as defined in entry F-054 of table F and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry F-054 of table F and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry F-054 of table F and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry F-054 of table F and $R^1$, $R^{5a}$, $R^{5b}$, $R^{5c}$ and X correspond in each case to a row of table D.

Table 55f: Compounds of formulae (Ia-1), (Ia-2) and (Ia-3), wherein Q is as defined in entry F-055 of table F and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry F-055 of table F and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry F-055 of table F and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry F-055 of table F and $R^1$, $R^{5a}$, $R^{5b}$, $R^{5c}$ and X correspond in each case to a row of table D.

Table 56f: Compounds of formulae (Ia-1), (Ia-2) and (Ia-3), wherein Q is as defined in entry F-056 of table F and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry F-056 of table F and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry F-056 of table F and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry F-056 of table F and $R^1$, $R^{5a}$, $R^{5b}$, $R^{5c}$ and X correspond in each case to a row of table D.

Table 57f: Compounds of formulae (Ia-1), (Ia-2) and (Ia-3), wherein Q is as defined in entry F-057 of table F and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry F-057 of table F and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry F-057 of table F and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry F-057 of table F and $R^1$, $R^{5a}$, $R^{5b}$, $R^{5c}$ and X correspond in each case to a row of table D.

Table 58f: Compounds of formulae (Ia-1), (Ia-2) and (Ia-3), wherein Q is as defined in entry F-058 of table F and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry F-058 of table F and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry F-058 of table F and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry F-058 of table F and $R^1$, $R^{5a}$, $R^{5b}$, $R^{5c}$ and X correspond in each case to a row of table D.

Table 59f: Compounds of formulae (Ia-1), (Ia-2) and (Ia-3), wherein Q is as defined in entry F-059 of table F and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry F-059 of table F and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry F-059 of table F and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry F-059 of table F and $R^1$, $R^{5a}$, $R^{5b}$, $R^{5c}$ and X correspond in each case to a row of table D.

Table 60f: Compounds of formulae (Ia-1), (Ia-2) and (Ia-3), wherein Q is as defined in entry F-060 of table F and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry F-060 of table F and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry F-060 of table F and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry F-060 of table F and $R^1$, $R^{5a}$, $R^{5b}$, $R^{5c}$ and X correspond in each case to a row of table D.

Table 61f: Compounds of formulae (Ia-1), (Ia-2) and (Ia-3), wherein Q is as defined in entry F-061 of table F and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry F-061 of table F and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry F-061 of table F and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry F-061 of table F and $R^1$, $R^{5a}$, $R^{5b}$, $R^{5c}$ and X correspond in each case to a row of table D.

Table 62f: Compounds of formulae (Ia-1), (Ia-2) and (Ia-3), wherein Q is as defined in entry F-062 of table F and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry F-062 of table F and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry F-062 of table F and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry F-062 of table F and $R^1$, $R^{5a}$, $R^{5b}$, $R^{5c}$ and X correspond in each case to a row of table D.

Table 63f: Compounds of formulae (Ia-1), (Ia-2) and (Ia-3), wherein Q is as defined in entry F-063 of table F and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry F-063 of table F and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry F-063 of table F and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry F-063 of table F and $R^1$, $R^{5a}$, $R^{5b}$, $R^{5c}$ and X correspond in each case to a row of table D.

Table 64f: Compounds of formulae (Ia-1), (Ia-2) and (Ia-3), wherein Q is as defined in entry F-064 of table F and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry F-064 of table F and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry F-064 of table F and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry F-064 of table F and $R^1$, $R^{5a}$, $R^{5b}$, $R^{5c}$ and X correspond in each case to a row of table D.

Table 65f: Compounds of formulae (Ia-1), (Ia-2) and (Ia-3), wherein Q is as defined in entry F-065 of table F and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry F-065 of table F and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry F-065 of table F and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry F-065 of table F and $R^1$, $R^{5a}$, $R^{5b}$, $R^{5c}$ and X correspond in each case to a row of table D.

Table 66f: Compounds of formulae (Ia-1), (Ia-2) and (Ia-3), wherein Q is as defined in entry F-066 of table F and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry F-066 of table F and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry F-066 of table F and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry F-066 of table F and $R^1$, $R^{5a}$, $R^{5b}$, $R^{5c}$ and X correspond in each case to a row of table D.

Table 67f: Compounds of formulae (Ia-1), (Ia-2) and (Ia-3), wherein Q is as defined in entry F-067 of table F and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry F-067 of table F and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry F-067 of table F and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry F-067 of table F and $R^1$, $R^{5a}$, $R^{5b}$, $R^{5c}$ and X correspond in each case to a row of table D.

Table 68f: Compounds of formulae (Ia-1), (Ia-2) and (Ia-3), wherein Q is as defined in entry F-068 of table F and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry F-068 of table F and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry F-068 of table F and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry F-068 of table F and $R^1$, $R^{5a}$, $R^{5b}$, $R^{5c}$ and X correspond in each case to a row of table D.

Table 69f: Compounds of formulae (Ia-1), (Ia-2) and (Ia-3), wherein Q is as defined in entry F-069 of table F and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry F-069 of table F and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry F-069 of table F and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry F-069 of table F and $R^1$, $R^{5a}$, $R^{5b}$, $R^{5c}$ and X correspond in each case to a row of table D.

Table 70f: Compounds of formulae (Ia-1), (Ia-2) and (Ia-3), wherein Q is as defined in entry F-070 of table F and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry F-070 of table F and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry F-070 of table F and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry F-070 of table F and $R^1$, $R^{5a}$, $R^{5b}$, $R^{5c}$ and X correspond in each case to a row of table D.

Table 71f: Compounds of formulae (Ia-1), (Ia-2) and (Ia-3), wherein Q is as defined in entry F-071 of table F and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry F-071 of table F and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry F-071 of table F and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry F-071 of table F and $R^1$, $R^{5a}$, $R^{5b}$, $R^{5c}$ and X correspond in each case to a row of table D.

Table 72f: Compounds of formulae (Ia-1), (Ia-2) and (Ia-3), wherein Q is as defined in entry F-072 of table F and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry F-072 of table F and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry F-072 of table F and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry F-072 of table F and $R^1$, $R^{5a}$, $R^{5b}$, $R^{5c}$ and X correspond in each case to a row of table D.

Table 73f: Compounds of formulae (Ia-1), (Ia-2) and (Ia-3), wherein Q is as defined in entry F-073 of table F and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry F-073 of table F and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry F-073 of table F and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29)

and (Id-30), wherein Q is as defined in entry F-073 of table F and $R^1$, $R^{5a}$, $R^{5b}$, $R^{5c}$ and X correspond in each case to a row of table D.

Table 74f: Compounds of formulae (Ia-1), (Ia-2) and (Ia-3), wherein Q is as defined in entry F-074 of table F and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry F-074 of table F and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry F-074 of table F and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry F-074 of table F and $R^1$, $R^{5a}$, $R^{5b}$, $R^{5c}$ and X correspond in each case to a row of table D.

Table 75f: Compounds of formulae (Ia-1), (Ia-2) and (Ia-3), wherein Q is as defined in entry F-075 of table F and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry F-075 of table F and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry F-075 of table F and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry F-075 of table F and $R^1$, $R^{5a}$, $R^{5b}$, $R^{5c}$ and X correspond in each case to a row of table D.

Table 76f: Compounds of formulae (Ia-1), (Ia-2) and (Ia-3), wherein Q is as defined in entry F-076 of table F and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry F-076 of table F and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry F-076 of table F and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry F-076 of table F and $R^1$, $R^{5a}$, $R^{5b}$, $R^{5c}$ and X correspond in each case to a row of table D.

Table 77f: Compounds of formulae (Ia-1), (Ia-2) and (Ia-3), wherein Q is as defined in entry F-077 of table F and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry F-077 of table F and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry F-077 of table F and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry F-077 of table F and $R^1$, $R^{5a}$, $R^{5b}$, $R^{5c}$ and X correspond in each case to a row of table D.

Table 78f: Compounds of formulae (Ia-1), (Ia-2) and (Ia-3), wherein Q is as defined in entry F-078 of table F and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry F-078 of table F and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry F-078 of table F and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry F-078 of table F and $R^1$, $R^{5a}$, $R^{5b}$, $R^{5c}$ and X correspond in each case to a row of table D.

Table 79f: Compounds of formulae (Ia-1), (Ia-2) and (Ia-3), wherein Q is as defined in entry F-079 of table F and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry F-079 of table F and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry F-079 of table F and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry F-079 of table F and $R^1$, $R^{5a}$, $R^{5b}$, $R^{5c}$ and X correspond in each case to a row of table D.

Table 80f: Compounds of formulae (Ia-1), (Ia-2) and (Ia-3), wherein Q is as defined in entry F-080 of table F and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry F-080 of table F and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry F-080 of table F and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry F-080 of table F and $R^1$, $R^{5a}$, $R^{5b}$, $R^{5c}$ and X correspond in each case to a row of table D.

Table 81f: Compounds of formulae (Ia-1), (Ia-2) and (Ia-3), wherein Q is as defined in entry F-081 of table F and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry F-081 of table F and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry F-081 of table F and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry F-081 of table F and $R^1$, $R^{5a}$, $R^{5b}$, $R^{5c}$ and X correspond in each case to a row of table D.

Table 82f: Compounds of formulae (Ia-1), (Ia-2) and (Ia-3), wherein Q is as defined in entry F-082 of table F and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry F-082 of table F and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry F-082 of table F and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry F-082 of table F and $R^1$, $R^{5a}$, $R^{5b}$, $R^{5c}$ and X correspond in each case to a row of table D.

Table 83f: Compounds of formulae (Ia-1), (Ia-2) and (Ia-3), wherein Q is as defined in entry F-083 of table F and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry F-083 of table F and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry F-083 of table F and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry F-083 of table F and $R^1$, $R^{5a}$, $R^{5b}$, $R^{5c}$ and X correspond in each case to a row of table D.

Table 84f: Compounds of formulae (Ia-1), (Ia-2) and (Ia-3), wherein Q is as defined in entry F-084 of table F and $R^1$, $R^5$ and X correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry F-084 of table F and $R^1$, $R^5$ and X correspond in each case to a row of table B; compounds of formulae (Ic-1), (Ic-2), (Ic-3), (Ic-4), (Ic-5), (Ic-6), (Ic-7), (Ic-8) and (Ic-9), wherein Q is as defined in entry F-084 of table F and $R^1$, $R^{5a}$, $R^{5b}$ and X correspond in each case to a row of table C; and compounds of formulae (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), (Id-21), (Id-22), (Id-23), (Id-24), (Id-25), (Id-26), (Id-27), (Id-28), (Id-29) and (Id-30), wherein Q is as defined in entry F-084 of table F and $R^1$, $R^{5a}$, $R^{5b}$, $R^{5c}$ and X correspond in each case to a row of table D.

Preparation Methods

The compounds of formula (I) according to the present invention can be prepared e.g. according to preparation methods and preparation schemes described below.

In the following schemes and methods, if not otherwise specified, the definition of the substituents, variables and indices in the formulae used correspond to the definitions given for formula (I) above.

Compounds of formula (I) can be prepared as shown in Scheme A below.

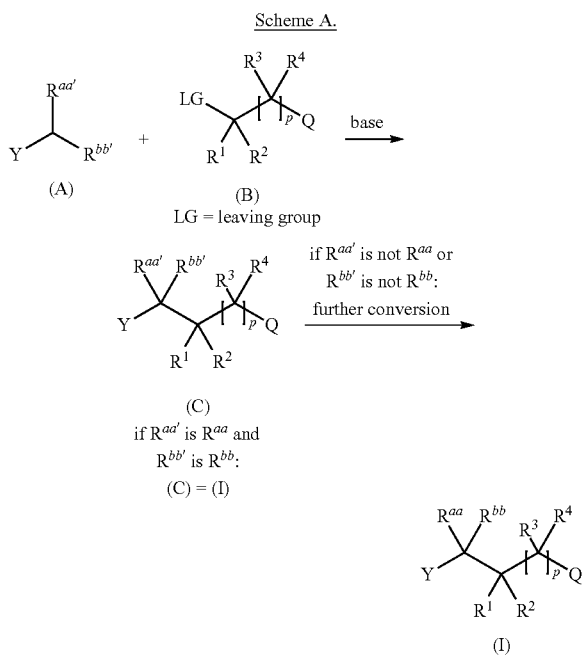

Compounds of formula (A) are reacted with compounds of formula (B) in the presence of a suitable base to give compounds of formula (C). A representative procedure is described in e.g. M. M. Meyers, J. Sun, K. E. Carlson, G. A. Marriner, B. S. Katzenellenbogen, J. A. Katzenellenbogen, J. Med. Chem. 2001, 44, 4230-4251. A further procedure is described in WO 2012/020130.

In the compounds of formula (C) $R^{aa'}$ is $R^{aa}$ or a precursor of $R^{aa}$, and $R^{bb'}$ is $R^{bb}$ or a precursor of $R^{bb}$. Compounds of formula (C) wherein $R^{aa'}$ is $R^{aa}$, and wherein $R^{bb'}$ is $R^{bb}$ correspond to compounds of formula (I). Compounds of formula (C) wherein $R^{aa'}$ is not $R^{aa}$, or wherein $R^{bb'}$ is not $R^{bb}$ represent synthetic intermediates, which can be further converted to compounds of formula (I).

A suitable precursor of $R^{aa}$ is, for example, —C(=O)O($C_1$-$C_4$-alkyl), preferably —C(=O)O($C_1$-$C_2$-alkyl), such as —C(=O)OMe or —C(=O)OEt, more preferably —C(=O)O($C_1$-alkyl). A suitable precursor of $R^{bb}$ is, for example, —C(=O)O($C_1$-$C_4$-alkyl), preferably —C(=O)O($C_1$-$C_2$-alkyl), such as —C(=O)OMe or —C(=O)OEt, more preferably —C(=O)O($C_1$-alkyl).

Compounds of formula (I) are preferably prepared from compounds of formula (C) wherein $R^{aa'}$ is a precursor of $R^{aa}$, for example, —C(=O)O($C_1$-$C_4$-alkyl), preferably —C(=O)O($C_1$-$C_2$-alkyl), such as —C(=O)OMe or —C(=O)OEt, more preferably —C(=O)O($C_1$-alkyl).

Compounds of formula (I) wherein $R^{bb}$ is CN are generally prepared from compounds of formula (C) wherein $R^{bb'}$ is CN, i.e. from compounds of formula (C) wherein $R^{bb'}$ is $R^{bb}$.

Compounds of formula (I) wherein $R^{bb}$ is not CN are preferably prepared from compounds of formula (C) wherein $R^{bb'}$ is a precursor of $R^{bb}$, for example, —C(=O)O($C_1$-$C_4$-alkyl), preferably —C(=O)O($C_1$-$C_2$-alkyl), such as —C(=O)OMe or —C(=O)OEt, more preferably —C(=O)O($C_1$-alkyl).

Compounds of formula (I) wherein $R^{aa}$ is —C(=O)N($R^{ff}$)$_2$ and wherein $R^{bb}$ is CN can, for example, be prepared from compounds of formula (C) wherein $R^{aa'}$ is —C(=O)O($C_1$-$C_4$-alkyl), preferably —C(=O)O($C_1$-$C_2$-alkyl), more preferably —C(=O)O($C_1$-alkyl), and wherein $R^{bb'}$ is CN by treatment with a suitable amine, NH($R^{ff}$)$_2$. In a particular embodiment of the invention, where $R^{ff}$ is H, the amine is $NH_3$.

Likewise, compounds of formula (I) wherein $R^{aa}$ and $R^{bb}$ are —C(=O)N($R^{ff}$)$_2$ can, for example, be prepared from compounds of formula (C) wherein $R^{aa'}$ and $R^{bb'}$ are —C(=O)O($C_1$-$C_4$-alkyl), preferably —C(=O)O($C_1$-$C_2$-alkyl), more preferably —C(=O)O($C_1$-alkyl), by treatment with a suitable amine, NH($R^{ff}$)$_2$. In a particular embodiment of the invention, where $R^{ff}$ is H, the amine is $NH_3$.

Compounds of formula (I) wherein $R^{aa}$ is —C(=S)N($R^{cc}$)$_2$ and wherein $R^{bb}$ is CN can, for example, be prepared from compounds of formula (C) wherein $R^{aa'}$ is —C(=O)O($C_1$-$C_4$-alkyl), preferably —C(=O)O($C_1$-$C_2$-alkyl), more preferably —C(=O)O($C_1$-alkyl), and wherein $R^{bb'}$ is CN by treatment with a suitable amine, NH($R^{cc}$)$_2$, followed by treatment of the resulting amide with e.g. $P_4S_{10}$ or Lawesson's reagent to obtain the corresponding thioamide. In a particular embodiment of the invention, where $R^C$ is H, the amine is $NH_3$.

Likewise, compounds of formula (I) wherein $R^{aa}$ and $R^{bb}$ are —C(=S)N($R^{cc}$)$_2$ can, for example, be prepared from compounds of formula (C) wherein $R^{aa'}$ and $R^{bb'}$ are —C(=O)O($C_1$-$C_4$-alkyl), preferably —C(=O)O($C_1$-$C_2$-alkyl), more preferably —C(=O)O($C_1$-alkyl), by treatment with a suitable amine, NH($R^{cc}$)$_2$, followed by treatment of the resulting amide with e.g. $P_4S_{10}$ or Lawesson's reagent to obtain the corresponding thioamide. In a particular embodiment of the invention, where $R^{cc}$ is H, the amine is $NH_3$.

Suitable functional group interconversions are described in e.g. WO 2003/99276; U.S. Pat. Nos. 4,740,228; 4,304,930; Journal of the American Chemical Society 1937, vol. 59, p. 1901; Synthesis 2004, p. 2625-2628; US 2011/183960; WO 2008/110488; Journal of Medicinal Chemistry 1994, vol. 37, p. 371-380; N. N. Dykhanov, Zhurnal Prikladnoi Khimii (Sankt Petersburg, Russian Federation) 1961, 34, p. 1588-91.

Compounds of formula (I) wherein $R^{aa}$ and/or $R^{bb}$ is —C(=$NR^{dd}$)$SR^{ee}$ can, for example, be prepared from the corresponding thioamides by treatment with an alkylating agent.

Compounds of formula (A) can be prepared by treatment of iodine compound A-1 with compound A-2 (Scheme B) as described in various publications. For example, this can be achieved in the presence of a base and a suitable palladium catalyst system as described in e.g. J. M. Atkins, S. A. Moteki, S. G. DiMagno, J. M. Takacs, Org. Lett. 2006, 13, 2759-2762. Alternatively, the reaction can also be carried out via copper catalysis in the presence of a base as described in e.g. M. Makosza, A. Chesnokov, Tetrahedron 2008, 64, 5925-5932. A further procedure is described in K. Okuro, M. Furuune, M. Miura, M. Nomura, Journal of Organic Chemistry 1993, 58(26), 7606-7.

Scheme B.

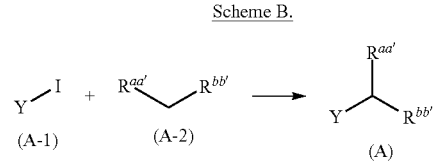

Compounds of formula (B) with p=0 like e.g. (B-5) in Scheme C that require a leaving group "LG" e.g. halogens or mesylates can be obtained starting from the respective halogenated compounds (B-1) as depicted below.

Scheme C.

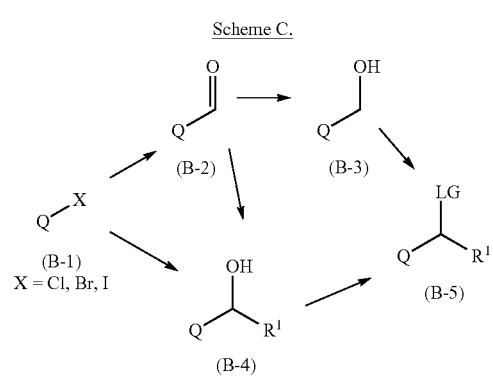

Reacting compounds of formula (B-1) with a lithium base followed by subsequent addition of DMF as described in e.g. WO 2012/058116 thus yields compounds of formula (B-2) which after reduction with e.g. a hydride reagent such as sodium borohydride yield (B-3) as described e.g. in WO 2012/022681.

Alternatively, compounds of formula (B-1) can also be treated with aldehydes e.g. acetaldehyde after reaction with a lithium base to directly yield compounds of formula (B-4) as described in e.g. Y. Zhang, J. P. Burgess, M. Brackeen, A. Gilliam, S. W. Mascarella, K. Page, H. H. Seltzman, B. F. Thomas, J. Med. Chem. 2008, 51, 3526-3539. Furthermore, various nucleophiles can be reacted with intermediates of formula (B-2) to yield mono- or disubstituted alcohols of formula (B-4) as described in e.g. J. A. Malona, K. Cariou, W. T. Spencer III, A. J. Frontier, J. Org. Chem. 2012, 77, 1891-1908.

Compounds of formula (B-3) or (B-4) can be converted into compounds of formula (B-5) by means of activating the hydroxyl group e.g. via mesylation or tosylation as described in WO 2012/085645. Alternatively, they can be treated with phosphortribromide to convert the hydroxyl group into the respective bromide as described in WO 2012/022487.

Compounds of formula (B) with p=1 like e.g. (B-6), (B-11), (B-12) or (B15) can be obtained starting from the respective carboxylic acid derivatives of formula (B-7), (B-9) or (B-13) as depicted in Schemes D to F.

α-Alkylation can be employed to introduce $R^3$ and $R^4$ substituents as described in e.g. WO 2012/058134. Substituents $R^1$ and $R^2$ can be introduced, for example, by treatment of compounds of formula (B-8), (B-9), (B-10) or (B-14) with e.g. hydride reagents or Grignard reagents as described in e.g. A. K. Ghosh, C. D. Martyr, C.-X. Xu, Org. Lett. 2012, 14, 2002-2005.

Scheme D.

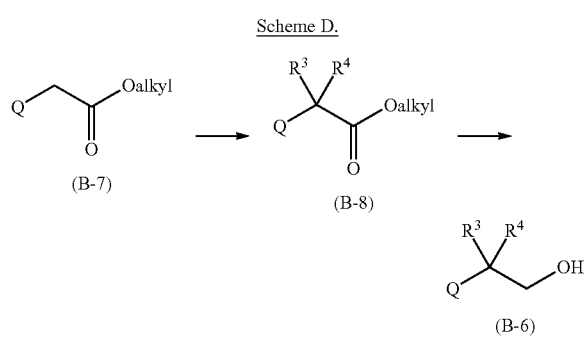

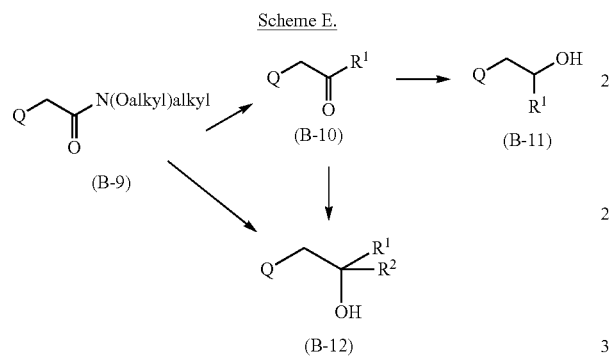

Scheme F.

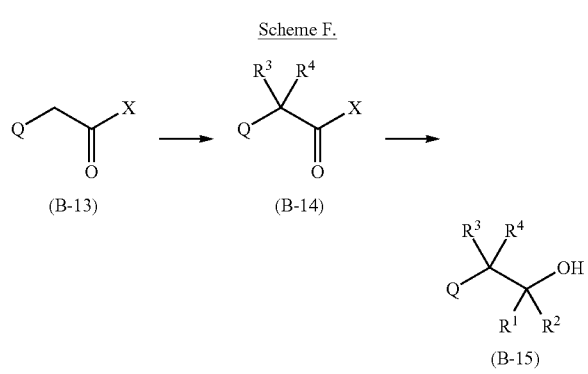

X = Oalkyl, N(Oalkyl)alkyl

The alcohols of formula (B-6), (B-11), (B-12) or (B15) can be further activated by similar methods as described above.

Iodo compounds of formula (A-1), chloro, bromo or iodo compounds of formula (B-1) as well as carboxylic acid derivatives needed for compounds of formula (B-7), (B-9) or (B-13) can be purchased or synthesized according to known literature methods.

As a rule, the compounds of formula (I) can be prepared by the methods described above. If individual compounds cannot be prepared via the above-described routes, they can be prepared by derivatization of other compounds (I) or by customary modifications of the synthesis routes described. For example, in individual cases, certain compounds (I) can advantageously be prepared from other compounds (I) by ester hydrolysis, amidation, esterification, ether cleavage, olefination, reduction, oxidation and the like.

The reaction mixtures are worked up in the customary manner, for example by mixing with water, separating the phases, and, if appropriate, purifying the crude products by chromatography, for example on alumina or silica gel. Some of the intermediates and end products may be obtained in the form of colorless or pale brown viscous oils, which are freed or purified from volatile components under reduced pressure and at moderately elevated temperature. If the intermediates and end products are obtained as solids, they may be purified by recrystallization or trituration with an appropriate solvent.

In a particularly preferred embodiment, where $R^{aa}$ is —C(=S)NH$_2$ or —C(=O)NH$_2$ and where $R^{bb}$ is CN, the compounds of formula (I) can, for example, be prepared according to the sequence illustrated in Scheme G.

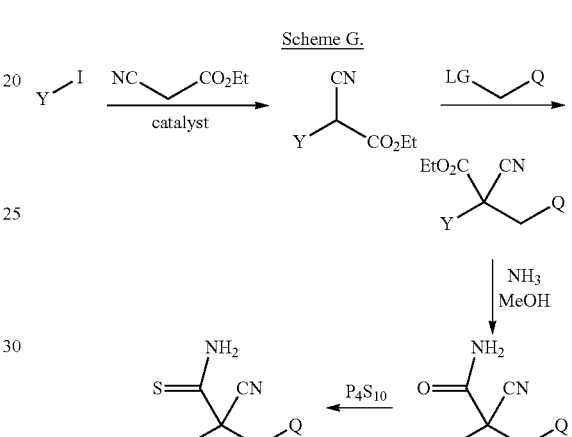

In a particularly preferred embodiment, where $R^{aa}$ and $R^{bb}$ are —C(=S)NH$_2$ or where $R^{aa}$ and $R^{bb}$ are —C(=O)NH$_2$, the compounds of formula (I) can, for example, be prepared according to the sequence illustrated in Scheme H.

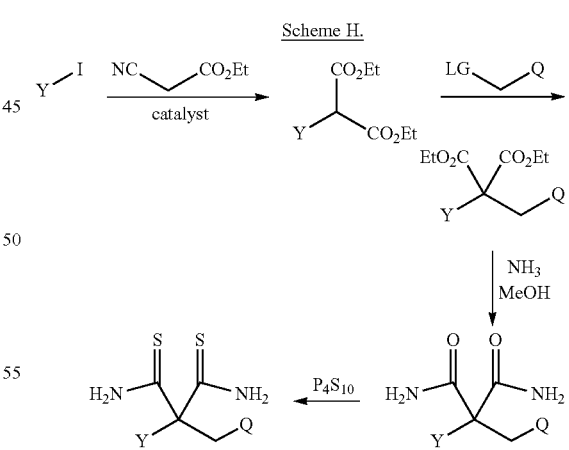

Compounds of formula (I) wherein $R^{aa}$ is —C(=S)NH$_2$ and wherein $R^{bb}$ is —C(=S)NH$_2$ or CN can, for example, be prepared from the corresponding dinitrile compounds by treatment with H$_2$S as illustrated in Scheme J. The reaction is preferably carried out in the presence of a base. Preferred bases include triethylamine, trimethylamine, N-ethyldiisopropylamine, triisopropylamine, ammonia, pyridine, lutidine, collidine, 4-(dimethylamino)pyridine (DMAP), imidazole, 1,8-diazabicyclo[5.4.0]undec-7-ene (DBU) or 1,5-diazabicyclo[4.3.0]non-5-ene (DBN). The reaction is preferably carried out in a solvent. Preferred solvents include dimethylformamide, dimethylacetamide, sulfolane, N-methylpyrrolidinone, 1,3-dimethylimazolidinone, dimethyl sulfoxide, water, dichloromethane, toluene, benzene, dioxane or mixtures thereof. $H_2S$ can be used as a gas. Alternatively, $H_2S$ can be used as a solution.

Scheme J.

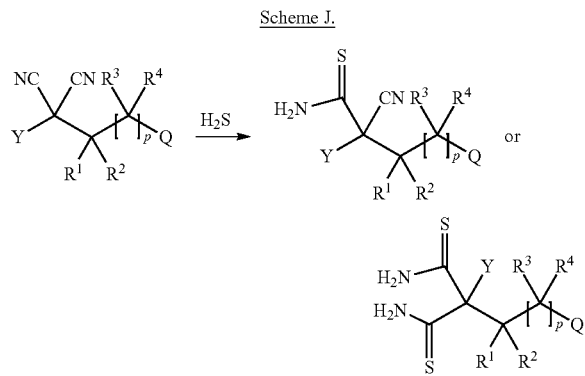

In yet a further aspect of the invention there is provided a method for preparing a compound of formula (I) according to any one of claims 1 to 20, 31 to 35 or a salt thereof, wherein $R^{aa}$ is $—C(=O)N(R^{ff})_2$; and $R^{bb}$ is $—C(=O)N(R^{ff})_2$ or CN; or wherein $R^{aa}$ is $—C(=S)N(R^{cc})_2$; and $R^{bb}$ is $—C(=S)N(R^{cc})_2$ or CN;
comprising the steps of
(i) reacting a compound of formula (XI),

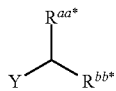 (XI)

wherein Y is defined as in formula (I);
$R^{aa*}$ is $—C(=O)O(C_1-C_4\text{-alkyl})$, preferably $—C(=O)O(C_1-C_2\text{-alkyl})$, more preferably $—C(=O)O(C_1\text{-alkyl})$;
$R^{bb*}$ is $—C(=O)O(C_1-C_4\text{-alkyl})$ or CN, preferably $—C(=O)O(C_1-C_2\text{-alkyl})$ or CN, more preferably $—C(=O)O(C_1\text{-alkyl})$ or CN,
provided that $R^{bb*}$ is CN when $R^{bb}$ is CN;
with a compound of formula (XII),

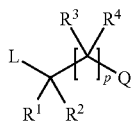 (XII)

wherein $R^1$, $R^2$, $R^3$, $R^4$, Q and p are defined as in formula (I);
L is a leaving group;
optionally in the presence of a base, to obtain a compound of formula (XIII),

 (XIII)

wherein $R^1$, $R^2$, $R^3$, $R^4$, Y, Q and p are defined as in formula (I);
$R^{aa*}$ and $R^{bb*}$ are defined as in formula (XI);
(ii) reacting the compound of formula (XIII) with an amine of formula (XIV), $NH(R^{xx})_2$ (XIV)

wherein $R^{xx}$ is $R^{cc}$ or $R^{ff}$ as defined in formula (I);
to obtain
a compound of formula (I), wherein $R^{aa}$ is $—C(=O)N(R^{ff})_2$; and $R^{bb}$ is $—C(=O)N(R^{ff})_2$ or CN;
or
a compound of formula (XV),

 (XV)

wherein $R^1$, $R^2$, $R^3$, $R^4$, Y, Q and p are defined as in formula (I);
$R^{aa**}$ is $—C(=O)N(R^{cc})_2$;
$R^{bb**}$ is $—C(=O)N(R^{cc})_2$ or CN,
wherein $R^{cc}$ is defined as in formula (I);
(iii) converting the compound of formula (XV) to a compound of formula (I), wherein $R^{aa}$ is $—C(=S)N(R)_2$; and $R^{bb}$ is $—C(=S)N(R^{cc})_2$ or CN.

In one embodiment the reaction of the compound of formula (XI) with the compound of formula (XII) is carried out in the absence of a base.

In a preferred embodiment the reaction of the compound of formula (XI) with the compound of formula (XII) is carried out in the presence of a base.

Preferred, more preferred, even more preferred and particularly preferred compounds of formula (XI) are the ones leading to the respective preferred, more preferred, even more preferred and particularly preferred compounds of formula (I).

Preferred, more preferred, even more preferred and particularly preferred compounds of formula (XII) are the ones leading to the respective preferred, more preferred, even more preferred and particularly preferred compounds of formula (I).

Preferred, more preferred, even more preferred and particularly preferred amines of formula (XIV) are the ones leading to the respective preferred, more preferred, even more preferred and particularly preferred compounds of formula (I). In a particular preferred embodiment the amine of formula (XIV) is $NH_3$.

Preference is given to compounds of formula (XII) wherein
L is halogen or $OS(O)_2R^\#$; and
$R^\#$ is $C_1-C_6$-alkyl, $C_1-C_6$-haloalkyl, $C_1-C_6$-nitroalkyl, $C_1-C_6$-alkoxy-$C_1-C_6$-alkyl, $C_3-C_6$-cycloalkyl, phenyl or phenyl-$C_1-C_6$-alkyl, wherein each phenyl is independently unsubstituted or substituted with up to 5 substituents selected from halogen, CN, $NO_2$, $C_1$-$C_6$-alkyl, $C_1$-$C_6$-haloalkyl or $C_1$-$C_6$-alkoxy.

Particular preference is given to compounds of formula (XII) wherein

L is Cl, Br, I or $OS(O)_2R^\#$; and $R^\#$ is $C_1$-$C_6$-alkyl, $C_1$-$C_6$-haloalkyl or phenyl, wherein phenyl is unsubstituted or substituted with up to 5 substituents selected from halogen, $NO_2$, $C_1$-$C_6$-alkyl or $C_1$-$C_6$-alkoxy.

Very particular preference is given to compounds of formula (XII) wherein

L is Cl, Br or $OS(O)_2R^*$; and $R^\#$ is Me, $CF_3$, $C_4F_9$, phenyl or toluyl.

The molar ratio of the compound of formula (XI) to the compound of formula (XII) is generally in the range of 1:0.5-2, preferably in the range of 1:0.5-1.5, more preferably in the range of 1:0.8-1.2.

Examples of suitable bases are carbonates such as lithium carbonate, sodium carbonate, potassium carbonate, cesium carbonate, magnesium carbonate, calcium carbonate, barium carbonate; hydrogen carbonates such as lithium hydrogen carbonate, sodium hydrogen carbonate, potassium hydrogen carbonate; hydroxides such as lithium hydroxide, sodium hydroxide, potassium hydroxide, magnesium hydroxide, calcium hydroxide, barium hydroxide, aluminum hydroxide; oxides such as lithium oxide, sodium oxide, potassium oxide, magnesium oxide, calcium oxide, barium oxide, iron oxide, silver oxide; hydrides such as lithium hydride, sodium hydride, potassium hydride, calcium hydride; phosphates such as potassium phosphate, calcium phosphate; alkoxides such sodium, potassium or magnesium alkoxides; nitrogen-containing bases such as triethylamine, trimethylamine, N-ethyldiisopropylamine, triisopropylamine, ammonia, pyridine, lutidine, collidine, 4-(dimethylamino)pyridine (DMAP), imidazole, 1,8-diazabicyclo[5.4.0]undec-7-ene (DBU) or 1,5-diazabicyclo[4.3.0]non-5-ene (DBN), lithium hexamethyldisilazide (LiHMDS), sodium hexamethyldisilazide (NaHMDS), potassium hexamethyldisilazide (KHMDS), lithium diisopropylamide (LDA), lithium tetramethylpiperidide (LiTMP).

Preferred bases include carbonates and hydrides. Particularly preferred bases include potassium carbonate, cesium carbonate and sodium hydride.

The term base as used herein also includes mixtures of two or more, preferably two of the above compounds. Particular preference is given to the use of one base.

The molar ratio of the compound of formula (XI) to the base is generally in the range of 1:0.8-3, preferably in the range of 1:1-2, more preferably in the range of 1:1-1.5.

Preferably, the reaction of the compound of formula (XI) with the compound of formula (XII) in the presence of a base is carried out in a solvent.

Examples of suitable solvents are dipolar aprotic solvents such as N,N-dimethylformamide (DMF), N,N-dimethylacetamide (DMAc), 1-methyl-2-pyrrolidinone (NMP), 1,3-dimethyl-2-imidazolidinone (DMI), N,N'-dimethylpropylene urea (DMPU), dimethyl sulfoxide (DMSO), sulfolane, acetonitrile, benzonitrile, acetone, methyl ethyl ketone, methyl butyl ketone, methyl isobutyl ketone, cyclohexanone, nitromethane, nitroethane, nitrobenzene; esters such as ethyl acetate, butyl acetate, isobutyl acetate; ethers such as diethylether, dibutylether, tert-butyl methyl ether (TBME), 1,2-dimethoxyethane, tetrahydrofurane (THF), cyclopentyl methyl ether, 1,4-dioxane; alcohols such as methanol, ethanol, isopropanol, 1-butanol, 2-butanol, isobutanol, tertbutanol, hexafluoro isopropanol; halogenated hydrocarbons such as dichloromethane, dichloroethane, carbon tetrachloride; aliphatic hydrocarbons such as hexane, cyclohexane; aromatic hydrocarbons such as benzene, toluene, xylenes, mesitylene, chlorobenzene.

Preferred solvents include acetone, DMF, DMAc, 1,2-dimethoxyethane, DMI, dichloromethane, diethylether and THF. Particularly preferred solvents include acetone, 1,2-dimethoxyethane, diethylether and THF.

The term solvent as used herein also includes mixtures of two or more of the above compounds.

The reaction of the compound of formula (XI) with the compound of formula (XII) in the presence of a base is generally carried out at a temperature in the range of from −40 to 80° C., preferably in the range of from −20 to 40° C., more preferably in the range of from 0 to 30° C.

Step (ii) is preferably carried out in the presence of a solvent. Preferred solvents include methanol, ethanol, dichloromethane, THF, DMF, acetonitrile, toluene, benzene, ethyl acetate, dioxane, tert-butyl methyl ether, or mixtures thereof. Particular preference is given to alcohols such as methanol or ethanol.

Step (ii) is preferably carried out at a temperature in the range of from −40 to 80° C., preferably in the range of from −20 to 40° C., more preferably in the range of from 0 to 30° C.

Preferred reagents for converting the compound of formula (XV) to the compound of formula (I), wherein $R^{aa}$ is $-C(=S)N(R^{cc})_2$; and $R^{bb}$ is $-C(=S)N(R^{cc})_2$ or CN, include $P_4S_{10}$ and Lawesson's reagent. A particular preferred reagent for the use in step (iii) is $P_4S_{10}$. In one embodiment $P_4S_{10}$ and hexamethyldisiloxane are used in step (iii).

Step (iii) is preferably carried out in the presence of a solvent. Preferred solvents include dichloromethane, THF, DMF, acetonitrile, toluene, benzene, ethyl acetate, dioxane, tert-butyl methyl ether, or mixtures thereof. More preferred solvents include toluene, dichloromethane, or mixtures thereof. Particular preference is given to a toluene/dichloromethane mixture, wherein the ratio of toluene to dichloromethane (vol:vol) is in the range of 2:1 to 1:2, preferably 1.2:1 to 1:1.2, more preferably about 1:1.

Step (iii) is preferably carried out at a temperature in the range of from 0 to 100° C., preferably in the range of from 20 to 80° C., more preferably in the range of from 50 to 70° C.

Pests

Preferred animal pests are invertebrate pests.

The term "invertebrate pest" as used herein encompasses animal populations, such as arthropod pests, including insects and arachnids, as well as nematodes, which may attack plants thereby causing substantial damage to the plants attacked, as well as ectoparasites which may infest animals, in particular warm blooded animals such as e.g. mammals or birds, or other higher animals such as reptiles, amphibians or fish, thereby causing substantial damage to the animals infested.

The compounds of the formula I, and their salts are in particular suitable for efficiently controlling arthropodal pests such as arachnids, myriapedes and insects as well as nematodes.

The compounds of the formula I are especially suitable for efficiently combating the following pests:

insects from the order of the lepidopterans (*Lepidoptera*), for example *Acronicta major, Adoxophyes orana, Aedia leucomelas, Agrotis* spp. such as *Agrotis fucosa, Agrotis segetum, Agrotis ypsilon; Alabama argillacea, Anticarsia gemmatalis, Anticarsia* spp., *Argyresthia conjugella, Autographa gamma, Barathra brassicae, Bucculatrix*

*thurberiella, Bupalus piniarius, Cacoecia murinana, Cacoecia podana, Capua reticulana, Carpocapsa pomonella, Cheimatobia brumata, Chilo* spp. such as *Chillo suppressalis; Choristoneura fumiferana, Choristoneura occidentalis, Cirphis unipuncta, Clysia ambiguella, Cnaphalocerus* spp., *Cydia pomonella, Dendrollimus pini, Diaphania nitidalis, Diatraea grandliosella, Earias insulana, Elasmopalpus lignosellus, Ephestia cautella, Ephestia kuehniella, Eupoecillia ambiguella, Euproctis chrysorrhoea, Euxoa* spp., *Evetria bouliana, Feltia* spp. such as *Feltia subterranean; Galleria mellonella, Grapholiltha funebrana, Grapholiltha molesta, Helicoverpa* spp. such as *Helicoverpa armigera, Helicoverpa zea, Heliothis* spp. such as *Heliothis armigera, Heliothis virescens, Heliothis zea; Hellula undalis, Hibernia defoliaria, Hofmannophilla pseudospretella, Homona magnanima, Hyphantria cunea, Hyponomeuta padella, Hyponomeuta malinellus, Keiferia lycopersicella, Lambdina fiscellaria, Laphygma* spp. such as *Laphygma exigua, Leucoptera coffeella, Leucoptera scitella, Lithocolletis blancardella, Lithophane antennata, Lobesia botrana, Loxagrotis albicosta, Loxostege sticticalis, Lymantria* spp. such as *Lymantria dispar, Lymantria monacha, Lyonetia clerkella, Malacosoma neustria, Mamestra* spp. such as *Mamestra brassicae; Mocis repanda, Mythimna separata, Orgyia pseudotsugata, Oria* spp., *Ostrinia* spp. such as *Ostrinia nubillallis; Oulema oryzae, Panolis flammea, Pectinophora* spp. such as *Pectinophora gossypiella, Peridroma saucla, Phalera bucephala, Phthorimaea* spp. such as *Phthorimaea operculella; Phyllocnistis citrella, Pieris* spp. such as *Pieris brassicae, Pieris rapae, Plathypena scabra, Putella maculipennis, Putella xylostella, Prodenia* spp., *Pseudaletia* spp., *Pseudoplusia includens, Pyrausta nubillallis, Rhyacionia frustrana, Scrobipalpula absoluta, Sitotroga cerealella, Sparganothis pilleriana, Spodoptera* spp. such as *Spodoptera frugiperda, Spodoptera littoralis, Spodoptera llltura, Thaumatopoea pityocampa, Thermesia gemmatalis, Tinea pellionella, Tineola bisselliella, Tortrix viridana, Trichoplusia* spp. such as *Trichoplusia ni; Tuta absoluta*, and *Zeiraphera canadensis*, beetles (*Coleoptera*), for example *Acanthoscehdes obtectus, Adoretus* spp., *Agelastica alni, Agrilus sinuatus, Agriotes* spp. such as *Agriotes fuscicollis, Agriotes llineatus, Agriotes obscurus; Amphimallus solstitialis, Anisandrus dispar, Anobium punctatum, Anomala rufocuprea, Anoplophora* spp. such as *Anoplophora glabripennis; Anthonomus* spp. such as *Anthonomus grandls, Anthonomus pomorum; Anthrenus* spp., *Aphthona euphoridae, Apogonia* spp., *Athous haemorrhoidalls, Atomaria* spp. such as *Atomaria llnearis; Attagenus* spp., *Aulacophora femorallis, Blastophagus piniperda, Blltophaga undata, Bruchidius obtectus, Bruchus* spp. such as *Bruchus lentis, Bruchus pisorum, Bruchus rufimanus; Byctlscus betulae, Calosobruchus chinensis, Cassida nebulosa, Cerotoma trifurcata, Cetonia aurata, Ceuthorhynchus* spp. such as *Ceuthorhynchus assimllls, Ceuthorhynchus napl; Chaetocnema tibialls, Cleonus mendicus, Conoderus* spp. such as *Conoderus vespertinus; Cosmopolites* spp., *Costelytra zealandica, Crioceris asparagi, Cryptorhynchus lapathi, Ctenicera* ssp. such as *Ctenicera destructor; Curcullio* spp., *Dectes texanus, Dermestes* spp., *Diabrotica* spp. such as *Diabrotica 12-punctata Diabrotica speciosa, Diabrotica longicornis, Diabrotica semipunctata, Diabrotica virgifera; Epilachna* spp. such as *Epilachna varivestis, Epilachna vigintioctomaculata; Epitrix* spp. such as *Epitrix hirtipennis; Eutinobothrus brasllensis, Faustinus cubae, Gibbium psylloides, Heteronychus arator, Hylamorpha elegans, Hylobius abletis, Hylotrupes bajulus, Hypera brunneipennis, Hypera postica, Hypothenemus* spp., *Ips typographus, Lachnosterna consanguinea, Lema bilineata, Lema melanopus, Leptinotarsa* spp. such as *Leptinotarsa decemlineata; Limonius californicus, Lissorhoptrus oryzophilus, Lissorhoptrus oryzophilus, Lixus* spp., *Lyctus* spp. such as *Lyctus bruneus; Melanotus communis, Meligethes* spp. such as *Meligethes aeneus; Melolontha hippocastani, Melolontha melolontha, Migdolus* spp., *Monochamus* spp. such as *Monochamus alternatus; Naupactus xanthographus, Niptus hololeucus, Oryctes rhinoceros, Oryzaephilus surinamensis, Otiorrhynchus sulcatus, Otlorrhynchus ovatus, Otlorrhynchus sulcatus, Oulema oryzae, Oxycetonia jucunda, Phaedon cochlearlae, Phyllobius pyrl Phyllopertha horticola, Phyllophaga* spp., *Phyllotreta* spp. such as *Phyllotreta chrysocephala, Phyllotreta nemorum, Phyllotreta striolata; Phyllophaga* spp., *Phyllopertha horticola, Popillla japonica, Premnotrypes* spp., *Psylliodes chrysocephala, Ptinus* spp., *Rhizobius ventralis, Rhizopertha dominica, Sitonalneatus, Sitophilus* spp. such as *Sitophilus granaria, Sitophilus zeamais; Sphenophorus* spp. such as *Sphenophorus levis; Sternechus* spp. such as *Sternechus sub signatus; Symphyletes* spp., *Tenebrio molltor, Tribolium* spp. such as *Tribollum castaneum; Trogoderma* spp., *Tychius* spp., *Xylotrechus* spp., and *Zabrus* spp. such as *Zabrus tenebrioldes*, flies, mosquitoes (*Diptera*), e.g. *Aedes* spp. such as *Aedes aegypti, Aedes albopictus, Aedes vexans; Anastrepha ludens, Anopheles* spp. such as *Anopheles albimanus, Anopheles crucians, Anopheles freeborni, Anopheles gambiae, Anopheles leucosphyrus, Anopheles macullpennis, Anopheles minimus, Anopheles quadrimaculatus, Anopheles sinensis; Bibio hortulanus, Calliphora erythrocephala, Calliphora vicina, Cerafitis capitata, Ceratltis capitata, Chrysomyia* spp. such as *Chrysomya bezziana, Chrysomya hominivorax, Chrysomya macellaria; Chrysops atlanticus, Chrysops discalis, Chrysops silacea, Cochliomyia* spp. such as *Cochliomyia hominivorax; Contarinia* spp. such as *Contarinia sorghicola; Cordylobia anthropophaga, Culex* spp. such as *Culex nigripalpus, Culex pipiens, Culex quinquefasciatus, Culex tarsalis, Culex tri taeniorhynchus; Culicoides furens, Culiseta inornata, Culiseta melanura, Cuterebra* spp., *Dacus cucurbitae, Dacus oleae, Dasineura brassicae, Delia* spp. such as *Delia antique, Delia coarctata, Delia platura, Delia radicum, Dermatobia hominis, Drosophila* spp., *Fannia* spp. such as *Fannia canicularis; Gastraphilus* spp. such as *Gasterophilus intestinalis; Geomyza Tripunctata, Glossina fuscipes, Glossina morsitans, Glossina palpalis, Glossina tachinoides, Haematobia irritans, Haplodiplosis equestris, Hippelates* spp., *Hylemyia* spp. such as *Hylemyia platura; Hypoderma* spp. such as *Hypoderma lineata; Hyppobosca* spp., *Leptoconops torrens, Liriomyza* spp. such as *Liriomyza sativae, Liriomyza trifoli; Lucilia* spp. such as *Lucilia caprina, Lucilia cuprina, Lucilia sericata; Lycoria pectoralis, Mansonia titillanus, Mayetiola* spp. such as *Mayetiola destructor; Musca* spp. such as *Musca autumnalis, Musca domestica; Muscina stabulans, Oestrus* spp. such as *Oestrus ovis; Opomyza florum, Oscinella* spp. such as *Oscinella frit; Pegomya hysocyami, Phlebotomus argentipes, Phorbia* spp. such as *Phorbia antiqua, Phorbia brassicae, Phorbia coarctata; Prosimulium mixtum, Pslila rosae, Psorophora columbiae, Psorophora discolor, Rhagoletis cerasi, Rhagoletis pomonella, Sarcophaga* spp. such as *Sar-* cophaga haemorrhoidalils; Simulium vittatum, Stomoxys spp. such as Stomoxys calcitrans; Tabanus spp. such as Tabanus atratus, Tabanus bovinus, Tabanus lineola, Tabanus simils; Tannia spp., Tipula oleracea, Tipula paludosa, and Wohlfahrtia spp., thrips (Thysanoptera), e.g. Baliothrips biformis, Dichromothrips corbettl, Dichromothrips ssp., Enneothrips flavens, Frankliniella spp. such as Frankliniella fusca, Frankliniella occidentalis, Frankliniella tritici; Heliothrips spp., Hercinothrips femoralis, Kakothrips spp., Rhipiphorothrips cruentatus, Scirtothrips spp. such as Scirtothrips citri; Taeniothrips cardamoni, Thrips spp. such as Thrips oryzae, Thrips palmi, Thrips tabac;

termites (Isoptera), e.g. Calotermes flavicollls, Coptotermes formosanus, Heterotermes aureus, Heterotermes longiceps, Heterotermes tenuis, Leucotermes flavipes, Odontotermes spp., Reticulitermes spp. such as Reticulitermes speratus, Reticulitermes flavipes, Reticulitermes grassei, Reticulitermes lucifugus, Reticulitermes santonensis, Reticulitermes virginicus, Termes natalensis, cockroaches (Blattaria-Blattodea), e.g. Acheta domesticus, Blatta orientalis, Blattella asahinae, Blattella germanica, Gryllotalpa spp., Leucophaea maderae, Locusta spp., Melanoplus spp., Periplaneta americana, Periplaneta australasiae, Periplaneta brunnea, Periplaneta fuligginosa, Periplaneta japonica, bugs, aphids, leafhoppers, whiteflies, scale insects, cicadas (Hemiptera), e.g. Acrosternum spp. such as Acrosternum hilare; Acyrthosipon spp. such as Acyrthosiphon onobrychis, Acyrthosiphon pisum; Adelges laricis, Aeneolamia spp., Agonoscena spp., Aleurodes spp., Aleurolobus barodensis, Aleurothrixus spp., Amrasca spp., Anasa tristis, Antestiopsis spp., Anuraphis cardui, Aonidiella spp., Aphanostigma piri Aphidula nasturtii, Aphis spp. such as Aphis fabae, Aphis forbesi Aphis gossypii, Aphis grossularlae, Aphis pomi, Aphis sambuci, Aphis schneider Aphis spiraecola, Arboridia apicalils, Arlilus critatus, Aspidiella spp., Aspidiotus spp., Atanus spp., Aulacorthum solani, Bemisia spp. such as Bemisia argentifoli, Bemisia tabac; Blissus spp. such as Blissus leucopterus; Brachycaudus cardul Brachycaudus helichrysi, Brachycaudus persicae, Brachycaudus prunicola, Brachycolus spp., Brevicoryne brassicae, Calligypona marginata, Calocoris spp., Campylomma livida, Capitophorus horni, Carneocephala fulgida, Cavelerius spp., Ceraplastes spp., Ceratovacuna lanigera, Cercopidae, Cerosipha gossypii, Chaetosiphon fragaefolll Chionaspis tegalensis, Chlorita onukli, Chromaphis juglandicola, Chrysomphalus ficus, Clcadulina mbila, Cimex spp. such as Clmex hemipterus, Clmex lectularius; Coccomytllus hali, Coccus spp., Creontiades dlilutus, Cryptomyzus ribis, Cryptomyzus ribhis, Cyrtopeltis notatus, Dalbulus spp., Dasynus piperis, Dialeurades spp., Diaphorina spp., Diaspis spp., Dichelops furcatus, Diconocoris hewetti, Doralis spp., Dreyfusia nordmannianae, Dreyfusia piceae, Drosicha spp., Dysaphis spp. such as Dysaphis plantaginea, Dysaphis pyri, Dysaphis radicola, Dysaulacorthum pseudosoani, Dysdercus spp. such as Dysdercus cingulatus, Dysdercus intermedius; Dysmicoccus spp., Empoasca spp. such as Empoasca fabae, Empoasca solana; Eriosoma spp., Erythroneura spp., Eurygaster spp. such as Eurygaster integriceps, Euscelis bilobatus, Euschistus spp. such as Euschistuos heros, Euschistus impictiventris, Euschistus servus; Geococcus coffeae, Halyomorpha spp. such as Halyomorpha halys; Helilopeltls spp., Homalodisca coagulata, Horcias nobilellus, Hyalopterus pruni, Hyperomyzus lactucae, Icerya spp., Idiocerus spp., Idioscopus spp., Laodelphax striatellus, Lecanium spp., Lepidosaphes spp., Leptocorisa spp., Leptoglossus phyllopus, Lipaphis erysimi, Lygus spp. such as Lygus hesperus, Lygus lineolaris, Lygus pratensis; Macropes excavatus, Macrosiphum spp. such as Macrosiphum rosae, Macrosiphum avenae, Macrosiphum euphorbiae; Mahanarva fimbriolata, Megacopta cribraria, Megoura viciae, Melanaphis pyrarius, Melanaphis sacchar Metcafiella spp., Metopolophium dirhodum, Miridae spp., Monelllia costals, Monellliopsis pecanis, Myzus spp. such as Myzus ascalonicus, Myzus cerasi, Myzus persicae, Myzus varians; Nasonovia ribis-nigr, Nephotettix spp. such as Nephotettix malayanus, Nephotettix nigropictus, Nephotettix parvus, Nephotettix virescens; Nezara spp. such as Nezara viridula; Nilaparvata lugens, Oebalus spp., Oncometopia spp., Orthezia praelonga, Parabemisia myricae, Paratrioza spp., Parlatoria spp., Pemphigus spp. such as Pemphigus bursarius; Pentomidae, Peregrinus maidis, Perkinsiella saccharicida, Phenacoccus spp., Phloeomyzus passerinii, Phorodon humui Phylloxera spp., Piesma quadrata, Piezodorus spp. such as Piezodorus guildinii, Pinnaspis aspidistrae, Planococcus spp., Protopulvinaria pyriformis, Psallus seriatus, Pseudacysta persea, Pseudaulacaspis pentagona, Pseudococcus spp. such as Pseudococcus comstocki; Psylla spp. such as Psylla mal Psylla pir; Pteromalus spp., Pyrilla spp., Quadraspidiotus spp., Quesada gigas, Rastrococcus spp., Reduvius senilis, Rhodnius spp., Rhopalomyzus ascalonicus, Rhopalosiphum spp. such as Rhopalosiphum pseudobrassicas, Rhopalosiphum insertum, Rhopalosiphum maidis, Rhopalosiphum padi Sagatodes spp., Sahlbergella singularis, Saissetia spp., Sappaphis mala, Sappaphis mal Scaphoides titanus, Schizaphis graminum, Schizoneura lanuginosa, Scotinophora spp., Selenaspidus articulatus, Sitobion avenae, Sogata spp., Sogatella furcifera, Solubea insularis, Stephanitis nashi, Stictocephala festina, Tenalaphara malayensis, Thyanta spp. such as Thyanta perditor; Tibraca spp., Tinocalllis caryaefoliae, Tomaspis spp., Toxoptera spp. such as Toxoptera aurantlii; Trialeurodes spp. such as Trialeurodes vaporariorum; Triatoma spp., Trioza spp., Typhlocyba spp., Unaspis spp. such as Unaspis yanonensis; and Viteus vitifolii, ants, bees, wasps, sawflies (Hymenoptera), e.g. Athallia rosae, Atta capiguara, Atta cephalotes, Atta cephalotes, Attalaevigata, Atta robusta, Atta sexdens, Atta texana, Bombus spp., Camponotus floridanus, Crematogaster spp., Dasymutilla occidentalis, Diprion spp., Dollchovespula maculata, Hoplocampa spp. such as Hoplocampa minuta, Hoplocampa testudinea; Lasius spp. such as Lasius niger, Linepithema humile, Monomorium pharaonis, Paravespula germanica, Paravespula pennsylvanica, Paravespula vulgaris, Pheidole megacephala, Pogonomyrmex barbatus, Pogonomyrmex callifornicus, Polistes rubiginosa, Solenopsis geminata, Solenopsis invicta, Solenopsis richteri, Solenopsis xyloni Vespa spp. such as Vespa crabro, and Vespula squamosa, crickets, grasshoppers, locusts (Orthoptera), e.g. Acheta domestica, Calliptamus italicus, Chortoicetes terminifera, Dociostaurus maroccanus, Gryllotalpa africana, Gryllotalpa gryllotalpa, Hieroglyphus daganensis, Kraussaria angullfera, Locusta migratoria, Locustana pardalina, Melanoplus bivittatus, Melanoplus femurrubrum, Melanoplus mexicanus, Melanoplus sanguinipes, Melanoplus spretus, Nomadacris septemfasciata, Oedaleus senegalensis, Schistocerca ameri cana, Schistocerca gregaria, Tachycines asynamorus, and Zonozerus variegatus, arachnids (*Arachnida*), such as *acari,e.g.* of the families *Argasidae, Ixodidae* and *Sarcoptidae*, such as *Amblyomma* spp. (*e.g. Amblyomma americanum, Amblyomma variegatum, Amblyomma maculatum*), *Argas* spp. (*e.g. Argas persicus*), *Boophilus* spp. (*e.g. Boophillus annulatus, Boophillus decoloratus, Boophillus microplus*), *Dermacentor sillvarum, Dermacentor andersoni, Dermacentor variabillis, Hyalomma* spp. (*e.g. Hyalomma truncatum*), *Ixodes* spp. (*e.g. Ixodes ricinus, Ixodes rubicundus, Ixodes scapularis, Ixodes holocyclus, Ixodes pacificus*), *Ornithodorus* spp. (*e.g. Ornithodorus moubata, Ornithodorus hermsi, Ornithodorus turicata*), *Ornithonyssus bacoti, Otobius megnini, Dermanyssus gallinae, Psoroptes* spp. (*e.g. Psoroptes ovis*), *Rhipicephalus* spp. (*e.g. Rhipicephalus sanguineus, Rhipicephalus appendiculatus, Rhipicephalus evertsi*), *Rhizoglyphus* spp., *Sarcoptes* spp. (*e.g. Sarcoptes scabilei*), and *Eriophyidae* spp. such as *Acaria sheldoni Aculops* spp. (*e.g. Aculops pelekassi*) *Aculus* spp. (*e.g. Aculus schlechtendali*), *Epitrimerus pyri, Phyllocoptruta oleivora* and *Eriophyes* spp. (*e.g. Eriophyes sheldonl*); *Tarsonemidae* spp. such as *Hemitarsonemus* spp., *Phytonemus pallidus* and *Polyphagotarsonemus latus, Stenotarsonemus* spp.; *Tenuipalpidae* spp. such as *Brevipalpus* spp. (*e.g. Brevipalpus phoenicis*); *Tetranychidae* spp. such as *Eotetranychus* spp., *Eutetranychus* spp., *Ollgonychus* spp., *Tetranychus cinnabarinus, Tetranychus kanzawai, Tetranychus pacificus, Tetranychus telarius* and *Tetranychus urticae; Bryobia praetiosa, Panonychus* spp. (*e.g. Panonychus ulmi, Panonychus citn*), *Metatetranychus* spp. and *Oligonychus* spp. (*e.g. Oligonychus pratensis*), *Vasates lycopersic, Araneida,* e.g. *Latrodectus mactans,* and *Loxosceles reclusa.* And *Acarus siro, Chorioptes* spp., *Scorpio maurus* fleas (*Siphonaptera*), e.g. *Ceratophyllus* spp., *Ctenocephalides fellis, Ctenocephalides canis, Xenopsylla cheopis, Pulex irritans, Tunga penetrans,* and *Nosopsyllus fasciatus,* silverfish, firebrat (*Thysanura*), e.g. *Lepisma saccharina* and *Thermobia domestica,* centipedes (*Chilopoda*), e.g. *Geophilus* spp., *Scutigera* spp. such as *Scutigera coleoptrata;* millipedes (*Diplopoda*), e.g. *Blaniulus guttulatus, Narceus* spp.,

Earwigs (*Dermaptera*), e.g. *forficula auricularia,* lice (*Phthiraptera*), e.g. *Damalinia* spp., *Pediculus* spp. such as *Pediculus humanus capitis, Pediculus humanus corporis; Pthirus pubis, Haematopinus* spp. such as *Haematopinus eurysternus, Haematopinus suis; Linognathus* spp. such as *Linognathus vituli; Bovicola bovis, Menopon gallinae, Menacanthus stramineus* and *Solenopotes capillatus, Trichodectes* spp., springtails (*Collembola*), e.g. *Onychiurus* ssp. such as *Onychiurus armatus,*

They are also suitable for controlling nematodes: plant parasitic nematodes such as root knot nematodes, *Meloidogyne hapla, Meloidogyne incognita, Meloidogyne javanica,* and other *Meloidogyne* species; cyst-forming nematodes, *Globodera rostochiensis* and other *Globodera* species; *Heterodera avenae, Heterodera glycines, Heterodera schachtii, Heterodera trifolii* and other *Heterodera* species; Seed gall nematodes, *Anguina* species; Stem and foliar nematodes, *Aphelenchoides* species such as *Aphelenchoides besseyi*; Sting nematodes, *Belonolaimus longicaudatus* and other *Belonolaimus* species; Pine nematodes, *Bursaphelenchus lignicolus Mamiya et Kiyohara, Bursaphelenchus xylophilus* and other *Bursaphelenchus* species; Ring nematodes, *Criconema* species, *Criconemella* species, *Criconemoides* species, *Mesocriconema* species; Stem and bulb nematodes, *Ditylenchus destructor, Ditylenchus dipsaci* and other *Ditylenchus* species; Awl nematodes, *Dolichodorus* species; Spiral nematodes, *Heliocotylenchus multicinctus* and other *Helicotylenchus* species; Sheath and sheathoid nematodes, *Hemicycliophora* species and *Hemicriconemoides* species; *Hirshmanniella* species; Lance nematodes, *Hoploaimus* species; false rootknot nematodes, *Nacobbus* species; Needle nematodes, *Longidorus elongatus* and other *Longidorus* species; Lesion nematodes, *Pratylenchus brachyurus, Pratylenchus neglectus, Pratylenchus penetrans, Pratylenchus curvitatus, Pratylenchus goodeyi* and other *Pratylenchus* species; Burrowing nematodes, *Radopholus similis* and other *Radopholus* species; Reniform nematodes, *Rotylenchus robustus, Rotylenchus reniformis* and other *Rotylenchus* species; *Scutellonema* species; Stubby root nematodes, *Trichodorus primitivus* and other *Trichodorus* species, *Paratrichodorus* species; Stunt nematodes, *Tylenchorhynchus cllaytoni, Tylenchorhynchus dubius* and other *Tylenchorhynchus* species; Citrus nematodes, *Tylenchulus* species such as *Tylenchulus semipenetrans,* Dagger nematodes, *Xiphinema* species; and other plant parasitic nematode species.

Examples of further pest species which may be controlled by compounds of fomula (I) include: from the class of the Bivalva, for example, *Dreissena* spp.; from the class of the Gastropoda, for example, *Arion* spp., *Biomphalaria* spp., *Bulinus* spp., *Deroceras* spp., *Galba* spp., *Lymnaea* spp., *Oncomelania* spp., *Succinea* spp.; from the class of the hellminths, for example, *Ancylostoma duodenale, Ancylostoma ceylanicum, Acylostoma braziliensis, Ancylostoma* spp., *Ascaris lumbricoides, Ascaris* spp., *Brugia malayi Brugia tinori, Bunostomum* spp., *Chabertia* spp., *Clonorchis* spp., *Cooperia* spp., *Dicrocoelilum* spp., *Dictyocaulus filaria, Diphyllobothrium latum, Dracunculus medinensis, Echinococcus granulosus, Echinococcus multilocularis, Enterobius vermicularis, Faciola* spp., *Haemonchus* spp. such as *Haemonchus contortus; Heterakis* spp., *Hymenolepis nana, Hyostrongulus* spp., *Loa Loa, Nematodirus* spp., *Oesophagostomum* spp., *Opisthorchis* spp., *Onchocerca volvulus, Ostertagia* spp., *Paragonimus* spp., *Schistosomen* spp., *Strongyloides fuelleborni, Strongyloides stercora lis, Stronyloides* spp., *Taenia saginata, Taenia solilum, Trichinella spiralis, Trichinella nativa, Trichinella britovi, Trichinella nelsonl Trichinella pseudopsiralils, Trichostrongulus* spp., *Trichuris trichiura, Wuchereria bancrofti*; from the order of the Isopoda, for example, *Armadllldium vulgare, Oniscus asellus, Porcellio scaber*; from the order of the Symphyla, for example, *Scutigerella immaculata.*

Further examples of pest species which may be controlled by compounds of formula (I) include: *Anisoplila austriaca, Apamea* spp., *Austroasca virldigrisea, Balilothrips biformis, Caenorhabditis elegans, Cephus* spp., *Ceutorhynchus napi Chaetocnema aridula, Chlilo auricillus, Chlilo indicus, Chlilo polychrysus, Chortiocetes termlinifera, Cnaphalocroci medinalis, Cnaphalocrosis* spp., *Colilas eurytheme, Collops* spp., *Cornitermes cumulans, Creontiades* spp., *Cyclocephala* spp., *Dalbulus maidis, Deraceras reticulatum, Diatrea saccharalls, Dichelops furcatus, Dicladispa armigera, Diloboderus* spp. such as *Diloboderus abderus; Edessa* spp., *Epinotia* spp., *Formlicidae, Geocoris* spp., *Globitermes sulfureus, Gryllotalpidae, Halotydeus destructor, Hipnodes bicolor, Hydrella philippina, Julus* spp., *Laodelphax* spp., *Leptocorsia acuta, Leptocorsia oratorius, Liogenys fuscus, Lucilllia* spp., *Lyogenys fuscus, Mahanarva* spp., *Maladera matrida, Marasmia* spp., *Mastotermes* spp., Mealybugs, Megascelis ssp, Metamasius hemipterus, Microtheca spp., *Mocls latipes*, *Murgantia* spp., *Mythemina separata*, *Neocapritermes opacus*, *Neocapritermes parvus*, *Neomegalotomus* spp., *Neotermes* spp., *Nymphula depunctalils*, *Oebalus pugnax*, *Orseolia* spp. such as *Orseolia oryzae; Oxycaraenus hyalilnipennis*, *Plusia* spp., *Pomacea canalilculata*, *Procornitermes ssp*, *Procornitermes triacifer*, *Psylloides* spp., *Rachiplusla* spp., *Rhodopholus* spp., *Scaptocoris castanea*, *Scaptocoris* spp., *Scirpophaga* spp. such as *Scirpophaga incertulas*, *Scirpophaga innotata*; *Scotinophara* spp. such as *Scotinophara coarctata*, *Sesamia* spp. such as *Sesamia inferens*, *Sogaella frucifera*, *Solenapsis geminata*, *Spissistlilus* spp., *Stalk borer*, *Stenchaetothrips biformis*, *Steneotarsonemus spinki Sylepta derogata*, *Telehin llcus*, *Trichostrongylus* spp.

Compounds of the formula I are particularly useful for controlling insects, preferably sucking or piercing insects such as insects from the genera *Thysanoptera*, *Diptera* and *Hemiptera*, in particular the following species:

Thysanoptera: *Frankllniellla fusca*, *Frankllniella occidentals*, *Frankllniella tritic Scirtothrips citri*, *Thrips oryzae*, *Thrips palmiand Thrips tabaci*, Diptera, e.g. *Aedes aegypti*, *Aedes albopictus*, *Aedes vexans*, *Anastrepha ludens*, *Anopheles maculipennis*, *Anopheles crucians*, *Anopheles albimanus*, *Anopheles gambiae*, *Anopheles freeborni*, *Anopheles leucosphyrus*, *Anopheles minimus*, *Anopheles quadrimaculatus*, *Calliphora vicina*, *Ceratitis capitata*, *Chrysomya bezziana*, *Chrysomya hominivorax*, *Chrysomya macellaria*, *Chrysops discalis*, *Chrysops silacea*, *Chrysops atllanticus*, *Cochliomyia hominivorax*, *Contarinia sorghicola Cordylobia anthropophaga*, *Culicoides furens*, *Culex pipiens*, *Culex nigripalpus*, *Culex quinquefasciatus*, *Culex tarsalis*, *Culiseta inornata*, *Culiseta melanura*, *Dacus cucurbitae*, *Dacus oleae*, *Dasineura brassicae*, *Delia antique*, *Delia coarctata*, *Delia platura*, *Delia radicum*, *Dermatobia hominis*, *Fannia canicularis*, *Geomyza Tripunctata*, *Gasterophilus intestinalis*, *Glossina morsitans*, *Glossina palpalis*, *Glossina fuscipes*, *Glossina tachinoides*, *Haematobia irritans*, *Haplodiplosis equestris*, *Hippelates* spp., *Hylemyia platura*, *Hypoderma lineata*, *Leptoconops torrens*, *Liriomyza sativae*, *Liriomyza trifolil Lucilia caprina*, *Lucilia cuprina*, *Lucilia sericata*, *Lycoria pectoralis*, *Mansonia titilllanus*, *Mayetiola destructor*, *Musca autumnalis*, *Musca domestica*, *Muscina stabulans*, *Oestrus ovis*, *Opomyza florum*, *Oscinella frit*, *Pegomya hysocyami*, *Phorbia antiqua*, *Phorbia brassicae*, *Phorbia coarctata*, *Phlebotomus argentipes*, *Psorophora columbiae*, *Psila rosae*, *Psorophora discolor*, *Prosimulium mixtum*, *Rhagoletis cerasi*, *Rhagoletis pomonellla*, *Sarcophaga haemorrhoidalis*, *Sarcophaga* spp., *Simulium vittatum*, *Stomoxys calcitrans*, *Tabanus bovinus*, *Tabanus atratus*, *Tabanus lineola*, and *Tabanus sinilils*, *Tipula oleracea*, and *Tipula paludosa;*

Hemiptera, in particular aphids: *Acyrthosiphon onobrychis*, *Adelges laricis*, *Aphidula nasturtii*, *Aphis fabae*, *Aphis forbesi*, *Aphis pomi*, *Aphis gossypi*, *Aphis grossulariae*, *Aphis schneideri*, *Aphis spiraecola*, *Aphis sambuci*, *Acyrthosiphon pisum*, *Aulacorthum solani*, *Brachycaudus cardui*, *Brachycaudus helichrysi*, *Brachycaudus persicae*, *Brachycaudus prunicola*, *Brevicoryne brassicae*, *Capitophorus horni*, *Cerosipha gossypii*, *Chaetosiphon fragaefolil Cryptomyzus ribis*, *Dreyfusia nordmannianae*, *Dreyfusia piceae*, *Dysaphis radicola*, *Dysaulacorthum pseudosolani*, *Dysaphis plantaginea*, *Dysaphis pyri*, *Empoasca fabae*, *Hyalopterus pruni*, *Hyperomyzus lactucae*, *Macrosiphum avenae*, *Macrosiphum euphorbiae*, *Macrosiphon rosae*, *Megoura viciae*, *Melanaphis pyrarius*, *Metopolophium dirhodum*, *Myzodes persicae*, *Myzus ascalonicus*, *Myzus cerasi*, *Myzus varians*, *Nasonovia ribis-nigri*, *Nilaparvata lugens*, *Pemphigus bursarius*, *Perkinsiella saccharicida*, *Phorodon humull Psylla mal Psylla piri*, *Rhopalomyzus ascalonicus*, *Rhopalosiphum maidis*, *Rhopalosiphum padi*, *Rhopalosiphum insertum*, *Sappaphis mala*, *Sappaphis mal Schizaphis graminum*, *Schizoneura lanuginosa*, *Sitobion avenae*, *Trialeurodes vaporariorum*, *Toxoptera aurantiiand*, and *Viteus vitifolil* Hemiptera, in particular *Nezara* spp. such as *Nezara viridula*.

Compounds of the formula I are particularly useful for controlling insects of the orders Hemiptera and Thysanoptera.

Compounds of the formula I are particularly useful for controlling Hemiptera, in particular *Nezara* spp. such as *Nezara viridula*.

Formulations

The invention also relates to agrochemical compositions comprising an auxiliary and at least one compound I according to the invention.

An agrochemical composition comprises a pesticidally effective amount of a compound I. The term "effective amount" denotes an amount of the composition or of the compounds I, which is sufficient for controlling harmful pests on cultivated plants or in the protection of materials and which does not result in a substantial damage to the treated plants. Such an amount can vary in a broad range and is dependent on various factors, such as the animal pests species to be controlled, the treated cultivated plant or material, the climatic conditions and the specific compound I used.

The compounds I and their salts can be converted into customary types of agrochemical compositions, e.g. solutions, emulsions, suspensions, dusts, powders, pastes, granules, pressings, capsules, and mixtures thereof. Examples for composition types are suspensions (e.g. SC, OD, FS), emulsifiable concentrates (e.g. EC), emulsions (e.g. EW, EO, ES, ME), capsules (e.g. CS, ZC), pastes, pastilles, wettable powders or dusts (e.g. WP, SP, WS, DP, DS), pressings (e.g. BR, TB, DT), granules (e.g. WG, SG, GR, FG, GG, MG), insecticidal articles (e.g. LN), as well as gel formulations for the treatment of plant propagation materials such as seeds (e.g. GF). These and further compositions types are defined in the "Catalogue of pesticide formulation types and international coding system", Technical Mono-graph No. 2, 6th Ed. May 2008, CropLife International.

The compositions are prepared in a known manner, such as described by Mollet and Grubemann, Formulation technology, Wiley VCH, Weinheim, 2001; or Knowles, New developments in crop protection product formulation, Agrow Reports DS243, T&F Informa, London, 2005.

Suitable auxiliaries are solvents, liquid carriers, solid carriers or fillers, surfactants, dispersants, emulsifiers, wetters, adjuvants, solubilizers, penetration enhancers, protective colloids, adhesion agents, thickeners, humectants, repellents, attractants, feeding stimulants, compatibilizers, bactericides, anti-freezing agents, anti-foaming agents, colorants, tackifiers and binders. Suitable solvents and liquid carriers are water and organic solvents, such as mineral oil fractions of medium to high boiling point, e.g. kerosene, diesel oil; oils of vegetable or animal origin; aliphatic, cyclic and aromatic hydrocarbons, e.g. toluene, paraffin, tetrahydronaphthalene, alkylated naphthalenes; alcohols, e.g. ethanol, propanol, butanol, benzylalcohol, cyclohexanol; glycols; DMSO; ketones, e.g. cyclohexanone; esters, e.g.

lactates, carbonates, fatty acid esters, gamma-butyrolactone; fatty acids; phosphonates; amines; amides, e.g. N-methylpyrrolidone, fatty acid dimethylamides; and mixtures thereof.

Suitable solid carriers or fillers are mineral earths, e.g. silicates, silica gels, talc, kaolins, limestone, lime, chalk, clays, dolomite, diatomaceous earth, bentonite, calcium sulfate, magnesium sulfate, magnesium oxide; polysaccharides, e.g. cellulose, starch; fertilizers, e.g. ammonium sulfate, ammonium phosphate, ammonium nitrate, ureas; products of vegetable origin, e.g. cereal meal, tree bark meal, wood meal, nutshell meal, and mixtures thereof.

Suitable surfactants are surface-active compounds, such as anionic, cationic, nonionic and amphoteric surfactants, block polymers, polyelectrolytes, and mixtures thereof. Such surfactants can be used as emulsifier, dispersant, solubilizer, wetter, penetration enhancer, protective colloid, or adjuvant. Examples of surfactants are listed in McCutcheon's, Vol. 1: Emulsifiers & Detergents, McCutcheon's Directories, Glen Rock, USA, 2008 (International Ed. or North American Ed.).

Suitable anionic surfactants are alkali, alkaline earth or ammonium salts of sulfonates, sulfates, phosphates, carboxylates, and mixtures thereof. Examples of sulfonates are alkylarylsulfonates, diphenylsulfonates, alpha-olefin sulfonates, lignine sulfonates, sulfonates of fatty acids and oils, sulfonates of ethoxylated alkylphenols, sulfonates of alkoxylated arylphenols, sulfonates of condensed naphthalenes, sulfonates of dodecyl- and tridecylbenzenes, sulfonates of naphthalenes and alkylnaphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Examples of carboxylates are alkyl carboxylates, and carboxylated alcohol or alkylphenol ethoxylates.

Suitable nonionic surfactants are alkoxylates, N-substituted fatty acid amides, amine oxides, esters, sugar-based surfactants, polymeric surfactants, and mixtures thereof. Examples of alkoxylates are compounds such as alcohols, alkylphenols, amines, amides, arylphenols, fatty acids or fatty acid esters which have been alkoxylated with 1 to 50 equivalents. Ethylene oxide and/or propylene oxide may be employed for the alkoxylation, preferably ethylene oxide. Examples of N-substituted fatty acid amides are fatty acid glucamides or fatty acid alkanolamides. Examples of esters are fatty acid esters, glycerol esters or monoglycerides. Examples of sugar-based surfactants are sorbitans, ethoxylated sorbitans, sucrose and glucose esters or alkylpolyglucosides. Examples of polymeric surfactants are home- or copolymers of vinylpyrrolidone, vinylalcohols, or vinylacetate.

Suitable cationic surfactants are quaternary surfactants, for example quaternary ammonium compounds with one or two hydrophobic groups, or salts of long-chain primary amines. Suitable amphoteric surfactants are alkylbetains and imidazolines. Suitable block polymers are block polymers of the A-B or A-B-A type comprising blocks of polyethylene oxide and polypropylene oxide, or of the A-B—C type comprising alkanol, polyethylene oxide and polypropylene oxide. Suitable polyelectrolytes are polyacids or polybases. Examples of polyacids are alkali salts of polyacrylic acid or polyacid comb polymers. Examples of polybases are polyvinylamines or polyethyleneamines.

Suitable adjuvants are compounds, which have a neglectable or even no pesticidal activity themselves, and which improve the biological performance of the compound I on the target. Examples are surfactants, mineral or vegetable oils, and other auxiliaries. Further examples are listed by Knowles, Adjuvants and additives, Agrow Reports DS256, T&F Informa UK, 2006, chapter 5.

Suitable thickeners are polysaccharides (e.g. xanthan gum, carboxymethylcellulose), anorganic clays (organically modified or unmodified), polycarboxylates, and silicates.

Suitable bactericides are bronopol and isothiazolinone derivatives such as alkylisothiazolinones and benzisothiazolinones.

Suitable anti-freezing agents are ethylene glycol, propylene glycol, urea and glycerin.

Suitable anti-foaming agents are silicones, long chain alcohols, and salts of fatty acids.

Suitable colorants (e.g. in red, blue, or green) are pigments of low water solubility and water-soluble dyes. Examples are inorganic colorants (e.g. iron oxide, titan oxide, iron hexacyanoferrate) and organic colorants (e.g. alizarin-, azo- and phthalocyanine colorants).

Suitable tackifiers or binders are polyvinylpyrrolidons, polyvinylacetates, polyvinyl alcohols, polyacrylates, biological or synthetic waxes, and cellulose ethers.

Examples for composition types and their preparation are:
i) Water-soluble concentrates (SL, LS)
   10-60 wt % of a compound I according to the invention and 5-15 wt % wetting agent (e.g. alcohol alkoxylates) are dissolved in water and/or in a water-soluble solvent (e.g. alcohols) ad 100 wt %. The active substance dissolves upon dilution with water.
ii) Dispersible concentrates (DC)
   5-25 wt % of a compound I according to the invention and 1-10 wt % dispersant (e.g. polyvinylpyrrolidone) are dissolved in organic solvent (e.g. cyclohexanone) ad 100 wt %. Dilution with water gives a dispersion.
iii) Emulsifiable concentrates (EC)
   15-70 wt % of a compound I according to the invention and 5-10 wt % emulsifiers (e.g. calcium dodecylbenzenesulfonate and castor oil ethoxylate) are dissolved in water-insoluble organic solvent (e.g. aromatic hydrocarbon) ad 100 wt %. Dilution with water gives an emulsion.
iv) Emulsions (EW, EO, ES)
   5-40 wt % of a compound I according to the invention and 1-10 wt % emulsifiers (e.g. calcium dodecylbenzenesulfonate and castor oil ethoxylate) are dissolved in 20-40 wt % water-insoluble organic solvent (e.g. aromatic hydrocarbon). This mixture is introduced into water ad 100 wt % by means of an emulsifying machine and made into a homogeneous emulsion. Dilution with water gives an emulsion.
v) Suspensions (SC, OD, FS)
   In an agitated ball mill, 20-60 wt % of a compound I according to the invention are comminuted with addition of 2-10 wt % dispersants and wetting agents (e.g. sodium lignosulfonate and alcohol ethoxylate), 0.1-2 wt % thickener (e.g. xanthan gum) and water ad 100 wt % to give a fine active substance suspension. Dilution with water gives a stable suspension of the active substance. For FS type composition up to 40 wt % binder (e.g. polyvinylalcohol) is added.
vi) Water-dispersible granules and water-soluble granules (WG, SG)
   50-80 wt % of a compound I according to the invention are ground finely with addition of dispersants and wetting agents (e.g. sodium lignosulfonate and alcohol ethoxylate) ad 100 wt % and prepared as water-dispersible or water-soluble granules by means of technical appliances (e.g. extrusion, spray tower, fluidized bed). Dilution with water gives a stable dispersion or solution of the active substance.

vii) Water-dispersible powders and water-soluble powders (WP, SP, WS)

50-80 wt % of a compound I according to the invention are ground in a rotor-stator mill with addition of 1-5 wt % dispersants (e.g. sodium lignosulfonate), 1-3 wt % wetting agents (e.g. alcohol ethoxylate) and solid carrier (e.g. silica gel) ad 100 wt %. Dilution with water gives a stable dispersion or solution of the active substance.

viii) Gel (GW, GF)

In an agitated ball mill, 5-25 wt % of a compound I according to the invention are comminuted with addition of 3-10 wt % dispersants (e.g. sodium lignosulfonate), 1-5 wt % thickener (e.g. carboxymethylcellulose) and water ad 100 wt % to give a fine suspension of the active substance. Dilution with water gives a stable suspension of the active substance.

iv) Microemulsion (ME)

5-20 wt % of a compound I according to the invention are added to 5-30 wt % organic solvent blend (e.g. fatty acid dimethylamide and cyclohexanone), 10-25 wt % surfactant blend (e.g. alkohol ethoxylate and arylphenol ethoxylate), and water ad 100%. This mixture is stirred for 1 h to produce spontaneously a thermodynamically stable microemulsion.

iv) Microcapsules (CS)

An oil phase comprising 5-50 wt % of a compound I according to the invention, 0-40 wt % water insoluble organic solvent (e.g. aromatic hydrocarbon), 2-15 wt % acrylic monomers (e.g. methylmethacrylate, methacrylic acid and a di- or triacrylate) are dispersed into an aqueous solution of a protective colloid (e.g. polyvinyl alcohol). Radical polymerization initiated by a radical initiator results in the formation of poly(meth)acrylate microcapsules. Alternatively, an oil phase comprising 5-50 wt % of a compound I according to the invention, 0-40 wt % water insoluble organic solvent (e.g. aromatic hydrocarbon), and an isocyanate monomer (e.g. diphenylmethene-4,4'-diisocyanatae) are dispersed into an aqueous solution of a protective colloid (e.g. polyvinyl alcohol). The addition of a polyamine (e.g. hexa-methylenediamine) results in the formation of a polyurea microcapsules. The monomers amount to 1-10 wt %. The wt % relate to the total CS composition.

ix) Dustable powders (DP, DS)

1-10 wt % of a compound I according to the invention are ground finely and mixed intimately with solid carrier (e.g. finely divided kaolin) ad 100 wt %.

x) Granules (GR, FG)

0.5-30 wt % of a compound I according to the invention is ground finely and associated with solid carrier (e.g. silicate) ad 100 wt %. Granulation is achieved by extrusion, spray-drying or the fluidized bed.

xi) Ultra-low volume liquids (UL)

1-50 wt % of a compound I according to the invention are dissolved in organic solvent (e.g. aromatic hydrocarbon) ad 100 wt %.

The compositions types i) to xi) may optionally comprise further auxiliaries, such as 0.1-1 wt % bactericides, 5-15 wt % anti-freezing agents, 0.1-1 wt % anti-foaming agents, and 0.1-1 wt % colorants.

The agrochemical compositions generally comprise between 0.01 and 95%, preferably between 0.1 and 90%, and in particular between 0.5 and 75%, by weight of active substance. The active substances are employed in a purity of from 90% to 100%, preferably from 95% to 100% (according to NMR spectrum).

Solutions for seed treatment (LS), Suspo-emulsions (SE), flowable concentrates (FS), powders for dry treatment (DS), water-dispersible powders for slurry treatment (WS), water-soluble powders (SS), emulsions (ES), emulsifiable concentrates (EC) and gels (GF) are usually employed for the purposes of treatment of plant propagation materials, particularly seeds. The compositions in question give, after two-to-tenfold dilution, active substance concentrations of from 0.01 to 60% by weight, preferably from 0.1 to 40% by weight, in the ready-to-use preparations. Application can be carried out before or during sowing. Methods for applying compound I and compositions thereof, respectively, on to plant propagation material, especially seeds include dressing, coating, pelleting, dusting, soaking and in-furrow application methods of the propagation material. Preferably, compound I or the compositions thereof, respectively, are applied on to the plant propagation material by a method such that germination is not induced, e.g. by seed dressing, pelleting, coating and dusting.

When employed in plant protection, the amounts of active substances applied are, depending on the kind of effect desired, from 0.001 to 2 kg per ha, preferably from 0.005 to 2 kg per ha, more preferably from 0.05 to 0.9 kg per ha, and in particular from 0.1 to 0.75 kg per ha. In treatment of plant propagation materials such as seeds, e.g. by dusting, coating or drenching seed, amounts of active substance of from 0.1 to 1000 g, preferably from 1 to 1000 g, more preferably from 1 to 100 g and most preferably from 5 to 100 g, per 100 kilogram of plant propagation material (preferably seeds) are generally required.

When used in the protection of materials or stored products, the amount of active substance applied depends on the kind of application area and on the desired effect. Amounts customarily applied in the protection of materials are 0.001 g to 2 kg, preferably 0.005 g to 1 kg, of active substance per cubic meter of treated material.

Various types of oils, wetters, adjuvants, fertilizer, or micronutrients, and further pesticides (e.g. herbicides, insecticides, fungicides, growth regulators, safeners) may be added to the active substances or the compositions comprising them as premix or, if appropriate not until immediately prior to use (tank mix). These agents can be admixed with the compositions according to the invention in a weight ratio of 1:100 to 100:1, preferably 1:10 to 10:1.

The user applies the composition according to the invention usually from a predosage device, a knapsack sprayer, a spray tank, a spray plane, or an irrigation system. Usually, the agrochemical composition is made up with water, buffer, and/or further auxiliaries to the desired application concentration and the ready-to-use spray liquor or the agrochemical composition according to the invention is thus obtained. Usually, 20 to 2000 liters, preferably 50 to 400 liters, of the ready-to-use spray liquor are applied per hectare of agricultural useful area.

According to one embodiment, individual components of the composition according to the invention such as parts of a kit or parts of a binary or ternary mixture may be mixed by the user himself in a spray tank and further auxiliaries may be added, if appropriate.

In a further embodiment, either individual components of the composition according to the invention or partially premixed components, e.g. components comprising compounds I, may be mixed by the user in a spray tank and further auxiliaries and additives may be added, if appropriate.

In a further embodiment, either individual components of the composition according to the invention or partially premixed components, e.g. components comprising compounds I, can be applied jointly (e.g. after tank mix) or consecutively.

Mixtures

According to one embodiment of the present invention, individual components of the composition according to the invention such as parts of a kit or parts of a binary or ternary mixture may be mixed by the user himself in a spray tank and further auxiliaries may be added, if appropriate. In a further embodiment, either individual components of the composition according to the invention or partially premixed components, e.g. components comprising compounds I and/or active substances from the groups M.1 to M.UN.X or F.I to F.XII, may be mixed by the user in a spray tank and further auxiliaries and additives may be added, if appropriate.

In a further embodiment, either individual components of the composition according to the invention or partially premixed components, e.g. components comprising compounds I and/or active substances from the groups M.1 to M.UN.X or F.I to F.XII, can be applied jointly (e.g. after tank mix) or consecutively.

The following list M of pesticides, grouped and numbered according the Mode of Action Classification of the Insecticide Resistance Action Committee (IRAC), together with which the compounds according to the invention can be used and with which potential synergistic effects might be produced, is intended to illustrate the possible combinations, but not to impose any limitation:

M.1 Acetylcholine esterase (AChE) inhibitors from the class of

M.1A carbamates, for example aldicarb, alanycarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, trimethacarb, XMC, xylylcarb and triazamate; or from the class of M.1B organophosphates, for example acephate, azamethiphos, azinphos-ethyl, azinphosmethyl, cadusafos, chlorethoxyfos, chlorfenvinphos, chlormephos, chlorpyrifos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isopropyl O-(methoxyaminothiophosphoryl) salicylate, isoxathion, malathion, mecarbam, methamidophos, methidathion, mevinphos, monocrotophos, naled, omethoate, oxydemeton-methyl, parathion, parathionmethyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, trichlorfon and vamidothion;

M.2. GABA-gated chloride channel antagonists such as:

M.2A cyclodiene organochlorine compounds, as for example endosulfan or chlordane; or M.2B fiproles (phenylpyrazoles), as for example ethiprole, fipronil, flufiprole, pyrafluprole and pyriprole;

M.3 Sodium channel modulators from the class of

M.3A pyrethroids, for example acrinathrin, allethrin, d-cis-trans allethrin, d-trans allethrin, bifenthrin, bioallethrin, bioallethrin S-cylclopentenyl, bioresmethrin, cyclopro-thrin, cyfluthrin, betacyfluthrin, cyhalothrin, lambda-cy-halothrin, gamma-cyhalothrin, cypermethrin, alphacypermethrin, beta-cypermethrin, theta-cypermethrin, zeta-cypermethrin, cyphenothrin, deltamethrin, empenthrin, esfenvalerate, etofenprox, fenpropathrin, fenvalerate, flucythrinate, flumethrin, tau-fluvalinate, halfenprox, imiprothrin, meperfluthrin, metofluthrin, momfluorothrin, permethrin, phenothrin, prallethrin, profluthrin, pyrethrin (pyrethrum), resmethrin, silafluofen, tefluthrin, tetramethylfluthrin, tetramethrin, tralomethrin and transfluthrin; or M.3B sodium channel modulators such as DDT or methoxychlor;

M.4 Nicotinic acetylcholine receptor agonists (nAChR) from the class of

M.4A neonicotinoids, for example acteamiprid, chlothianidin, dinotefuran, imidacloprid, nitenpyram, thiacloprid and thiamethoxam; or the compounds M.4A.1: 1-[(6-chloro-3-pyridinyl)methyl]-2,3,5,6,7,8-hexahydro-9-nitro-(5S,8R)-5,8-Epoxy-1Himidazo[1,2-a]azepine; or M.4A.2: 1-[(6-chloro-3-pyridyl)methyl]-2-nitro-1-[(E)-pentylideneamino]guanidine; or M4.A.3: 1-[(6-chloro-3-pyridyl)methyl]-7-methyl-8-nitro-5-propoxy-3,5,6,7-tetrahydro-2H-imidazo[1,2-a]pyridine;

or M.4B nicotine.

M.5 Nicotinic acetylcholine receptor allosteric activators from the class of spinosyns, for example spinosad or spinetoram;

M.6 Chloride channel activators from the class of avermectins and milbemycins, for example abamectin, emamectin benzoate, ivermectin, lepimectin or milbemectin;

M.7 Juvenile hormone mimics, such as

M.7A juvenile hormone analogues as hydroprene, kinoprene and methoprene; or others as M.7B fenoxycarb or M.7C pyriproxyfen;

M.8 miscellaneous non-specific (multi-site) inhibitors, for example

M.8A alkyl halides as methyl bromide and other alkyl halides, or

M.8B chloropicrin, or M.8C sulfuryl fluoride, or M.8D borax, or M.8E tartar emetic;

M.9 Selective homopteran feeding blockers, for example M.9B pymetrozine, or M.9C flonicamid;

M.10 Mite growth inhibitors, for example

M.10A clofentezine, hexythiazox and diflovidazin, or M.10B etoxazole;

M.11 Microbial disruptors of insect midgut membranes, for example *bacillus thuringiensis* or *bacillus sphaericus* and the insecticdal proteins they produce such as *bacillus thuringiensis* subsp. *israelensis, bacillus sphaericus, bacillus thuringiensis* subsp. *aizawai bacillus thuringiensis* subsp. *kurstakiand bacillus thuringiensis* subsp. *tenebrionis*, or the Bt crop proteins: Cry1Ab, Cry1Ac, Cry1Fa, Cry2Ab, mCry3A, Cry3Ab, Cry3Bb and Cry34/35Ab1;

M.12 Inhibitors of mitochondrial ATP synthase, for example

M.12A diafenthiuron, or

M.12B organotin miticides such as azocyclotin, cyhexatin or fenbutatin oxide, or M.12C propargite, or M.12D tetradifon;

M.13 Uncouplers of oxidative phosphorylation via disruption of the proton gradient, for example chlorfenapyr, DNOC or sulfluramid;

M.14 Nicotinic acetylcholine receptor (nAChR) channel blockers, for example nereistoxin analogues as bensultap, cartap hydrochloride, thiocyclam or thiosultap sodium;

M.15 Inhibitors of the chitin biosynthesis type 0, such as benzoylureas as for example bistrifluron, chlorfluazuron, diflubenzuron, flucycloxuron, flufenoxuron, hexaflumuron, lufenuron, novaluron, noviflumuron, teflubenzuron or triflumuron;

M.16 Inhibitors of the chitin biosynthesis type 1, as for example buprofezin;

M.17 Moulting disruptors, Dipteran, as for example cyromazine;

M.18 Ecdyson receptor agonists such as diacylhydrazines, for example methoxyfenozide, tebufenozide, halofenozide, fufenozide or chromafenozide;

M.19 Octopamin receptor agonists, as for example amitraz;

M.20 Mitochondrial complex III electron transport inhibitors, for example

M.20A hydramethylnon, or M.20B acequinocyl, or M.20C fluacrypyrim;

M.21 Mitochondrial complex I electron transport inhibitors, for example

M.21A METI acaricides and insecticides such as fenazaquin, fenpyroximate, pyrimidifen, pyridaben, tebufenpyrad or tolfenpyrad, or M.21B rotenone;

M.22 Voltage-dependent sodium channel blockers, for example

M.22A indoxacarb, or M.22B metaflumizone, or M.22C 1-[(E)-[2-(4-cyanophenyl)-1-[3-(trifluoromethyl)phenyl]ethylidene]amino]-3-[4-(difluoromethoxy)phenyl]urea;

M.23 Inhibitors of the of acetyl CoA carboxylase, such as Tetronic and Tetramic acid derivatives, for example spirodiclofen, spiromesifen or spirotetramat;

M.24 Mitochondrial complex IV electron transport inhibitors, for example

M.24A phosphine such as aluminium phosphide, calcium phosphide, phosphine or zinc phosphide, or M.24B cyanide.

M.25 Mitochondrial complex II electron transport inhibitors, such as beta-ketonitrile derivatives, for example cyenopyrafen or cyflumetofen;

M.28 Ryanodine receptor-modulators from the class of diamides, as for example flubendiamide, chlorantraniliprole (Rynaxypyr®), cyantraniliprole (Cyazypyr®), or the phthalamide compounds M.28.1: (R)-3-Chlor-N1-{2-methyl-4-[1,2,2,2-tetrafluor-1-(trifluormethyl)ethyl]phenyl}-N2-(1-methyl-2-methylsulfonylethyl)phthalamid and M.28.2: (S)-3-Chlor-N1-{2-methyl-4-[1,2,2,2-tetrafluor-1-(trifluormethyl)ethyl]phenyl}-N2-(1-methyl-2-methylsulfonylethyl)phthalamid, or the compound M.28.3: 3-bromo-N-{2-bromo-4-chloro-6-[(1-cyclopropylethyl)carbamoyl]phenyl}-1-(3-chlorpyridin-2-yl)-1H-pyrazole-5-carboxamide (proposed ISO name: cyclaniliprole), or the compound M.28.4: methyl-2-[3,5-dibromo-2-({[3-bromo-1-(3-chlorpyridin-2-yl)-1H-pyrazol-5-yl]carbonyl}amino)benzoyl]-1,2-dimethylhydrazinecarboxylate; or a compound selected from M.28.5a) to M.28.5l):

M.28.5a) N-[4,6-dichloro-2-[(diethyl-lambda-4-sulfanylidene)carbamoyl]-phenyl]-2-(3-chloro-2-pyridyl)-5-(trifluoromethyl)pyrazole-3-carboxamide;

M.28.5b) N-[4-chloro-2-[(diethyl-lambda-4-sulfanylidene)carbamoyl]-6-methyl-phenyl]-2-(3-chloro-2-pyridyl)-5-(trifluoromethyl)pyrazole-3-carboxamide;

M.28.5c) N-[4-chloro-2-[(di-2-propyl-lambda-4-sulfanylidene)carbamoyl]-6-methyl-phenyl]-2-(3-chloro-2-pyridyl)-5-(trifluoromethyl)pyrazole-3-carboxamide;

M.28.5d) N-[4,6-dichloro-2-[(di-2-propyl-lambda-4-sulfanylidene)carbamoyl]-phenyl]-2-(3-chloro-2-pyridyl)-5-(trifluoromethyl)pyrazole-3-carboxamide;

M.28.5e) N-[4,6-dichloro-2-[(diethyl-lambda-4-sulfanylidene)carbamoyl]-phenyl]-2-(3-chloro-2-pyridyl)-5-(difluoromethyl)pyrazole-3-carboxamide;

M.28.5f) N-[4,6-dibromo-2-[(di-2-propyl-lambda-4-sulfanylidene)carbamoyl]-phenyl]-2-(3-chloro-2-pyridyl)-5-(trifluoromethyl)pyrazole-3-carboxamide;

M.28.5g) N-[4-chloro-2-[(di-2-propyl-lambda-4-sulfanylidene)carbamoyl]-6-cyano-phenyl]-2-(3-chloro-2-pyridyl)-5-(trifluoromethyl)pyrazole-3-carboxamide;

M.28.5h) N-[4,6-dibromo-2-[(diethyl-lambda-4-sulfanylidene)carbamoyl]-phenyl]-2-(3-chloro-2-pyridyl)-5-(trifluoromethyl)pyrazole-3-carboxamide;

M.28.5i) N-[2-(5-amino-1,3,4-thiadiazol-2-yl)-4-chloro-6-methyl-phenyl]-5-bromo-2-(3-chloro-2-pyridyl)pyrazole-3-carboxamide;

M.28.5j) 5-chloro-2-(3-chloro-2-pyridyl)-N-[2,4-dichloro-6-[(1-cyano-1-methyl-ethyl)carbamoyl]phenyl]pyrazole-3-carboxamide;

M.28.5k) 5-bromo-N-[2,4-dichloro-6-(methylcarbamoyl)phenyl]-2-(3,5-dichloro-2-pyridyl)pyrazole-3-carboxamide;

M.28.5l) N-[2-(tert-butylcarbamoyl)-4-chloro-6-methyl-phenyl]-2-(3-chloro-2-pyridyl)-5-(fluoromethoxy)pyrazole-3-carboxamide; or a compound selected from M.28.6 N2-(1-cyano-1-methyl-ethyl)-N1-(2,4-dimethylphenyl)-3-iodo-phthalamide; or M.28.7 3-chloro-N2-(1-cyano-1-methyl-ethyl)-N1-(2,4-dimethylphenyl)phthalamide;

M.UN.X insecticidal active compounds of unknown or uncertain mode of action, as for example afidopyropen, azadirachtin, amidoflumet, benzoximate, bifenazate, bromopropylate, chinomethionat, cryolite, dicofol, flufenerim, flometoquin, fluensulfone, flupyradifurone, piperonyl butoxide, pyridalyl, pyrifluquinazon, sulfoxaflor, pyflubumide or the compounds M.UN.X.1: 4-[5-(3,5-Dichloro-phenyl)-5-trifluoromethyl-4,5-dihydro-isoxazol-3-yl]-2-methyl-N-[(2,2,2-trifluoroethylcarbamoyl)-methyl]-benzamide, or the compound M.UN.X.2: 4-[5-[3-chloro-5-(trifluoromethyl)phenyl]-5-(trifluoromethyl)-4H-isoxazol-3-yl]-N-[2-oxo-2-(2,2,2-trifluoroethylamino)ethyl]naphthalene-1-carboxamide, or the compound M.UN.X.3: 11-(4-chloro-2,6-dimethylphenyl)-12-hydroxy-1,4-dioxa-9-azadispiro[4.2.4.2]-tetradec-11-en-10-one, or the compound M.UN.X.4: 3-(4'-fluoro-2,4-dimethylbiphenyl-3-yl)-4-hydroxy-8-oxa-1-azaspiro[4.5]dec-3-en-2-one, or the compound M.UN.X.5: 1-[2-fluoro-4-methyl-5-[(2,2,2-trifluoroethyl)sulfinyl]phenyl]-3-(trifluoromethyl)-1H-1,2,4-triazole-5-amine, or actives on basis of *bacillus firmus* (Votivo, 1-1582); or M.UN.X.6; a compound selected from the group of M.UN.X.6a) (E/Z)—N-[1-[(6-chloro-3-pyridyl)methyl]-2-pyridylidene]-2,2,2-trifluoro-acetamide;

M.UN.X.6b) (E/Z)—N-[1-[(6-chloro-5-fluoro-3-pyridyl)methyl]-2-pyridylidene]-2,2,2-trifluoro-acetamide;

M.UN.X.6c) (E/Z)-2,2,2-trifluoro-N-[1-[(6-fluoro-3-pyridyl)methyl]-2-pyridylidene]acetamide;

M.UN.X.6d) (E/Z)—N-[1-[(6-bromo-3-pyridyl)methyl]-2-pyridylidene]-2,2,2-trifluoro-acetamide;

M.UN.X.6e) (E/Z)—N-[1-[1-(6-chloro-3-pyridyl)ethyl]-2-pyridylidene]-2,2,2-trifluoro-acetamide;

M.UN.X.6f) (E/Z)—N-[1-[(6-chloro-3-pyridyl)methyl]-2-pyridylidene]-2,2-difluoro-acetamide;

M.UN.X.6g) (E/Z)-2-chloro-N-[1-[(6-chloro-3-pyridyl)methyl]-2-pyridylidene]-2,2-difluoro-acetamide;

M.UN.X.6h) (E/Z)—N-[1-[(2-chloropyrimidin-5-yl)methyl]-2-pyridylidene]-2,2,2-trifluoro-acetamide and M.UN.X.6i) (E/Z)—N-[1-[(6-chloro-3-pyridyl)methyl]-2-pyridylidene]-2,2,3,3,3-pentafluoropropanamide.); or of the compounds M.UN.X.7: 3-[3-chloro-5-(trifluoromethyl)phenyl]-4-oxo-1-(pyrimidin-5-ylmethyl)pyrido[1,2-a]pyrimidin-1-ium-2-olate; or M.UN.X.8: 8-chloro-N-[2-chloro-5-methoxyphenyl)sulfonyl]-6-trifluoromethyl)-imidazo[1,2-a]pyridine-2-carboxamide; or M.UN.X.9: 4-[5-(3,5-dichlorophenyl)-5-(trifluoromethyl)-4H-isoxazol-3-yl]-2-methyl-N-(1-oxothietan-3-yl)benzamide; or M.UN.X.10: 5-[3-[2,6-dichloro-4-(3,3-dichloroallyloxy)phenoxy]propoxy]-1H-pyrazole.

The commercially available compounds of the group M listed above may be found in The Pesticide Manual, 15th Edition, C. D. S. Tomlin, British Crop Protection Council (2011) among other publications.

The quinoline derivative flometoquin is shown in WO2006/013896. The aminofuranone compounds flupyradifurone is known from WO 2007/115644. The sulfoximine compound sulfoxaflor is known from WO2007/149134. The pyrethroid momfluorothrin is known from U.S. Pat. No. 6,908,945. The pyrazole acaricide pyflubumide is known from WO2007/020986. The isoxazoline compounds have been described likewise M.UN.X.1 in WO2005/085216, M.UN.X2. in WO2009/002809 and in WO2011/149749 and the isoxazoline M.UN.X.9 in WO2013/050317. The pyripyropene derivative afidopyropen has been described in WO 2006/129714. The spiroketal-substituted cyclic ketoenol derivative M.UN.X.3 is known from WO2006/089633 and the biphenyl-substituted spirocyclic ketoenol derivative M.UN.X.4 from WO2008/067911. Finally triazoylphenylsulfide like M.UN.X.5 have been described in WO2006/043635 and biological control agents on basis of *bacillus firmus* in WO2009/124707. The neonicotinoids 4A.1 is known from WO20120/069266 and WO2011/06946, the M.4.A.2 from WO2013/003977, the M4.A.3. from WO2010/069266. The Metaflumizone analogue M.22C is described in CN 10171577. The phthalamides M.28.1 and M.28.2 are both known from WO 2007/101540. The anthranilamide M.28.3 has been described in WO2005/077934. The hydrazide compound M.28.4 has been described in WO 2007/043677. The anthranilamides M.28.5a) to M.28.5h) can be prepared as described in WO 2007/006670, WO2013/024009 and WO2013/024010, the anthranilamide M.28.5i) is described in WO2011/085575, the M.28.5j) in WO2008/134969, the M.28.5k) in US2011/046186 and the M.28.5l) in WO2012/034403. The diamide compounds M.28.6 and M.28.7 can be found in CN102613183. The compounds M.UN.X.6a) to M.UN.X.6i) listed in M.UN.X.6 have been described in WO2012/029672. The mesoionic antagonist compound M.UN.X.7 was described in WO2012/092115, the nematicide M.UN.X.8 in WO2013/055584 and the Pyridalyl-type analogue M.UN.X.10 in WO2010/060379.

The following list of active fungicidal substances, in conjunction with which the compounds according to the invention can be used, is intended to illustrate the possible combinations but does not limit them:

F.I) Respiration Inhibitors

F.I-1) Inhibitors of complex III at Qo site (e.g. strobilurins) strobilurins: azoxystrobin, dimoxystrobin, enestroburin, fluoxastrobin, kresoxim-methyl, metominostrobin, orysastrobin, picoxystrobin, pyraclostrobin, pyrametostrobin, pyraoxystrobin, pyribencarb, trifloxystrobin, methyl (2-chloro-5 [1-(3-methylbenzyloxyimino)ethyl]benzyl)carbamate and 2 (2-(3-(2,6-dichlorophenyl)-1-methyl-allylideneaminooxymethyl)-phenyl)-2-methoxy-imino-N methyl-acetamide;

oxazolidinediones and imidazolinones: famoxadone, fenamidone;

F.I-2) Inhibitors of complex II (e.g. carboxamides):

carboxanilides: benodanil, bixafen, boscalid, carboxin, fenfuram, fenhexamid, fluopyram, flutolanil, furametpyr, isopyrazam, isotianil, mepronil, oxycarboxin, penflufen, penthiopyrad, sedaxane, tecloftalam, thifluzamide, tiadinil, 2-amino-4 methyl-thiazole-5-carboxanilide, N-(3', 4',5' trifluorobiphenyl-2 yl)-3-difluoromethyl-1-methyl-1H-pyrazole-4 carboxamide, N-(4'-trifluoromethylthiobiphenyl-2-yl)-3 difluoromethyl-1-methyl-1H pyrazole-4-carboxamide and N-(2-(1,3,3-trimethyl-butyl)-phenyl)-1,3-dimethyl-5 fluoro-1H-pyrazole-4 carboxamide;

F.I-3) Inhibitors of complex III at Qi site: cyazofamid, amisulbrom;

F.I-4) Other respiration inhibitors (complex I, uncouplers) diflumetorim; tecnazen; ferimzone; ametoctradin; silthiofam; nitrophenyl derivates: binapacryl, dinobuton, dinocap, fluazinam, nitrthal-isopropyl, organometal compounds: fentin salts, such as fentin-acetate, fentin chloride or fentin hydroxide;

F.II) Sterol biosynthesis inhibitors (SBI fungicides)

F.II-1) C14 demethylase inhibitors (DMI fungicides, e.g. triazoles, imidazoles) triazoles: azaconazole, bitertanol, bromuconazole, cyproconazole, difenoconazole, diniconazole, diniconazole-M, epoxiconazole, fenbuconazole, fluquinconazole, flusilazole, flutriafol, hexaconazole, imibenconazole, ipconazole, metconazole, myclobutanil, paclobutrazole, penconazole, propiconazole, prothioconazole, simeconazole, tebuconazole, tetraconazole, triadimefon, triadimenol, triticonazole, uniconazole;

imidazoles: imazalil, pefurazoate, oxpoconazole, prochloraz, triflumizole;

pyrimidines, pyridines and piperazines: fenarimol, nuarimol, pyrifenox, triforine;

F.II-2) Delta14-reductase inhibitors (Amines, e.g. morpholines, piperidines) morpholines: aldimorph, dodemorph, dodemorph-acetate, fenpropimorph, tridemorph;

piperidines: fenpropidin, piperalin;

spiroketalamines: spiroxamine;

F.II-3) Inhibitors of 3-keto reductase: hydroxyanilides: fenhexamid;

F.III) Nucleic acid synthesis inhibitors

F.III-1) RNA, DNA synthesis phenylamides or acyl amino acid fungicides: benalaxyl, benalaxyl-M, kiralaxyl, metalaxyl, metalaxyl-M (mefenoxam), ofurace, oxadixyl;

isoxazoles and iosothiazolones: hymexazole, octhilinone;

F.III-2) DNA topisomerase inhibitors: oxolinic acid;

F.III-3) Nucleotide metabolism (e.g. adenosin-deaminase) hydroxy (2-amino)-pyrimidines: bupirimate;

F.IV) Inhibitors of cell division and or cytoskeleton

F.IV-1) Tubulin inhibitors: benzimidazoles and thiophanates: benomyl, carbendazim, fuberidazole, thiabendazole, thiophanate-methyl;

triazolopyrimidines: 5-chloro-7 (4-methylpiperidin-1-yl)-6-(2,4,6-trifluorophenyl)[1,2,4]triazolo[1,5a]pyrimidine F.IV-2) Other cell division inhibitors benzamides and phenyl acetamides: diethofencarb, ethaboxam, pencycuron, fluopicolide, zoxamide;

F.IV-3) Actin inhibitors: benzophenones: metrafenone;

F.V) Inhibitors of amino acid and protein synthesis

F.V-1) Mmethionine synthesis inhibitors (anilino-pyrimidines) anilino-pyrimidines: cyprodinil, mepanipyrim, nitrapyrin, pyrimethanil;

F.V-2) Protein synthesis inhibitors (anilino-pyrimidines) antibiotics: blasticidin-S, kasugamycin, kasugamycin hydrochloride-hydrate, mildiomycin, streptomycin, oxytetracyclin, polyoxine, validamycin A;

F.VI) Signal transduction inhibitors

F.VI-1) MAP/Histidine kinase inhibitors (e.g. anilino-pyrimidines) dicarboximides: fluoroimid, iprodione, procymidone, vinclozolin;

phenylpyrroles: fenpiclonil, fludioxonil;

F.VI-2) G protein inhibitors: quinolines: quinoxyfen;

F.VII) Lipid and membrane synthesis inhibitors

F.VII-1) Phospholipid biosynthesis inhibitors organophosphorus compounds: edifenphos, iprobenfos, pyrazophos;

dithiolanes: isoprothiolane;

F.VII-2) Lipid peroxidation aromatic hydrocarbons: dicloran, quintozene, tecnazene, tolclofos-methyl, biphenyl, chloroneb, etridiazole;

F.VII-3) Carboxyl acid amides (CAA fungicides) cinnamic or mandelic acid amides: dimethomorph, flumorph, mandiproamid, pyrimorph;

valinamide carbamates: benthiavalicarb, iprovalicarb, pyribencarb, valifenalate and N-(1-(1-(4-cyano-phenyl)ethanesulfonyl)-but-2-yl) carbamic acid-(4-fluorophenyl) ester;

F.VII-4) Compounds affecting cell membrane permeability and fatty acides carbamates: propamocarb, propamocarb-hydrochlorid F.VIII) Inhibitors with Multi Site Action F.VIII-1) Inorganic active substances: Bordeaux mixture, copper acetate, copper hydroxide, copper oxychloride, basic copper sulfate, sulfur;

F.VIII-2) Thio- and dithiocarbamates: ferbam, mancozeb, maneb, metam, methasulphocarb, metiram, propineb, thiram, zineb, ziram;

F.VIII-3) Organochlorine compounds (e.g. phthalimides, sulfamides, chloronitriles): anilazine, chlorothalonil, captafol, captan, folpet, dichlofluanid, dichlorophen, flusulfamide, hexachlorobenzene, pentachlorphenole and its salts, phthalide, tolylfluanid, N-(4-chloro-2-nitrophenyl)-N-ethyl-4-methyl-benzenesulfonamide;

F.VIII-4) Guanidines: guanidine, dodine, dodine free base, guazatine, guazatine-acetate, iminoctadine, iminoctadine-triacetate, iminoctadine-tris(albesilate);

F.VIII-5) Ahtraquinones: dithianon;

F.IX) Cell wall synthesis inhibitors

F.IX-1) Inhibitors of glucan synthesis: validamycin, polyoxin B;

F.IX-2) Melanin synthesis inhibitors: pyroquilon, tricyclazole, carpropamide, dicyclomet, fenoxanil;

F.X) Plant defence inducers

F.X-1) Salicylic acid pathway: acibenzolar-S-methyl;

F.X-2) Others: probenazole, isotianil, tiadinil, prohexadione-calcium;

phosphonates: fosetyl, fosetyl-aluminum, phosphorous acid and its salts;

F.XI) Unknown mode of action:

bronopol, chinomethionat, cyflufenamid, cymoxanil, dazomet, debacarb, diclomezine, difenzoquat, difenzoquat-methylsulfate, diphenylamin, flumetover, flusulfamide, flutianil, methasulfocarb, oxin-copper, proquinazid, tebufloquin, tecloftalam, triazoxide, 2-butoxy-6-iodo-3-propylchromen-4-one, N-(cyclopropylmethoxyimino-(6-difluoro-methoxy-2,3-difluoro-phenyl)methyl)-2-phenyl acetamide, N'-(4-(4-chloro-3-trifluoromethyl-phenoxy)-2,5-dimethyl-phenyl)-N-ethyl-N methyl formamidine, N'(4-(4-fluoro-3-trifluoromethyl-phenoxy)-2,5-dimethyl-phenyl)-N-ethyl-N-methyl formamidine, N'-(2-methyl-5-trifluoromethyl-4-(3-trimethylsilanyl-propoxy)phenyl)-N-ethyl-N-methyl formamidine, N'-(5-difluoromethyl-2 methyl-4-(3-trimethylsilanyl-propoxy)-phenyl)-N-ethyl-N-methyl formamidine, 2-{1-[2-(5-methyl-3-trifluoromethyl-pyrazole-1-yl)-acetyl]-piperidin-4-yl}-thiazole-4-carboxylic acid methyl-(1,2,3,4-tetrahydro-naphthalen-1-yl)amide, 2-{1-[2-(5-methyl-3-trifluoromethyl-pyrazole-1-yl)-acetyl]-piperidin-4-yl}-thiazole-4-carboxylic acid methyl-(R)-1,2,3,4-tetrahydro-naphthalen-1-yl-amide, methoxy-acetic acid 6-tert-butyl-8-fluoro-2,3-dimethyl-quinolin-4-yl ester and N-Methyl-2-{1-[(5-methyl-3-trifluoromethyl-1H-pyrazol-1-yl)-acetyl]-piperidin-4-yl}-N-[(1R)-1,2,3,4-tetrahydronaphthalen-1-yl]-4-thiazolecarboxamide, 3-[5-(4-chloro-phenyl)-2,3-dimethyl-isoxazolidin-3 yl]-pyridine, 3-[5-(4-methyl-phenyl)-2,3-dimethyl-isoxazolidin-3-yl]-pyridine, 5-amino-2-isopropyl-3-oxo-4-ortho-tolyl-2,3-dihydro-pyrazole-1 carbothioic acid S-allyl ester, N-(6-methoxy-pyridin-3-yl) cyclopropane-carboxylic acid amide, 5-chloro-1 (4,6-dimethoxy-pyrimidin-2-yl)-2-methyl-1H-benzoimidazole, 2-(4-chloro-phenyl)-N-[4-(3,4-dimethoxy-phenyl)-isoxazol-5-yl]-2-prop-2-ynyloxy-acetamide;

F.XI) Growth regulators:

abscisic acid, amidochlor, ancymidol, 6-benzylaminopurine, brassinolide, butralin, chlormequat (chlormequat chloride), choline chloride, cyclanilide, daminozide, dikegulac, dimethipin, 2,6-dimethylpuridine, ethephon, flumetralin, flurprimidol, fluthiacet, forchlorfenuron, gibberellic acid, inabenfide, indole-3-acetic acid, maleic hydrazide, mefluidide, mepiquat (mepiquat chloride), naphthaleneacetic acid, N 6 benzyladenine, paclobutrazol, prohexadione (prohexadione-calcium), prohydrojasmon, thidiazuron, triapenthenol, tributyl phosphorotrithioate, 2,3,5 tri iodobenzoic acid, trinexapac-ethyl and uniconazole;

F.XII) Biological control agents antifungal biocontrol agents: *Bacillus* substilis strain with NRRL No. B-21661 (e.g. RHAPSODY®, SERENADE® MAX and SERENADE® ASO from AgraQuest, Inc., USA.), *Bacillus* pumilus strain with NRRL No. B-30087 (e.g. SONATA® and BALLAD® Plus from AgraQuest, Inc., USA), Ulocladium oudemansii (e.g. the product BOTRY-ZEN from BotriZen Ltd., New Zealand), Chitosan (e.g. ARMOUR-ZEN from BotriZen Ltd., New Zealand).

Applications

The animal pest, i.e. the insects, arachnids and nematodes, the plant, soil or water in which the plant is growing can be contacted with the present compounds of formula I or composition(s) containing them by any application method known in the art. As such, "contacting" includes both direct contact (applying the compounds/compositions directly on the animal pest or plant—typically to the foliage, stem or roots of the plant) and indirect contact (applying the compounds/compositions to the locus of the animal pest or plant).

The compounds of formula I or the pesticidal compositions comprising them may be used to protect growing plants and crops from attack or infestation by animal pests, especially insects, acaridae or arachnids by contacting the plant/crop with a pesticidally effective amount of compounds of formula I. The term "crop" refers both to growing and harvested crops.

The compounds of the present invention and the compositions comprising them are particularly important in the control of a multitude of insects on various cultivated plants, such as cereal, root crops, oil crops, vegetables, spices, ornamentals, for example seed of durum and other wheat, barley, oats, rye, maize (fodder maize and sugar maize/sweet and field corn), soybeans, oil crops, crucifers, cotton, sunflowers, bananas, rice, oilseed rape, turnip rape, sugarbeet, fodder beet, eggplants, potatoes, grass, lawn, turf, fodder grass, tomatoes, leeks, pumpkin/squash, cabbage, iceberg lettuce, pepper, cucumbers, melons, Brassica species, melons, beans, peas, garlic, onions, carrots, tuberous plants such as potatoes, sugar cane, tobacco, grapes, petunias, geranium/pelargoniums, pansies and impatiens.

The compounds of the present invention are employed as such or in form of compositions by treating the insects or the plants, plant propagation materials, such as seeds, soil, surfaces, materials or rooms to be protected from insecticidal attack with a insecticidally effective amount of the active compounds. The application can be carried out both before and after the infection of the plants, plant propagation materials, such as seeds, soil, surfaces, materials or rooms by the insects.

The present invention also includes a method of combating animal pests which comprises contacting the animal pests, their habit, breeding ground, food supply, cultivated plants, seed, soil, area, material or environment in which the animal pests are growing or may grow, or the materials, plants, seeds, soils, surfaces or spaces to be protected from animal attack or infestation with a pesticidally effective amount of a mixture of at least one active compound I.

Moreover, animal pests may be controlled by contacting the target pest, its food supply, habitat, breeding ground or its locus with a pesticidally effective amount of compounds of formula I. As such, the application may be carried out before or after the infection of the locus, growing crops, or harvested crops by the pest.

The compounds of the invention can also be applied preventively to places at which occurrence of the pests is expected.

The compounds of formula I may be also used to protect growing plants from attack or infestation by pests by contacting the plant with a pesticidally effective amount of compounds of formula I. As such, "contacting" includes both direct contact (applying the compounds/compositions directly on the pest and/or plant—typically to the foliage, stem or roots of the plant) and indirect contact (applying the compounds/compositions to the locus of the pest and/or plant). "Locus" means a habitat, breeding ground, plant, seed, soil, area, material or environment in which a pest or parasite is growing or may grow.

The term "plant propagation material" is to be understood to denote all the generative parts of the plant such as seeds and vegetative plant material such as cuttings and tubers (e.g. potatoes), which can be used for the multiplication of the plant. This includes seeds, roots, fruits, tubers, bulbs, rhizomes, shoots, sprouts and other parts of plants. Seedlings and young plants, which are to be transplanted after germination or after emergence from soil, may also be included. These plant propagation materials may be treated prophylactically with a plant protection compound either at or before planting or transplanting.

The term "cultivated plants" is to be understood as including plants which have been modified by breeding, mutagenesis or genetic engineering. Genetically modified plants are plants, which genetic material has been so modified by the use of recombinant DNA techniques that under natural circumstances cannot readily be obtained by cross breeding, mutations or natural recombination. Typically, one or more genes have been integrated into the genetic material of a genetically modified plant in order to improve certain properties of the plant. Such genetic modifications also include but are not limited to targeted post-transitional modification of protein(s) (oligo- or polypeptides) poly for example by glycosylation or polymer additions such as prenylated, acetylated or farnesylated moieties or PEG moieties (e.g. as disclosed in Biotechnol Prog. 2001 July-August; 17(4):720-8., Protein Eng Des Sel. 2004 January; 17(1):57-66, Nat Protoc. 2007; 2(5):1225-35., Curr Opin Chem Biol. 2006 October; 10(5):487-91. Epub 2006 Aug. 28., Bio-materials. 2001 March; 22(5):405-17, Bioconjug Chem. 2005 January-February; 16(1):113-21).

The term "cultivated plants" is to be understood also including plants that have been rendered tolerant to applications of specific classes of herbicides, such as hydroxyphenylpyruvate dioxygenase (HPPD) inhibitors; acetolactate synthase (ALS) inhibitors, such as sulfonyl ureas (see e.g. U.S. Pat. No. 6,222,100, WO 01/82685, WO 00/26390, WO 97/41218, WO 98/02526, WO 98/02527, WO 04/106529, WO 05/20673, WO 03/14357, WO 03/13225, WO 03/14356, WO 04/16073) or imidazolinones (see e.g. U.S. Pat. No. 6,222,100, WO 01/82685, WO 00/26390, WO 97/41218, WO 98/02526, WO 98/02527, WO 04/106529, WO 05/20673, WO 03/14357, WO 03/13225, WO 03/14356, WO 04/16073); enolpyruvylshikimate-3-phosphate synthase (EPSPS) inhibitors, such as glyphosate (see e.g. WO 92/00377); glutamine synthetase (GS) inhibitors, such as glufosinate (see e.g. EP-A-0242236, EP-A-242246) or oxynil herbicides (see e.g. U.S. Pat. No. 5,559,024) as a result of conventional methods of breeding or genetic engineering. Several cultivated plants have been rendered tolerant to herbicides by conventional methods of breeding (mutagenesis), for example Clearfield® summer rape (Canola) being tolerant to imidazolinones, e.g. imazamox. Genetic engineering methods have been used to render cultivated plants, such as soybean, cotton, corn, beets and rape, tolerant to herbicides, such as glyphosate and glufosinate, some of which are commercially available under the trade names RoundupReady® (glyphosate) and LibertyLink® (glufosinate).

The term "cultivated plants" is to be understood also including plants that are by the use of recombinant DNA techniques capable to synthesize one or more insecticidal proteins, especially those known from the bacterial genus Bacillus, particularly from Bacillus thuringiensis, such as ä-endotoxins, e.g. CryIA(b), CryIA(c), CryIF, CryIF(a2), CryIIA(b), CryIIIA, CryIIIB(b1) or Cry9c; vegetative insecticidal proteins (VIP), e.g. VIP1, VIP2, VIP3 or VIP3A; insecticidal proteins of bacteria colonizing nematodes, for example Photorhabdus spp. or Xenorhabdus spp.; toxins produced by animals, such as scorpion toxins, arachnid toxins, wasp toxins, or other insect-specific neurotoxins; toxins produced by fungi, such Streptomycetes toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxysteroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. In the context of the present invention these insecticidal proteins or toxins are to be understood expressly also as pre-toxins, hybrid proteins, truncated or otherwise modified proteins. Hybrid proteins are characterized by a new combination of protein domains, (see, for example WO 02/015701). Further examples of such toxins or genetically-modified plants capable of synthesizing such toxins are disclosed, for example, in EP-A 374 753, WO 93/007278, WO 95/34656, EP-A 427 529, EP-A 451 878, WO 03/018810 and WO 03/052073. The methods for producing such genetically modified plants are generally known to the person skilled in the art and are described, for example, in the publications mentioned above. These insecticidal proteins contained in the genetically modified plants impart to the plants producing these proteins protection from harmful pests from certain taxonomic groups of arthropods, particularly to beetles (*Coleoptera*), flies (*Diptera*), and butterflies and moths (*Lepidoptera*) and to plant parasitic nematodes (Nematoda).

The term "cultivated plants" is to be understood also including plants that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, for example EP-A 0 392 225), plant disease resistance genes (for example potato cultivars, which express resistance genes acting against *Phytophthora infestans* derived from the mexican wild potato *Solanum bulbocastanum*) or T4-lysozym (e.g. potato cultivars capable of synthesizing these proteins with increased resistance against bacteria such as *Erwinia amylvora*). The methods for producing such genetically modified plants are generally known to the person skilled in the art and are described, for example, in the publications mentioned above.

The term "cultivated plants" is to be understood also including plants that are by the use of recombinant DNA techniques capable to synthesize one or more proteins to increase the productivity (e.g. bio mass production, grain yield, starch content, oil content or protein content), tolerance to drought, salinity or other growth-limiting environmental factors or tolerance to pests and fungal, bacterial or viral pathogens of those plants.

The term "cultivated plants" is to be understood also including plants that contain by the use of recombinant DNA techniques a modified amount of substances of content or new substances of content, specifically to improve human or animal nutrition, for example oil crops that produce health-promoting long-chain omega-3 fatty acids or unsaturated omega-9 fatty acids (e.g. Nexera® rape).

The term "cultivated plants" is to be understood also including plants that contain by the use of recombinant DNA techniques a modified amount of substances of content or new substances of content, specifically to improve raw material production, for example potatoes that produce increased amounts of amylopectin (e.g. Amflora® potato).

In general, "pesticidally effective amount" means the amount of active ingredient needed to achieve an observable effect on growth, including the effects of necrosis, death, retardation, prevention, and removal, destruction, or otherwise diminishing the occurrence and activity of the target organism. The pesticidally effective amount can vary for the various compounds/compositions used in the invention. A pesticidally effective amount of the compositions will also vary according to the prevailing conditions such as desired pesticidal effect and duration, weather, target species, locus, mode of application, and the like.

In the case of soil treatment or of application to the pests dwelling place or nest, the quantity of active ingredient ranges from 0.0001 to 500 g per 100 m$^2$, preferably from 0.001 to 20 g per 100 m$^2$.

Customary application rates in the protection of materials are, for example, from 0.01 g to 1000 g of active compound per m$^2$ treated material, desirably from 0.1 g to 50 g per m$^2$.

Insecticidal compositions for use in the impregnation of materials typically contain from 0.001 to 95 weight %, preferably from 0.1 to 45 weight %, and more preferably from 1 to 25 weight % of at least one repellent and/or insecticide.

For use in treating crop plants, the rate of application of the active ingredients of this invention may be in the range of 0.1 g to 4000 g per hectare, desirably from 25 g to 600 g per hectare, more desirably from 50 g to 500 g per hectare.

The compounds of formula I are effective through both contact (via soil, glass, wall, bed net, carpet, plant parts or animal parts), and ingestion (bait, or plant part).

The compounds of the invention may also be applied against non-crop insect pests, such as ants, termites, wasps, flies, mosquitoes, crickets, or cockroaches. For use against said non-crop pests, compounds of formula I are preferably used in a bait composition.

The bait can be a liquid, a solid or a semisolid preparation (e.g. a gel). Solid baits can be formed into various shapes and forms suitable to the respective application e.g. granules, blocks, sticks, disks. Liquid baits can be filled into various devices to ensure proper application, e.g. open containers, spray devices, droplet sources, or evaporation sources. Gels can be based on aqueous or oily matrices and can be formulated to particular necessities in terms of stickyness, moisture retention or aging characteristics.

The bait employed in the composition is a product, which is sufficiently attractive to incite insects such as ants, termites, wasps, flies, mosquitoes, crickets etc. or cockroaches to eat it. The attractiveness can be manipulated by using feeding stimulants or sex pheromones. Food stimulants are chosen, for example, but not exclusively, from animal and/or plant proteins (meat-, fish- or blood meal, insect parts, egg yolk), from fats and oils of animal and/or plant origin, or mono-, oligo- or polyorganosaccharides, especially from sucrose, lactose, fructose, dextrose, glucose, starch, pectin or even molasses or honey. Fresh or decaying parts of fruits, crops, plants, animals, insects or specific parts thereof can also serve as a feeding stimulant. Sex pheromones are known to be more insect specific. Specific pheromones are described in the literature and are known to those skilled in the art.

For use in bait compositions, the typical content of active ingredient is from 0.001 weight % to weight %, desirably from 0.001 weight % to 5% weight % of active compound.

Formulations of compounds of formula I as aerosols (e.g. in spray cans), oil sprays or pump sprays are highly suitable for the non-professional user for controlling pests such as flies, fleas, ticks, mosquitoes or cockroaches. Aerosol recipes are preferably composed of the active compound, solvents such as lower alcohols (e.g. methanol, ethanol, propanol, butanol), ketones (e.g. acetone, methyl ethyl ketone), paraffin hydrocarbons (e.g. kerosenes) having boiling ranges of approximately 50 to 250° C., dimethylformamide, N-methylpyrrolidone, dimethyl sulfoxide, aromatic hydrocarbons such as toluene, xylene, water, furthermore auxiliaries such as emulsifiers such as sorbitol monooleate, oleyl ethoxylate having 3-7 mol of ethylene oxide, fatty alcohol ethoxylate, perfume oils such as ethereal oils, esters of medium fatty acids with lower alcohols, aromatic carbonyl compounds, if appropriate stabilizers such as sodium benzoate, amphoteric surfactants, lower epoxides, triethyl orthoformate and, if required, propellants such as propane, butane, nitrogen, compressed air, dimethyl ether, carbon dioxide, nitrous oxide, or mixtures of these gases.

The oil spray formulations differ from the aerosol recipes in that no propellants are used.

For use in spray compositions, the content of active ingredient is from 0.001 to 80 weights %, preferably from 0.01 to 50 weight % and most preferably from 0.01 to 15 weight %.

The compounds of formula I and its respective compositions can also be used in mosquito and fumigating coils, smoke cartridges, vaporizer plates or long-term vaporizers and also in moth papers, moth pads or other heat-independent vaporizer systems.

Methods to control infectious diseases transmitted by insects (e.g. malaria, dengue and yellow fever, lymphatic filariasis, and leishmaniasis) with compounds of formula I and its respective compositions also comprise treating surfaces of huts and houses, air spraying and impregnation of curtains, tents, clothing items, bed nets, tsetse-fly trap or the like. Insecticidal compositions for application to fibers, fabric, knitgoods, nonwovens, netting material or foils and tarpaulins preferably comprise a mixture including the insecticide, optionally a repellent and at least one binder. Suitable repellents for example are N,N-Diethyl-meta-toluamide (DEET), N,N-diethylphenylacetamide (DEPA), 1-(3-cyclohexan-1-yl-carbonyl)-2-methylpiperine, (2-hydroxymethylcyclohexyl) acetic acid lactone, 2-ethyl-1,3-hexandiol, indalone, Methylneodecanamide (MNDA), a pyrethroid not used for insect control such as {(+/−)-3-allyl-2-methyl-4-oxocyclopent-2-(+)-enyl-(+)-trans-chrysantemate (Esbiothrin), a repellent derived from or identical with plant extracts like limonene, eugenol, (+)-Eucamalol (1), (−)-1-epi-eucamalol or crude plant extracts from plants like *Eucalyptus maculata, Vitex rotundifolia, Cymbopogan martinii, Cymbopogan citratus* (lemon grass), *Cymopogan nartdus* (citronella). Suitable binders are selected for example from polymers and copolymers of vinyl esters of aliphatic acids (such as such as vinyl acetate and vinyl versatate), acrylic and methacrylic esters of alcohols, such as butyl acrylate, 2-ethylhexylacrylate, and methyl acrylate, mono- and diethylenically unsaturated hydrocarbons, such as styrene, and aliphatic diens, such as butadiene.

The impregnation of curtains and bednets is done in general by dipping the textile material into emulsions or dispersions of the insecticide or spraying them onto the nets.

The compounds of formula I and its compositions can be used for protecting wooden materials such as trees, board fences, sleepers, etc. and buildings such as houses, outhouses, factories, but also construction materials, furniture, leathers, fibers, vinyl articles, electric wires and cables etc. from ants and/or termites, and for controlling ants and termites from doing harm to crops or human being (e.g. when the pests invade into houses and public facilities). The compounds of formula I are applied not only to the surrounding soil surface or into the under-floor soil in order to protect wooden materials but it can also be applied to lumbered articles such as surfaces of the under-floor concrete, alcove posts, beams, plywoods, furniture, etc., wooden articles such as particle boards, half boards, etc. and vinyl articles such as coated electric wires, vinyl sheets, heat insulating material such as styrene foams, etc. In case of application against ants doing harm to crops or human beings, the ant controller of the present invention is applied to the crops or the surrounding soil, or is directly applied to the nest of ants or the like.

Seed Treatment

The compounds of formula I are also suitable for the treatment of seeds in order to protect the seed from insect pest, in particular from soil-living insect pests and the resulting plant's roots and shoots against soil pests and foliar insects.

The compounds of formula I are particularly useful for the protection of the seed from soil pests and the resulting plant's roots and shoots against soil pests and foliar insects. The protection of the resulting plant's roots and shoots is preferred. More preferred is the protection of resulting plant's shoots from piercing and sucking insects, wherein the protection from aphids is most preferred.

The present invention therefore comprises a method for the protection of seeds from insects, in particular from soil insects and of the seedling's roots and shoots from insects, in particular from soil and foliar insects, said method comprising contacting the seeds before sowing and/or after pregermination with a compound of the general formula I or a salt thereof. Particularly preferred is a method, wherein the plant's roots and shoots are protected, more preferably a method, wherein the plants shoots are protected form piercing and sucking insects, most preferably a method, wherein the plants shoots are protected from aphids.

The term seed embraces seeds and plant propagules of all kinds including but not limited to true seeds, seed pieces, suckers, corms, bulbs, fruit, tubers, grains, cuttings, cut shoots and the like and means in a preferred embodiment true seeds.

The term seed treatment comprises all suitable seed treatment techniques known in the art, such as seed dressing, seed coating, seed dusting, seed soaking and seed pelleting. The present invention also comprises seeds coated with or containing the active compound.

The term "coated with and/or containing" generally signifies that the active ingredient is for the most part on the surface of the propagation product at the time of application, although a greater or lesser part of the ingredient may penetrate into the propagation product, depending on the method of application. When the said propagation product is (re)planted, it may absorb the active ingredient.

Suitable seed is seed of cereals, root crops, oil crops, vegetables, spices, ornamentals, for example seed of durum and other wheat, barley, oats, rye, maize (fodder maize and sugar maize/sweet and field corn), soybeans, oil crops, crucifers, cotton, sunflowers, bananas, rice, oilseed rape, turnip rape, sugarbeet, fodder beet, eggplants, potatoes, grass, lawn, turf, fodder grass, tomatoes, leeks, pumpkin/squash, cabbage, iceberg lettuce, pepper, cucumbers, melons, *Brassica* species, melons, beans, peas, garlic, onions, carrots, tuberous plants such as potatoes, sugar cane, tobacco, grapes, petunias, geranium/pelargoniums, pansies and impatiens.

In addition, the active compound may also be used for the treatment of seeds from plants, which tolerate the action of herbicides or fungicides or insecticides owing to breeding, including genetic engineering methods.

For example, the active compound can be employed in treatment of seeds from plants, which are resistant to herbicides from the group consisting of the sulfonylureas, imidazolinones, glufosinate-ammonium or glyphosate-isopropylammonium and analogous active substances (see for example, EP-A-0242236, EP-A-242246) (WO 92/00377) (EP-A-0257993, U.S. Pat. No. 5,013,659) or in transgenic crop plants, for example cotton, with the capability of producing *Bacillus thuringiensis* toxins (Bt toxins) which make the plants resistant to certain pests (EP-A -0142924, EP-A-0193259), Furthermore, the active compound can be used also for the treatment of seeds from plants, which have modified characteristics in comparison with existing plants consist, which can be generated for example by traditional breeding methods and/or the generation of mutants, or by recombinant procedures). For example, a number of cases have been described of recombinant modifications of crop plants for the purpose of modifying the starch synthesized in the plants (e.g. WO 92/11376, WO 92/14827, WO 91/19806) or of transgenic crop plants having a modified fatty acid composition (WO 91/13972).

The seed treatment application of the active compound is carried out by spraying or by dusting the seeds before sowing of the plants and before emergence of the plants.

Compositions which are especially useful for seed treatment are e.g.:
A Soluble concentrates (SL, LS)
D Emulsions (EW, EO, ES)
E Suspensions (SC, OD, FS)
F Water-dispersible granules and water-soluble granules (WG, SG)
G Water-dispersible powders and water-soluble powders (WP, SP, WS)
H Gel-Formulations (GF)
I Dustable powders (DP, DS)

Conventional seed treatment formulations include for example flowable concentrates FS, solutions LS, powders for dry treatment DS, water dispersible powders for slurry treatment WS, water-soluble powders SS and emulsion ES and EC and gel formulation GF. These formulations can be applied to the seed diluted or undiluted. Application to the seeds is carried out before sowing, either directly on the seeds or after having pregerminated the latter.

In a preferred embodiment a FS formulation is used for seed treatment. Typically, a FS formulation may comprise 1-800 g/l of active ingredient, 1-200 g/I Surfactant, 0 to 200 g/I antifreezing agent, 0 to 400 g/l of binder, 0 to 200 g/l of a pigment and up to 1 liter of a solvent, preferably water.

Especially preferred FS formulations of compounds of formula I for seed treatment usually comprise from 0.1 to 80% by weight (1 to 800 g/I) of the active ingredient, from 0.1 to 20% by weight (1 to 200 g/I) of at least one surfactant, e.g. 0.05 to 5% by weight of a wetter and from 0.5 to 15% by weight of a dispersing agent, up to 20% by weight, e.g. from 5 to 20% of an anti-freeze agent, from 0 to 15% by weight, e.g. 1 to 15% by weight of a pigment and/or a dye, from 0 to 40% by weight, e.g. 1 to 40% by weight of a binder (sticker/adhesion agent), optionally up to 5% by weight, e.g. from 0.1 to 5% by weight of a thickener, optionally from 0.1 to 2% of an anti-foam agent, and optionally a preservative such as a biocide, antioxidant or the like, e.g. in an amount from 0.01 to 1% by weight and a filler/vehicle up to 100% by weight.

Seed treatment formulations may additionally also comprise binders and optionally colorants.

Binders can be added to improve the adhesion of the active materials on the seeds after treatment. Suitable binders are homo- and copolymers from alkylene oxides like ethylene oxide or propylene oxide, polyvinylacetate, polyvinylalcohols, polyvinylpyrrolidones, and copolymers thereof, ethylene-vinyl acetate copolymers, acrylic homo- and copolymers, polyethyleneamines, polyethyleneamides and polyethyleneimines, polysaccharides like celluloses, tylose and starch, polyolefin homo- and copolymers like olefin/maleic anhydride copolymers, polyurethanes, polyesters, polystyrene homo and copolymers Optionally, also colorants can be included in the formulation. Suitable colorants or dyes for seed treatment formulations are Rhodamin B, C.I. Pigment Red 112, C.I. Solvent Red 1, pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

An example of a gelling agent is carrageen (Satiagel®).

In the treatment of seed, the application rates of the compounds I are generally from 0.1 g to 10 kg per 100 kg of seed, preferably from 1 g to 5 kg per 100 kg of seed, more preferably from 1 g to 1000 g per 100 kg of seed and in particular from 1 g to 200 g per 100 kg of seed.

The invention therefore also relates to seed comprising a compound of the formula I, or an agriculturally useful salt of I, as defined herein. The amount of the compound I or the agriculturally useful salt thereof will in general vary from 0.1 g to 10 kg per 100 kg of seed, preferably from 1 g to 5 kg per 100 kg of seed, in particular from 1 g to 1000 g per 100 kg of seed. For specific crops such as lettuce the rate can be higher.

Animal Health

The compounds of formula I or veterinarily acceptable salts thereof are in particular also suitable for being used for combating parasites in and on animals.

An object of the present invention is therefore also to provide new methods to control parasites in and on animals. Another object of the invention is to provide safer pesticides for animals. Another object of the invention is further to provide pesticides for animals that may be used in lower doses than existing pesticides. And another object of the invention is to provide pesticides for animals, which provide a long residual control of the parasites.

The invention also relates to compositions containing a parasiticidally effective amount of compounds of formula I or veterinarily acceptable salts thereof and an acceptable carrier, for combating parasites in and on animals.

The present invention also provides a method for treating, controlling, preventing and protecting animals against infestation and infection by parasites, which comprises orally, topically or parenterally administering or applying to the animals a parasiticidally effective amount of a compound of formula I or veterinarily acceptable salts thereof or a composition comprising it.

The invention also provides a process for the preparation of a composition for treating, controlling, preventing or protecting animals against infestation or infection by parasites which comprises a parasiticidally effective amount of a compound of formula I or veterinarily acceptable salts thereof or a composition comprising it.

Activity of compounds against agricultural pests does not suggest their suitability for control of endo- and ectoparasites in and on animals which requires, for example, low, non-emetic dosages in the case of oral application, metabolic compatibility with the animal, low toxicity, and a safe handling.

Surprisingly it has now been found that compounds of formula I are suitable for combating endo- and ectoparasites in and on animals.

Compounds of formula I or veterinarily acceptable salts thereof and compositions comprising them are preferably used for controlling and preventing infestations and infections animals including warm-blooded animals (including humans) and fish. They are for example suitable for controlling and preventing infestations and infections in mammals such as cattle, sheep, swine, camels, deer, horses, pigs, poultry, rabbits, goats, dogs and cats, water buffalo, donkeys, fallow deer and reindeer, and also in fur-bearing animals such as mink, chinchilla and raccoon, birds such as hens, geese, turkeys and ducks and fish such as fresh- and salt-water fish such as trout, carp and eels.

Compounds of formula I or veterinarily acceptable salts thereof and compositions comprising them are preferably used for controlling and preventing infestations and infections in domestic animals, such as dogs or cats.

Infestations in warm-blooded animals and fish include, but are not limited to, lice, biting lice, ticks, nasal bots, keds, biting flies, muscoid flies, flies, myiasitic fly larvae, chiggers, gnats, mosquitoes and fleas.

The compounds of formula I or veterinarily acceptable salts thereof and compositions comprising them are suitable for systemic and/or non-systemic control of ecto- and/or endoparasites. They are active against all or some stages of development.

The compounds of formula I are especially useful for combating ectoparasites.

The compounds of formula I are especially useful for combating parasites of the following orders and species, respectively:

fleas (Siphonaptera), e.g. *Ctenocephalides felis, Ctenocephalides canis, Xenopsylla cheopis, Pulex irritans, Tunga penetrans*, and *Nosopsyus fasciatus*, cockroaches (Blattaria—Blattodea), e.g. *Blattella germanica, Blattella asahinae, Periplaneta americana, Periplaneta japonica, Periplaneta brunnea, Periplaneta fuligginosa, Periplaneta australasiae*, and *Blatta orientalis*, flies, mosquitoes (Diptera), e.g. *Aedes aegypti, Aedes albopictus, Aedes vexans, Anastrepha ludens, Anopheles maculipennis, Anopheles crucians, Anopheles albimanus, Anopheles gambiae, Anopheles freeborni, Anopheles leucosphyrus, Anopheles minimrus, Anopheles quadrimaculatus, Calliphora vicina, Chrysomya bezziana, Chrysomya hominivorax, Chrysomya macellaria, Chrysops discalli, Chrysops silacea, Chrysops atlanticus, Cochliomyra hominivorax, Cordylobia anthropophaga, Culicoides furens, Culex pipiens, Culex nigrpalpus, Culex quinquefasciatus, Culex tarsalis, Culiseta inornata, Culiseta melanura, Dermatobia hominlis, Fannia canicularis, Gasterophilus intestinalis, Glossina morsitans, Glossina palpalis, Glossina fuscipes, Glossina tachinoides, Haematobia irritans, Haplodiplosis equestris, Hippelates spp., Hypoderma lineata, Leptoconops torrens, Lucilia caprina, Lucilia cuprina, Lucilia sericata, Lycoria pectoralis, Mansonia spp., Musca domestica, Muscina stabulans, Oestrus ovis, Phlebotomus argentipes, Psorophora columbiae, Psorophora discolor, Prosimulium mixtum, Sarcophaga haemorrhoidalis, Sarcophaga sp., Simulium vittatum, Stomoxys calcitrans, Tabanus bovinus, Tabanus atratus, Tabanus lineola*, and *Tabanus similis*, lice (Phthiraptera), e.g. *Pediculus humanus capitis, Pediculus humanus corporis, Pthirus pubis, Haematopinus eurysternus, Haematopinus suis, Linognathus vituli, Bovicola bovis, Menopon gallinae, Menacanthus stramineus* and *Solenopotes capillatus*.

ticks and parasitic mites (Parasitiformes): ticks (Ixodida), e.g. *Ixodes scapularis, Ixodes holocyclus, Ixodes pacificus, Rhiphicephalus sanguineus, Dermacentor andersoni, Dermacentor variabilis, Amblyomma americanum, Ambryomma maculatum, Ornithodorus hermsi, Ornithodorus turicata* and parasitic mites (Mesostigmata), e.g. *Ornithonyssus bacoti* and *Dermanyssus gallinae*, Actinedida (Prostigmata) and Acaridida (Astigmata) e.g. *Acarapis* spp., *Cheyletiella* spp., *Omithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., and *Laminosioptes* spp, Bugs (Heteropterida): *Cimex lectularius, Cimex hemrnipterus, Reduvius senilis, Triatoma* spp., *Rhodnius* ssp., *Panstrongylus* ssp. and *Arilus critatus*, Anoplurida, e.g. *Haematopinus* spp., *Linognathus* spp., *Pediculus* spp., *Phtirus* spp., and *Solenopotes* spp, Mallophagida (suborders Arnblycerina and Ischnocerina), e.g. *Trimenopon* spp., *Menopon* spp., *Trinoton* spp., *Bovicola* spp., *Werneckiella* spp., *Lepikentron* spp., *Trichodectes* spp., and *Felicola*spp, Roundworms Nematoda:

Wipeworms and Trichinosis (Trichosyringida), e.g. Trichinellidae (*Trichinella* spp.), (Trichuridae) *Trichuris* spp., *Capillaria* spp, Rhabditida, e.g. *Rhabditis* spp, *Strongyloides* spp., *Helicephalobus* spp, Strongylida, e.g. *Strongylus* spp., *Ancylostoma* spp., *Necator americanus, Bunostomum* spp. (Hookworm), *Trichostrongylus* spp., *Haemonchus contortus., Ostertagia* spp., *Cooperia* spp., *Nematodirus* spp., *Dictyocaulus* spp., *Cyathostoma* spp., *Oesophagostomum* spp., *Stephanurus dentatus, Ollulanus* spp., *Chabertia* spp., *Stephanurus dentatus, Syngamus trachea, Ancylostoma* spp., *Uncinaria* spp., *Globocephalus* spp., *Necator* spp., *Metastrongylus* spp., *Muellerius capllaris, Protostrongylus* spp., *Angiostrongylus* spp., *Parelaphostrongylus* spp. *Aleurostrongylus abstrusus*, and *Dioctophyma renale*, Intestinal roundworms (Ascaridida), e.g. *Ascaris lumbricoides, Ascaris suum, Ascaridia galli, Parascaris equorum, Enterobius vermicularis* (Threadworm), *Toxocara canis, Toxascaris leonine, Skrjabinema* spp., and *Oxyuris equ*, Camallanida, e.g. *Dracunculus medinensis* (guinea worm)

Spirurida, e.g. *Thelazia* spp. *Wuchereria* spp., *Brugia* spp., *Onchocerca* spp., *Dirofiari* spp.a, *Dipetalonema* spp., *Setaria* spp., *Elaeophora* spp., *Spirocerca lupi*, and *Habronema* spp., Thorny headed worms (Acanthocephala), e.g. *Acanthocephalus* spp., *Macracanthorhynchus hirudinaceus* and *Oncicola* spp, Planarians (Plathelminthes):

Flukes (Trematoda), e.g. *Faciola* spp., *Fascioloides magna, Paragonlmus* spp., *Dicrocoelium*spp., *Fasciolopsis buski, Clonorchis sinensis, Schistosoma* spp., *Trichobilharzia* spp., *Alaria alata, Paragonimus* spp., and *Nanocyetes* spp, Cercomeromorpha, in particular Cestoda (Tapeworms), e.g. *Diphyllobothrium* spp., *Tenia* spp., *Echinococcus* spp., *Dipylidium canlinum, Mullticeps* spp., *Hymenolepis* spp.,

*Mesocestoides* spp., *Vampirolepis* spp., *Moniezia* spp., *Anoplocephala* spp., *Sirometra* spp., *Anoplocephala* spp., and *Hymenolepis* spp.

The compounds of formula I and compositions containing them are particularly useful for the control of pests from the orders Diptera, Siphonaptera and Ixodida.

Moreover, the use of the compounds of formula I and compositions containing them for combating mosquitoes is especially preferred.

The use of the compounds of formula I and compositions containing them for combating flies is a further preferred embodiment of the present invention.

Furthermore, the use of the compounds of formula I and compositions containing them for combating fleas is especially preferred.

The use of the compounds of formula I and compositions containing them for combating ticks is a further preferred embodiment of the present invention.

The compounds of formula I also are especially useful for combating endoparasites (roundworms nematoda, thorny headed worms and planarians).

Administration can be carried out both prophylactically and therapeutically.

Administration of the active compounds is carried out directly or in the form of suitable preparations, orally, topically/dermally or parenterally.

For oral administration to warm-blooded animals, the formula I compounds may be formulated as animal feeds, animal feed premixes, animal feed concentrates, pills, solutions, pastes, suspensions, drenches, gels, tablets, boluses and capsules. In addition, the formula I compounds may be administered to the animals in their drinking water. For oral administration, the dosage form chosen should provide the animal with 0.01 mg/kg to 100 mg/kg of animal body weight per day of the formula I compound, preferably with 0.5 mg/kg to 100 mg/kg of animal body weight per day.

Alternatively, the formula I compounds may be administered to animals parenterally, for example, by intraruminal, intramuscular, intravenous or subcutaneous injection. The formula I compounds may be dispersed or dissolved in a physiologically acceptable carrier for subcutaneous injection. Alternatively, the formula I compounds may be formulated into an implant for subcutaneous administration. In addition the formula I compound may be transdermally administered to animals. For parenteral administration, the dosage form chosen should provide the animal with 0.01 mg/kg to 100 mg/kg of animal body weight per day of the formula I compound.

The formula I compounds may also be applied topically to the animals in the form of dips, dusts, powders, collars, medallions, sprays, shampoos, spot-on and pour-on formulations and in ointments or oil-in-water or water-in-oil emulsions. For topical application, dips and sprays usually contain 0.5 ppm to 5,000 ppm and preferably 1 ppm to 3,000 ppm of the formula I compound. In addition, the formula I compounds may be formulated as ear tags for animals, particularly quadrupeds such as cattle and sheep.

Suitable preparations are:
Solutions such as oral solutions, concentrates for oral administration after dilution, solutions for use on the skin or in body cavities, pouring-on formulations, gels;
Emulsions and suspensions for oral or dermal administration; semi-solid preparations;
Formulations in which the active compound is processed in an ointment base or in an oil-in-water or water-in-oil emulsion base;
Solid preparations such as powders, premixes or concentrates, granules, pellets, tablets, boluses, capsules; aerosols and inhalants, and active compound-containing shaped articles.

Compositions suitable for injection are prepared by dissolving the active ingredient in a suitable solvent and optionally adding further ingredients such as acids, bases, buffer salts, preservatives, and solubilizers. The solutions are filtered and filled sterile.

Suitable solvents are physiologically tolerable solvents such as water, alkanols such as ethanol, butanol, benzyl alcohol, glycerol, propylene glycol, polyethylene glycols, N-methyl-pyrrolidone, 2-pyrrolidone, and mixtures thereof.

The active compounds can optionally be dissolved in physiologically tolerable vegetable or synthetic oils which are suitable for injection.

Suitable solubilizers are solvents which promote the dissolution of the active compound in the main solvent or prevent its precipitation. Examples are polyvinylpyrrolidone, polyvinyl alcohol, polyoxyethylated castor oil, and polyoxyethylated sorbitan ester.

Suitable preservatives are benzyl alcohol, trichlorobutanol, p-hydroxybenzoic acid esters, and n-butanol.

Oral solutions are administered directly. Concentrates are administered orally after prior dilution to the use concentration. Oral solutions and concentrates are prepared according to the state of the art and as described above for injection solutions, sterile procedures not being necessary.

Solutions for use on the skin are trickled on, spread on, rubbed in, sprinkled on or sprayed on.

Solutions for use on the skin are prepared according to the state of the art and according to what is described above for injection solutions, sterile procedures not being necessary.

In general, "parasiticidally effective amount" means the amount of active ingredient needed to achieve an observable effect on growth, including the effects of necrosis, death, retardation, prevention, and removal, destruction, or otherwise diminishing the occurrence and activity of the target organism. The parasiticidally effective amount can vary for the various compounds/compositions used in the invention. A parasiticidally effective amount of the compositions will also vary according to the prevailing conditions such as desired parasiticidal effect and duration, target species, mode of application, and the like.

The compositions which can be used in the invention can comprise generally from about 0.001 to 95% of the compound of formula I.

Generally it is favorable to apply the compounds of formula I in total amounts of 0.5 mg/kg to 100 mg/kg per day, preferably 1 mg/kg to 50 mg/kg per day.

Ready-to-use preparations contain the compounds acting against parasites, preferably ectoparasites, in concentrations of 10 ppm to 80 percent by weight, preferably from 0.1 to 65 percent by weight, more preferably from 1 to 50 percent by weight, most preferably from 5 to 40 percent by weight.

Preparations which are diluted before use contain the compounds acting against ectoparasites in concentrations of 0.5 to 90 percent by weight, preferably of 1 to 50 percent by weight.

Furthermore, the preparations comprise the compounds of formula I against endoparasites in concentrations of 10 ppm to 2 percent by weight, preferably of 0.05 to 0.9 percent by weight, very particularly preferably of 0.005 to 0.25 percent by weight.

In a preferred embodiment of the present invention, the compositions comprising the compounds of formula I them are applied dermally/topically.

In a further preferred embodiment, the topical application is conducted in the form of compound containing shaped articles such as collars, medallions, ear tags, bands for fixing at body parts, and adhesive strips and foils.

Generally it is favorable to apply solid formulations which release compounds of formula I in total amounts of 10 mg/kg to 300 mg/kg, preferably 20 mg/kg to 200 mg/kg, most preferably 25 mg/kg to 160 mg/kg body weight of the treated animal in the course of three weeks.

For the preparation of the shaped articles, thermoplastic and flexible plastics as well as elastomers and thermoplastic elastomers are used. Suitable plastics and elastomers are polyvinyl resins, polyurethane, polyacrylate, epoxy resins, cellulose, cellulose derivatives, polyamides and polyester which are sufficiently compatible with the compounds of formula I. A detailed list of plastics and elastomers as well as preparation procedures for the shaped articles is given e.g. in WO 03/086075.

The invention is illustrated by the following examples without being limited thereby.

EXAMPLES

A. Preparation Examples

With appropriate modification of the starting materials, the procedures given in the synthesis examples below were used to obtain further compounds II and Ill. The compounds obtained in this manner are listed in the tables that follow, together with physical data.

The products shown below were characterized by NMR spectroscopy.

Procedure for the preparation of II-1:

Preparation of ethyl 2-cyano-2-phenylacetate (Ex-1)

A mixture of iodobenzene (4.08 g, 21.6 mmol), ethyl cyanoacetate (4.52 g, 40 mmol), potassium carbonate (11.0 g, 79.8 mmol) and copper(I)iodide (0.38 g, 2.0 mmol) in anhydrous dimethyl sulfoxide (50 mL) was stirred at 120° C. for 20 h under nitrogen atmosphere. The resulting reaction mixture was then poured into HCl (2N, 100 mL), and extracted with methyl t-butyl ether (3×100 mL). The combined organic layers were washed with brine (50 mL), dried with anhydrous sodium sulfate and concentrated under reduced pressure. The residue was purified by column chromatography (silica gel, 9:1 hexanes/EtOAc) to afford ethyl 2-cyano-2-phenylacetate (Ex-1, 2.8 g, 76%) as pale yellow oil.

Preparation of ethyl 2-cyano-3-(4-ethynylphenyl)-2-phenylpropanoate (Ex-2)

To a stirred ice-cold suspension of sodium hydride (60% in mineral oil, 0.44 g, 18.5 mmol, prewashed with hexanes, 2×5 mL) in anhydrous DMF (5 mL), a solution of ethyl 2-cyano-2-phenylacetate (Ex-1, 2.02 g, 10.7 mmol) in anhydrous DMF (5 mL) was added dropwise. The mixture was then allowed to warm to room temperature over a period of 1h upon stirring. 1-(Bromomethyl)-4-ethynylbenzene (1.8 g, 18.5 mmol) was added, and the mixture was stirred at room temperature for 4h. After reaction completion (TLC), the mixture was cooled to 0° C., quenched with HCl (2N, 2.0 mL), diluted with water (30 mL), and extracted with methyl t-butyl ether (3×100 mL). The combined organic layers were washed with brine (20 mL), dried with anhydrous sodium sulfate and concentrated under reduced pressure. The residue was purified by column chromatography (silica gel, 9:1 hexanes/EtOAc) to afford ethyl 2-cyano-3-(4-ethynylphenyl)-2-phenylpropanoate (Ex-2, 2.7 g, 96%) as colorless viscous liquid.

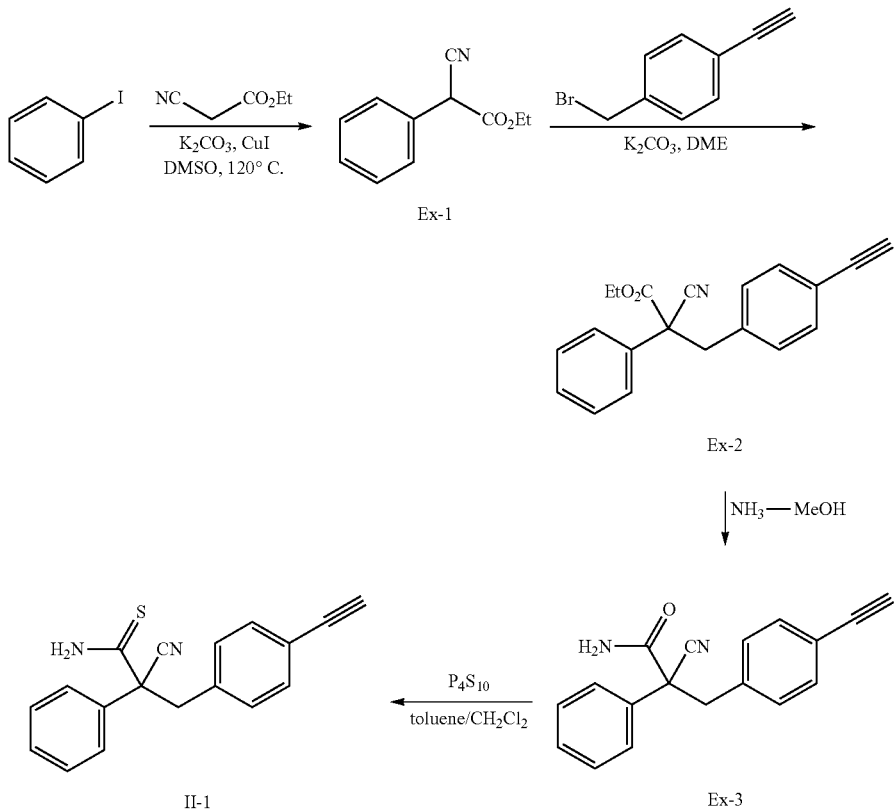

Preparation of 2-cyano-3-(4-ethynylphenyl)-2-phenylpropanamide (Ex-3)

A mixture of ethyl 2-cyano-3-(4-ethynylphenyl)-2-phenylpropanoate (Ex-2, 2.6 g, 8.6 mmol) and ammonia in methanol (7N, 50 mL) were stirred at room temperature for 2 days. After reaction completion (TLC), the solvent was removed under reduced pressure, and the residue was purified by column chromatography (silica gel, 7:3 hexanes/EtOAc) to afford 2-cyano-3-(4-ethynylphenyl)-2-phenylpropanamide (Ex-3, 2.0 g, 86%) as off-white solid.

Preparation of 2-cyano-3-(4-ethynylphenyl)-2-phenylpropanethioamide (II-1)

A mixture of 2-cyano-3-(4-ethynylphenyl)-2-phenylpropanamide (0.70 g, 2.55 mmol), $P_4S_{10}$ (0.23 g, 0.51 mmol) and hexamethyldisiloxane (1.12 mL, 5.26 mmol) in a mixture of toluene and $CH_2Cl_2$ (1:1, 10 mL) was stirred and heated at 60° C. for about 12h. When reaction was completed by ca. 80% (TLC) (formation of side products was observed), the mixture was cooled to room temperature, followed by addition of $K_2CO_3$ (5M aq., 1 mL). The reaction mixture was stirred for 30 min at room temperature and then extracted with ethyl acetate (3×100 mL). The combined organic layers were washed with brine (50 mL), dried with anhydrous sodium sulfate and concentrated under reduced pressure. The residue was purified by column chromatography (silica gel, hexanes/EtOAc, gradient 8.5:1.5 to 7:3) to afford 2-cyano-3-(4-ethynylphenyl)-2-phenylpropanethioamide (II-1, 0.224 g, 30%) as a purple solid.

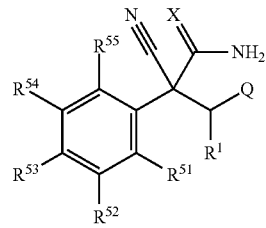

(II)

| Comp. | X | $R^{51}$ | $R^{52}$ | $R^{53}$ | $R^{54}$ | $R^{55}$ | $R^1$ | Q |
|---|---|---|---|---|---|---|---|---|
| II-1 | S | H | H | H | H | H | H | 4-ethynylphenyl |
| II-2 | O | H | H | F | H | H | H | 4-(trifluoromethyl)phenyl |
| II-3 | O | H | H | F | H | H | H | 4-ethynylphenyl |
| II-4 | S | H | H | F | H | H | H | 4-(trifluoromethyl)phenyl |
| II-5 | O | H | H | $OCF_3$ | H | H | H | 6-(trifluoromethyl)pyridin-3-yl |
| II-6 | S | H | H | F | H | H | H | 4-ethynylphenyl |
| II-7 | S | H | F | H | F | H | H | 4-(trifluoromethyl)phenyl |
| II-8 | S | H | F | H | F | H | H | 4-ethynylphenyl |
| II-9 | S | H | F | F | F | H | H | 4-ethynylphenyl |
| II-10 | S | H | F | F | F | H | H | 4-(trifluoromethyl)phenyl |
| II-11 | S | H | H | F | H | H | $CH_3$ | 4-(trifluoromethyl)phenyl |
| II-12 | S | H | F | H | F | H | $CH_3$ | 4-(trifluoromethyl)phenyl |
| II-13 | S | H | F | F | F | H | $CH_3$ | 4-(trifluoromethyl)phenyl |
| II-14 | S | H | F | H | F | H | $CH_3$ | 5-(trifluoromethyl)-2-pyridyl |
| II-15 | S | H | H | F | H | H | $CH_3$ | 5-(trifluoromethyl)-2-pyridyl |
| II-16 | S | H | F | F | F | H | $CH_3$ | 5-(trifluoromethyl)-2-pyridyl |
| II-17 | O | H | F | H | F | H | H | 4-(trifluoromethyl)phenyl |
| II-18 | O | H | F | F | F | H | H | 4-(trifluoromethyl)phenyl |
| II-19 | O | H | H | F | H | H | $CH_3$ | 4-(trifluoromethyl)phenyl |
| II-20 | O | H | F | F | F | H | $CH_3$ | 4-(trifluoromethyl)phenyl |
| II-21 | S | H | F | H | F | H | H | 3-fluoro-4-(trifluoromethyl)phenyl |
| II-22 | S | H | F | F | F | H | $CH_3$ | 4-bromophenyl |
| II-23 | S | H | F | H | F | H | H | 2-fluoro-4-(trifluoromethyl)phenyl |
| II-24 | O | H | F | H | F | H | H | 2-fluoro-4-(trifluoromethyl)phenyl |
| II-25 | S | H | H | F | H | H | H | trans-4-ethynylcyclohexyl |

Procedure for the preparation of III-1 and III-4:

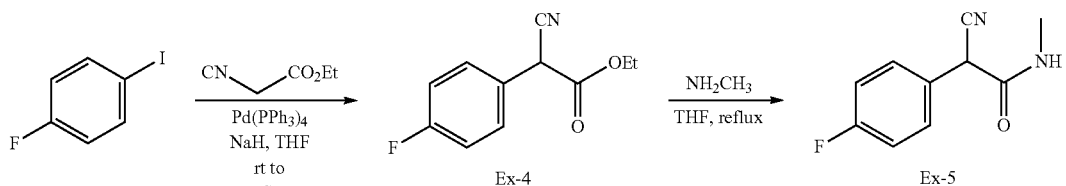

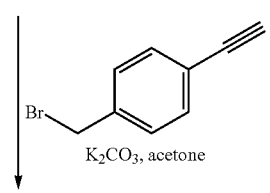

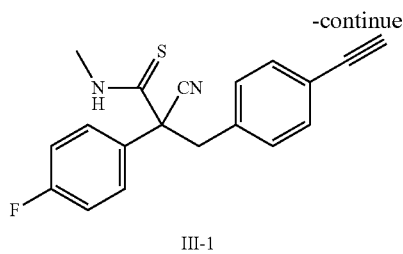 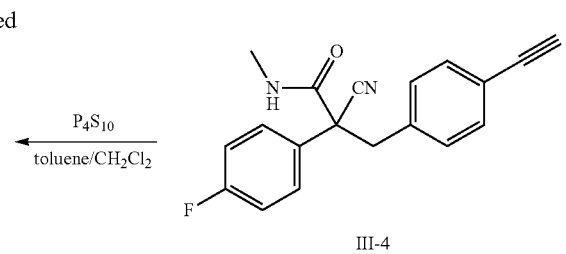

III-1           III-4

Preparation of ethyl 2-cyano-2-(4-fluorophenyl)acetate (Ex-4)

A solution of ethyl 2-cyanoacetate (2.55 g, 0.023 mol) in 250 ml tetrahydrofuran was added dropwise to a stirred and cooled mixture of sodium hydride (1.8 g, 60%, 0.045 mol) in 150 ml tetrahydrofuran. The reaction mixture was stirred for 1 h at room temperature and 1-fluoro-4-iodobenzene (5 g, 0.023 mol) and Pd(PPh$_3$)$_4$ (1.99 g, 1.7 mmol) were added. The reaction mixture was heated to reflux and stirring was continued for 3.5 h. The mixture was poured on an ice/water mixture (100 g/100 g) and filtered, discarding the formed precipitate. The mother liquor was concentrated, kept at 0° C. overnight and the newly formed precipitate was again filtered off. The mother liquor (pH=11) was then washed with dichloromethane twice. Finally the aqueous layer was acidified with hydrochloric acid (10% aqueous solution) to pH 3.4, extracted with dichloromethane (2×300 ml) and the organic layers were washed with brine, dried over anhydrous sodium sulfate and filtered. The solvent was removed under reduced pressure to afford ethyl 2-cyano-2-(4-fluorophenyl)acetate (Ex-4, 4 g, 50.5%).

Preparation of 2-cyano-2-(4-fluorophenyl)-N-methyl-acetamide (Ex-5)

A solution of ethyl 2-cyano-2-(4-fluorophenyl)acetate (Ex-4, 2 g) in 10 mL NH$_2$CH$_3$ in THF was heated at reflux overnight. The solvent was removed under reduced pressure and the residue was purified by column chromatography (silica gel, pentane: EtOAc=20:1) to afford 2-cyano-2-(4-fluorophenyl)-N-methyl-acetamide (Ex-5, 1.1 g, 60%).

Preparation of 2-cyano-3-(4-ethynylphenyl)-2-(4-fluorophenyl)-N-methyl-propanamide (III-4)

To a solution of 2-cyano-2-(4-fluorophenyl)-N-methyl-acetamide (Ex-5, 0.2 g, 0.001 mol) in 100 mL anhydrous acetone was added 1-(bromomethyl)-4-ethynyl-benzene (0.2 g, 0.001 mol) and K$_2$CO$_3$ (0.3 g, 0.002 mol) at room temperature under N$_2$, then the reaction was stirred at this temperature overnight. The reaction mixture was filtered and the solvent was removed under reduced pressure. The residue was purified by column chromatography (silica gel, pentane:EtOAc=10:1) to yield 2-cyano-3-(4-ethynylphenyl)-2-(4-fluorophenyl)-N-methylpropanamide (III-4, 0.2 g, 60%).

Preparation of 2-cyano-3-(4-ethynylphenyl)-2-(4-fluorophenyl)-N-methyl-propanethioamide (III-1)

To a solution of 2-cyano-3-(4-ethynylphenyl)-2-(4-fluorophenyl)-N-methyl-propanamide (III-4, 0.1 g, 0.032 mmol) in toluene (6 mL) was added Lawesson's reagent (0.2 g, 0.49 mmol). The mixture was heated in the microwave at 150° C. for 50 min. The solvent was removed under reduced pressure and the residue was purified by column chromatography (silica gel, pentane:EtOAc=8:1) to yield 2-cyano-3-(4-ethynylphenyl)-2-(4-fluorophenyl)-N-methylpropanethioamide (III-1, 0.1 g, 10%).

(III)

| Comp. | X | R$^{51}$ | R$^{52}$ | R$^{53}$ | R$^{54}$ | R$^{55}$ | R$^1$ | Q |
|---|---|---|---|---|---|---|---|---|
| III-1 | S | H | H | F | H | H | H | 4-ethynylphenyl |
| III-2 | S | H | F | H | F | H | H | 4-ethynylphenyl |
| III-3 | S | H | F | F | F | H | H | 4-ethynylphenyl |
| III-4 | O | H | H | F | H | H | H | 4-ethynylphenyl |
| III-5 | O | H | F | H | F | H | H | 4-ethynylphenyl |
| III-6 | O | H | F | F | F | H | H | 4-ethynylphenyl |

Analytical Data:

| Comp. | solvent | $^1$H-NMR-data (400 MHz, δ in ppm) |
|---|---|---|
| II-1 | (CD$_3$)$_2$CO | 3.60 (s, 1H), 3.98, 3.70 (ABq, 2H), 7.12 (d, 2H), 7.31 (d, 2H), 7.42-7.36 (m, 3H), 7.59-7.54 (m, 2H) |
| II-2* | CDCl$_3$ | 3.3 (d, 1H), 3.78 (d, 1H), 5.61 (bs, 1H), 6.10 (bs, 1H), 7.11 (t, 2H), 7.26-7.28 (m, 2H), 7.53 (d, 2H), 7.55-7.58 (m, 2H) |
| II-3* | CDCl$_3$ | 3.08 (s, 1H), 3.25 (d, 1H), 3.71 (d, 1H), 5.51 (bs, 1H), 6.08 (bs, 1H), 7.08-7.12 (m, 4H), 7.39 (d, 2H), 7.54-7.56 (m, 2H) |
| II-4 | CDCl$_3$ | 3.62 (d, 1H), 4.00 (d, 1H), 7.07-7.12 (m, 2H), 7.23 (d, 2H), 7.49 (d, 2H), 7.52-7.56 (m, 2H) |
| II-5 | CDCl$_3$ | 3.31 (d, 1H), 3.85 (d, 1H), 6.19 (bs, 1H), 6.27 (bs, 1H), 7.29 (d, 2H), 7.62-7.67 (m, 3H), 7.76 (dd, 1H), 8.55 (d, 1H) |
| II-6 | (CD$_3$)$_2$SO | 10.224 (s, 1H), 9.357 (s, 1H), 7.597-7.574 (m, 2H), 7.379-7.358 (m, 2H), 7.320-7.275 (m, 2H), 7.163-7.143 (m, 2H), 4.164 (s, 1H), 3.918-3.884 (m, 1H), 3.699-3.664 (m, 1H) |

-continued

| Comp. | solvent | $^1$H-NMR-data (400 MHz, δ in ppm) |
|---|---|---|
| II-7 | CDCl$_3$ | 7.541-7.521 (m, 2H), 7.315-7.295 (m, 2H), 7.166-7.151 (m, 2H), 6.896-6.848 (m, 1H), 4.048-4.019 (m, 1H), 3.635-3.600 (m, 1H) |
| II-8 | (CD$_3$)$_2$SO | 10.327 (s, 1H), 9.415 (s, 1H), 7.402-7.355 (m, 3H), 7.268-7.251 (m, 2H), 7.205-7.184 (m, 2H), 4.175 (s, 1H), 3.931-3.897 (m, 1H), 3.754-3.720 (m, 1H) |
| II-9 | (CD$_3$)$_2$SO | 10.342 (s, 1H), 9.378 (s, 1H), 7.499-7.462 (m, 2H), 7.407-7.387 (m, 2H), 7.214-7.194 (m, 2H), 4.176 (s, 1H), 3.934-3.898 (m, 1H), 3.745-3.710 (m, 1H) |
| II-10 | (CD$_3$)$_2$SO | 10.351 (s, 1H), 9.393 (s, 1H), 7.675-7.654 (m, 2H), 7.513-7.474 (m, 2H), 7.422-7.402 (m, 2H), 4.006-3.971 (m, 1H), 3.837-3.802 (m, 1H) |
| II-11 | CDCl$_3$ | 7.822-7.608 (m, 2H), 7.595-7.573 (m, 2H), 7.386-7.366 (m, 1H), 7.264-7.139 (m, 2H), 6.906-6.885 (m, 2H), 4.457-4.355 (m, 1H), 1.666-1.379 (m, 3H) |
| II-12 | (CD$_3$)$_2$SO | 10.464 (s, 0.5H), 10.031 (s, 0.5H), 9.664 (s, 0.5H), 9.216 (s, 0.5H), 7.801-7.739 (m, 2H), 7.563-7.526 (m, 2H), 7.416-7.396 (m, 1H), 7.155-7.139 (m, 2H), 4.506-4.415 (m, 1H), 1.558-1.284 (m, 3H) |
| II-13 | (CD$_3$)$_2$SO | 10.476 (s, 0.5H), 10.041 (s, 0.5H), 9.653 (s, 0.5H), 9.197 (s, 0.5H), 7.787-7.733 (m, 3H), 7.577-7.556 (m, 2H), 7.442-7.375 (m, 2H), 4.487-4.404 (m, 1H), 1.552-1.288 (m, 3H) |
| II-14 | CDCl$_3$ | 8.836-8.734 (s, 1H), 8.032-7.462 (m, 3H), 7.255-7.234 (m, 1H), 6.927-6.672 (m, 1H), 1.662-1.399 (m, 3H) |
| II-15 | CDCl$_3$ | 8.824 (s, 0.2H), 8.697 (s, 0.5H), 8.022-7.612 (m, 4H), 7.207-7.136 (m, 1H), 6.906-6.863 (m, 1H), 1.662-1.373 (m, 3H) |
| II-16 | CDCl$_3$ | 8.818-8.721 (s, 1H), 7.915-7.643 (m, 2H), 7.460-7.359 (m, 2H), 4.710-4.384 (m, 1H), 1.626-1.370 (m, 3H) |
| II-17 | CDCl$_3$ | 7.575 (d, J = 7.78 Hz, 2 H), 7.350 (d, J = 7.78 Hz, 2 H), 7.210 (d, J = 6.27 Hz, 2 H), 6.885 (t, J = 8.41 Hz, 1 H), 6.145 (br. s., 1 H), 5.545 (br. s., 1 H), 3.804 (d, J = 13.30 Hz, 1 H), 3.292 (d, J = 13.55 Hz, 1 H) |
| II-18 | CDCl$_3$ | 7.590 (d, J = 7.94 Hz, 2 H), 7.319-7.391 (m, 4 H), 6.167 (br. s., 1 H), 5.449-5.638 (m, 1 H), 3.779 (d, J = 13.67 Hz, 1 H), 3.260 (d, J = 13.67 Hz, 1 H) |
| II-19 | (CD$_3$)$_2$SO | 7.912-7.737 (m, 4H), 7.515-7.495 (m, 2 H), 7.378-7.344 (m, 2 H), 7.286-7.267 (m, 1 H), 7.142-7.120 (m, 1 H), 4.186-4.077 (m, 1 H), 1.523-1.507 (d, J = 6.40 Hz, 2 H), 1.132-1.114 (d, J = 7.2 Hz, 1 H) |
| II-20 | (CD$_3$)$_2$SO | 8.005-7.959 (d, J = 8.40 Hz, 1 H), 7.729-7.714 (d, J = 6.0 Hz, 1 H), 7.590-7.545 (m, 2 H), 7.380-7.360 (d, J = 8.0 Hz, 1H), 7.248-7.226 (m, 1H), 4.242-4.114 (m, 1 H), 1.503-1.487 (d, J = 6.40 Hz, 2 H), 1.155-1.137 (d, J = 7.2 Hz, 1 H) |
| II-21 | CDCl$_3$ | 7.595-7.522 (m, 2H), 7.310-7.285 (m, 1H), 7.200-7.185 (m, 2H), 7.110-7.093 (m, 2H), 7.068-6.911 (m, 1H), 4.054-4.019 (m, 1H), 3.631-3.597 (m, 1H) |
| II-22 | CDCl$_3$ | 7.629 (s, 1H), 7.363-7.306 (m, 4H), 7.061-7.040 (m, 2H), 4.291-4.241 (m, 1H), 1.613-1.577 (m, 3H) |
| II-23 | CDCl$_3$ | 7.849 (s, 1H), 7.395-7.261 (m, 4H), 7.171-7.151 (m, 2H), 6.870-6.865 (m, 1H), 3.984-3.950 (m, 1H), 3.840-3.804 (m, 1H) |
| II-24 | CDCl$_3$ | 7.363-7.270 (m, 3H), 7.192-7.177 (m, 2H), 6.902-6.865 (m, 1H), 6.214 (s, 2H), 5.789 (s, 1H), 3.758-3.724 (m, 1H), 3.561-3.525 (m, 1H) |
| II-25 | CDCl$_3$ | 7.55 (d, 2H), 7.35 (t, 2H), 2.61 (dd, 1 H), 2.25-2.11 (m, 2H), 2.06-1.81 (m, 4H), 1.79-1.68 (m, 1H), 1.56-0.95 (m, 1H), 1.94-1.28 (m, 2H), 1.20-0.98 (m, 2H) |
| III-1 | CD$_3$OD | 7.499-7.466 (m, 2H), 7.288-7.269 (m, 2H), 7.134-7.113 (m, 2H), 7.092-7.007 (m, 2H), 3.935-3.901 (m, 1H), 3.695-3.661 (m, 1H), 3.458 (s, 1H), 3.053 (s, 3H) |
| III-2 | CD$_3$OD | 7.320-7.300 (m, 2H), 7.113-7.066 (m, 4H), 6.987-6.965 (m, 1H), 3.945-3.911 (m, 1H), 3.706-3.672 (m, 1H), 3.452 (s, 1H), 3.065 (s, 3H) |
| III-3 | CD$_3$OD | 7.343-7.261 (m, 4H), 7.116-7.095 (m, 2H), 3.949-3.915 (m, 1H), 7.092-7.007 (m, 1H), 3.696-3.662 (m, 1H), 3.475 (s, 1H), 3.062 (s, 3H) |
| III-4 | CD$_3$OD | 7.525-7.490 (m, 2H), 7.330-7.310 (m, 2H), 7.172-7.084 (m, 4H), 3.733-3.699 (m, 1H), 3.462-3.376 (m, 2H), 2.722 (s, 3H) |

-continued

| Comp. | solvent | $^1$H-NMR-data (400 MHz, δ in ppm) |
|---|---|---|
| III-5 | CD$_3$OD | 7.357-7.337 (m, 2H), 7.154-7.134 (m, 2H), 7.043-6.999 (m, 1H), 3.752-3.718 (m, 1H), 3.472 (s, 1H), 3.388-3.355 (m, 2H), 2.732 (s, 3H) |
| III-6 | CDCl$_3$ | 7.443-7.423 (m, 2H), 7.352-7.316 (m, 2H), 7.168-7.148 (m, 2H), 6.219 (s, 1H), 3.736-3.702 (m, 1H), 3.223-3.189 (m, 1H), 3.107 (s, 1H), 2.822 (s, 3H) |

*measured with 500 MHz

B. Biological Examples

The activity of the compounds of formula II and III of the present invention could be demonstrated and evaluated in biological tests described in the following.

If not otherwise specified the test solutions are prepared as follows:

The active compound is dissolved at the desired concentration in a mixture of 1:1 (vol:vol) distilled water:acetone. The test solution is prepared at the day of use and in general at concentrations of ppm (wt/vol).

B.1 Mediterranean Fruitfly (*Ceratitis capitata*)

For evaluating control of Mediterranean fruitfly (*Ceratitis capitata*) the test unit consisted of microtiter plates containing an insect diet and 50-80 *C. capitata* eggs. The compounds were formulated using a solution containing 75% v/v water and 25% v/v DMSO. Different concentrations of formulated compounds were sprayed onto the insect diet at 5 µl, using a custom built micro atomizer, at two replications. After application, microtiter plates were incubated at about 28±1° C. and about 80±5% relative humidity for 5 days. Egg and larval mortality was then visually assessed.

In this test, the compounds II-3, II-4, II-10, II-11, II-12, II-13, II-14, II-15, II-16, II-17, II-18, II-19, II-21, II-22, II-23, II-24, II-25, II-6, II-8, II-9 and III-4, respectively, at 2500 ppm showed a mortality of at least 75% in comparison with untreated controls.

B.2 Green Peach Aphid (*Myzus persicae*)

For evaluating control of green peach aphid (*Myzus persicae*) through systemic means the test unit consisted of 96-well-microtiter plates containing liquid artificial diet under an artificial membrane. The compounds were formulated using a solution containing 75% v/v water and 25% v/v DMSO. Different concentrations of formulated compounds were pipetted into the aphid diet, using a custom built pipetter, at two replications. After application, 5-8 adult aphids were placed on the artificial membrane inside the microtiter plate wells. The aphids were then allowed to suck on the treated aphid diet and incubated at about 23+1° C. and about 50+5% relative humidity for 3 days. Aphid mortality and fecundity was then visually assessed.

In this test, the compounds II-4, II-10, II-11, II-12, II-13, II-14, II-15, II-16, II-21, II-25, II-8 and II-9, respectively, at a concentration of the test solution of 2500 mg/L showed a mortality of at least 75%.

B.3 Orchid Thrips (*Dichromothrips Corbetti*)

*Dichromothrips corbetti* adults used for bioassay are obtained from a colony maintained continuously under laboratory conditions. For testing purposes, the test compound is diluted to a concentration of 300 ppm (wt compound: vol diluent) in a 1:1 mixture of acetone:water (vol:vol), plus 0.01% vol/vol Kinetic® surfactant. Thrips potency of each compound is evaluated by using a floral-immersion technique. Plastic petri dishes are used as test arenas. All petals of individual, intact orchid flowers are dipped into treatment solution and allowed to dry. Treated flowers are placed into individual petri dishes along with 10-15 adult thrips. The petri dishes are then covered with lids. All test arenas are held under continuous light and a temperature of about 28° C. for duration of the assay. After 4 days, the numbers of live thrips are counted on each flower, and along inner walls of each petri dish. The level of thrips mortality is extrapolated from pre-treatment thrips numbers.

In this test, the compounds II-4, II-10, II-11, II-12, II-13, II-14, II-15, II-16, II-17, II-18, II-19, II-21, II-22, II-23, II-24, II-6, II-7, II-8, II-9, II-2, II-3, II-4 and III-6, respectively, at 500 ppm showed a mortality of at least 75% in comparison with untreated controls.

B.4 Silverleaf Whitefly (*Bemisia argentifolii*)

The active compounds were formulated in cyclohexanone as a 10,000 ppm solution supplied in 1.3 ml ABgene® tubes. These tubes were inserted into an automated electrostatic sprayer equipped with an atomizing nozzle and they served as stock solutions for which lower dilutions were made in 50% acetone:50% water (v/v). A nonionic surfactant (Kinetic®) was included in the solution at a volume of 0.01% (v/v). Cotton plants at the cotyledon stage (one plant per pot) were sprayed by an automated electrostatic plant sprayer equipped with an atomizing spray nozzle. The plants were dried in the sprayer fume hood and then removed from the sprayer. Each pot was placed into a plastic cup and 10 to 12 whitefly adults (approximately 3-5 days old) were introduced. The insects were collected using an aspirator and 0.6 cm, nontoxic Tygon® tubing (R-3603) connected to a barrier pipette tip. The tip, containing the collected insects, was then gently inserted into the soil containing the treated plant, allowing insects to crawl out of the tip to reach the foliage for feeding. Cups were covered with a reusable screened lid (150-micron mesh polyester screen PeCap from Tetko, Inc.). Test plants were maintained in a growth room at 25° C. and 20-40% relative humidity for 3 days, avoiding direct exposure to fluorescent light (24 hour photoperiod) to prevent trapping of heat inside the cup. Mortality was assessed 3 days after treatment, compared to untreated control plants.

In this test, the compounds II-1, II-6 and II-7, respectively, at 500 ppm showed a mortality of at least 75% in comparison with untreated controls.

B.5 Southern Armyworm (*Spodoptera eridania*)

The active compounds were formulated in cyclohexanone as a 10,000 ppm solution supplied in 1.3 ml ABgene® tubes. These tubes were inserted into an automated electrostatic sprayer equipped with an atomizing nozzle and they served as stock solutions for which lower dilutions were made in 50% acetone:50% water (v/v). A nonionic surfactant (Kinetic®) was included in the solution at a volume of 0.01% (v/v). Lima bean plants (variety Sieva) were grown 2 plants to a pot and selected for treatment at the 1st true leaf stage. Test solutions were sprayed onto the foliage by an automated electro-static plant sprayer equipped with an atomizing spray nozzle. The plants were dried in the sprayer fume hood and then removed from the sprayer. Each pot was placed into perforated plastic bags with a zip closure. Ten to 11 armyworm larvae were placed into the bag and the bags zipped closed. Test plants were maintained in a growth room at at 25° C. and 20-40% relative humidity for 4 days, avoiding direct exposure to fluorescent light (24 hour photoperiod) to prevent trapping of heat inside the bags. Mortality and reduced feeding were assessed 4 days after treatment, compared to untreated control plants.

In this test, the compound II-2 at 500 ppm showed a mortality of at least 75% in comparison with untreated controls.

B.6 Boll Weevil (*Anthonomus grandis*)

For evaluating control of boll weevil (*Anthonomus grandis*) the test unit consisted of 24-well-microtiter plates containing an insect diet and 20-30 *A. grandis* eggs. The compounds were formulated using a solution containing 75% v/v water and 25% v/v DMSO. Different concentrations of formulated compounds were sprayed onto the insect diet at 20 µl, using a custom built micro atomizer, at two replications. After application, microtiter plates were incubated at about 23±1° C. and about 50±5% relative humidity for 5 days. Egg and larval mortality was then visually assessed.

In this test, the compounds II-1, II-3, II-4, II-10, II-11, II-12, II-13, II-14, II-15, II-16, II-17, II-18, II-19, II-20, II-21, II-22, II-23, II-24, II-25, II-6, II-7, II-8, II-9, III-1, III-2, III-3, III-4 and III-5, respectively, at 2500 ppm showed a mortality of at least 75% in comparison with untreated controls.

B.7 Red Spider Mite (*Tetranychus kanzawai*)

The active compound is dissolved at the desired concentration in a mixture of 1:1 (vol:vol) distilled water:acetone. Add surfactant (Alkamuls® EL 620) at the rate of 0.1% (vol/vol). The test solution is prepared at the day of use. Potted cowpea beans of 7-10 days of age were cleaned with tap water and sprayed with 5 ml of the test solution using air driven hand atomizer. The treated plants were allowed to air dry and afterwards inculated with 20 or more mites by clipping a cassava leaf section with known mite population. Treated plants were placed inside a holding room at about 25-27° C. and about 50-60% relative humidity. Percent mortality was assessed 72 hours after treatment.

In this test, the compounds II-2 and II-11, respectively, at 500 ppm showed a mortality of at least 75% in comparison with untreated controls.

B.8 Rice Brown Plant Hopper (*Nilaparvata lugens*)

Rice seedlings were cleaned and washed 24 hours before spraying. The active compounds were formulated in 50:50 acetone:water (vol:vol) and 0.1% vol/vol surfactant (EL 620) was added. Potted rice seedlings were sprayed with 5 ml test solution, air dried, placed in cages and inoculated with 10 adults. Treated rice plants were kept at about 28-29° C. and relative humidity of about 50-60%. Percent mortality was recorded after 72 hours.

In this test, the compounds II-3, II-4, II-10, II-11, II-12, II-13, II-14, II-16, II-21, II-22, II-23, II-6, II-7, II-8, II-9, III-2, III-3, III-5 and III-6, respectively, at 500 ppm showed a mortality of at least 75% in comparison with untreated controls.

B.9 Yellow Fever Mosquito (*Aedes aegypti*)

For evaluating control of yellow fever mosquito (*Aedes aegypti*) the test unit consisted of 96-well-microtiter plates containing 200 µl of tap water per well and 5-15 freshly hatched *A. aegypti* larvae. The compounds or mixtures were formulated using a solution containing 75% water and 25% DMSO. Different concentrations of formulated compounds or mixtures were sprayed onto the insect diet at 2.5 µl, using a custom built micro atomizer, at two replications. After application, microtiter plates were incubated at 28±1° C., 80±5% RH for 2 days. Larval mortality was then visually assessed.

In this test, the compounds III-1, II-2, II-3, II-4, II-5, II-10, II-11, II-12, II-13, II-14, II-15, II-16, II-17, II-18, II-19, II-20, II-21, II-22, II-23, II-24, II-25, II-6, II-7, II-8, II-9, III-2 and III-3, respectively, at 2500 ppm showed a mortality of at least 75% in comparison with untreated controls.

B.10 Green Soldier Stink Bug (*Nezara viridula*)

The active compound is dissolved at the desired concentration in a mixture of 1:1 (vol:vol) distilled water:aceteone. Surfactant (Kinetic HV) is added at a rate of 0.01% (vol/vol). The test solution is prepared at the day of use. Soybean pods were placed in microwavable plastic cups lined with moist filter paper and inoculated with ten 3rd instar *N. viridula*. Using a hand atomizer, an approximately 2 ml solution is sprayed into each cup. Treated cups were kept at about 28-29° C. and relative humidity of about 50-60%. Percent mortality was recorded after 5 days.

In this test, the compounds II-1, II-3, II-4, II-10, II-11, II-12, II-13, II-14, II-15, II-16 and II-9, respectively, at 500 ppm showed a mortality of at least 75% in comparison with untreated controls.

The invention claimed is:

1. A method for combating invertebrate animal pests which attack plants, which method comprises contacting the pests, breeding ground, food supply, plant, seed, soil, area, material or environment in which the pests are growing or may grow, or the materials, plants, seeds, soils, surfaces or spaces to be protected from animal attack or infestation with a pesticidally effective amount of at least one compound of formula (I)

or a salt thereof, wherein

Y is phenyl unsubstituted or substituted with 1, 2, 3, 4 or 5 substituents $R^5$; or naphthyl unsubstituted or substituted with 1, 2, 3, 4, 5, 6 or 7 substituents $R^5$;

Q is phenyl unsubstituted or substituted with 1, 2, 3, 4 or 5 substituents $R^6$; $C_3$-$C_8$ cycloalkyl unsubstituted or substituted with one or more substituents $R^6$; $C_3$-$C_8$ cycloalkenyl unsubstituted or substituted with one or more substituents $R^6$; or a 6-membered aromatic heterocyclic ring containing 1, 2, 3 or 4 nitrogen atoms in the ring, wherein the aforementioned ring is unsubstituted or substituted with 1, 2, 3 or 4 substituents $R^6$;

$R^1$ is selected from the group consisting of hydrogen, halogen, cyano, hydroxy, $C_1$-$C_6$-alkyl, $C_2$-$C_6$-alkenyl, $C_2$-$C_6$-alkynyl, $C_3$-$C_8$-cycloalkyl, $C_3$-$C_8$-cycloalkenyl, $C_1$-$C_6$-alkoxy, $C_2$-$C_6$-alkenyloxy, $C_1$-$C_6$-alkylthio, ($C_1$-$C_6$-alkoxy)carbonyl, wherein the carbon atoms of the aforementioned aliphatic or cycloaliphatic radicals are unsubstituted or substituted with 1, 2 or 3 substituents $R^7$;

$R^2$ is hydrogen or halogen;

or
$R^1$ and $R^2$ form together with the carbon atom to which they are attached a methylene group or a cyclopropyl group;
$R^3$ is selected from the group consisting of hydrogen, halogen, cyano, hydroxy, $C_1$-$C_6$-alkyl, $C_2$-$C_6$-alkenyl, $C_2$-$C_6$-alkynyl, $C_3$-$C_8$-cycloalkyl, $C_3$-$C_8$-cycloalkenyl, $C_1$-$C_6$-alkoxy, $C_2$-$C_6$-alkenyloxy, $C_1$-$C_6$-alkylthio, ($C_1$-$C_6$-alkoxy)carbonyl, wherein the carbon atoms of the aforementioned aliphatic or cycloaliphatic radicals are unsubstituted or substituted with 1, 2 or 3 substituents $R^7$;
$R^4$ is hydrogen or halogen;
or
$R^3$ and $R^4$ form together with the carbon atom to which they are attached a methylene group or a cyclopropyl group;
each $R^5$, $R^6$ is independently selected from the group consisting of halogen, cyano, azido, nitro, —SCN, $SF_5$, $C_1$-$C_6$ alkyl, $C_2$-$C_6$ alkenyl, $C_2$-$C_6$ alkynyl, wherein the carbon atoms of the aforementioned aliphatic radicals are unsubstituted or substituted with one or more $R^a$;
$C_3$-$C_8$ cycloalkyl or $C_3$-$C_8$ cycloalkenyl, wherein the carbon atoms of the aforementioned cycloaliphatic radicals are unsubstituted or substituted with one or more $R^b$;
phenyl unsubstituted or substituted with up to 5 $R^c$;
a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO, $SO_2$, wherein the aforementioned ring is unsubstituted or substituted with up to 5 $R^d$;
$Si(R^e)_3$, $OR^f$, $SR^f$, $OS(O)_xR^h$, $S(O)_xR^h$, $N(R^i)_2$, $N(R^i)C(=O)R^m$, $OC(=O)R^m$, $C(=O)R^m$, $C(=O)OR^f$, $C(=NR^i)R^m$, $C(=S)R^m$;
or
two $R^5$ on two adjacent carbon atoms present on one phenyl ring are together a bridge selected from the group consisting of $CH_2CH_2CH_2CH_2$, N=CH—CH=CH, CH=N—CH=CH, N=CH—N=CH, N=CH—CH=N, $OCH_2CH_2CH_2$, $OCH_2$=CHCH$_2$, $CH_2OCH_2CH_2$, $OCH_2CH_2O$, $OCH_2OCH_2$, $CH_2CH_2CH_2$, CH=CHCH$_2$, $CH_2CH_2O$, CH=CHO, $CH_2OCH_2$, $CH_2C(=O)O$, $C(=O)OCH_2$, $O(CH_2)O$, $SCH_2CH_2CH_2$, SCH=CHCH$_2$, $CH_2SCH_2CH_2$, $SCH_2CH_2S$, $SCH_2SCH_2$, $CH_2CH_2S$, CH=CHS, $CH_2SCH_2$, $CH_2C(=S)S$, $C(=S)SCH_2$, $S(CH_2)S$, $CH_2CH_2NR^K$, $CH_2CH=N$, CH=CH—$NR^K$, OCH=N, SCH=N and form together with the carbon atoms the two $R^5$ are bonded to a 5- or 6-membered partially unsaturated or aromatic carbocyclic or heterocyclic ring, wherein the ring is unsubstituted or substituted with 1 or 2 substituents selected from the group consisting of =O, OH, $CH_3$, $OCH_3$, halogen, halomethyl and halomethoxy;
each $R^7$ is independently selected from the group consisting of halogen, cyano, hydroxy, $C_1$-$C_6$-alkyl, $C_2$-$C_6$-alkenyl, $C_2$-$C_6$-alkynyl, $C_3$-$C_8$-cycloalkyl, $C_3$-$C_8$-cycloalkenyl, $C_1$-$C_6$-alkoxy, $C_2$-$C_6$-alkenyloxy, $C_1$-$C_6$-alkylthio, ($C_1$-$C_6$-alkoxy)carbonyl, $OSi(R^e)_3$, wherein the carbon atoms of the aforementioned aliphatic or cycloaliphatic radicals are unsubstituted, partially or fully halogenated and/or oxygenated;
$R^{aa}$ is —C(=S)N($R^{cc}$)$_2$, —C(=NR$^{dd}$)SR$^{ee}$, or —C(=O)N($R^{ff}$)$_2$;

$R^{bb}$ is —C(=S)N($R^{cc}$)$_2$, —C(=NR$^{dd}$)SR$^{ee}$, —C(=O)N($R^{ff}$)$_2$, or CN;
each $R^{cc}$ is independently selected from the group consisting of hydrogen, cyano, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_6$-cycloalkyl, $C_3$-$C_6$-halocycloalkyl, $C_1$-$C_6$-alkoxy-$C_1$-$C_6$-alkyl, $C_1$-$C_6$-haloalkoxy-$C_1$-$C_6$-alkyl, $C_1$-$C_6$-alkylthio-$C_1$-$C_6$-alkyl, $C_1$-$C_6$-haloalkylthio-$C_1$-$C_6$-alkyl;
each $R^{dd}$ is independently selected from the group consisting of hydrogen, cyano, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_6$-cycloalkyl, $C_3$-$C_6$-halocycloalkyl, $C_1$-$C_6$-alkoxy-$C_1$-$C_6$-alkyl, $C_1$-$C_6$-haloalkoxy-$C_1$-$C_6$-alkyl, $C_1$-$C_6$-alkylthio-$C_1$-$C_6$-alkyl, $C_1$-$C_6$-haloalkylthio-$C_1$-$C_6$-alkyl;
each $R^{ee}$ is independently selected from the group consisting of cyano, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_6$-cycloalkyl, $C_3$-$C_6$-halocycloalkyl, $C_1$-$C_6$-alkoxy-$C_1$-$C_6$-alkyl, $C_1$-$C_6$-haloalkoxy-$C_1$-$C_6$-alkyl, $C_1$-$C_6$-alkylthio-$C_1$-$C_6$-alkyl, $C_1$-$C_6$-haloalkylthio-$C_1$-$C_6$-alkyl;
each $R^{ff}$ is independently selected from the group consisting of hydrogen, cyano, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_6$-cycloalkyl, $C_3$-$C_6$-halocycloalkyl, $C_1$-$C_6$-alkoxy-$C_1$-$C_6$-alkyl, $C_1$-$C_6$-haloalkoxy-$C_1$-$C_6$-alkyl, $C_1$-$C_6$-alkylthio-$C_1$-$C_6$-alkyl, $C_1$-$C_6$-haloalkylthio-$C_1$-$C_6$-alkyl;
each $R^a$ is independently selected from the group consisting of halogen, cyano, azido, nitro, —SCN, $SF_5$, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$ haloalkynyl, $C_1$-$C_6$-alkyl-$C_3$-$C_8$-cycloalkyl,
$Si(R^e)_3$, $OR^A$, $SR^A$, $OSO_2R^B$, $S(O)_xR^B$, —$S(O)_xN(R^D)_2$, $N(R^D)_2$, $C(=O)N(R^D)_2$, $C(=S)N(R^D)_2$, $C(=O)OR^A$,
phenyl unsubstituted or substituted with up to 5 $R^E$;
a 3-, 4-, 5-, 6- or 7-membered saturated, partially unsaturated or aromatic heterocyclic ring containing 1, 2 or 3 heteroatoms or heteroatom groups selected from N, O, S, NO, SO, $SO_2$, wherein the aforementioned ring is unsubstituted or substituted with up to 5 $R^E$,
or
two $R^a$ present on one carbon atom are together =O, =C($R^F$)$_2$, =NR$^D$, =NOR$^A$, =NNR$^D$,
or
two $R^a$ form a 3-, 4-, 5-, 6-, 7- or 8-membered saturated or partially unsaturated carbocyclic or heterocyclic ring together with the carbon atoms the two $R^a$ are bonded to;
each $R^b$ is independently selected from the group consisting of halogen, cyano, azido, nitro, —SCN, $SF_5$, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$ haloalkynyl, $C_1$-$C_6$-alkyl-$C_3$-$C_8$-cycloalkyl,
$Si(R^G)_3$, $OR^H$, $SR^H$, $OSO_2R^J$, $S(O)_xR^J$, —$S(O)_xN(R^K)_2$, $N(R^K)_2$, $C(=O)N(R^K)_2$, $C(=S)N(R^K)_2$, $C(=O)OR^H$,
or
two $R^b$ present on one carbon atom are together =O, =C($R^L$)$_2$, =NR$^K$, =NOR$^H$, =NNR$^K$, or two $R^b$ form a 3-, 4-, 5-, 6-, 7- or 8-membered saturated or partially unsaturated carbocyclic or heterocyclic ring together with the carbon atoms the two $R^b$ are bonded to;

each $R^c$ is independently selected from the group consisting of halogen, cyano, azido, nitro, —SCN, $SF_5$, $C_1$-$C_6$-alkyl, $C_2$-$C_6$-alkenyl, $C_2$-$C_6$-alkynyl, $C_3$-$C_8$-cycloalkyl, wherein the carbon atoms of the aforementioned aliphatic or cycloaliphatic radicals are unsubstituted or substituted with one or more $R^M$;

$Si(R^G)_3$, $OR^H$, $SR^H$, $OS(O)_xR^J$, $S(O)_xR^J$, —$S(O)_xN(R^K)_2$, $N(R^K)_2$, $C(=O)R^N$, $C(=O)OR^H$, $C(=NR^K)R^N$, $C(=O)N(R^K)_2$, $C(=S)N(R^K)_2$;

each $R^d$ is independently selected from the group consisting of halogen, cyano, azido, nitro, —SCN, $SF_5$, $C_1$-$C_6$-alkyl, $C_2$-$C_6$-alkenyl, $C_2$-$C_6$-alkynyl, $C_3$-$C_8$-cycloalkyl, wherein the carbon atoms of the aforementioned aliphatic or cycloaliphatic radicals are unsubstituted or substituted with one or more $R^M$;

$Si(R^G)_3$, $OR^H$, $SR^H$, $OS(O)_xR^J$, $S(O)_xR^J$, —$S(O)_xN(R^K)_2$, $N(R^K)_2$, $C(=O)R^N$, $C(=O)OR^H$, $C(=NR^K)R^N$, $C(=O)N(R^K)_2$, $C(=S)N(R^K)_2$, or two $R^d$ present on one atom of a saturated or partially unsaturated heterocyclic ring are together =O, =C($R^L$)$_2$; =$NR^K$, =$NOR^H$ or =$NNR^K$;

each $R^e$ is independently selected from the group consisting of halogen, $C_1$-$C_6$ alkyl, $C_1$-$C_6$ haloalkyl, $C_1$-$C_6$ alkoxyalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_8$ cycloalkyl, $C_3$-$C_8$ halocycloalkyl, $C_1$-$C_6$ haloalkoxyalkyl, phenyl, a 3-, 4-, 5-, 6- or 7-membered saturated, partially unsaturated or aromatic heterocyclic ring containing 1, 2 or 3 heteroatoms or heteroatom groups selected from N, O, S, NO, SO, $SO_2$;

each $R^f$ is independently selected from the group consisting of hydrogen, cyano, $C_1$-$C_6$-alkyl, $C_1$-$C_6$-alkylsulfinyl, $C_1$-$C_6$-alkylsulfonyl, $C_3$-$C_8$-cycloalkyl, $C_2$-$C_6$-alkenyl, $C_2$-$C_6$-alkynyl, wherein the carbon atoms of the aforementioned aliphatic or cycloaliphatic radicals are unsubstituted or substituted with one or more $R^M$;

$Si(R^e)_3$, $S(O)_xR^B$, —$S(O)_xN(R^D)_2$, $N(R^D)_2$, —N=C($R^F$)$_2$, $C(=O)R^Q$, $C(=O)N(R^D)_2$, $C(=S)N(R^D)_2$, $C(=O)OR^A$, phenyl, a 3-, 4-, 5-, 6- or 7-membered saturated, partially unsaturated or aromatic heterocyclic ring containing 1, 2 or 3 heteroatoms or heteroatom groups selected from N, O, S, NO, SO, $SO_2$;

each $R^h$ is independently selected from the group consisting of hydrogen, cyano, $C_1$-$C_6$-alkyl, $C_1$-$C_6$-alkoxy, $C_1$-$C_6$-alkylthio, $C_3$-$C_8$-cycloalkyl, $C_2$-$C_6$-alkenyl, $C_2$-$C_6$-alkynyl, wherein the carbon atoms of the aforementioned aliphatic or cycloaliphatic radicals are unsubstituted or substituted with one or more $R^M$;

$N(R^D)_2$, —N=C($R^F$)$_2$, $C(=O)R^Q$, $C(=O)N(R^D)_2$, $C(=S)N(R^D)_2$, $C(=O)OR^A$, phenyl, a 3-, 4-, 5-, 6- or 7-membered saturated, partially unsaturated or aromatic heterocyclic ring containing 1, 2 or 3 heteroatoms or heteroatom groups selected from N, O, S, NO, SO, $SO_2$;

each $R^i$ is independently selected from the group consisting of hydrogen, $C_1$-$C_6$-alkyl, $C_1$-$C_6$-alkoxy, $C_1$-$C_6$-alkylthio, $C_3$-$C_8$-cycloalkyl, $C_2$-$C_6$-alkenyl, $C_2$-$C_6$-alkynyl, wherein the carbon atoms of the aforementioned aliphatic or cycloaliphatic radicals are unsubstituted or substituted with one or more $R^M$;

$S(O)_xR^B$, —$S(O)_xN(R^D)_2$, $C(=O)R^S$, $C(=O)OR^A$, $C(=O)N(R^D)_2$, $C(=S)R^S$, $C(=S)SR^A$, $C(=S)N(R^D)_2$, $C(=NR^D)R^S$, phenyl unsubstituted or substituted with up to 5 $R^E$;

a 3-, 4-, 5-, 6- or 7-membered saturated, partially unsaturated or aromatic heterocyclic ring containing 1, 2 or 3 heteroatoms or heteroatom groups selected from N, O, S, NO, SO, $SO_2$, wherein the aforementioned ring is unsubstituted or substituted with up to 5 $R^E$, or two $R^i$ on one nitrogen atom are together a $C_2$-$C_7$ alkylene chain and form together with the nitrogen atom they are bonded to a 3-, 4-, 5-, 6-, 7- or 8-membered saturated, partially unsaturated or aromatic ring, wherein the alkylene chain may contain 1 or 2 heteroatoms or heteroatom groups selected from N, O, S, NO, SO, $SO_2$, and wherein the alkylene chain is unsubstituted or substituted with halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_2$-$C_6$-alkenyl, $C_2$-$C_6$-haloalkenyl, $C_2$-$C_6$-alkynyl, $C_2$-$C_6$-haloalkynyl;

each $R^m$ is independently selected from the group consisting of hydrogen, —SCN, $SF_5$, $C_1$-$C_6$-alkyl, $C_1$-$C_6$-alkoxy, $C_1$-$C_6$-alkylthio, $C_3$-$C_8$-cycloalkyl, $C_2$-$C_6$-alkenyl, $C_2$-$C_6$-alkynyl, wherein the carbon atoms of the aforementioned aliphatic or cycloaliphatic radicals are unsubstituted or substituted with one or more $R^M$;

$Si(R^e)_3$, $OR^A$, $SR^A$, $OSO_2R^B$, $N(R^D)_2$, $C(=O)N(R^D)_2$, $C(=S)N(R^D)_2$, $C(=O)OR^A$, phenyl unsubstituted or substituted with up to 5 $R^E$;

a 3-, 4-, 5-, 6- or 7-membered saturated, partially unsaturated or aromatic heterocyclic ring containing 1, 2 or 3 heteroatoms or heteroatom groups selected from N, O, S, NO, SO, $SO_2$, wherein the aforementioned ring is unsubstituted or substituted with up to 5 $R^E$;

each $R^A$ is independently selected from the group consisting of hydrogen, cyano, $C_1$-$C_6$-alkylsulfinyl, $C_1$-$C_6$-alkylsulfonyl, trimethylsilyl, triethylsilyl, tert-butyldimethylsilyl, $C_1$-$C_6$-alkyl, $C_2$-$C_6$-alkenyl, $C_2$-$C_6$-alkynyl, $C_3$-$C_8$-cycloalkyl, wherein the four last mentioned radicals are unsubstituted, partially or fully halogenated and/or oxygenated and/or carry 1 or 2 radicals selected from $C_1$-$C_4$ alkoxy;

phenyl, benzyl, pyridyl, phenoxy, wherein the four last mentioned radicals are unsubstituted, partially or fully halogenated and/or carry 1, 2 or 3 substituents selected from $C_1$-$C_6$-alkyl, $C_1$-$C_6$-haloalkyl, $C_1$-$C_6$-alkoxy, $C_1$-$C_6$ haloalkoxy and ($C_1$-$C_6$-alkoxy)carbonyl;

each $R^B$ is independently selected from the group consisting of hydrogen, cyano, $C_1$-$C_6$-alkoxy, $C_1$-$C_6$-haloalkoxy, $C_1$-$C_6$-alkylthio, $C_1$-$C_6$-haloalkylthio, trimethylsilyl, triethylsilyl, tert-butyldimethylsilyl, $C_1$-$C_6$-alkyl, $C_2$-$C_6$-alkenyl, $C_2$-$C_6$-alkynyl, $C_3$-$C_8$-cycloalkyl, wherein the four last mentioned radicals are unsubstituted, partially or fully halogenated and/or oxygenated and/or carry 1 or 2 radicals selected from $C_1$-$C_4$ alkoxy;

phenyl, benzyl, pyridyl, phenoxy, wherein the four last mentioned radicals are unsubstituted, partially or fully halogenated and/or carry 1, 2 or 3 substituents selected from $C_1$-$C_6$-alkyl, $C_1$-$C_6$-haloalkyl, $C_1$-$C_6$-alkoxy, $C_1$-$C_6$ haloalkoxy and ($C_1$-$C_6$-alkoxy)carbonyl;

each $R^D$ is independently selected from the group consisting of hydrogen, cyano, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, trimethylsilyl, triethylsilyl, tert-butyldimethylsilyl, $C_1$-$C_6$-alkyl, $C_2$-$C_6$-alkenyl, $C_2$-$C_6$-alkynyl, $C_3$-$C_8$-cycloalkyl, wherein the four last mentioned radicals are unsubstituted, partially or fully halogenated and/or oxygenated and/or carry 1 or 2 radicals selected from $C_1$-$C_4$-alkoxy;

phenyl, benzyl, pyridyl, phenoxy, wherein the four last mentioned radicals are unsubstituted, partially or fully halogenated and/or carry 1, 2 or 3 substituents selected from $C_1$-$C_6$-alkyl, $C_1$-$C_6$-haloalkyl, $C_1$-$C_6$-alkoxy, $C_1$-$C_6$ haloalkoxy and ($C_1$-$C_6$-alkoxy)carbonyl, or two $R^D$ on one nitrogen atom are together a $C_2$-$C_6$ alkylene chain and form together with the nitrogen atom they are bonded to a 3-, 4-, 5-, 6-, or 7-membered saturated, partially unsaturated or aromatic ring, wherein the alkylene chain may contain 1 or 2 heteroatoms or heteroatom groups selected from N, O, S, NO, SO, $SO_2$, and wherein the alkylene chain is unsubstituted or substituted with halogen, $C_1$-$C_4$-haloalkyl, $C_1$-$C_4$-alkoxy or $C_1$-$C_4$-haloalkoxy;

each $R^E$ is independently selected from the group consisting of cyano, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, trimethylsilyl, triethylsilyl, tert-butyldimethylsilyl, $C_1$-$C_6$-alkyl, $C_2$-$C_6$-alkenyl, $C_2$-$C_6$-alkynyl, wherein the four last mentioned radicals are unsubstituted, partially or fully halogenated and/or oxygenated and/or carry 1 or 2 radicals selected from $C_1$-$C_4$-alkoxy, or two $R^E$ present on one atom of a saturated or partially unsaturated heterocyclic ring are together =O, =N($C_1$-$C_6$-alkyl), =NO($C_1$-$C_6$-alkyl), =CH($C_1$-$C_4$-alkyl) or =C($C_1$-$C_4$-alkyl)$C_1$-$C_4$-alkyl;

each $R^F$ is independently selected from the group consisting of $C_1$-$C_4$ alkyl, $C_1$-$C_6$ cycloalkyl, $C_1$-$C_4$ alkoxyalkyl, phenyl and benzyl;

each $R^G$ is independently selected from the group consisting of halogen, $C_1$-$C_6$ alkyl, $C_1$-$C_6$ haloalkyl, $C_1$-$C_6$ alkoxyalkyl, $C_2$-$C_6$ alkenyl, $C_2$-$C_6$ haloalkenyl, $C_2$-$C_6$ alkynyl, $C_2$-$C_6$ haloalkynyl, $C_1$-$C_6$ haloalkoxyalkyl;

each $R^H$ is independently selected from the group consisting of hydrogen, cyano, $C_1$-$C_6$-alkyl sulfinyl, $C_1$-$C_6$-alkylsulfonyl, trimethylsilyl, triethylsilyl, tert-butyldimethylsilyl, $C_1$-$C_6$-alkyl, $C_2$-$C_6$-alkenyl, $C_2$-$C_6$-alkynyl, wherein the three last mentioned radicals are unsubstituted, partially or fully halogenated and/or oxygenated and/or carry 1 or 2 radicals selected from $C_1$-$C_4$ alkoxy;

each $R^J$ is independently selected from the group consisting of hydrogen, cyano, $C_1$-$C_6$-alkoxy, $C_1$-$C_6$-haloalkoxy, $C_1$-$C_6$-alkylthio, $C_1$-$C_6$-haloalkylthio, trimethylsilyl, triethylsilyl, tert-butyldimethylsilyl, $C_1$-$C_6$-alkyl, $C_2$-$C_6$-alkenyl, $C_2$-$C_6$-alkynyl, wherein the three last mentioned radicals are unsubstituted, partially or fully halogenated and/or oxygenated and/or carry 1 or 2 radicals selected from $C_1$-$C_4$ alkoxy;

each $R^K$ is independently selected from the group consisting of hydrogen, cyano, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, trimethylsilyl, triethylsilyl, tert-butyldimethylsilyl, $C_1$-$C_6$-alkyl, $C_2$-$C_6$-alkenyl, $C_2$-$C_6$-alkynyl, wherein the three last mentioned radicals are unsubstituted, partially or fully halogenated and/or oxygenated and/or carry 1 or 2 radicals selected from $C_1$-$C_4$-alkoxy;

each $R^L$ is independently selected from the group consisting of $C_1$-$C_4$ alkyl and $C_1$-$C_4$ alkoxyalkyl;

each $R^M$ is independently selected from the group consisting of halogen, cyano, azido, nitro, OH, SH, —SCN, $SF_5$, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, trimethylsilyl, triethylsilyl, tert-butyldimethylsilyl, $C_1$-$C_6$-alkyl, $C_2$-$C_6$-alkenyl, $C_2$-$C_6$-alkynyl, $C_3$-$C_8$-cycloalkyl, $C_1$-$C_6$-alkyl-$C_3$-$C_8$-cycloalkyl, wherein the five last mentioned radicals are unsubstituted, partially or fully halogenated and/or oxygenated and/or carry 1 or 2 radicals selected from $C_1$-$C_4$ alkoxy, or two $R^M$ present on one carbon atom are together =O, =CH($C_1$-$C_4$-alkyl), =C($C_1$-$C_4$-alkyl)$C_1$-$C_4$-alkyl, =N($C_1$-$C_6$-alkyl) or =NO($C_1$-$C_6$-alkyl);

each $R^N$ is independently selected from the group consisting of hydrogen, OH, SH, —SCN, $SF_5$, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, trimethylsilyl, triethylsilyl, tert-butyldimethylsilyl, $C_1$-$C_6$-alkyl, $C_2$-$C_6$-alkenyl, $C_2$-$C_6$-alkynyl, wherein the three last mentioned radicals are unsubstituted, partially or fully halogenated and/or oxygenated and/or carry 1 or 2 radicals selected from $C_1$-$C_4$ alkoxy;

each $R^Q$ is independently selected from the group consisting of hydrogen, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, trimethylsilyl, triethylsilyl, tert-butyldimethylsilyl, $C_1$-$C_6$-alkyl, $C_2$-$C_6$-alkenyl, $C_2$-$C_6$-alkynyl, $C_3$-$C_8$-cycloalkyl, wherein the four last mentioned radicals are unsubstituted, partially or fully halogenated and/or oxygenated and/or carry 1 or 2 radicals selected from $C_1$-$C_4$ alkoxy;

phenyl, benzyl, pyridyl, phenoxy, wherein the four last mentioned radicals are unsubstituted, partially or fully halogenated and/or carry 1, 2 or 3 substituents selected from $C_1$-$C_6$-alkyl, $C_1$-$C_6$-haloalkyl, $C_1$-$C_6$-alkoxy, $C_1$-$C_6$ haloalkoxy and ($C_1$-$C_6$-alkoxy)carbonyl;

each $R^S$ is independently selected from the group consisting of hydrogen, OH, SH, —SCN, $SF_5$, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, trimethylsilyl, triethylsilyl, tert-butyldimethylsilyl, $C_1$-$C_6$-alkyl, $C_2$-$C_6$-alkenyl, $C_2$-$C_6$-alkynyl, $C_3$-$C_8$-cycloalkyl, wherein the four last mentioned radicals are unsubstituted, partially or fully halogenated and/or oxygenated and/or carry 1 or 2 radicals selected from $C_1$-$C_4$ alkoxy;

phenyl, benzyl, pyridyl, phenoxy, wherein the four last mentioned radicals are unsubstituted, partially or fully halogenated and/or carry 1, 2 or 3 substituents selected from $C_1$-$C_6$-alkyl, $C_1$-$C_6$-haloalkyl, $C_1$-$C_6$-alkoxy, $C_1$-$C_6$ haloalkoxy, ($C_1$-$C_6$-alkoxy)carbonyl, ($C_1$-$C_6$-alkyl)amino and di-($C_1$-$C_6$-alkyl)amino;

p is 0 or 1;

x is 1 or 2.

2. The method of claim 1, wherein

Y is phenyl unsubstituted or substituted with 1, 2, 3, 4 or 5 substituents $R^5$; or naphthyl unsubstituted or substituted with 1 or 2 substituents $R^5$;

Q is phenyl unsubstituted or substituted with 1, 2, 3 or 4 substituents $R^6$; cyclohexyl unsubstituted or substituted with 1 or 2 substituents $R^6$; cyclopentyl unsubstituted or substituted with 1 or 2 substituents $R^6$; or a 6-membered aromatic heterocyclic ring containing 1, 2 or 3 nitrogen atoms in the ring, wherein the aforementioned ring is unsubstituted or substituted with 1, 2, 3 or 4 substituents $R^6$;

$R^1$ is selected from the group consisting of H, halogen, cyano, $C_1$-$C_6$-alkyl, $C_2$-$C_6$-alkenyl, $C_2$-$C_6$-alkynyl, $C_3$-$C_6$-cycloalkyl or ($C_1$-$C_6$-alkoxy)carbonyl, wherein the five radicals last mentioned are unsubstituted or substituted with 1, 2 or 3 substituents selected from halogen, cyano, hydroxy, $OSi(C_1$-$C_6$-alkyl$)_3$, $C_1$-$C_6$-alkyl, $C_2$-$C_6$-alkenyl, $C_2$-$C_6$-alkynyl, $C_3$-$C_6$-cycloalkyl, $C_1$-$C_6$-alkoxy and ($C_1$-$C_6$-alkoxy)carbonyl, wherein the six radicals last mentioned are unsubstituted or partially or fully halogenated;

$R^2$ is selected from the group consisting of H and halogen; or $R^1$ and $R^2$ form together with the carbon atom to which they are attached a methylene group;

$R^3$ is selected from the group consisting of H, halogen, cyano, $C_1$-$C_6$-alkyl, $C_2$-$C_6$-alkenyl, $C_2$-$C_6$-alkynyl, $C_3$-$C_6$-cycloalkyl or ($C_1$-$C_6$-alkoxy)carbonyl, wherein the five radicals last mentioned are unsubstituted or substituted with 1, 2 or 3 substituents selected from halogen, cyano, hydroxy, $OSi(C_1$-$C_6$-alkyl$)_3$, $C_1$-$C_6$-alkyl, $C_2$-$C_6$-alkenyl, $C_2$-$C_6$-alkynyl, $C_3$-$C_6$-cycloalkyl, $C_1$-$C_6$-alkoxy and ($C_1$-$C_6$-alkoxy)carbonyl, wherein the six radicals last mentioned are unsubstituted or partially or fully halogenated;

$R^4$ is selected from the group consisting of H and halogen; or $R^3$ and $R^4$ form together with the carbon atom to which they are attached a methylene group;

$R^5$ is selected from the group consisting of halogen, cyano, $SF_5$, tri-($C_1$-$C_4$)silyl-$C_2$-$C_4$-alkynyl, ($C_1$-$C_6$-alkyl)aminocarbonyl, di-($C_1$-$C_6$-alkyl)aminocarbonyl, $C_1$-$C_6$-alkyl, $C_2$-$C_6$-alkenyl, $C_2$-$C_6$-alkynyl, $C_3$-$C_6$-cycloalkyl, phenyl, $C_1$-$C_6$-alkoxy, $C_1$-$C_6$-alkylthio, $C_1$-$C_6$-alkylsulfinyl, $C_1$-$C_6$-alkylsulfonyl, ($C_1$-$C_6$-alkoxy)carbonyl, ($C_1$-$C_6$-alkyl)amino, di-($C_1$-$C_6$-alkyl)amino, ($C_1$-$C_6$-alkyl)carbonyl or ($C_1$-$C_6$-alkyl)carbonyloxy, wherein the 14 radicals last mentioned are unsubstituted or substituted with one or more substituents selected from halogen, cyano, $C_1$-$C_4$-alkyl-$C_3$-$C_6$-cycloalkyl, $C_1$-$C_6$-alkyl, $C_2$-$C_6$-alkenyl, $C_2$-$C_6$-alkynyl, $C_3$-$C_6$-cycloalkyl and $C_1$-$C_6$-alkoxy, wherein the five radicals last mentioned are unsubstituted or partially or fully halogenated;

or two $R^5$ on two adjacent carbon atoms present on one phenyl ring are together a bridge selected from N=CH—CH=CH, N=CH—CH=N, $OCH_2CH_2O$, $O(CH_2)O$ and form together with the carbon atoms the two $R^5$ are bonded to a 5- or 6-membered partially unsaturated or aromatic heterocyclic ring, wherein the ring is unsubstituted;

$R^6$ is selected from the group consisting of halogen, nitro, cyano, $SF_5$, tri-($C_1$-$C_4$)silyl-$C_2$-$C_4$-alkynyl, 2,2,2-trifluoro-1-hydroxy-1-(trifluoromethyl)ethyl, ($C_1$-$C_6$-alkyl)aminocarbonyl, di-($C_1$-$C_6$-alkyl)aminocarbonyl, dimethylcarbamoylsulfanyl, morpholine-4-carbonyl, acetamido, pyridyl, pyrrolyl, pyrazolyl, imidazolyl, triazolyl, $C_1$-$C_6$-alkyl, $C_2$-$C_6$-alkenyl, $C_2$-$C_6$-alkynyl, $C_3$-$C_6$-cycloalkyl, phenyl, $C_1$-$C_6$-alkoxy, $C_3$-$C_6$-cycloalkoxy, phenoxy, $C_1$-$C_6$-alkylthio, $C_1$-$C_6$-alkylsulfinyl, $C_1$-$C_6$-alkylsulfonyl, ($C_1$-$C_6$-alkoxy)carbonyl, ($C_1$-$C_6$-alkyl)amino, di-($C_1$-$C_6$-alkyl)amino, ($C_1$-$C_6$-alkyl)carbonyl or ($C_1$-$C_6$-alkyl)carbonyloxy, wherein the 16 radicals last mentioned are unsubstituted or substituted with one or more substituents selected from halogen, cyano, $C_1$-$C_4$-alkyl-$C_3$-$C_6$-cycloalkyl, $C_1$-$C_6$-alkyl, $C_2$-$C_6$-alkenyl, $C_2$-$C_6$-alkynyl, $C_3$-$C_6$-cycloalkyl and $C_1$-$C_6$-alkoxy, wherein the five radicals last mentioned are unsubstituted or partially or fully halogenated;

$R^{aa}$ is selected from the group consisting of —C(=S)N($R^{cc}$)$_2$ and —C(=O)N($R^{ff}$)$_2$;

$R^{bb}$ is CN;

each $R^{cc}$ is independently selected from the group consisting of hydrogen, $C_1$-$C_4$-alkyl, $C_2$-$C_4$-alkenyl, $C_2$-$C_4$-alkynyl, $C_3$-$C_6$-cycloalkyl, $C_1$-$C_4$-alkoxy-$C_1$-$C_2$-alkyl;

each $R^{ff}$ is independently selected from the group consisting of hydrogen, $C_1$-$C_4$-alkyl, $C_2$-$C_4$-alkenyl, $C_2$-$C_4$-alkynyl, $C_3$-$C_6$-cycloalkyl, $C_1$-$C_4$-alkoxy-$C_1$-$C_2$-alkyl;

p is 0 or 1.

3. The method of claim 1, wherein $R^1$ is selected from the group consisting of H, Me, Et, iPr, cPr, $CH_2CN$, $CF_3$, $CHF_2$, $CH_2F$, $CH_2CH_2F$, $CH_2CHF_2$, $CH_2CF_3$, CN, halogen, $CH_2OH$, $CH_2OMe$, $CH_2OEt$, $CO_2Me$, $CO_2Et$, $CH_2CO_2Me$, $CH_2CO_2Et$, $CH_2OSi(Me)_3$ and $CH_2OSi(Et)_3$.

4. The method of claim 1, wherein $R^3$ is selected from the group consisting of H, Me, Et, iPr, cPr, $CH_2CN$, $CF_3$, $CHF_2$, $CH_2F$, $CH_2CH_2F$, $CH_2CHF_2$, $CH_2CF_3$, CN, halogen, $CH_2OH$, $CH_2OMe$, $CH_2OEt$, $CO_2Me$, $CO_2Et$, $CH_2CO_2Me$, $CH_2CO_2Et$, $CH_2OSi(Me)_3$ and $CH_2OSi(Et)_3$.

5. The method of claim 1, wherein $R^5$ is selected from the group consisting of halogen, Me, Et, iPr, cPr, OMe, OEt, OiPr, ethynyl, (trimethylsilyl)ethynyl, vinyl, Ph, CN, $CF_3$, $OCF_3$, $SF_5$, $CHF_2$, $OCHF_2$, SMe, S(O)Me, S(O)$_2$Me, $SCF_3$, S(O)$CF_3$, S(O)$_2CF_3$, $SCHF_2$, S(O)$CHF_2$, S(O)$_2CHF_2$, $CO_2Me$, $CO_2Et$, C(O)Me, OAc, C(O)NHMe, C(O)NMe$_2$, $CH_2OMe$ and $CH_2OEt$;

or two $R^5$ on two adjacent carbon atoms present on one phenyl ring are together a bridge selected from the group consisting of N=CH—CH=CH, N=CH—CH=N, $OCH_2CH_2O$, $O(CH_2)O$ and form together with the carbon atoms the two $R^5$ are bonded to a 5- or 6-membered partially unsaturated or aromatic heterocyclic ring, wherein the ring is unsubstituted.

6. The method of claim 1, wherein $R^6$ is selected from the group consisting f halogen, Me, Et, iPr, cPr, tBu, OMe, OEt, OnPr, OiPr, OtBu, OPh, ethynyl, (trimethylsilyl)ethynyl, vinyl, Ph, $NO_2$, CN, $CF_3$, $OCF_3$, $SF_5$, $CHF_2$, $OCHF_2$, SMe, S(O)Me, S(O)$_2$Me, $SCF_3$, S(O)$CF_3$, S(O)$_2CF_3$, $SCHF_2$, S(O)$CHF_2$, S(O)$_2CHF_2$, $CO_2Me$, $CO_2Et$, $CO_2iPr$, C(O)Me, OAc, C(O)NHMe, C(O)NMe$_2$, $CH_2OMe$, $CH_2OEt$, fluoromethyl, 2,2,2-trifluoroethyl, 1,2,2,2-tetrafluoro-1-(trifluoromethyl)ethyl, 2,2,2-trifluoro-1-hydroxy-1-(trifluoromethyl)ethyl, dimethoxymethyl, chloro(difluoro)methoxy, 2,2,2-trifluoroethoxy, 2,2-difluorocyclopropoxy, tert-butylsulfanyl, dimethylcarbamoylsulfanyl, morpholine-4-carbonyl, acetamido, 2-pyridyl, 3-pyridyl, 4-pyridyl, pyrrol-1-yl, pyrazol-1-yl, imidazol-1-yl and 1,2,4-triazol-1-yl.

7. The method of claim 1, wherein
Y is phenyl unsubstituted or substituted with 1, 2, 3, 4 or 5 substituents $R^5$; or naphthyl unsubstituted or substituted with 1 substituent $R^5$;
Q is phenyl unsubstituted or substituted with 1, 2 or 3 substituents $R^6$; cyclohexyl unsubstituted or substituted with 1 substituent $R^6$; or a 6-membered aromatic heterocyclic ring containing 1, 2 or 3 nitrogen atoms in the ring, wherein the aforementioned ring is unsubstituted or substituted with 1, 2 or 3 substituents $R^6$;
$R^1$ is selected from the group consisting of H, Me, Et, CN, $CH_2CN$, $CH_2CF_3$, halogen, $CH_2OH$, $CH_2OMe$, $CH_2OEt$, $CH_2CO_2Me$, $CH_2CO_2Et$, $CH_2OSi(Me)_3$ and $CH_2OSi(Et)_3$;
$R^2$ is selected from the group consisting of H and halogen;
$R^3$ is selected from the group consisting of H, Me, Et, CN, $CH_2CN$, $CH_2CF_3$, halogen, $CH_2OH$, $CH_2OMe$, $CH_2OEt$, $CH_2CO_2Me$, $CH_2CO_2Et$, $CH_2OSi(Me)_3$ and $CH_2OSi(Et)_3$;
$R^4$ is selected from the group consisting of H and halogen;
$R^5$ is selected from the group consisting of halogen, cyano, tri-$(C_1$-$C_4)$silyl-$C_2$-$C_4$-alkynyl, $C_1$-$C_6$-alkyl, $C_2$-$C_6$-alkenyl, $C_2$-$C_6$-alkynyl, $C_3$-$C_6$-cycloalkyl, phenyl, $C_1$-$C_6$-alkoxy, $C_1$-$C_6$-alkylthio and $(C_1$-$C_6$-alkoxy)carbonyl,
wherein the eight radicals last mentioned are unsubstituted or partially or fully halogenated;
or
two $R^5$ on two adjacent carbon atoms present on one phenyl ring are together a bridge selected from the group consisting of N=CH—CH=CH, N=CH—CH=N, $OCH_2CH_2O$, $O(CH_2)O$ and form together with the carbon atoms the two $R^5$ are bonded to a 5- or 6-membered partially unsaturated or aromatic heterocyclic ring, wherein the ring is unsubstituted;
$R^6$ is selected from the group consisting of halogen, nitro, cyano, tri-$(C_1$-$C_4)$silyl-$C_2$-$C_4$-alkynyl, 2,2,2-trifluoro-1-hydroxy-1-(trifluoromethyl)ethyl, dimethoxymethyl, dimethylcarbamoylsulfanyl, morpholine-4-carbonyl, acetamido, pyridyl, pyrrolyl, pyrazolyl, imidazolyl, triazolyl, $C_1$-$C_6$-alkyl, $C_2$-$C_6$-alkenyl, $C_2$-$C_6$-alkynyl, $C_3$-$C_6$-cycloalkyl, phenyl, $C_1$-$C_6$-alkoxy, $C_3$-$C_6$-cycloalkoxy, phenoxy, $C_1$-$C_6$-alkylthio, $C_1$-$C_6$-alkylsulfonyl and $(C_1$-$C_6$-alkoxy)carbonyl,
wherein the eleven radicals last mentioned are unsubstituted or partially or fully halogenated;
$R^{aa}$ is —C(=S)N($R^{cc}$)$_2$;
$R^{bb}$ is CN;
each $R^{cc}$ is independently selected from the group consisting of H, Me, Et, propargyl, allyl, $CH_2OMe$, $CH_2OEt$;
p is 0 or 1.

8. The method of claim 1, wherein $R^5$ is selected from the group consisting of halogen, Me, OMe, CN, $CF_3$, $OCF_3$ and ethynyl.

9. The method of claim 1, wherein $R^6$ is selected from the group consisting of halogen, Me, OMe, CN, $CF_3$, $OCF_3$ and ethynyl.

10. The method of claim 1, wherein
Y is phenyl unsubstituted or substituted with 1, 2 or 3 substituents $R^5$;
Q is phenyl unsubstituted or substituted with 1 or 2 substituents $R^6$; pyridyl, pyrimidinyl, pyrazinyl or pyridazinyl, wherein the four rings last mentioned are unsubstituted or substituted with 1 or 2 substituents $R^6$;
$R^1$ is selected from the group consisting of H, F, Me, Et, CN, $CH_2CN$ and $CH_2OMe$;
$R^2$ is H;
$R^5$ is selected from the group consisting of F, Cl, Br and $CF_3$;
$R^6$ is selected from the group consisting of F, ethynyl and $CF_3$;
$R^{aa}$ is —C(=S)$NH_2$;
$R^{bb}$ is CN;
p is 0.

11. The method of claim 1, wherein $R^1$ is H.

12. The method of claim 1, wherein $R^3$ is H.

13. The method of claim 1, wherein p is 0.

14. The method of claim 1, wherein Q is phenyl unsubstituted or substituted with one or more $R^6$.

15. The method of claim 1, wherein Q is pyridyl or pyrimidinyl, wherein the aforementioned rings are unsubstituted or substituted with one or more $R^6$.

16. The method of claim 1, wherein $R^{cc}$ is H when $R^{bb}$ is CN.

17. The method of claim 1, wherein $R^{aa}$ is —C(=S)$NH_2$ or —C(=O)$NH_2$.

18. The method of claim 1, wherein $R^{bb}$ is CN.

19. The method of claim 1, wherein $R^{aa}$ is —C(=S)$NH_2$ and $R^{bb}$ is CN.

20. The method of claim 1, wherein $R^1$ and $R^2$ are H and p is 0.

21. A method for protecting crops from attack or infestation by invertebrate animal pests, which comprises contacting the crop with a pesticidally effective amount of at least one compound of formula (I) of formula (I)

$$Y-\underset{R^1\ R^2}{C}(R^{aa})(R^{bb})-\underset{}{C}(R^3)(R^4)-_pQ \quad (I)$$

wherein
Y is phenyl unsubstituted or substituted with 1, 2, 3, 4 or 5 substituents $R^5$; or naphthyl unsubstituted or substituted with 1, 2, 3, 4, 5, 6 or 7 substituents $R^5$;
Q is phenyl unsubstituted or substituted with 1, 2, 3, 4 or 5 substituents $R^6$; $C_3$-$C_8$ cycloalkyl unsubstituted or substituted with one or more substituents $R^6$; $C_3$-$C_8$ cycloalkenyl unsubstituted or substituted with one or more substituents $R^6$; 6-membered aromatic heterocyclic ring containing 1, 2, 3 or 4 nitrogen atoms in the ring, wherein the aforementioned ring is unsubstituted or substituted with 1, 2, 3 or 4 substituents $R^6$;
$R^1$ is selected from the group consisting of hydrogen, halogen, cyano, hydroxy, $C_1$-$C_6$-alkyl, $C_2$-$C_6$-alkenyl, $C_2$-$C_6$-alkynyl, $C_3$-$C_8$-cycloalkyl, $C_3$-$C_8$-cycloalkenyl, $C_1$-$C_6$-alkoxy, $C_2$-$C_6$-alkenyloxy, $C_1$-$C_6$-alkylthio, $(C_1$-$C_6$-alkoxy)carbonyl, wherein the carbon atoms of the aforementioned aliphatic or cycloaliphatic radicals are unsubstituted or substituted with 1, 2 or 3 substituents $R^7$;
$R^2$ is hydrogen or halogen;
or
$R^1$ and $R^2$ form together with the carbon atom to which they are attached a methylene group or a cyclopropyl group;
$R^3$ is selected from the group consisting of hydrogen, halogen, cyano, hydroxy, $C_1$-$C_6$-alkyl, $C_2$-$C_6$-alkenyl, $C_2$-$C_6$-alkynyl, $C_3$-$C_8$-cycloalkyl, $C_3$-$C_8$-cycloalkenyl, $C_1$-$C_6$-alkoxy, $C_2$-$C_6$-alkenyloxy, $C_1$-$C_6$-alkylthio, $(C_1$-

$C_6$-alkoxy)carbonyl, wherein the carbon atoms of the aforementioned aliphatic or cycloaliphatic radicals are unsubstituted or substituted with 1, 2 or 3 substituents $R^7$;

$R^4$ is hydrogen or halogen;

or $R^3$ and $R^4$ form together with the carbon atom to which they are attached a methylene group or a cyclopropyl group;

each $R^5$, $R^6$ is independently selected from the group consisting of halogen, cyano, azido, nitro, —SCN, $SF_5$, $C_1$-$C_6$ alkyl, $C_2$-$C_6$ alkenyl, $C_2$-$C_6$ alkynyl, wherein the carbon atoms of the aforementioned aliphatic radicals are unsubstituted or substituted with one or more $R^a$;

$C_3$-$C_8$ cycloalkyl or $C_3$-$C_8$ cycloalkenyl, wherein the carbon atoms of the aforementioned cycloaliphatic radicals are unsubstituted or substituted with one or more $R^b$;

phenyl unsubstituted or substituted with up to 5 $R^c$;

a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO, $SO_2$, wherein the aforementioned ring is unsubstituted or substituted with up to 5 $R^d$;

$Si(R^e)_3$, $OR^f$, $SR^f$, $OS(O)_xR^h$, $S(O)_xR^h$, $N(R^i)_2$, $N(R^i)C(=O)R^m$, $OC(=O)R^m$, $C(=O)R^m$, $C(=O)OR^f$, $C(=NR^i)R^m$, $C(=S)R^m$;

or two $R^5$ on two adjacent carbon atoms present on one phenyl ring are together a bridge selected from the group consisting of $CH_2CH_2CH_2CH_2$, N=CH—CH=CH, CH=N—CH=CH, N=CH—N=CH, N=CH—CH=N, $OCH_2CH_2CH_2$, OCH=CHCH$_2$, $CH_2OCH_2CH_2$, $OCH_2CH_2O$, $OCH_2OCH_2$, $CH_2CH_2CH_2$, CH=CHCH$_2$, $CH_2CH_2O$, CH=CHO, $CH_2OCH_2$, $CH_2C(=O)O$, $C(=O)OCH_2$, $O(CH_2)O$, $SCH_2CH_2CH_2$, SCH=CHCH$_2$, $CH_2SCH_2CH_2$, $SCH_2CH_2S$, $SCH_2SCH_2$, $CH_2CH_2S$, CH=CHS, $CH_2SCH_2$, $CH_2C(=S)S$, $C(=S)SCH_2$, $S(CH_2)S$, $CH_2CH_2NR^K$, $CH_2CH=N$, CH=CH—$NR^K$, OCH=N, SCH=N and form together with the carbon atoms the two $R^5$ are bonded to a 5- or 6-membered partially unsaturated or aromatic carbocyclic or heterocyclic ring, wherein the ring is unsubstituted or substituted with 1 or 2 substituents selected from the group consisting of =O, OH, $CH_3$, $OCH_3$, halogen, halomethyl and halomethoxy;

each $R^7$ is independently selected from the group consisting of halogen, cyano, hydroxy, $C_1$-$C_6$-alkyl, $C_2$-$C_6$-alkenyl, $C_2$-$C_6$-alkynyl, $C_3$-$C_8$-cycloalkyl, $C_3$-$C_8$-cycloalkenyl, $C_1$-$C_6$-alkoxy, $C_2$-$C_6$-alkenyloxy, $C_1$-$C_6$-alkylthio, ($C_1$-$C_6$-alkoxy)carbonyl, $OSi(R^e)_3$, wherein the carbon atoms of the aforementioned aliphatic or cycloaliphatic radicals are unsubstituted, partially or fully halogenated and/or oxygenated;

$R^{aa}$ is —C(=S)N($R^{cc}$)$_2$, —C(=N$R^{dd}$)$SR^{ee}$, or —C(=O)N($R^{ff}$)$_2$;

$R^{bb}$ is —C(=S)N($R^{cc}$)$_2$, —C(=N$R^{dd}$)$SR^{ee}$, —C(=O)N($R^{ff}$)$_2$, or CN;

each $R^{cc}$ is independently selected from the group consisting of hydrogen, cyano, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_6$-cycloalkyl, $C_3$-$C_6$-halocycloalkyl, $C_1$-$C_6$-alkoxy-$C_1$-$C_6$-alkyl, $C_1$-$C_6$-haloalkoxy-$C_1$-$C_6$-alkyl, $C_1$-$C_6$-alkylthio-$C_1$-$C_6$-alkyl, $C_1$-$C_6$-haloalkylthio-$C_1$-$C_6$-alkyl;

each $R^{dd}$ is independently selected from the group consisting of hydrogen, cyano, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_6$-cycloalkyl, $C_3$-$C_6$-halocycloalkyl, $C_1$-$C_6$-alkoxy-$C_1$-$C_6$-alkyl, $C_1$-$C_6$-haloalkoxy-$C_1$-$C_6$-alkyl, $C_1$-$C_6$-alkylthio-$C_1$-$C_6$-alkyl, $C_1$-$C_6$-haloalkylthio-$C_1$-$C_6$-alkyl;

each $R^{ee}$ is independently selected from the group consisting of cyano, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_6$-cycloalkyl, $C_3$-$C_6$-halocycloalkyl, $C_1$-$C_6$-alkoxy-$C_1$-$C_6$-alkyl, $C_1$-$C_6$-haloalkoxy-$C_1$-$C_6$-alkyl, $C_1$-$C_6$-alkylthio-$C_1$-$C_6$-alkyl, $C_1$-$C_6$-haloalkylthio-$C_1$-$C_6$-alkyl;

each $R^{ff}$ is independently selected from the group consisting of hydrogen, cyano, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_6$-cycloalkyl, $C_3$-$C_6$-halocycloalkyl, $C_1$-$C_6$-alkoxy-$C_1$-$C_6$-alkyl, $C_1$-$C_6$-haloalkoxy-$C_1$-$C_6$-alkyl, $C_1$-$C_6$-alkylthio-$C_1$-$C_6$-alkyl, $C_1$-$C_6$-haloalkylthio-$C_1$-$C_6$-alkyl;

each $R^a$ is independently selected from the group consisting of halogen, cyano, azido, nitro, —SCN, $SF_5$, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$ haloalkynyl, $C_1$-$C_6$-alkyl-$C_3$-$C_8$-cycloalkyl, $Si(R^e)_3$, $OR^A$, $SR^A$, $OSO_2R^B$, $S(O)_xR^B$, —$S(O)_xN(R^D)_2$, $N(R^D)_2$, $C(=O)N(R^D)_2$, $C(=S)N(R^D)_2$, $C(=O)OR^A$, phenyl unsubstituted or substituted with up to 5 $R^E$;

a 3-, 4-, 5-, 6- or 7-membered saturated, partially unsaturated or aromatic heterocyclic ring containing 1, 2 or 3 heteroatoms or heteroatom groups selected from N, O, S, NO, SO, $SO_2$, wherein the aforementioned ring is unsubstituted or substituted with up to 5 $R^E$, or two $R^a$ present on one carbon atom are together =O, =C($R^F$)$_2$, =$NR^D$, =$NOR^A$, =$NNR^D$, or two $R^a$ form a 3-, 4-, 5-, 6-, 7- or 8-membered saturated or partially unsaturated carbocyclic or heterocyclic ring together with the carbon atoms the two $R^a$ are bonded to;

each $R^b$ is independently selected from the group consisting of halogen, cyano, azido, nitro, —SCN, $SF_5$, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$ haloalkynyl, $C_1$-$C_6$-alkyl-$C_3$-$C_8$-cycloalkyl, $Si(R^G)_3$, $OR^H$, $SR^H$, $OSO_2R^J$, $S(O)_xR^J$, —$S(O)_xN(R^K)_2$, $N(R^K)_2$, $C(=O)N(R^K)_2$, $C(=S)N(R^K)_2$, $C(=O)OR^H$, or two $R^b$ present on one carbon atom are together =O, =C($R^L$)$_2$, =$NR^K$, =$NOR^H$, =$NNR^K$, or two $R^b$ form a 3-, 4-, 5-, 6-, 7- or 8-membered saturated or partially unsaturated carbocyclic or heterocyclic ring together with the carbon atoms the two $R^b$ are bonded to;

each $R^c$ is independently selected from the group consisting of halogen, cyano, azido, nitro, —SCN, $SF_5$, $C_1$-$C_6$-alkyl, $C_2$-$C_6$-alkenyl, $C_2$-$C_6$-alkynyl, $C_3$-$C_8$-cycloalkyl, wherein the carbon atoms of the aforementioned aliphatic or cycloaliphatic radicals are unsubstituted or substituted with one or more $R^M$;
$Si(R^G)_3$, $OR^H$, $SR^H$, $OS(O)_xR^J$, $S(O)_xR^J$, $-S(O)_xN(R^K)_2$, $N(R^K)_2$, $C(=O)R^N$, $C(=O)OR^H$, $C(=NR^K)R^N$, $C(=O)N(R^K)_2$, $C(=S)N(R^K)_2$;

each $R^d$ is independently selected from the group consisting of halogen, cyano, azido, nitro, —SCN, $SF_5$, $C_1$-$C_6$-alkyl, $C_2$-$C_6$-alkenyl, $C_2$-$C_6$-alkynyl, $C_3$-$C_8$-cycloalkyl, wherein the carbon atoms of the aforementioned aliphatic or cycloaliphatic radicals are unsubstituted or substituted with one or more $R^M$;
$Si(R^G)_3$, $OR^H$, $SR^H$, $OS(O)_xR^J$, $S(O)_xR^J$, $-S(O)_xN(R^K)_2$, $N(R^K)_2$, $C(=O)R^N$, $C(=O)OR^H$, $C(=NR^K)R^N$, $C(=O)N(R^K)_2$, $C(=S)N(R^K)_2$,
or
two $R^d$ present on one atom of a saturated or partially unsaturated heterocyclic ring are together =O, $=C(R^L)_2$; $=NR^K$, $=NOR^H$ or $=NNR^K$;

each $R^e$ is independently selected from the group consisting of halogen, $C_1$-$C_6$ alkyl, $C_1$-$C_6$ haloalkyl, $C_1$-$C_6$ alkoxyalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_8$ cycloalkyl, $C_3$-$C_8$ halocycloalkyl, $C_1$-$C_6$ haloalkoxyalkyl, phenyl, a 3-, 4-, 5-, 6- or 7-membered saturated, partially unsaturated or aromatic heterocyclic ring containing 1, 2 or 3 heteroatoms or heteroatom groups selected from N, O, S, NO, SO, $SO_2$, each $R^f$ is independently selected from the group consisting of hydrogen, cyano, $C_1$-$C_6$-alkyl, $C_1$-$C_6$-alkylsulfinyl, $C_1$-$C_6$-alkylsulfonyl, $C_3$-$C_8$-cycloalkyl, $C_2$-$C_6$-alkenyl, $C_2$-$C_6$-alkynyl, wherein the carbon atoms of the aforementioned aliphatic or cycloaliphatic radicals are unsubstituted or substituted with one or more $R^M$;
$Si(R^e)_3$, $S(O)_xR^B$, $-S(O)_xN(R^D)_2$, $N(R^D)_2$, $-N=C(R^F)_2$, $C(=O)R^Q$, $C(=O)N(R^D)_2$, $C(=S)N(R^D)_2$, $C(=O)OR^A$,
phenyl, a 3-, 4-, 5-, 6- or 7-membered saturated, partially unsaturated or aromatic heterocyclic ring containing 1, 2 or 3 heteroatoms or heteroatom groups selected from N, O, S, NO, SO, $SO_2$;

each $R^h$ is independently selected from the group consisting of hydrogen, cyano, $C_1$-$C_6$-alkyl, $C_1$-$C_6$-alkoxy, $C_1$-$C_6$-alkylthio, $C_3$-$C_8$-cycloalkyl, $C_2$-$C_6$-alkenyl, $C_2$-$C_6$-alkynyl, wherein the carbon atoms of the aforementioned aliphatic or cycloaliphatic radicals are unsubstituted or substituted with one or more $R^M$;
$N(R^D)_2$, $-N=C(R^F)_2$, $C(=O)R^Q$, $C(=O)N(R^D)_2$, $C(=S)N(R^D)_2$, $C(=O)OR^A$,
phenyl, a 3-, 4-, 5-, 6- or 7-membered saturated, partially unsaturated or aromatic heterocyclic ring containing 1, 2 or 3 heteroatoms or heteroatom groups selected from N, O, S, NO, SO, $SO_2$;

each $R^i$ is independently selected from the group consisting of hydrogen, $C_1$-$C_6$-alkyl, $C_1$-$C_6$-alkoxy, $C_1$-$C_6$-alkylthio, $C_3$-$C_8$-cycloalkyl, $C_2$-$C_6$-alkenyl, $C_2$-$C_6$-alkynyl, wherein the carbon atoms of the aforementioned aliphatic or cycloaliphatic radicals are unsubstituted or substituted with one or more $R^M$;
$S(O)_xR^B$, $-S(O)_xN(R^D)_2$, $C(=O)R^S$, $C(=O)OR^A$, $C(=O)N(R^D)_2$, $C(=S)R^S$, $C(=S)SR^A$, $C(=S)N(R^D)_2$, $C(=NR^D)R^S$,
phenyl unsubstituted or substituted with up to 5 $R^E$;
a 3-, 4-, 5-, 6- or 7-membered saturated, partially unsaturated or aromatic heterocyclic ring containing 1, 2 or 3 heteroatoms or heteroatom groups selected from N, O, S, NO, SO, $SO_2$, wherein the aforementioned ring is unsubstituted or substituted with up to 5 $R^E$, or
two $R^i$ on one nitrogen atom are together a $C_2$-$C_7$ alkylene chain and form together with the nitrogen atom they are bonded to a 3-, 4-, 5-, 6-, 7- or 8-membered saturated, partially unsaturated or aromatic ring, wherein the alkylene chain may contain 1 or 2 heteroatoms or heteroatom groups selected from N, O, S, NO, SO, $SO_2$, and wherein the alkylene chain is unsubstituted or substituted with halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_2$-$C_6$-alkenyl, $C_2$-$C_6$-haloalkenyl, $C_2$-$C_6$-alkynyl, $C_2$-$C_6$-haloalkynyl;

each $R^m$ is independently selected from the group consisting of hydrogen, —SCN, $SF_5$, $C_1$-$C_6$-alkyl, $C_1$-$C_6$-alkoxy, $C_1$-$C_6$-alkylthio, $C_3$-$C_8$-cycloalkyl, $C_2$-$C_6$-alkenyl, $C_2$-$C_6$-alkynyl, wherein the carbon atoms of the aforementioned aliphatic or cycloaliphatic radicals are unsubstituted or substituted with one or more $R^M$;
$Si(R^e)_3$, $OR^A$, $SR^A$, $OSO_2R^B$, $N(R^D)_2$, $C(=O)N(R^D)_2$, $C(=S)N(R^D)_2$, $C(=O)OR^A$,
phenyl unsubstituted or substituted with up to 5 $R^E$;
a 3-, 4-, 5-, 6- or 7-membered saturated, partially unsaturated or aromatic heterocyclic ring containing 1, 2 or 3 heteroatoms or heteroatom groups selected from N, O, S, NO, SO, $SO_2$, wherein the aforementioned ring is unsubstituted or substituted with up to 5 $R^E$;

each $R^A$ is independently selected from the group consisting of hydrogen, cyano, $C_1$-$C_6$-alkylsulfinyl, $C_1$-$C_6$-alkylsulfonyl, trimethylsilyl, triethylsilyl, tert-butyldimethylsilyl,
$C_1$-$C_6$-alkyl, $C_2$-$C_6$-alkenyl, $C_2$-$C_6$-alkynyl, $C_3$-$C_8$-cycloalkyl, wherein the four last mentioned radicals are unsubstituted, partially or fully halogenated and/or oxygenated and/or carry 1 or 2 radicals selected from $C_1$-$C_4$ alkoxy;
phenyl, benzyl, pyridyl, phenoxy, wherein the four last mentioned radicals are unsubstituted, partially or fully halogenated and/or carry 1, 2 or 3 substituents selected from $C_1$-$C_6$-alkyl, $C_1$-$C_6$-haloalkyl, $C_1$-$C_6$-alkoxy, $C_1$-$C_6$ haloalkoxy and $(C_1$-$C_6$-alkoxy)carbonyl;

each $R^B$ is independently selected from the group consisting of hydrogen, cyano, $C_1$-$C_6$-alkoxy, $C_1$-$C_6$-haloalkoxy, $C_1$-$C_6$-alkylthio, $C_1$-$C_6$-haloalkylthio, trimethylsilyl, triethylsilyl, tert-butyldimethylsilyl, $C_1$-$C_6$-alkyl, $C_2$-$C_6$-alkenyl, $C_2$-$C_6$-alkynyl, $C_3$-$C_8$-cycloalkyl, wherein the four last mentioned radicals are unsubstituted, partially or fully halogenated and/or oxygenated and/or carry 1 or 2 radicals selected from $C_1$-$C_4$ alkoxy;
phenyl, benzyl, pyridyl, phenoxy, wherein the four last mentioned radicals are unsubstituted, partially or fully halogenated and/or carry 1, 2 or 3 substituents selected from $C_1$-$C_6$-alkyl, $C_1$-$C_6$-haloalkyl, $C_1$-$C_6$-alkoxy, $C_1$-$C_6$ haloalkoxy and $(C_1$-$C_6$-alkoxy)carbonyl;

each $R^D$ is independently selected from the group consisting of hydrogen, cyano, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, trimethylsilyl, triethylsilyl, tert-butyldimethylsilyl,
$C_1$-$C_6$-alkyl, $C_2$-$C_6$-alkenyl, $C_2$-$C_6$-alkynyl, $C_3$-$C_8$-cycloalkyl, wherein the four last mentioned radicals are unsubstituted, partially or fully halogenated and/or oxygenated and/or carry 1 or 2 radicals selected from $C_1$-$C_4$-alkoxy;
phenyl, benzyl, pyridyl, phenoxy, wherein the four last mentioned radicals are unsubstituted, partially or fully halogenated and/or carry 1, 2 or 3 substituents selected from $C_1$-$C_6$-alkyl, $C_1$-$C_6$-haloalkyl, $C_1$-$C_6$-alkoxy, $C_1$-$C_6$ haloalkoxy and ($C_1$-$C_6$-alkoxy)carbonyl, or two $R^D$ on one nitrogen atom are together a $C_2$-$C_6$ alkylene chain and form together with the nitrogen atom they are bonded to a 3-, 4-, 5-, 6-, or 7-membered saturated, partially unsaturated or aromatic ring, wherein the alkylene chain may contain 1 or 2 heteroatoms or heteroatom groups selected from N, O, S, NO, SO, $SO_2$, and wherein the alkylene chain is unsubstituted or substituted with halogen, $C_1$-$C_4$-haloalkyl, $C_1$-$C_4$-alkoxy or $C_1$-$C_4$-haloalkoxy;

each $R^E$ is independently selected from the group consisting of cyano, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, trimethylsilyl, triethylsilyl, tert-butyldimethylsilyl, $C_1$-$C_6$-alkyl, $C_2$-$C_6$-alkenyl, $C_2$-$C_6$-alkynyl, wherein the four last mentioned radicals are unsubstituted, partially or fully halogenated and/or oxygenated and/or carry 1 or 2 radicals selected from $C_1$-$C_4$-alkoxy, or two $R^E$ present on one atom of a saturated or partially unsaturated heterocyclic ring are together =O, =N($C_1$-$C_6$-alkyl), =NO($C_1$-$C_6$-alkyl), =CH($C_1$-$C_4$-alkyl) or =C($C_1$-$C_4$-alkyl)$C_1$-$C_4$-alkyl;

each $R^F$ is independently selected from the group consisting of $C_1$-$C_4$ alkyl, $C_1$-$C_6$ cycloalkyl, $C_1$-$C_4$ alkoxyalkyl, phenyl and benzyl;

each $R^G$ is independently selected from the group consisting of halogen, $C_1$-$C_6$ alkyl, $C_1$-$C_6$ haloalkyl, $C_1$-$C_6$ alkoxyalkyl, $C_2$-$C_6$ alkenyl, $C_2$-$C_6$ haloalkenyl, $C_2$-$C_6$ alkynyl, $C_2$-$C_6$ haloalkynyl, $C_1$-$C_6$ haloalkoxyalkyl;

each $R^H$ is independently selected from the group consisting of hydrogen, cyano, $C_1$-$C_6$-alkylsulfinyl, $C_1$-$C_6$-alkylsulfonyl, trimethylsilyl, trimethylsilyl, tert-butyldimethylsilyl, $C_1$-$C_6$-alkyl, $C_2$-$C_6$-alkenyl, $C_2$-$C_6$-alkynyl, wherein the three last mentioned radicals are unsubstituted, partially or fully halogenated and/or oxygenated and/or carry 1 or 2 radicals selected from $C_1$-$C_4$ alkoxy;

each $R^J$ is independently selected from the group consisting of hydrogen, cyano, $C_1$-$C_6$-alkoxy, $C_1$-$C_6$-haloalkoxy, $C_1$-$C_6$-alkylthio, $C_1$-$C_6$-haloalkylthio, trimethylsilyl, triethylsilyl, tert-butyldimethylsilyl, $C_1$-$C_6$-alkyl, $C_2$-$C_6$-alkenyl, $C_2$-$C_6$-alkynyl, wherein the three last mentioned radicals are unsubstituted, partially or fully halogenated and/or oxygenated and/or carry 1 or 2 radicals selected from $C_1$-$C_4$ alkoxy;

each $R^K$ is independently selected from the group consisting of hydrogen, cyano, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, trimethylsilyl, triethylsilyl, tert-butyldimethylsilyl, $C_1$-$C_6$-alkyl, $C_2$-$C_6$-alkenyl, $C_2$-$C_6$-alkynyl, wherein the three last mentioned radicals are unsubstituted, partially or fully halogenated and/or oxygenated and/or carry 1 or 2 radicals selected from $C_1$-$C_4$-alkoxy;

each $R^L$ is independently selected from the group consisting of $C_1$-$C_4$ alkyl and $C_1$-$C_4$ alkoxyalkyl;

each $R^M$ is independently selected from the group consisting of halogen, cyano, azido, nitro, OH, SH, —SCN, $SF_5$, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, trimethylsilyl, triethylsilyl, tert-butyldimethylsilyl, $C_1$-$C_6$-alkyl, $C_2$-$C_6$-alkenyl, $C_2$-$C_6$-alkynyl, $C_3$-$C_8$-cycloalkyl, $C_1$-$C_6$-alkyl-$C_3$-$C_8$-cycloalkyl, wherein the five last mentioned radicals are unsubstituted, partially or fully halogenated and/or oxygenated and/or carry 1 or 2 radicals selected from $C_1$-$C_4$ alkoxy, or two $R^M$ present on one carbon atom are together =O, =CH($C_1$-$C_4$-alkyl), =C($C_1$-$C_4$-alkyl)$C_1$-$C_4$-alkyl, =N($C_1$-$C_6$-alkyl) or =NO($C_1$-$C_6$-alkyl);

each $R^N$ is independently selected from the group consisting of hydrogen, OH, SH, —SCN, $SF_5$, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, trimethylsilyl, triethylsilyl, tert-butyldimethylsilyl, $C_1$-$C_6$-alkyl, $C_2$-$C_6$-alkenyl, $C_2$-$C_6$-alkynyl, wherein the three last mentioned radicals are unsubstituted, partially or fully halogenated and/or oxygenated and/or carry 1 or 2 radicals selected from $C_1$-$C_4$ alkoxy;

each $R^Q$ is independently selected from the group consisting of hydrogen, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, trimethylsilyl, triethylsilyl, tert-butyldimethylsilyl, $C_1$-$C_6$-alkyl, $C_2$-$C_6$-alkenyl, $C_2$-$C_6$-alkynyl, $C_3$-$C_8$-cycloalkyl, wherein the four last mentioned radicals are unsubstituted, partially or fully halogenated and/or oxygenated and/or carry 1 or 2 radicals selected from $C_1$-$C_4$ alkoxy;

phenyl, benzyl, pyridyl, phenoxy, wherein the four last mentioned radicals are unsubstituted, partially or fully halogenated and/or carry 1, 2 or 3 substituents selected from $C_1$-$C_6$-alkyl, $C_1$-$C_6$-haloalkyl, $C_1$-$C_6$-alkoxy, $C_1$-$C_6$ haloalkoxy and ($C_1$-$C_6$-alkoxy)carbonyl;

each $R^S$ is independently selected from the group consisting of hydrogen, OH, SH, —SCN, $SF_5$, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, trimethylsilyl, triethylsilyl, tert-butyldimethylsilyl, $C_1$-$C_6$-alkyl, $C_2$-$C_6$-alkenyl, $C_2$-$C_6$-alkynyl, $C_3$-$C_8$-cycloalkyl, wherein the four last mentioned radicals are unsubstituted, partially or fully halogenated and/or oxygenated and/or carry 1 or 2 radicals selected from $C_1$-$C_4$ alkoxy;

phenyl, benzyl, pyridyl, phenoxy, wherein the four last mentioned radicals are unsubstituted, partially or fully halogenated and/or carry 1, 2 or 3 substituents selected from $C_1$-$C_6$-alkyl, $C_1$-$C_6$-haloalkyl, $C_1$-$C_6$-alkoxy, $C_1$-$C_6$ haloalkoxy, ($C_1$-$C_6$-alkoxy)carbonyl, ($C_1$-$C_6$-alkyl)amino and di-($C_1$-$C_6$-alkyl)amino;

p is 0 or 1;

x is 1 or 2;

or a salt thereof.

22. A method for protecting seeds from soil insects and the seedlings' roots and shoots from soil and foliar insects, which comprises contacting the seeds before sowing and/or after pregermination with at least one compound of formula (I)

wherein
Y is phenyl unsubstituted or substituted with 1, 2, 3, 4 or 5 substituents $R^5$; or naphthyl unsubstituted or substituted with 1, 2, 3, 4, 5, 6 or 7 substituents $R^5$;

Q is phenyl unsubstituted or substituted with 1, 2, 3, 4 or 5 substituents $R^6$; $C_3$-$C_8$ cycloalkyl unsubstituted or substituted with one or more substituents $R^6$; $C_3$-$C_8$ cycloalkenyl unsubstituted or substituted with one or more substituents $R^6$; or a 6-membered aromatic heterocyclic ring containing 1, 2, 3 or 4 nitrogen atoms in the ring, wherein the aforementioned ring is unsubstituted or substituted with 1, 2, 3 or 4 substituents $R^6$;

$R^1$ is selected from the group consisting of hydrogen, halogen, cyano, hydroxy, $C_1$-$C_6$-alkyl, $C_2$-$C_6$-alkenyl, $C_2$-$C_6$-alkynyl, $C_3$-$C_8$-cycloalkyl, $C_3$-$C_8$-cycloalkenyl, $C_1$-$C_6$-alkoxy, $C_2$-$C_6$-alkenyloxy, $C_1$-$C_6$-alkylthio, ($C_1$-$C_6$-alkoxy)carbonyl, wherein the carbon atoms of the aforementioned aliphatic or cycloaliphatic radicals are unsubstituted or substituted with 1, 2 or 3 substituents $R^7$;

$R^2$ is hydrogen or halogen;

or $R^1$ and $R^2$ form together with the carbon atom to which they are attached a methylene group or a cyclopropyl group;

$R^3$ is selected from the group consisting of hydrogen, halogen, cyano, hydroxy, $C_1$-$C_6$-alkyl, $C_2$-$C_6$-alkenyl, $C_2$-$C_6$-alkynyl, $C_3$-$C_8$-cycloalkyl, $C_3$-$C_8$-cycloalkenyl, $C_1$-$C_6$-alkoxy, $C_2$-$C_6$-alkenyloxy, $C_1$-$C_6$-alkylthio, ($C_1$-$C_6$-alkoxy)carbonyl, wherein the carbon atoms of the aforementioned aliphatic or cycloaliphatic radicals are unsubstituted or substituted with 1, 2 or 3 substituents $R^7$;

$R^4$ is hydrogen or halogen;

or $R^3$ and $R^4$ form together with the carbon atom to which they are attached a methylene group or a cyclopropyl group;

each $R^5$, $R^6$ is independently selected from the group consisting of halogen, cyano, azido, nitro, —SCN, $SF_5$, $C_1$-$C_6$ alkyl, $C_2$-$C_6$ alkenyl, $C_2$-$C_6$ alkynyl, wherein the carbon atoms of the aforementioned aliphatic radicals are unsubstituted or substituted with one or more $R^a$;

$C_3$-$C_8$ cycloalkyl or $C_3$-$C_8$ cycloalkenyl, wherein the carbon atoms of the aforementioned cycloaliphatic radicals are unsubstituted or substituted with one or more $R^b$;

phenyl unsubstituted or substituted with up to 5 $R^c$;

a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO, $SO_2$, wherein the aforementioned ring is unsubstituted or substituted with up to 5 $R^d$;

$Si(R^e)_3$, $OR^f$, $SR^f$, $OS(O)_xR^h$, $S(O)_xR^h$, $N(R^i)_2$, $N(R^i)C(=O)R^m$, $OC(=O)R^m$, $C(=O)R^m$, $C(=O)OR^f$, $C(=NR^i)R^m$, $C(=S)R^m$;

or two $R^5$ on two adjacent carbon atoms present on one phenyl ring are together a bridge selected from the group consisting of $CH_2CH_2CH_2CH_2$, N=CH—CH=CH, CH=N—CH=CH, N=CH—N=CH, N=CH—CH=N, $OCH_2CH_2CH_2$, $OCH=CHCH_2$, $CH_2OCH_2CH_2$, $OCH_2CH_2O$, $OCH_2OCH_2$, $CH_2CH_2CH_2O$, CH=CHCH_2O, $CH_2CH_2O$, CH=CHO, $CH_2OCH_2$, $CH_2C(=O)O$, $C(=O)OCH_2$, $O(CH_2)O$, $SCH_2CH_2CH_2$, SCH=CHCH_2, $CH_2SCH_2CH_2$, $SCH_2CH_2S$, $SCH_2SCH_2$, $CH_2CH_2S$, CH=CHS, $CH_2SCH_2$, $CH_2C(=S)S$, $C(=S)SCH_2$, $S(CH_2)S$, $CH_2CH_2NR^K$, $CH_2CH=N$, CH=CH—$NR^K$, OCH=N, SCH=N and form together with the carbon atoms the two $R^5$ are bonded to a 5- or 6-membered partially unsaturated or aromatic carbocyclic or heterocyclic ring, wherein the ring is unsubstituted or substituted with 1 or 2 substituents selected from the group consisting of =O, OH, $CH_3$, $OCH_3$, halogen, halomethyl and halomethoxy;

each $R^7$ is independently selected from the group consisting of halogen, cyano, hydroxy, $C_1$-$C_6$-alkyl, $C_2$-$C_6$-alkenyl, $C_2$-$C_6$-alkynyl, $C_3$-$C_8$-cycloalkyl, $C_3$-$C_8$-cycloalkenyl, $C_1$-$C_6$-alkoxy, $C_2$-$C_6$-alkenyloxy, $C_1$-$C_6$-alkylthio, ($C_1$-$C_6$-alkoxy)carbonyl, $OSi(R^e)_3$, wherein the carbon atoms of the aforementioned aliphatic or cycloaliphatic radicals are unsubstituted, partially or fully halogenated and/or oxygenated;

$R^{aa}$ is —C(=S)N($R^{cc}$)$_2$, —C(=$NR^{dd}$)$SR^{ee}$, or —C(=O)N($R^{ff}$)$_2$;

$R^{bb}$ is —C(=S)N($R^{cc}$)$_2$, —C(=$NR^{dd}$)$SR^{ee}$, —C(=O)N($R^{ff}$)$_2$, or CN;

each $R^{cc}$ is independently selected from the group consisting of hydrogen, cyano, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_6$-cycloalkyl, $C_3$-$C_6$-halocycloalkyl, $C_1$-$C_6$-alkoxy-$C_1$-$C_6$-alkyl, $C_1$-$C_6$-haloalkoxy-$C_1$-$C_6$-alkyl, $C_1$-$C_6$-alkylthio-$C_1$-$C_6$-alkyl, $C_1$-$C_6$-haloalkylthio-$C_1$-$C_6$-alkyl;

each $R^{dd}$ is independently selected from the group consisting of hydrogen, cyano, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_6$-cycloalkyl, $C_3$-$C_6$-halocycloalkyl, $C_1$-$C_6$-alkoxy-$C_1$-$C_6$-alkyl, $C_1$-$C_6$-haloalkoxy-$C_1$-$C_6$-alkyl, $C_1$-$C_6$-alkylthio-$C_1$-$C_6$-alkyl, $C_1$-$C_6$-haloalkylthio-$C_1$-$C_6$-alkyl;

each $R^{ee}$ is independently selected from the group consisting of cyano, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_6$-cycloalkyl, $C_3$-$C_6$-halocycloalkyl, $C_1$-$C_6$-alkoxy-$C_1$-$C_6$-alkyl, $C_1$-$C_6$-haloalkoxy-$C_1$-$C_6$-alkyl, $C_1$-$C_6$-alkylthio-$C_1$-$C_6$-alkyl, $C_1$-$C_6$-haloalkylthio-$C_1$-$C_6$-alkyl;

each $R^{ff}$ is independently selected from the group consisting of hydrogen, cyano, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_6$-cycloalkyl, $C_3$-$C_6$-halocycloalkyl, $C_1$-$C_6$-alkoxy-$C_1$-$C_6$-alkyl, $C_1$-$C_6$-haloalkoxy-$C_1$-$C_6$-alkyl, $C_1$-$C_6$-alkylthio-$C_1$-$C_6$-alkyl, $C_1$-$C_6$-haloalkylthio-$C_1$-$C_6$-alkyl;

each $R^a$ is independently selected from the group consisting of halogen, cyano, azido, nitro, —SCN, $SF_5$, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$ haloalkynyl, $C_1$-$C_6$-alkyl-$C_3$-$C_8$-cycloalkyl, $Si(R^e)_3$, $OR^A$, $SR^A$, $OSO_2R^B$, $S(O)_xR^B$, —$S(O)_xN(R^D)_2$, $N(R^D)_2$, $C(=O)N(R^D)_2$, $C(=S)N(R^D)_2$, $C(=O)OR^A$, phenyl unsubstituted or substituted with up to 5 $R^E$;

a 3-, 4-, 5-, 6- or 7-membered saturated, partially unsaturated or aromatic heterocyclic ring containing 1, 2 or 3 heteroatoms or heteroatom groups selected from N, O, S, NO, SO, $SO_2$, wherein the aforementioned ring is unsubstituted or substituted with up to 5 $R^E$, or two $R^a$ present on one carbon atom are together =O, =C($R^F$)$_2$, =N$R^D$, =NO$R^A$, =NN$R^D$, or two $R^a$ form a 3-, 4-, 5-, 6-, 7- or 8-membered saturated or partially unsaturated carbocyclic or heterocyclic ring together with the carbon atoms the two $R^a$ are bonded to;

each $R^b$ is independently selected from the group consisting of halogen, cyano, azido, nitro, —SCN, SF$_5$, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$ haloalkynyl, $C_1$-$C_6$-alkyl-$C_3$-$C_8$-cycloalkyl, Si($R^G$)$_3$, O$R^H$, S$R^H$, OSO$_2R^J$, S(O)$_xR^J$, —S(O)$_x$N($R^K$)$_2$, N($R^K$)$_2$, C(=O)N($R^K$)$_2$, C(=S)N($R^K$)$_2$, C(=O)O$R^H$, or two $R^b$ present on one carbon atom are together =O, =C($R^L$)$_2$, =N$R^K$, =NO$R^H$, =NN$R^K$, or two $R^b$ form a 3-, 4-, 5-, 6-, 7- or 8-membered saturated or partially unsaturated carbocyclic or heterocyclic ring together with the carbon atoms the two $R^b$ are bonded to;

each $R^c$ is independently selected from the group consisting of halogen, cyano, azido, nitro, —SCN, SF$_5$, $C_1$-$C_6$-alkyl, $C_2$-$C_6$-alkenyl, $C_2$-$C_6$-alkynyl, $C_3$-$C_8$-cycloalkyl, wherein the carbon atoms of the aforementioned aliphatic or cycloaliphatic radicals are unsubstituted or substituted with one or more $R^M$;

Si($R^G$)$_3$, O$R^H$, S$R^H$, OS(O)$_xR^J$, S(O)$_xR^J$, —S(O)$_x$N($R^K$)$_2$, N($R^K$)$_2$, C(=O)$R^N$, C(=O)O$R^H$, C(=N$R^K$)$R^N$, C(=O)N($R^K$)$_2$, C(=SN($R^K$)$_2$;

each $R^d$ is independently selected from the group consisting of halogen, cyano, azido, nitro, —SCN, SF$_5$, $C_1$-$C_6$-alkyl, $C_2$-$C_6$-alkenyl, $C_2$-$C_6$-alkynyl, $C_3$-$C_8$-cycloalkyl, wherein the carbon atoms of the aforementioned aliphatic or cycloaliphatic radicals are unsubstituted or substituted with one or more $R^M$;

Si($R^G$)$_3$, O$R^H$, S$R^H$, OS(O)$_xR^J$, S(O)$_xR^J$, —S(O)$_x$N($R^K$)$_2$, N($R^K$)$_2$, C(=O)$R^N$, C(=O)O$R^H$, C(=N$R^K$)$R^N$, C(=O)N($R^K$)$_2$, C(=S)N($R^K$)$_2$, or two $R^d$ present on one atom of a saturated or partially unsaturated heterocyclic ring are together =O, =C($R^L$)$_2$; =N$R^K$, =NO$R^H$ or =NN$R^K$;

each $R^e$ is independently selected from the group consisting of halogen, $C_1$-$C_6$ alkyl, $C_1$-$C_6$ haloalkyl, $C_1$-$C_6$ alkoxyalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_8$ cycloalkyl, $C_3$-$C_8$ halocycloalkyl, $C_1$-$C_6$ haloalkoxyalkyl, phenyl, a 3-, 4-, 5-, 6- or 7-membered saturated, partially unsaturated or aromatic heterocyclic ring containing 1, 2 or 3 heteroatoms or heteroatom groups selected from N, O, S, NO, SO, SO$_2$;

each $R^f$ is independently selected from the group consisting of hydrogen, cyano, $C_1$-$C_6$-alkyl, $C_1$-$C_6$-alkylsulfinyl, $C_1$-$C_6$-alkylsulfonyl, $C_3$-$C_8$-cycloalkyl, $C_2$-$C_6$-alkenyl, $C_2$-$C_6$-alkynyl, wherein the carbon atoms of the aforementioned aliphatic or cycloaliphatic radicals are unsubstituted or substituted with one or more $R^M$;

Si($R^e$)$_3$, S(O)$_xR^B$, —S(O)$_x$N($R^D$)$_2$, N($R^D$)$_2$, —N=C($R^F$)$_2$, C(=O)$R^Q$, C(=O)N($R^D$)$_2$, C(=S)N($R^D$)$_2$, C(=O)O$R^A$, phenyl, a 3-, 4-, 5-, 6- or 7-membered saturated, partially unsaturated or aromatic heterocyclic ring containing 1, 2 or 3 heteroatoms or heteroatom groups selected from N, O, S, NO, SO, SO$_2$;

each $R^h$ is independently selected from the group consisting of hydrogen, cyano, $C_1$-$C_6$-alkyl, $C_1$-$C_6$-alkoxy, $C_1C_6$-alkylthio, $C_3$-$C_8$-cycloalkyl, $C_2$-$C_6$-alkenyl, $C_2$-$C_6$-alkynyl, wherein the carbon atoms of the aforementioned aliphatic or cycloaliphatic radicals are unsubstituted or substituted with one or more $R^M$;

N($R^D$)$_2$, —N=C($R^F$)$_2$, C(=O)$R^Q$, C(=O)N($R^D$)$_2$, C(=S)N($R^D$)$_2$, C(=O)O$R^A$, phenyl, a 3-, 4-, 5-, 6- or 7-membered saturated, partially unsaturated or aromatic heterocyclic ring containing 1, 2 or 3 heteroatoms or heteroatom groups selected from N, O, S, NO, SO, SO$_2$;

each $R^i$ is independently selected from the group consisting of hydrogen, $C_1C_6$-alkyl, $C_1$-$C_6$-alkoxy, $C_1C_6$-alkylthio, $C_3$-$C_8$-cycloalkyl, $C_2$-$C_6$-alkenyl, $C_2$-$C_6$-alkynyl, wherein the carbon atoms of the aforementioned aliphatic or cycloaliphatic radicals are unsubstituted or substituted with one or more $R^M$;

S(O)$_xR^B$, —S(O)$_x$N($R^D$)$_2$, C(=O)$R^S$, C(=O)O$R^A$, C(=O)N($R^D$)$_2$, C(=S)$R^S$, C(=S)S$R^A$, C(=S)N($R^D$)$_2$, C(=N$R^D$)$R^S$, phenyl unsubstituted or substituted with up to 5 $R^E$;

a 3-, 4-, 5-, 6- or 7-membered saturated, partially unsaturated or aromatic heterocyclic ring containing 1, 2 or 3 heteroatoms or heteroatom groups selected from N, O, S, NO, SO, SO$_2$, wherein the aforementioned ring is unsubstituted or substituted with up to 5 $R^E$;

or two $R^i$ on one nitrogen atom are together a $C_2$-$C_7$ alkylene chain and form together with the nitrogen atom they are bonded to a 3-, 4-, 5-, 6-, 7- or 8-membered saturated, partially unsaturated or aromatic ring, wherein the alkylene chain may contain 1 or 2 heteroatoms or heteroatom groups selected from N, O, S, NO, SO, SO$_2$, and wherein the alkylene chain is unsubstituted or substituted with halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_2$-$C_6$-alkenyl, $C_2$-$C_6$-haloalkenyl, $C_2$-$C_6$-alkynyl, $C_2$-$C_6$-haloalkynyl;

each $R^m$ is independently selected from the group consisting of hydrogen, —SCN, SF$_5$, $C_1$-$C_6$-alkyl, $C_1$-$C_6$-alkoxy, $C_1$-$C_6$-alkylthio, $C_3$-$C_8$-cycloalkyl, $C_2$-$C_6$-alkenyl, $C_2$-$C_6$-alkynyl, wherein the carbon atoms of the aforementioned aliphatic or cycloaliphatic radicals are unsubstituted or substituted with one or more $R^M$;

Si($R^e$)$_3$, O$R^A$, S$R^A$, OSO$_2R^B$, N($R^D$)$_2$, C(=O)N($R^D$)$_2$, C(=S)N($R^D$)$_2$, C(=O)O$R^A$, phenyl unsubstituted or substituted with up to 5 $R^E$;

a 3-, 4-, 5-, 6- or 7-membered saturated, partially unsaturated or aromatic heterocyclic ring containing 1, 2 or 3 heteroatoms or heteroatom groups selected from N, O, S, NO, SO, SO$_2$, wherein the aforementioned ring is unsubstituted or substituted with up to 5 $R^E$;

each $R^A$ is independently selected from the group consisting of hydrogen, cyano, $C_1$-$C_6$-alkylsulfinyl, $C_1$-$C_6$-alkylsulfonyl, trimethylsilyl, triethylsilyl, tert-butyldimethylsilyl, $C_1$-$C_6$-alkyl, $C_2$-$C_6$-alkenyl, $C_2$-$C_6$-alkynyl, $C_3$-$C_8$-cycloalkyl, wherein the four last mentioned radicals are unsubstituted, partially or fully halogenated and/or oxygenated and/or carry 1 or 2 radicals selected from $C_1$-$C_4$ alkoxy;

phenyl, benzyl, pyridyl, phenoxy, wherein the four last mentioned radicals are unsubstituted, partially or fully halogenated and/or carry 1, 2 or 3 substituents selected from $C_1$-$C_6$-alkyl, $C_1$-$C_6$-haloalkyl, $C_1$-$C_6$-alkoxy, $C_1$-$C_6$ haloalkoxy and ($C_1$-$C_6$-alkoxy)carbonyl;

each $R^B$ is independently selected from the group consisting of hydrogen, cyano, $C_1$-$C_6$-alkoxy, $C_1$-$C_6$-haloalkoxy, $C_1$-$C_6$-alkylthio, $C_1$-$C_6$-haloalkylthio, trimethylsilyl, triethylsilyl, tert-butyldimethylsilyl, $C_1$-$C_6$-alkyl, $C_2$-$C_6$-alkenyl, $C_2$-$C_6$-alkynyl, $C_3$-$C_8$-cycloalkyl, wherein the four last mentioned radicals are unsubstituted, partially or fully halogenated and/or oxygenated and/or carry 1 or 2 radicals selected from $C_1$-$C_4$ alkoxy;

phenyl, benzyl, pyridyl, phenoxy, wherein the four last mentioned radicals are unsubstituted, partially or fully halogenated and/or carry 1, 2 or 3 substituents selected from $C_1$-$C_6$-alkyl, $C_1$-$C_6$-haloalkyl, $C_1$-$C_6$-alkoxy, $C_1$-$C_6$ haloalkoxy and ($C_1$-$C_6$-alkoxy)carbonyl;

each $R^D$ is independently selected from the group consisting of hydrogen, cyano, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, trimethylsilyl, triethylsilyl, tert-butyldimethylsilyl, $C_1$-$C_6$-alkyl, $C_2$-$C_6$-alkenyl, $C_2$-$C_6$-alkynyl, $C_3$-$C_8$-cycloalkyl, wherein the four last mentioned radicals are unsubstituted, partially or fully halogenated and/or oxygenated and/or carry 1 or 2 radicals selected from $C_1$-$C_4$-alkoxy;

phenyl, benzyl, pyridyl, phenoxy, wherein the four last mentioned radicals are unsubstituted, partially or fully halogenated and/or carry 1, 2 or 3 substituents selected from $C_1$-$C_6$-alkyl, $C_1$-$C_6$-haloalkyl, $C_1$-$C_6$-alkoxy, $C_1$-$C_6$ haloalkoxy and ($C_1$-$C_6$-alkoxy)carbonyl, or two $R^D$ on one nitrogen atom are together a $C_2$-$C_6$ alkylene chain and form together with the nitrogen atom they are bonded to a 3-, 4-, 5-, 6-, or 7-membered saturated, partially unsaturated or aromatic ring, wherein the alkylene chain may contain 1 or 2 heteroatoms or heteroatom groups selected from N, O, S, NO, SO, $SO_2$, and wherein the alkylene chain is unsubstituted or substituted with halogen, $C_1$-$C_4$-haloalkyl, $C_1$-$C_4$-alkoxy or $C_1$-$C_4$-haloalkoxy;

each $R^E$ is independently selected from the group consisting of cyano, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, trimethylsilyl, triethylsilyl, tert-butyldimethylsilyl, $C_1$-$C_6$-alkyl, $C_2$-$C_6$-alkenyl, $C_2$-$C_6$-alkynyl, wherein the four last mentioned radicals are unsubstituted, partially or fully halogenated and/or oxygenated and/or carry 1 or 2 radicals selected from $C_1$-$C_4$-alkoxy, or two $R^E$ present on one atom of a saturated or partially unsaturated heterocyclic ring are together =O, =N($C_1$-$C_6$-alkyl), =NO($C_1$-$C_6$-alkyl), =CH($C_1$-$C_4$-alkyl) or =C($C_1$-$C_4$-alkyl)$C_1$-$C_4$-alkyl;

each $R^F$ is independently selected from the group consisting of $C_1$-$C_4$ alkyl, $C_1$-$C_6$ cycloalkyl, $C_1$-$C_4$ alkoxyalkyl, phenyl and benzyl;

each $R^G$ is independently selected from the group consisting of halogen, $C_1$-$C_6$ alkyl, $C_1$-$C_6$ haloalkyl, $C_1$-$C_6$ alkoxyalkyl, $C_2$-$C_6$ alkenyl, $C_2$-$C_6$ haloalkenyl, $C_2$-$C_6$ alkynyl, $C_2$-$C_6$ haloalkynyl, $C_1$-$C_6$ haloalkoxyalkyl;

each $R^H$ is independently selected from the group consisting of hydrogen, cyano, $C_1$-$C_6$-alkylsulfinyl, $C_1$-$C_6$-alkylsulfonyl, trimethylsilyl, triethylsilyl, tert-butyldimethylsilyl, $C_1$-$C_6$-alkyl, $C_2$-$C_6$-alkenyl, $C_2$-$C_6$-alkynyl, wherein the three last mentioned radicals are unsubstituted, partially or fully halogenated and/or oxygenated and/or carry 1 or 2 radicals selected from $C_1$-$C_4$ alkoxy;

each $R^J$ is independently selected from the group consisting of hydrogen, cyano, $C_1$-$C_6$-alkoxy, $C_1$-$C_6$-haloalkoxy, $C_1$-$C_6$-alkylthio, $C_1$-$C_6$-haloalkylthio, trimethylsilyl, triethylsilyl, tert-butyldimethylsilyl, $C_1$-$C_6$-alkyl, $C_2$-$C_6$-alkenyl, $C_2$-$C_6$-alkynyl, wherein the three last mentioned radicals are unsubstituted, partially or fully halogenated and/or oxygenated and/or carry 1 or 2 radicals selected from $C_1$-$C_4$ alkoxy;

each $R^K$ is independently selected from the group consisting of hydrogen, cyano, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, trimethylsilyl, triethylsilyl, tert-butyldimethylsilyl, $C_1$-$C_6$-alkyl, $C_2$-$C_6$-alkenyl, $C_2$-$C_6$-alkynyl, wherein the three last mentioned radicals are unsubstituted, partially or fully halogenated and/or oxygenated and/or carry 1 or 2 radicals selected from $C_1$-$C_4$-alkoxy;

each $R^L$ is independently selected from the group consisting of $C_1$-$C_4$ alkyl and $C_1$-$C_4$ alkoxyalkyl;

each $R^M$ is independently selected from the group consisting of halogen, cyano, azido, nitro, OH, SH, —SCN, $SF_5$, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, trimethylsilyl, triethylsilyl, tert-butyldimethylsilyl, $C_1$-$C_6$-alkyl, $C_2$-$C_6$-alkenyl, $C_2$-$C_6$-alkynyl, $C_3$-$C_8$-cycloalkyl, $C_1$-$C_6$-alkyl-$C_3$-$C_8$-cycloalkyl, wherein the five last mentioned radicals are unsubstituted, partially or fully halogenated and/or oxygenated and/or carry 1 or 2 radicals selected from $C_1$-$C_4$ alkoxy, or two $R^M$ present on one carbon atom are together =O, =CH($C_1$-$C_4$-alkyl), =C($C_1$-$C_4$-alkyl)$C_1$-$C_4$-alkyl, =N($C_1$-$C_6$-alkyl) or =NO($C_1$-$C_6$-alkyl);

each $R^N$ is independently selected from the group consisting of hydrogen, OH, SH, —SCN, $SF_5$, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, trimethylsilyl, triethylsilyl, tert-butyldimethylsilyl, $C_1$-$C_6$-alkyl, $C_2$-$C_6$-alkenyl, $C_2$-$C_6$-alkynyl, wherein the three last mentioned radicals are unsubstituted, partially or fully halogenated and/or oxygenated and/or carry 1 or 2 radicals selected from $C_1$-$C_4$ alkoxy;

each $R^Q$ is independently selected from the group consisting of hydrogen, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, trimethylsilyl, triethylsilyl, tert-butyldimethylsilyl, $C_1$-$C_6$-alkyl, $C_2$-$C_6$-alkenyl, $C_2$-$C_6$-alkynyl, $C_3$-$C_8$-cycloalkyl, wherein the four last mentioned radicals are unsubstituted, partially or fully halogenated and/or oxygenated and/or carry 1 or 2 radicals selected from $C_1$-$C_4$ alkoxy;

phenyl, benzyl, pyridyl, phenoxy, wherein the four last mentioned radicals are unsubstituted, partially or fully halogenated and/or carry 1, 2 or 3 substituents selected from $C_1$-$C_6$-alkyl, $C_1$-$C_6$-haloalkyl, $C_1$-$C_6$-alkoxy, $C_1$-$C_6$ haloalkoxy and ($C_1$-$C_6$-alkoxy)carbonyl;

each $R^S$ is independently selected from the group consisting of hydrogen, OH, SH, —SCN, $SF_5$, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, trimethylsilyl, triethylsilyl, tert-butyldimethylsilyl, $C_1$-$C_6$-alkyl, $C_2$-$C_6$-alkenyl, $C_2$-$C_6$-alkynyl, $C_3$-$C_8$-cycloalkyl, wherein the four last mentioned radicals are unsubstituted, partially or fully halogenated and/or oxygenated and/or carry 1 or 2 radicals selected from $C_1$-$C_4$ alkoxy;

phenyl, benzyl, pyridyl, phenoxy, wherein the four last mentioned radicals are unsubstituted, partially or fully halogenated and/or carry 1, 2 or 3 substituents selected from $C_1$-$C_6$-alkyl, $C_1$-$C_6$-haloalkyl, $C_1$-$C_6$-alkoxy, $C_1$-$C_6$ haloalkoxy, ($C_1$-$C_6$-alkoxy)carbonyl, ($C_1$-$C_6$-alkyl)amino and di-($C_1$-$C_6$-alkyl)amino;

p is 0 or 1;

x is 1 or 2; or a salt thereof.

23. The method of claim 21, wherein

Y is phenyl unsubstituted or substituted with 1, 2, 3, 4 or 5 substituents $R^5$; or naphthyl unsubstituted or substituted with 1 or 2 substituents $R^5$;

Q is phenyl unsubstituted or substituted with 1, 2, 3 or 4 substituents $R^6$; cyclohexyl unsubstituted or substituted with 1 or 2 substituents $R^6$; cyclopentyl unsubstituted or substituted with 1 or 2 substituents $R^6$; or a 6-membered aromatic heterocyclic ring containing 1, 2 or 3 nitrogen atoms in the ring, wherein the aforementioned ring is unsubstituted or substituted with 1, 2, 3 or 4 substituents $R^6$;

$R^1$ is selected from the group consisting of H, halogen, cyano, $C_1$-$C_6$-alkyl, $C_2$-$C_6$-alkenyl, $C_2$-$C_6$-alkynyl, $C_3$-$C_6$-cycloalkyl or ($C_1$-$C_6$-alkoxy)carbonyl, wherein the five radicals last mentioned are unsubstituted or substituted with 1, 2 or 3 substituents selected from halogen, cyano, hydroxy, $OSi(C_1$-$C_6$-alkyl)$_3$, $C_1$-$C_6$-alkyl, $C_2$-$C_6$-alkenyl, $C_2$-$C_6$-alkynyl, $C_3$-$C_6$-cycloalkyl, $C_1$-$C_6$-alkoxy and ($C_1$-$C_6$-alkoxy)carbonyl, wherein the six radicals last mentioned are unsubstituted or partially or fully halogenated;

$R^2$ is selected from the group consisting of H and halogen; or $R^1$ and $R^2$ form together with the carbon atom to which they are attached a methylene group;

$R^3$ is selected from the group consisting of H, halogen, cyano, $C_1$-$C_6$-alkyl, $C_2$-$C_6$-alkenyl, $C_2$-$C_6$-alkynyl, $C_3$-$C_6$-cycloalkyl or ($C_1$-$C_6$-alkoxy)carbonyl, wherein the five radicals last mentioned are unsubstituted or substituted with 1, 2 or 3 substituents selected from halogen, cyano, hydroxy, $OSi(C_1$-$C_6$-alkyl)$_3$, $C_1$-$C_6$-alkyl, $C_2$-$C_6$-alkenyl, $C_2$-$C_6$-alkynyl, $C_3$-$C_6$-cycloalkyl, $C_1$-$C_6$-alkoxy and ($C_1$-$C_6$-alkoxy)carbonyl, wherein the six radicals last mentioned are unsubstituted or partially or fully halogenated;

$R^4$ is selected from the group consisting of H and halogen; or $R^3$ and $R^4$ form together with the carbon atom to which they are attached a methylene group;

$R^5$ is selected from the group consisting of halogen, cyano, $SF_5$, tri-($C_1$-$C_4$)silyl-$C_2$-$C_4$-alkynyl, ($C_1$-$C_6$-alkyl)aminocarbonyl, di-($C_1$-$C_6$-alkyl)aminocarbonyl, $C_1$-$C_6$-alkyl, $C_2$-$C_6$-alkenyl, $C_2$-$C_6$-alkynyl, $C_3$-$C_6$-cycloalkyl, phenyl, $C_1$-$C_6$-alkoxy, $C_1$-$C_6$-alkylthio, $C_1$-$C_6$-alkylsulfinyl, $C_1$-$C_6$-alkylsulfonyl, ($C_1$-$C_6$-alkoxy)carbonyl, ($C_1$-$C_6$-alkyl)amino, di-($C_1$-$C_6$-alkyl)amino, ($C_1$-$C_6$-alkyl)carbonyl or ($C_1$-$C_6$-alkyl)carbonyloxy, wherein the 14 radicals last mentioned are unsubstituted or substituted with one or more substituents selected from halogen, cyano, $C_1$-$C_4$-alkyl-$C_3$-$C_6$-cycloalkyl, $C_1$-$C_6$-alkyl, $C_2$-$C_6$-alkenyl, $C_2$-$C_6$-alkynyl, $C_3$-$C_6$-cycloalkyl and $C_1$-$C_6$-alkoxy, wherein the five radicals last mentioned are unsubstituted or partially or fully halogenated;

or two $R^5$ on two adjacent carbon atoms present on one phenyl ring are together a bridge selected from N=CH—CH=CH, N=CH—CH=N, $OCH_2CH_2O$, $O(CH_2)O$ and form together with the carbon atoms the two $R^5$ are bonded to a 5- or 6-membered partially unsaturated or aromatic heterocyclic ring, wherein the ring is unsubstituted;

$R^6$ is selected from the group consisting of halogen, nitro, cyano, $SF_5$, tri-($C_1$-$C_4$)silyl-$C_2$-$C_4$-alkynyl, 2,2,2-trifluoro-1-hydroxy-1-(trifluoromethyl)ethyl, ($C_1$-$C_6$-alkyl)aminocarbonyl, di-($C_1$-$C_6$-alkyl)aminocarbonyl, dimethylcarbamoylsulfanyl, morpholine-4-carbonyl, acetamido, pyridyl, pyrrolyl, pyrazolyl, imidazolyl, triazolyl, $C_1$-$C_6$-alkyl, $C_2$-$C_6$-alkenyl, $C_2$-$C_6$-alkynyl, $C_3$-$C_6$-cycloalkyl, phenyl, $C_1$-$C_6$-alkoxy, $C_3$-$C_6$-cycloalkoxy, phenoxy, $C_1$-$C_6$-alkylthio, $C_1$-$C_6$-alkylsulfinyl, $C_1$-$C_6$-alkylsulfonyl, ($C_1$-$C_6$-alkoxy)carbonyl, ($C_1$-$C_6$-alkyl)amino, di-($C_1$-$C_6$-alkyl)amino, ($C_1$-$C_6$-alkyl)carbonyl or ($C_1$-$C_6$-alkyl)carbonyloxy, wherein the 16 radicals last mentioned are unsubstituted or substituted with one or more substituents selected from halogen, cyano, $C_1$-$C_4$-alkyl-$C_3$-$C_6$-cycloalkyl, $C_1$-$C_6$-alkyl, $C_2$-$C_6$-alkenyl, $C_2$-$C_6$-alkynyl, $C_3$-$C_6$-cycloalkyl and $C_1$-$C_6$-alkoxy, wherein the five radicals last mentioned are unsubstituted or partially or fully halogenated;

$R^{aa}$ is selected from the group consisting of —C(=S)N($R^{cc}$)$_2$ and —C(=O)N($R^{ff}$)$_2$;

$R^{bb}$ is CN;

each $R^{cc}$ is independently selected from the group consisting of hydrogen, $C_1$-$C_4$-alkyl, $C_2$-$C_4$-alkenyl, $C_2$-$C_4$-alkynyl, $C_3$-$C_6$-cycloalkyl, $C_1$-$C_4$-alkoxy-$C_1$-$C_2$-alkyl;

each $R^{ff}$ is independently selected from the group consisting of hydrogen, $C_1$-$C_4$-alkyl, $C_2$-$C_4$-alkenyl, $C_2$-$C_4$-alkynyl, $C_3$-$C_6$-cycloalkyl, $C_1$-$C_4$-alkoxy-$C_1$-$C_2$-alkyl;

p is 0 or 1.

24. The method of claim 21, wherein $R^1$ is selected from the group consisting of H, Me, Et, iPr, cPr, $CH_2CN$, $CF_3$, $CHF_2$, $CH_2F$, $CH_2CH_2F$, $CH_2CHF_2$, $CH_2CF_3$, CN, halogen, $CH_2OH$, $CH_2OMe$, $CH_2OEt$, $CO_2Me$, $CO_2Et$, $CH_2CO_2Me$, $CH_2CO_2Et$, $CH_2OSi(Me)_3$ and $CH_2OSi(Et)_3$.

25. The method of claim 21, wherein $R^3$ is selected from the group consisting of H, Me, Et, iPr, cPr, $CH_2CN$, $CF_3$, $CHF_2$, $CH_2F$, $CH_2CH_2F$, $CH_2CHF_2$, $CH_2CF_3$, CN, halogen, $CH_2OH$, $CH_2OMe$, $CH_2OEt$, $CO_2Me$, $CO_2Et$, $CH_2CO_2Me$, $CH_2CO_2Et$, $CH_2OSi(Me)_3$ and $CH_2OSi(Et)_3$.

26. The method of claim 21, wherein $R^5$ is selected from the group consisting of halogen, Me, Et, iPr, cPr, OMe, OEt, OiPr, ethynyl, (trimethylsilyl)ethynyl, vinyl, Ph, CN, $CF_3$, $OCF_3$, $SF_5$, $CHF_2$, $OCHF_2$, SMe, S(O)Me, S(O)$_2$Me, $SCF_3$, S(O)$CF_3$, S(O)$_2$CF$_3$, SCHF$_2$, S(O)CHF$_2$, S(O)$_2$CHF$_2$, CO$_2$Me, CO$_2$Et, C(O)Me, OAc, C(O)NHMe, C(O)NMe$_2$, CH$_2$OMe and CH$_2$OEt;

or two R$^5$ on two adjacent carbon atoms present on one phenyl ring are together a bridge selected from the group consisting of N=CH—CH=CH, N=CH—CH=N, OCH$_2$CH$_2$O, O(CH$_2$)O and form together with the carbon atoms the two R$^5$ are bonded to a 5- or 6-membered partially unsaturated or aromatic heterocyclic ring, wherein the ring is unsubstituted.

27. The method of claim 21, wherein

R$^6$ is selected from the group consisting of halogen, Me, Et, iPr, cPr, tBu, OMe, OEt, OnPr, OiPr, OtBu, OPh, ethynyl, (trimethylsilyl)ethynyl, vinyl, Ph, NO$_2$, CN, CF$_3$, OCF$_3$, SF$_5$, CHF$_2$, OCHF$_2$, SMe, S(O)Me, S(O)$_2$Me, SCF$_3$, S(O)CF$_3$, S(O)$_2$CF$_3$, SCHF$_2$, S(O)CHF$_2$, S(O)$_2$CHF$_2$, CO$_2$Me, CO$_2$Et, CO$_2$iPr, C(O)Me, OAc, C(O)NHMe, C(O)NMe$_2$, CH$_2$OMe, CH$_2$OEt, fluoromethyl, 2,2,2 trifluoroethyl, 1,2,2,2-tetrafluoro-1-(trifluoromethyl)ethyl, 2,2,2-trifluoro-1-hydroxy-1-(trifluoromethyl)ethyl, dimethoxymethyl, chloro(difluoro)methoxy, 2,2,2-trifluoroethoxy, 2,2 difluorocyclopropoxy, tert-butylsulfanyl, dimethylcarbamoylsulfanyl, morpholine-4-carbonyl, acetamido, 2-pyridyl, 3-pyridyl, 4-pyridyl, pyrrol-1-yl, pyrazol-1-yl, imidazol-1-yl and 1,2,4-triazol-1-yl.

28. The method of claim 21, wherein

Y is phenyl unsubstituted or substituted with 1, 2, 3, 4 or 5 substituents R$^5$; or naphthyl unsubstituted or substituted with 1 substituent R$^5$;

Q is phenyl unsubstituted or substituted with 1, 2 or 3 substituents R$^6$; cyclohexyl unsubstituted or substituted with 1 substituent R$^6$; or a 6-membered aromatic heterocyclic ring containing 1, 2 or 3 nitrogen atoms in the ring, wherein the aforementioned ring is unsubstituted or substituted with 1, 2 or 3 substituents R$^6$;

R$^1$ is selected from the group consisting of H, Me, Et, CN, CH$_2$CN, CH$_2$CF$_3$, halogen, CH$_2$OH, CH$_2$OMe, CH$_2$OEt, CH$_2$CO$_2$Me, CH$_2$CO$_2$Et, CH$_2$OSi(Me)$_3$ and CH$_2$OSi(Et)$_3$;

R$^2$ is selected from the group consisting of H and halogen;

R$^3$ is selected from the group consisting of H, Me, Et, CN, CH$_2$CN, CH$_2$CF$_3$, halogen, CH$_2$OH, CH$_2$OMe, CH$_2$OEt, CH$_2$CO$_2$Me, CH$_2$CO$_2$Et, CH$_2$OSi(Me)$_3$ and CH$_2$OSi(Et)$_3$;

R$^4$ is selected from the group consisting of H and halogen;

R$^5$ is selected from the group consisting of halogen, cyano, tri-(C$_1$-C$_4$)silyl-C$_2$-C$_4$-alkynyl, C$_1$-C$_6$-alkyl, C$_2$-C$_6$-alkenyl, C$_2$-C$_6$-alkynyl, C$_3$-C$_6$-cycloalkyl, phenyl, C$_1$-C$_6$-alkoxy, C$_1$-C$_6$-alkylthio and (C$_1$-C$_6$-alkoxy)carbonyl, wherein the eight radicals last mentioned are unsubstituted or partially or fully halogenated;

or two R$^5$ on two adjacent carbon atoms present on one phenyl ring are together a bridge selected from the group consisting of N=CH—CH=CH, N=CH—CH=N, OCH$_2$CH$_2$O, O(CH$_2$)O and form together with the carbon atoms the two R$^5$ are bonded to a 5- or 6-membered partially unsaturated or aromatic heterocyclic ring, wherein the ring is unsubstituted;

R$^6$ is selected from the group consisting of halogen, nitro, cyano, tri-(C$_1$-C$_4$)silyl-C$_2$-C$_4$-alkynyl, 2,2,2-trifluoro-1-hydroxy-1-(trifluoromethyl)ethyl, dimethoxymethyl, dimethylcarbamoylsulfanyl, morpholine-4-carbonyl, acetamido, pyridyl, pyrrolyl, pyrazolyl, imidazolyl, triazolyl, C$_1$-C$_6$-alkyl, C$_2$-C$_6$-alkenyl, C$_2$-C$_6$-alkynyl, C$_3$-C$_6$-cycloalkyl, phenyl, C$_1$-C$_6$-alkoxy, C$_3$-C$_6$-cycloalkoxy, phenoxy, C$_1$-C$_6$-alkylthio, C$_1$-C$_6$-alkylsulfonyl and (C$_1$-C$_6$-alkoxy)carbonyl, wherein the eleven radicals last mentioned are unsubstituted or partially or fully halogenated;

R$^{aa}$ is —C(=S)N(R$^{cc}$)$_2$;

R$^{bb}$ is CN;

each R$^{cc}$ is independently selected from the group consisting of H, Me, Et, propargyl, allyl, CH$_2$OMe, CH$_2$OEt;

p is 0 or 1.

29. The method of claim 21, wherein R$^5$ is selected from the group consisting of halogen, Me, OMe, CN, CF$_3$, OCF$_3$ and ethynyl.

30. The method of claim 21, wherein R$^6$ is selected from the group consisting of halogen, Me, OMe, CN, CF$_3$, OCF$_3$ and ethynyl.

* * * * *